United States Patent
Knutsen et al.

(10) Patent No.: US 11,147,788 B2
(45) Date of Patent: *Oct. 19, 2021

(54) COMPOUNDS FOR THE TREATMENT OF NEUROMUSCULAR DISORDERS

(71) Applicant: NMD PHARMA A/S, Aarhus N (DK)

(72) Inventors: Lars J. S. Knutsen, Essex (GB); Thomas Holm Pedersen, Risskov (DK); Martin Broch-Lipps, Skøstrup (DK); Claus Elsborg Olesen, Åbyhøj (DK); Marc Labelle, Bedford, NH (US); Ole Baekgaard Nielsen, Egå (DK)

(73) Assignee: NMD PHARMA A/S, Århus N (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/842,807

(22) Filed: Dec. 14, 2017

(65) Prior Publication Data

US 2019/0183833 A1    Jun. 20, 2019

(51) Int. Cl.
| | | |
|---|---|---|
| *A61K 31/216* | (2006.01) | |
| *A61K 31/085* | (2006.01) | |
| *A61K 31/055* | (2006.01) | |
| *A61P 21/04* | (2006.01) | |
| *C07K 14/705* | (2006.01) | |

(52) U.S. Cl.
CPC .......... *A61K 31/216* (2013.01); *A61K 31/055* (2013.01); *A61K 31/085* (2013.01); *A61P 21/04* (2018.01); *C07K 14/705* (2013.01); *C07K 14/70571* (2013.01)

(58) Field of Classification Search
CPC .. A61K 31/216; A61K 31/055; A61K 31/085; A61P 21/04; C07K 14/7057
See application file for complete search history.

(56) References Cited

U.S. PATENT DOCUMENTS

| | | | |
|---|---|---|---|
| 3,544,560 A | 12/1970 | Ludwig et al. | |
| 3,984,411 A | 10/1976 | Claverie et al. | |
| 4,056,628 A | 11/1977 | Winternitz | |
| 4,283,472 A | 8/1981 | Gompf et al. | |
| 4,337,267 A | 6/1982 | Eistetter et al. | |
| 4,803,301 A | 2/1989 | Sakakibara et al. | |
| 5,025,031 A | 6/1991 | Lo et al. | |
| 5,192,785 A | 3/1993 | Lo et al. | |
| 8,163,793 B2 | 4/2012 | Sánchez et al. | |
| 2002/0013295 A1 | 1/2002 | Slusher et al. | |
| 2003/0096802 A1 | 5/2003 | Ohuchida et al. | |
| 2003/0171411 A1* | 9/2003 | Kodra | A61K 31/16 514/357 |
| 2005/0054630 A1 | 3/2005 | Dolle et al. | |
| 2005/0165033 A1 | 7/2005 | Baxter et al. | |
| 2006/0211765 A1 | 9/2006 | Pairaudeau et al. | |
| 2006/0264435 A1 | 11/2006 | Bonnert et al. | |
| 2008/0200499 A1 | 8/2008 | Fischer et al. | |
| 2009/0158637 A1 | 6/2009 | McCall et al. | |
| 2009/0239897 A1 | 9/2009 | Boehm et al. | |
| 2009/0250376 A1 | 10/2009 | Brandvold et al. | |
| 2010/0292517 A1 | 11/2010 | Debuisschert et al. | |
| 2011/0230632 A1 | 9/2011 | Abhari | |
| 2013/0197039 A1 | 8/2013 | Fernandez et al. | |
| 2013/0261101 A1 | 10/2013 | Combs | |
| 2014/0288030 A1 | 9/2014 | Cohen et al. | |
| 2016/0221965 A1 | 8/2016 | Straub et al. | |
| 2016/0237059 A1 | 8/2016 | Straub et al. | |

FOREIGN PATENT DOCUMENTS

| | | |
|---|---|---|
| CA | 676827 A | 12/1963 |
| CN | 101402537 A | 4/2009 |
| CN | 102771479 A | 11/2012 |
| CN | 104059055 A | 9/2014 |
| EA | 200700316 A1 | 6/2007 |
| EP | 0046590 A2 | 3/1982 |
| EP | 0117675 A1 | 9/1984 |
| EP | 0257378 A1 | 3/1988 |
| EP | 0582198 A2 | 2/1994 |
| EP | 0623605 A2 | 11/1994 |
| EP | 2554049 A1 | 2/2013 |
| FR | 1451171 A | 1/1966 |
| FR | 2 551 063 A1 | 3/1985 |
| GB | 573476 A | 11/1945 |
| GB | 822199 A | 10/1959 |
| JP | S52-019632 U | 2/1977 |
| JP | 2009-515943 A | 4/2009 |
| JP | 2010-512387 A | 4/2010 |
| JP | 2014-524886 A | 9/2014 |
| JP | 2015231988 A | 12/2015 |
| KR | 10-2017-0037154 A | 4/2017 |
| RU | 2 372 330 C2 | 11/2009 |
| WO | 86/07353 A1 | 12/1986 |

(Continued)

OTHER PUBLICATIONS

Rouhi, A.M. Chem. & Eng. News, (2003), 81(8), 32-35.*
Morissette, Sherry. Adv. Drug Delivery Rev. (2004), 56, 275-300.*
Rangwala, Shamina M. Chirality (1997) 9:37-47.*
Moon, Lomary. J. Org. Chem. (2010), 75, 5487-5498.*
Wermuth, Camille. Molecular Variations Based on Isoteric Replacements. The Practice of Medicinal Chemistry. Academic Press, 1996. pp. 203-237.*
Andres, Janet. Polymorphs in Pharmaceutical Products. PowerPoint. Created 2008.*

(Continued)

*Primary Examiner* — Tracy Vivlemore
*Assistant Examiner* — Ebenezer O Sackey
(74) *Attorney, Agent, or Firm* — Buchanan Ingersoll & Rooney PC

(57) ABSTRACT

The present invention relates to compounds suitable for treating, ameliorating and/or preventing neuromuscular disorders, including the reversal of drug-induced neuromuscular blockade. The compounds as defined herein preferably inhibit the CIC-1 ion channel.

16 Claims, 12 Drawing Sheets

(56) References Cited

FOREIGN PATENT DOCUMENTS

| | | |
|---|---|---|
| WO | 92/19651 A1 | 11/1992 |
| WO | 98/42670 A1 | 10/1998 |
| WO | 01/68592 A1 | 9/2001 |
| WO | 2002/057222 | 7/2002 |
| WO | 02074768 A1 | 9/2002 |
| WO | 2002/092087 | 11/2002 |
| WO | 03/016259 A2 | 2/2003 |
| WO | 2004/089885 A1 | 10/2004 |
| WO | 2004/094386 A1 | 11/2004 |
| WO | 2005/105727 | 11/2005 |
| WO | 2006/037982 | 4/2006 |
| WO | 2006/037982 A2 | 4/2006 |
| WO | 2007/062678 | 6/2006 |
| WO | 2007030885 A1 | 3/2007 |
| WO | 2007/057767 A2 | 5/2007 |
| WO | 2007/062773 | 6/2007 |
| WO | 2007/062773 A1 | 6/2007 |
| WO | 2008/073311 A2 | 6/2008 |
| WO | 2008138889 A2 | 11/2008 |
| WO | 2011/133920 | 10/2011 |
| WO | 2012/004722 A1 | 1/2012 |
| WO | 2012/155199 A1 | 11/2012 |
| WO | 2013010082 A2 | 1/2013 |
| WO | 2013/042138 A2 | 3/2013 |
| WO | 2016/011019 A1 | 1/2016 |
| WO | 2016/202341 | 12/2016 |
| WO | 2016202341 A1 | 12/2016 |
| WO | 2017/106064 A1 | 6/2017 |
| WO | 2017106064 A1 | 6/2017 |
| WO | 2018/124000 A1 | 7/2018 |
| WO | 2019/115781 A1 | 6/2019 |

OTHER PUBLICATIONS

Angelini C. Spectrum of metabolic myopathies. Biochim Biophys Acta. Apr. 2015; 1852(4):615-621.

Ansar V, Valadi N. Guillain-Barré Syndrome. Prim Care. Jun. 2015;42(2): 189-193.

Birk TJ1. Poliomyelitis and the post-polio syndrome: exercise capacities and adaptation—current research, future directions, and widespread applicability. Med Sci Sports Exerc. Apr. 1993;25(4):466-72.

Burton A. Take your pyridostigmine: that's an (ethical?) order! Lancet Neurol. May 2003;2(5):268.

Finlayson S1, Beeson D, Palace J. Congenital myasthenic syndromes: an update. Pract Neurol. Apr. 2013; 13(2):80-91.

Fletcher SN1, Kennedy DD, Ghosh IR, Misra VP, Kiff K, Coakley JH, Hinds CJ. Persistent neuromuscular and neurophysiologic abnormalities in long-term survivors of prolonged critical illness. Crit Care Med. Apr. 2003; 31(4): 1012-6.

Garcia CC, Potian JG, Hognason K, Thyagarajan B, Sultatos LG, Souayah N, Routh VH, McArdle JJ. Acetylcholinesterase deficiency contributes to neuromuscular junction dysfunction in type 1 diabetic neuropathy. Am J Physiol Endocrinol Metab. Aug. 15, 2012;303(4):E551-61.

Giniatullin RA, Khazipov RN, Oranska TI, Nikolsky EE, Voronin VA, Vyskocil F. The effect of non-quantal acetylcholine release on quantal miniature currents at mouse diaphragm. J Physiol. Jul. 1993; 466:105-14.

Howard JF Jr1. Adverse drug effects on neuromuscular transmission. Semin Neurol. Mar. 1990;10(1):89-102.

Kawamura Y, Kihara M, Nishimoto K, Taki M. Efficacy of a half dose of oral pyridostigmine in the treatment of chronic fatigue syndrome: three case reports. Pathophysiology. May 2003;9(3):189-194.

Killian JM1, Wilfong AA, Burnett L, Appel SH, Boland D. Decremental motor responses to repetitive nerve stimulation in ALS. Muscle Nerve. Jul. 1994;17(7):747-54.

Kwiecinski H1, Lehmann-Horn F, Rüdel R. Drug-induced myotonia in human intercostal muscle. Muscle Nerve. Jun. 1988;11(6):576-81.

Kwiecinski H, Lehmann-Horn F, Rüdel R. Membrane currents in human intercostal muscle at varied extracellular potassium. Muscle Nerve. Jul.-Aug. 1984;7(6):465-9.

Latronico N, Bolton CF. Critical illness polyneuropathy and myopathy: a major cause of muscle weakness and paralysis. Lancet Neurol. 2011 10(10):931-41.

Le Panse R1, Berrih-Aknin S. Autoimmune myasthenia gravis: autoantibody mechanisms and new developments on immune regulation. Curr Opin Neurol. Oct. 2013; 26(5):569-76.

Liantonio A, Accardi A, Carbonara G, Fracchiolla G, Loiodice F, Tortorella P, Traverso S, Guida P, Pierno S, De Luca A, Camerino DC, Pusch M. Molecular requisites for drug binding to muscle CLC-1 and renal CLC-K channel revealed by the use of phenoxyalkyl derivatives of 2-(p-chlorophenoxy)propionic acid. Mol Pharmacol. Aug. 2002;62(2):265-71.

Mehndiratta MM, Pandey S, Kuntzer T. Acetylcholinesterase inhibitor treatment for myasthenia gravis. Cochrane Database Syst Rev. Oct. 13, 2014.

Milone M1, Wong LJ. Diagnosis of mitochondrial myopathies. Mol Genet Metab. Sep.-Oct. 2013;110(1-2):35-41.

Overgaard K, Nielsen OB. Activity-induced recovery of excitability in K(+)-depressed rat soleus muscle. Am J Physiol Regul Integr Comp Physiol. Jan. 2001; 280(1):R48-55.

Pedersen, T.H., F. de Paoli, and O.B. Nielsen. 2005. Increased excitability of acidified skeletal muscle role of chloride conductance. J. Gen. Physiol. 125:237-246.

Plomp JJ, Morsch M, Phillips WD, Verschuuren JJ. Electrophysiological analysis of neuromuscular synaptic function in myasthenia gravis patients and animal models. Exp Neurol. 2015. 270:41-54.

Riisager A, Duehmke R, Nielsen OB, Huang CL, Pedersen TH. Determination of cable parameters in skeletal muscle fibres during repetitive firing of action potentials. J Physiol. Oct. 15, 2014; 592(Pt 20):4417-29.

Roberts M1, Willison HJ, Vincent A, Newsom-Davis J. Multifocal motor neuropathy human sera block distal motor nerve conduction in mice. Ann Neurol. Jul. 1995; 38(1):111-8.

Skov M, De Paoli FV, Lausten J, Nielsen OB, Pedersen TH. Extracellular magnesium and calcium reduce myotonia in isolated ClC-1 chloride channel-inhibited human muscle. Muscle Nerve. Jan. 2015; 51(1):65-71.

Srivastava A, Hunter JM. Reversal of neuromuscular block. Br J Anaesth. 2009. 103(1):115-29.

Stevie, Z.a, Peric, S.a , Pavlovic, S.b, Basta, I.a, Lavrnic, D.a. Myasthenic symptoms in a patient with Kennedy's disorder Acta Neurologica Belgica (Letter) vol. 114, Issue 1, Mar. 2014, pp. 71-73.

Titulaer MJ, Lang B, Verschuuren JJ. Lambert-Eaton myasthenic syndrome: from clinical characteristics to therapeutic strategies. Lancet Neurol. Dec. 2011;10(12):1098-107.

Trojan DA1, Gendron D, Cashman NR. Electrophysiology and electrodiagnosis of the post-polio motor unit. Orthopedics. Dec. 1991;14(12):1353-61.

Wadman RI1, Vrancken AF, van den Berg LH, van der Pol WL. Dysfunction of the neuromuscular junction in spinal muscular atrophy types 2 and 3. Neurology. Nov. 13, 2012;79(20):2050-5.

Wittbrodt, Drugs and myasthenia gravis. An update. Arch. Intern. Med., 157, 399-408, 1997.

Wood SJ, Slater CR. Safety factor at the neuromuscular junction. Prog Neurobiol. Jul. 2001; 64(4):393-429.

Yamada, M.ab, Inaba, A.a, Shiojiri, T.a. X-linked spinal and bulbar muscular atrophy with myasthenic symptoms (Article) Journal of the Neurological Sciences. vol. 146, Issue 2, Mar. 10, 1997, pp. 183-185.

Aromataris, E.C., Pharmacology of the ClC-1 Chloride Channel, PhD Thesis, Dicipline of Physiology, school of Molecular and Biomedical Science, The University of Adelaide, 2009.

Bansagi B, Griffin H, Whittaker RG, Antoniadi T, Evangelista T, Miller J, Greenslade M, Forester N, Duff J, Bradshaw A, Kleinle S, Boczonadi V, Steele H, Ramesh V, Franko E, Pyle A, Lochmüller H, Chinnery PF, Horvath R. Genetic heterogeneity of motor neuropathies. Neurology. 2017 28; 88(13):1226-1234.

Bettoni, G. et al., J. Med. Chem. 1987, 30, 1267-1270.

(56) References Cited

OTHER PUBLICATIONS

Conte-Camerino, D., Mambrini, M., DeLuca, A., Tricarico, D., Bryant, S.H., Tortorella, V., Bettoni, G. Enantiomers of clofibric acid analogs have opposite actions on rat skeletal muscle chloride channels, Pflugers Archiv., 1988, 413, 105-107.
Feller, D.R., Kamanna, V.S., Newman, H.A.I., Romstedt, K.J., Witiak, D.T., Bettoni, G., Bryant, S.H., Conte-Camerino, D., Loiodice, F., Tortorella, V. Dissociation of hypolipidemic and antiplatelet actions from adverse myotonic effects of clofibric acid related enantiomers. J. Med. Chem., 1987, 30, 1265-1267.
Gilhus, N.E. New England Journal of Medicine, 2016, 375, 2570-2581.
Gilhus, N.E., Owe, J.F., Hoff, J.M., Romi, F., Skeie, G.O., Aarli, J.A. Myasthenia Gravis: A Review of Available Treatment Approaches, Autoimmune Diseases, 2011, Article ID 84739).
Gilmore KJ, Morat T, Doherty TJ4, Rice CL. Motor unit number estimation and neuromuscular fidelity in 3 stages of sarcopenia. 2017 55(5):676-684).
Hwee, D.T., Kennedy, A.R., Hartman, J.J., Ryans, J., Durham, N., Malik, F.I., Jasper, J.R. The small-molecule fast skeletal troponin activator, CK-2127107, improves exercise tolerance in a rat model of heart failure. Journal of Pharmacology and Experimental Therapeutics, 2015, 353, 159-168).
Liantonio, A. et al., Structural requisites of 2-(p-chlorophenoxy)propionic acid analogues for activity on native rat skeletal muscle chloride conductance and on heterologously expressed CLC-1. Br. J. Phamacol., 2003, 129, 1255-1264.
Liantonio, A. Pusch, M., Picollo, A., Guida, P., De Luca, A., Pierno, S., Fracchiolla, G., Loiodice, F., Tortorella, P., Conte-Camerino, D. Investigations of pharmacologic properties of the renal CLC-K1 chloride channel co-expressed with barttin by the use of 2-(p-chlorophenoxy)propionic acid derivatives and other structurally unrelated chloride hannels blockers. J. Am. Soc. Nephrol., 2004, 15, 13-20.
Murphy GS, Brull SJ. Residual neuromuscular block: lessons unlearned. Part I: definitions, incidence, and adverse physiologic effects of residual neuromuscular block. Anesth Analg. 2010 111(1):120-8).
Pedersen, T.H., Riisager, A., Vincenzo de Paoli, F., Chen, T-Y, Nielsen, O.B. Role of physiological ClC-1 Cl-ion channel regulation for the excitability and function of working skeletal muscle. J. Gen. Physiol. 2016, 147, 291-308.
Pusch, M., Liantonio, A., Bertorello, L., Accardi, A., De Luca, A., Pierno, S., Tortorella, V., Conte-Camerino, D. Pharmacological characterization of chloride channels belonging to the ClC family by the use of chiral clofibric acid derivatives. Molecular Pharmacology, 2000, 58, 498-507.
Sandham, D.A. et al., Bioorganic & Medicinal Letters, 17, 4347-4350, (2007).
Bettoni, S. et al., Chiral beta-Aryloxy Acetic Acids: Synthesis, Absolute Configuration, Chemical Resolution, and Direct Separation by HPLC, Chirality, 1992, 4:193-203.
Maria Grazia Perrone et al., Stereoselective prostereogenic 3-oxo ester reduction mediated by a novel yeast alcohol dehydrogenase derived from Kluyveromyces marxianus CBS 6556, Advanced Synthesis & Catalysis (2007), 349(7), 1111-1118.
Giuseppe Fracchiolla et al., Synthesis, biological evaluation, and molecular modeling investigation of chiral phenoxyacetic acid analogues with PPARα and PPARγ agonist activity, ChemMedChem (2007), 2(5), 641-654.
Maria Grazia Perrone et al., Screening yeasts for the stereoselective reduction of oxoester clofibrate analogues, Tetrahedron: Asymmetry (2005), 16(8), 1473-1477.
Maria Grazia Perrone et al., Reaction of cesium 4-chlorophenate and chlorohydrins from threonines: synthesis of clofibrate analogs, Tetrahedron: Asymmetry (2005), 16(4), 783-792.
Maria Grazia Perrone et al., Synthesis and biological evaluation of new clofibrate analogues as potential PPARα agonists, European Journal of Medicinal Chemistry (2005), 40(2), 143-154.
Maria Grazia Perrone et al., Diastereo- and enantioselective bioreduction of ethyl 2-(4-chlorophenoxy)-3-oxobutanoate clofibrate analogues by Kluyveromyces marxianus and other whole cell biocatalysts, Tetrahedron: Asymmetry (2004), 15(22), 3511-3517.
Maria Grazia Perrone et al., Baker's yeast-mediated reduction of ethyl 2-(4-chlorophenoxy)-3-oxoalkanoates intermediates for potential PPARα ligands, Tetrahedron: Asymmetry (2004), 15(22), 3501-3510.
Fulvio Gualtieri et al., Presynaptic Cholinergic Modulators as Potent Cognition Enhancers and Analgesic Drugs. 2. 2-Phenoxy-, 2-(Phenylthio)-, and 2-(Phenylamino)alkanoic Acid Esters, Journal of Medicinal Chemistry (1994), 37(11), 1712-19.
FCH Group, Chemical Catalog, 2167656-52-0 Registry, Jan. 1, 2018.
Ukrorgsyntez Ltd., Chemical Catalog, 1874151-65-1 Registry, Feb. 25, 2016.
Ukrorgsyntez Ltd., Chemical Catalog, 1855714-49-6 Registry, Jan. 29, 2016.
International Search Report and Written Opinion dated Apr. 3, 2019 in counterpart International Application No. PCT/EP2018/084989.
Database Registry [Online], Chemical Abstracts Service, Columbus, Ohio, US; Propanoic acid, 2-[2-(2-benzothiazolyl)phenoxy]—(CA Index Name), XP002789551, Mar. 13, 2007, retrieved from STN Database accession No. RN-926236-33-1.
Fabio Del Bello et al, Fruitful Adrenergic [alpha] 2C-Agonism/[alpha] 2A-Antagonism Combination to Prevent and Contrast Morphine Tolerance and Dependence ( 1), +, Journal of Medicinal Chemistry. 53 (21)7825-7835, Nov. 11, 2010, XP055484778, ISSN: 0022-2623, DOI: 10.1021/jm100977d.
Francesco Gentili et al., [alpha] 2-Adrenoreceptors Profile Modulation. 2. 1 Biphenyline Analogues as Tools for Selective Activation of the [alpha] 2C-Subtype, Journal of Medicinal Chemistry, 47(25):6160-6173, Dec. 1, 2004, XP055484835, ISSN: 0022-2623, DOI: 10.1021/jm0408215.
Ram, Bhagat et al., Database CA [Online] Chemical Abstracts Service, Columbus, Ohio, US; Potential hypolipidemic agents part VI: synthesis and biological activity of some new 4-chloro/methyl-2-yrazolylphenoxy alkanoates, XP002782149, retrieved from STN Database accession No. 1992:255529.
Campiani G et al, Pyrrolobenzothiazepinones and Pyrrolobenzoxazepinones: Novel and Specific Non-Nucleoside HIV-1 Reverse Transcriptase Inhibitors with Antiviral Activity, Journal of Medicinal Chemistry, 39(14):2672-2680, Jan. 1, 1996 (Jan. 1, 1996), XP002564131, American Chemical Society ISSN 0022-2623, DOI: 10.1021/JM950702C [retrieved on Jun. 1, 1996].
M. A. Mikhaleva et al., Use of the Amidomethylation Reaction for the Sysnthesis of 2-(Aryloxy)-3-Alanines, Novosibirsk Institute o f Organic Chemistry, Siberian Division, Academy o f Sciences, USSR Translated from Zhurnal Obshchei Khimii, 34(7):2153-2157, Jul. 1964.
A. Chiriac et al., Quantitative Structure-Activity Relations With the MTD Procedure for Plant Growth-Regulation Optically Active Acetic Acid Derivatives, Revue Roumaine de Chimie, 27 (4):561-568, 1982.
G. Fracchiolla et al., Synthesis, biological evaluation, and molecular modeling investigation of chiral 2-(4-chloro-phenoxy)-3-phenyl-propanoic acid derivatives with PPARa and PPARc agonist activity, Bioorganic & Medicinal Chemistry 16:9498-9510, 2008.
A. Chiriac et al., Qunatitiavie Structure-Citostatic Activity Relations for Diketonato-Complexes of Tetravalent Transitional Metals, Universitatea din timisoara, Facultatea de Stiinte ale Naturii, Serie Chimie, 4:1-6,1989.
L. J. Edgerton et al., The Effect of Some Growth Substances on Leaf Petiole Abscission and Preharvest Drop of Several Apple Varieties, Proceedings of the American Society for Horticultural Science, 62:159-166, 1953.
G. Fracchiolla et al., Supporting Information, Synthesis, biological evaluation, and molecular modeling investigation of chiral 2-(4-chloro-phenoxy)-3-phenyl-propanoic acid derivatives with PPARa and PPARc agonist activity, 2008.
J. D. Williams et al., Synthesis and structure-activity relationships of novel phenoxyacetamide inhibitors of the Pseudomonas aeruginosa type III secretion system (T3SS), 23(5):1027-1043, 2015.

(56) References Cited

OTHER PUBLICATIONS

K. Hayashi et al., Small-molecule agonists and antagonists of F-box protein-substrate interactions in auxin perception and signaling, PNAS, 105(14): 5632-5637, Apr. 8, 2008.
R. C. Brian, Action of Plant Growth Regulators III, Adsorption of Aromatic Acids to Oat Monolayers, Plant Physiology, 35(6):773-782, Nov. 1960.
E. Duintjer et al., Synthetic Plant Hormones, VI. Preparation of some alpha-Phenoxy and alpha-1-Naphtohoxy fatty Acids (Addition to Part IV), Short Communications, Part V. Aeta Chem. Scand., 8(119):1493-1494, 1954.
M. Matell, On the Use of 2-Amino-1-phenyl-propane (Benzedrine) for Optical Resolution of Acids, Short Communications, Aeta Chem Scand. 7(4):698-699, 1953.
N. M. White (edited), Eurosensors XII, 1:511-514, Sep. 1998.
E. J. Lien et al., Quantitative Structure-Activity Correlation of Optical Isomers: a Molecular Basis for Pfeiffer's Rule, Molecular Pharmacology, 12:598-604, Aug. 22, 1975.
M. Ochiai et al., Studies on Herbicides and Plant Growth Regulators. II. Synthesis and Some Reactions of 1-Aryloxyacylpyrazoles, Chem. Pharm. Bull., 14(6):628-641, 1966.
C. Stanley, Derivatization of Pesticide-Related Acids and Phenols for Gas Chromatographic Determination, 14 (3):321-323, May-Jun. 1966.
M. Alexander, Persistence and Biological Reactions of Pesticides in Soils, Soil Science Society of America Proceedings, 29(1):1-7, Jan.-Feb. 1965.
C. A. Bache et al., Absence of Phenoxyacid Herbicide Residues in the Milk of Dairy Cows at High Feeding Levels, Journal of Dairy Science, 47(3):298-299, Mar. 1964.
K. Burger et al., Decomposition of Phenoxyalkyl Carboxylic Acids, Soil Science Society of America Proceedings, 26 (3):243-246, May-Jun. 1962.
M. Alexander et al., Effect of Chemical Structure on Microbial Decomposition of Aromatic Herbicides, Agricultural and Food Chemistry, 9(1):44-47, Jan.-Feb. 1961.
B. Sjoberg, Stereochemical studies. XI The relationship between optical rotatory dispersion and configuration for some ketones, Arkiv for Kemi Band 15(5):473-480, 1960.
B. Sjoberg, Stereochemical studies. X The relationship between optical rotatory dispersion and configuration for some carboxylic acids, Arkiv for Kemi Band 15(5):473-480, 1960.
D. Gowing et al., Uncommon Plant Growth Regulators for the control of Nutgrass and Oxalis, Weeds, pp. 279-283, 1960.
W. C. Shaw et al., The Selective Herbicidal Properties of Several Variously Substituted Phenoxyalkylcarboxylic Acids, Journal of the Weed Society of America, V(2):75-92, Apr. 1957.
C. H. Fawcett et al., Investigations on Fungicides, ii. Aryloxy- and Arylthio-Alkanecarboxylic Acids and Their Activity as Fungicides and Systemic Fungicides, Ann. appl. Biol., 45(r): 158-176, 1957.
J. A. Zwar et al., Inhibition of Transport of Indole-3-Acetic Acid in the Etiolated Hypocotyl of *Phaseolus vulgaris* L., Inhibition of IAA Transport, Jun. 11, 1956.
C. H. Fawcett et al., Studies on Plant Growth-Regulationg Substances, VIII. The Growth Promoting Activity of Certain Aryloxy- and Arylthio-Alkeanecarboxylic Acids, Ann. appl. Biol., 43(3): 342-354, 1955.
A. W. Galston et al., The Adaptive Formation and Physiological Signaificance of Indoleacetic Acid Oxidase, American Journal of Botany, 41(5):373-380, May 1954.
M. Matell, Stereochemical studies on plant growth regulators. VII, Optically active alpha-(2-methyl-4-chlorophenoxy)-propionic acid and alpha-(2,4-dichlorophenoxy)-n-butyric acid and their steric relations, Arkiv for Kemi, 6(4):365-373, 1953.
M. Matell, Stereochemical Studies on Plant Growth Substances, Kungl. Lantbruks-Hogskolans Annaler, 20:206-240, 1953.
C. H. Fawcett et al., Studies on Plant Growth-Regulating Substances, vi. Side-Chain Structure in Relation to Growth-Regulating Activity in the Aryloxyalkylcarboxylic Acids, 40 (2):231-243, Jun. 1953.
J. Munch-Petersen, alpha-Aryloxyesters. II. Further Studies on Certain Self-Condesations, Acta Chemica Scandinavica, 7:14-20, 1953.
J. Munch-Petersen, Aryloxyesters. The Reacitivity of the alpha-Hydrogen and the Carbonyl Carbon towards GBasic Reagents, Acta Chemica Scandinavica, 5:519-528, 1951.
C. M. Hill et al., The Synthesis, Propertis and Dehydrohalogenation of Some alpha-Phenoxy and 2,4-Dichlorophenoxy Substituted Acid Chlorides, Phenoxy Substituted Acid Chlorides, 73:1660-1662, Aug. 24, 1950.
J. Munch-Petersen et al., Acylations of Certain alpha-Alkoxy and alpha-Aryloxy Ketones and Esters, University of Claifornia Los Angeles, 71:770-773, Mar. 1949.
L. Haskelberg, The Halogenation of Aryloxyacetic Acids and Their Homologs, Daniel Sieff Research Institute, pp. 426-433, Dec. 16, 1946.
H. E. Thompson et al., New Growth-Regulating Compounds. I. Summary of Growth-Inhibitory Activities of Some Organic Compounds as Determined By Three Tests, Botanical Gazette, pp. 476-507, 1946.
C. Zhang et al., Synthesis and Bioactivity of Novel Inhibitors for Type III Secretion System of Pseudomonas aeruginosa PAO1, Chinese Journal of Organic Chemistry, 33:1309-1318, 2013.
C. Temporini et al., Enantiomeric separation of 2-aryloxyalkyl- and 2-arylalkyl-2-aryloxyacetic acids on a Penicillin G Acylase-based chiral stationary phase: Influence of the chemical structure on retention and enantioselectivity ESJPBA, ISSN: 0731-7085, 45(2):211-218, 2007.
A. Liantonio et al., Investigations of Pharmacologic Properties of the Renal CLCK1 Chloride Channel Co-expressed with Barttin by the Use of 2-(p-Chlorophenoxy)Propionic Acid Derivatives and Other Structurally Unrelated Chloride Channels Blockers, J Am Soc Nephrol. 15:13-20, 2004.
Kirkiacharian et al., Structure-activity relationships of some 3-substituted-4-hydroxycoumarins as HIV-1 protease inhibitors; EFARMA, ISSN: 0014-827X, 57(9):703-708, 2002.
O. H. Rubio et al., A molecular receptor selective for zwitterionic alanine, Org. Biomol. Chem., 15:477-485, 2017.
O. H. Rubio et al., A molecular receptor selective for zwitterionic alanine, Supplementary Material (ESI) for Organic & Biomolecular Chemistry, The Royal Society of Chemistry, 2016.
N. Shams et al., Four-component reaction of alkyl isocyanide, acetylenic esters, phenols and pyrrole; synthesis of dialkyl 2-[(alkylimino)(1 H-pyrrol-2-yl)methyl]-3-(aryloxy) succinate, Journal of Chemical Research, 39:270-273, May 2015.
I. D. Jurberg et al., Synthesis of Functionalized Chromenes and Benzofurans from Aryloxy Proparagyl Malonates, Israel Journal of Chemistry, 53:915-922, 2013.
I. D. Jurberg et al., A gold(I)-Catalyzed Cyclization / Photochemical Rearrangement Sequence for the Synthesis of Functionalized Benzofurans from Aryloxy Propargyl Malonates Supporting Information, 2013.
G. Fracchiolla et al., Synthesis, biological evaluation and molecular investigation of fluorinated peroxisome proliferator-activated receptors a/c dual agonists, Bioorganic & Medicinal Chemistry 20:2141-2151, 2012.
M. Bolli et al., 2-Imino-thiazolidin-4-one Derivatives as Potent, Orally Active S1P1 Receptor Agonists, J. Med. Chem., 53:4198-4211, 2010.
M. Bolli et al., Supporting Information, 2-Imino-thiazolidin-4-one Derivatives as Potent, Orally Active S1P1 Receptor Agonists, 2010.
G. Fracchiolla et al., Synthesis, Biological Evaluation, and Molecular Modeling Investigation of Chiral Phenoxyacetic Acid Analogues with PPARa and PPARg Agonist Activity, ChemMedChem, 2:641-654, 2007.
A. Ramazani et al., Dipotassium Hydrogen Phosphate-Catalyzed Synthesis of Dialkyl 2-(4-Fluoro-Phenoxy)-2-Butendioates from Stabilized Phosphorus Ylides in Solven-Free Conditions, Phosphorus, Sulfur and Silicon, 182:413-417, 2007.
G. Carbonara et al., Carboxylic acids and skeletal muscle chloride channel conductance: effects on the biological activity induced by

(56) References Cited

OTHER PUBLICATIONS the introduction of an aryloxyalkyl group alpha to the carboxylic function of 4-chloro-phenoxyacetic acid, Il Farmaco, 56:749-754, 2001.

M. Protiva et al., Potential Cerebral Stimulants: Esters of 2-Dimethyl-Aminoethanol With Some Lipophilic Carboxylic Acids, Collect. Czech. Chem., 55:1278-1289, 1990.

G. W. K. Cavill et al., The Chemistry of Plant Growth-regulators. Part II. Modification of the Side-chain of 2:4-Dichlorophenoxyacetic Acid, University of California—Los Angeles, pp. 1388-1391, 1954.

K. Gasanov et al., Synthesis and Research of TRI-n-Butylstannyl Ester of 2,4-Dichlorophenoxy-α-Butyric Acid, Academic Council of the Institute of Petrochemical Processes of the Academy of Sciences of Azerbaijan SSR, Deposited Doc. 309:10, 1980.

V.P. Mamaev et al., Synthese of-aryloxy—alanines, SSSR, News Bulletin of the Siberian Department of the USSR Academy of Science, 11:145-148, 1962.

V. V. Dovlattan et al., 5-aryloxypyrimidines, Academy of the Agricultural Sciences of Armenia, 56(1-2): 102-108, 2003.

R. Nakashima et al., Effect of α-Substituted Carboxilyc Acids and Their Ethyl Esters on the Growth of Lettuces seedings, Japan Society of Agricultural Chemistry, 65(12): 1777-1780, 1991.

K. Gasanov et al., Proton NMR study of solavation of lead derivatives of aryloxy carboxylic acids, Azerbaidzhanskii Khimicheskii Zhurnal, 2:58-61, 1988.

D. Khydyrov et al., Synthesis and herbicide activity of N-methylcarbamate derivatives of 2-hydroxyethyl 2,4-dichloroaryloxyalkanoates, Akademiya Nauk Azerbaidzhanskoi SSR, 43(1):38-41, 1987.

V. D. Cihimil, Determination of Chlorophenoxylkankarbronic Acids and Chlorphenols in Water by the Method of Gas-Liquidchromatography in the Form of 2,2,2-Trichlorethyl and Pentaftorbenzyl Ether and Pentaftorbenzyl Etherand Pentaf Etherether ЧМИЛЬ В. Д , Journal of Analytical Chemistry, XXXI(4):711-714, 1984.

K. Gasanov et al., Synthesis and carbon-13 NMR study of some organosilicon derivatives of aryloxycarboxylic acids, Azerbaidzhanskii Khimicheskii Zhurnal, 5:47-50, 1982.

G. Zeiger et al., Aryloxyalkanoic acids, their esters and cycling products as pesticide-active compounds, Scientific Journal of the "Karl Liebknecht" University of Pedagogic of Potsdam, 21(1):29-46, 1977.

S. Mamedov et al., Synthesis of Complex Ethers of 3-Chlorethyl Ether α-(2,4-Dichlorophenoxy) Butyric Acid, Chemical Magazine of Azerbaijan, 4:79-82, 1977.

A. I. Karaev et al., About the Injuries Healing Properties of Synthetic Growth Regulators, Reports of the Academy of Sciences of Azerbaijan SSR, IX(1):1-4, Sep. 18, 1952.

S. N. Lutokhin, Parthenocarpy in *Cucurbita maxima* L. Induced by Phytohormones With Glycerin, Reports of the Academy of Sciences of USSR, LVIII(7):1-3, 1947.

V. V. Feofilaktov et al., Synthesis of α-(2,4-Dichloro-Phenoxy) -n.-Butyric Acid, Magazine General Chemistry, XVII(2):253-256, 1947.

C. Rivalle et al., III. —Study of diversely-substituted α-aryloxy pinacolones. Newsletter of the French Chemistry Society BSCFAS, 7:2555-3002, 1972.

B. S. Kirkiacharian, No. 293.—Thermal free radicals: study of malonic and cyanoacetic esters, No. 5, 1971.

M. Julia, No. 158.—Plant growth factors. VIII.—On some aliphatic α-dichloro-phenoxy-diacids, pp. 396-399, Jun. 1955.

V. Koula et al., Analysis of the analogues of 2,4-dichlorophenoxyacetic acid and related substances, Annals of the Czechoslovak Academy of Agricultural Sciences, XXVII(A-4):289-294, 1954.

Watanabe et al., "Effects of Substituent and Temperature on Enantioselectivity for Lipase-Catalyzed Esterification of 2-(4-Substituted Phenoxy) Propionic Acids in Organic Solvents," Bioorganic Chemistry, (Apr. 1, 2001), vol. 29, No. 2, pp. 65-76.

Office Action (Communication pursuant to Article 94(3) EPC) dated Sep. 9, 2019, by the European Patent Office in corresponding European Patent Application No. 16 738 352.0-1114. (6 pages).

Database Registry [Online] Chemical Abstracts Service, Columbus Ohio, US; (Sep. 2016), XP002796472, retrieved from STN Database accession No. 1989185-38-7 (abstract only).

Nugiel et al., "De Novo Design of a Picomolar Nonbasic 5-HT1B Receptor Antagonist," Journal of Medicinal Chemistry, (Jan. 1, 2010), vol. 53, No. 4, pp. 1876-1880.

The partial European Search Report dated Jan. 2, 2020, by the European Patent Office in corresponding European Application No. 19181253.6-1109. (17 pages).

The extended European Search Report dated Jan. 3, 2020, by the European Patent Office in corresponding European Patent Application No. 19181240.3-1109. (8 pages).

Fernandes et al., "Synthesis of Some New 2-[2-(5-Phenyl-3-isoxazolyl) phenoxy methyl]-4H-1-benzopyran-4-ones," Journal of the Indian Chemical Society, (Jan. 1, 1984), vol. 61, pp. 604-606.

Ferorelli et al., "Carboxylic acids and skeletal muscle chloride channel conductance: effects on the biological activity induced by the introduction of methyl groups on the aromatic ring of chiral α-(4-chloro-phenoxy)alkanoic acids," Il Farmaco, (2001), vol. 56, No. 3, pp. 239-246.

Ito et al., "A Simple Synthetic Method of trans-5-Aryl and 5-Cyclopropyl Derivatives of 2-Isoxazolin-4-ol via Intramolecular Ring Opening of α,β-Epoxy Ketone Oximes," Bulletin of the Chemical Society of Japan, (Sep. 1, 1990), vol. 63, No. 9, pp. 2739-2741.

Roth et al., "Zur Kondensation von Chalkinoxiden mit Hydroxylamin," Archiv Der Pharmazie, (Jan. 1, 1961), vol. 294, No. 12, pp. 769-774.

The extended European Search Report dated Oct. 11, 2019, by the European Patent Office in corresponding European Patent Application No. 19181262.7-1110. (7 pages).

Search Report dated Oct. 1, 2019, by the Russian Patent Office in corresponding Russian Patent Application No. 2017143609/04(075061). (2 pages).

Office Action dated Feb. 11, 2020, by the Intellectual Property India in India Patent Application No. 201717046494 with an English Translation of the Office Action. (6 pages).

Ukrorgsyntez Ltd., Chemical Catalog, 1704952-69-1 Registry, Entered STN: May 15, 2015.

Office Action dated Jul. 15, 2020, by the Brazil Patent Office in Brazil Patent Application No. BR112017026739-0. (4 pages).

Office Action dated Aug. 13, 2020, by the Intellectual Property Corporation of Malaysia in Malaysia Patent Application No. PI 2017704383. (3 pages).

Shields et al., "ORg 25969 (sugammadex), a selective relaxant binding agent for antagonism of prolonged rocuronium-induced neuromuscular block," British Journal of Anaesthesia, (Month unknown, 2006), vol. 96, No. 1, pp. 36-43.

Verkman et al., "Chloride channel as drug targets," Nature Reviews Drug Discovery, (Feb. 2009), vol. 8, No. 2, pp. 153-171.

Office Action (Examination report No. 1 for standard patent application) dated Sep. 24, 2020, by the Australian Patent Office in corresponding Australian Patent Application No. 2016279486. (9 pages).

Sandham et al., "2-Cycloalkyl Phenoxyacetic Acid CRTh2 Receptor Antagonists," Bioorganic & Medicinal Chemistry Letters, (2007), vol. 17, pp. 4347-4350.

Final Office Action issued by the U.S. Patent and Trademark Office in the U.S. Appl. No. 16/221,069, dated Jan. 15, 2021, U.S. Patent and Trademark Office, Alexandria, VA. (14 pages).

* cited by examiner

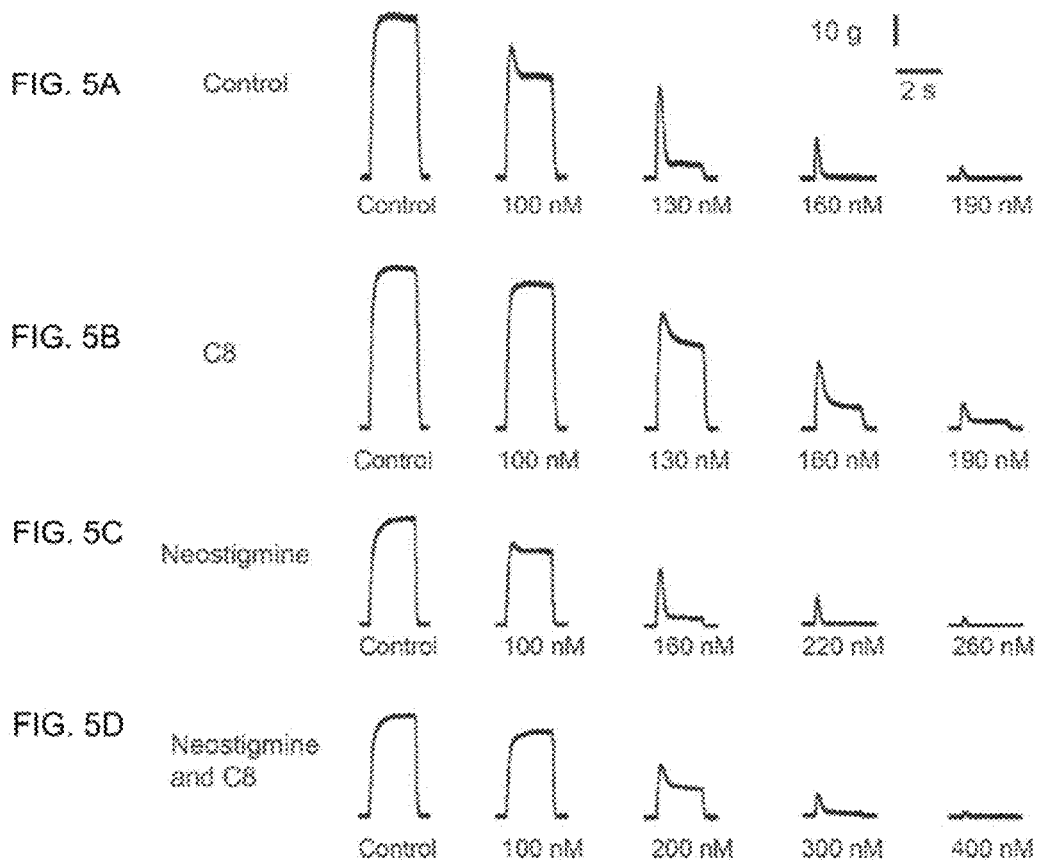
FIG. 5A Control
FIG. 5B C8
FIG. 5C Neostigmine
FIG. 5D Neostigmine and C8
FIG. 5E
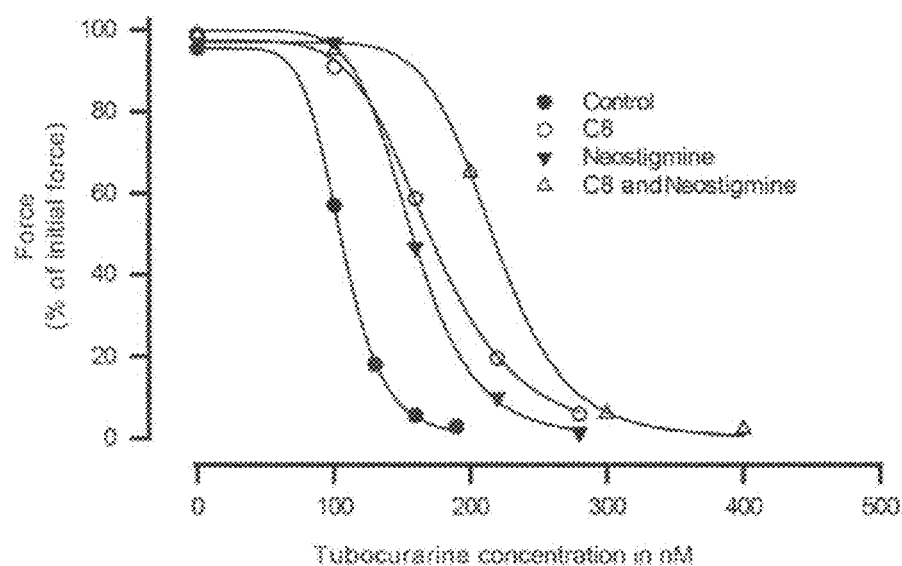

FIG. 6A Control 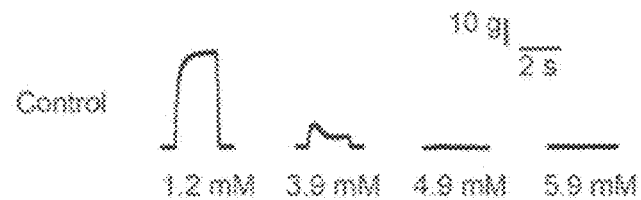
FIG. 6B C8 
FIG. 6C 3,4-AP 
FIG. 6D 3,4-AP and C8 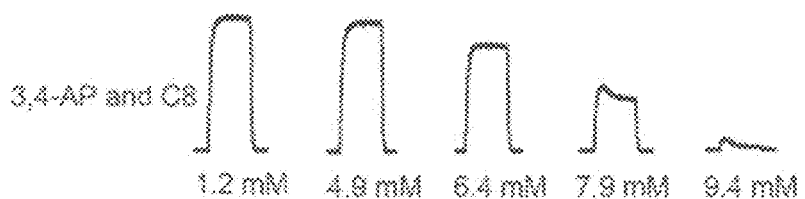

COMPOUNDS FOR THE TREATMENT OF NEUROMUSCULAR DISORDERS

FIELD OF INVENTION

The present invention relates to compounds for use in treating, ameliorating and/or preventing neuromuscular disorders, including the reversal of drug-induced neuromuscular blockade. The compounds as defined herein preferably inhibit the CIC-1 ion channel. The invention further relates to methods of treating, preventing and/or ameliorating neuromuscular disorders, by administering said composition to a person in need thereof.

BACKGROUND

Walking, breathing, and eye movement are examples of essential everyday physiological activities that are powered by contractile activity of skeletal muscle. Skeletal muscles are inherently resting and contractile activity exclusively occurs in response to commands from the central nervous system. Such neuronal commands take the form of action potentials that travel from the brain to the muscle fibers in several steps. The neuromuscular junction (NMJ) is the highly specialized membrane area on muscle fibers where motor neurons come into close contact with the muscle fibers, and it is at NMJ that neuronal action potentials are transmitted to muscular action potentials in a one-to-one fashion via synaptic transmission.

Neuromuscular transmission refers to the sequence of cellular events at the NMJ whereby an action potential in the lower motor neuron is transmitted to a corresponding action potential in a muscle fiber. When a neuronal action potential arrives at the pre-synaptic terminal it triggers influx of $Ca^{2+}$ through voltage gated P/Q-type $Ca^{2+}$ channels in the nerve terminal membrane. This influx causes a rise in cytosolic $Ca^{2+}$ in the nerve terminal that triggers exocytosis of acetylcholine (ACh). Released ACh next diffuses across the synaptic cleft to activate nicotinic ACh receptors in the post-synaptic, muscle fiber membrane. Upon activation, ACh receptors convey an excitatory current flow of $Na^+$ into the muscle fiber, which results in a local depolarization of the muscle fiber at the NMJ that is known as the endplate potential (EPP). If the EPP is sufficiently large, voltage gated $Na^+$ channels in the muscle fiber will activate and an action potential in the muscle fiber will ensue. This action potential then propagates from NMJ throughout the muscle fiber and triggers the $Ca^{2+}$ release from the sarcoplasmic reticulum. The released $Ca^{2+}$ activates the contractile proteins within the muscle fibers thus resulting in contraction of the fiber.

Failure in the neuromuscular transmission can arise from both pre-synaptic dysfunction (Lambert Eaton syndrome, amyotrophic lateral sclerosis, spinal muscular atrophy) and as a result of post-synaptic dysfunction as occurs in myasthenia gravis. Failure to excite and/or propagate action potentials in muscle can also arise from reduced muscle excitability such as in critical illness myopathy (CIM). In Lambert Eaton syndrome, an autoimmune attack against the pre-synaptic P/Q-type $Ca^{2+}$ channels results in markedly reduced $Ca^{2+}$ influx into the nerve terminal during the pre-synaptic action potential and, consequently, a reduced release of ACh into the synaptic cleft. In myasthenia gravis the most common finding is an autoimmune attack on the post-synaptic membrane either against the nicotinic ACh receptors or the musk-receptor in the muscle fiber membrane. Congenital forms of myasthenia are also known. Common to disorders with neuromuscular transmission failure (Lambert Eaton syndrome, amyotrophic lateral sclerosis, spinal muscular atrophy and myasthenia gravis) is that the current flow generated by ACh receptor activation is markedly reduced, and EPPs therefore become insufficient to trigger muscle fiber action potentials. Neuromuscular blocking agents also reduce EPP by antagonizing ACh receptors. In CIM with reduced muscle excitability, the EPP may be of normal amplitude but they are still insufficient to trigger muscle fiber action potentials because the membrane potential threshold for action potential excitation has become more depolarized because of loss-of-function of voltage gated $Na^+$ channels in the muscle fibers.

While ACh release (Lambert Eaton, amyotrophic lateral sclerosis, spinal muscular atrophy), ACh receptor function (myasthenia gravis, neuromuscular blockade) and function of voltage gated $Na^+$ channels (CIM) are essential components in the synaptic transmission at NMJ, the magnitude of the EPP is also affected by inhibitory currents flowing in the NMJ region of muscle fibers. These currents tend to outbalance excitatory current through ACh receptors and, expectedly, they thereby tend to reduce EPP amplitude. The most important ion channel for carrying such inhibitory membrane currents in muscle fibers is the muscle-specific CIC-1 $Cl^-$ ion channel.

ACh esterase (AChE) inhibitors are traditionally used in the treatment of myasthenia gravis. This treatment leads to improvement in most patients but it is associated with side effects, some of which are serious. Because ACh is an import neurotransmitter in the autonomic nervous system, delaying it's breakdown can lead to gastric discomfort, diarrhea, salivation and muscle cramping. Overdosing is a serious concern as it can lead to muscle paralysis and respiratory failure, a situation commonly referred to as cholinergic crisis. Despite the serious side effects of AChE inhibitors, these drugs are today the treatment of choice for a number of disorders involving neuromuscular impairment. In patients where pyridostigmine (a parasympathomimetic and a reversible ACHE inhibitor) is insufficient, corticosteroid treatment (prednisone) and immunosuppressive treatment (azathioprine) is used. Plasma exchange can be used to obtain a fast but transient improvement.

Unfortunately, all of the currently employed myasthenia gravis drug regimens are associated with deleterious long-term consequences. In addition, the otherwise safe use of common drugs such as anti-infectives, cardiovascular drugs, anticholinergics, anticonvulsants, antirheumatics and others have been reported to worsen the symptoms of myasthenia gravis patients.

The CIC-1 ion channel is emerging as a target for potential drugs, although its potential has been largely unrealized.

SUMMARY

The present inventors have identified a group of compounds that alleviate neuromuscular junction disorders through inhibition of CIC-1 channels.

Thus, for the first time, it has been found that compounds that inhibit the CIC-1 ion channels are capable of restoring neuromuscular transmission, as evidenced by the data generated by investigation of the compound set in biological models described herein. These compounds thus constitute a new group of drugs that can be used to treat or ameliorate muscle weakness and muscle fatigue in neuromuscular junction disorders caused by disease or by neuromuscular blocking agents.

The present invention thus concerns the use of CIC-1 ion channel inhibitors in the treatment of a range of conditions, such as reversal of block, ALS and myasthenic conditions, in which muscle activation by the nervous system is compromised and symptoms of weakness and fatigue are prominent.

In one aspect the invention concerns a composition comprising a compound of Formula (II):

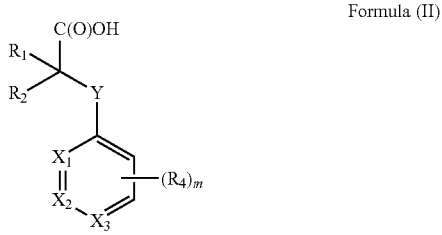

Formula (II)

or a pharmaceutically acceptable salt, solvate, polymorph, or tautomer thereof;
wherein
m is 0, 1, 2, 3, 4 or 5;
Y is selected from the group consisting of O, NH, N—CH$_3$, CH$_2$, CH$_2$—O, S and SO$_2$;
X$_1$, X$_2$ and X$_3$ are independently selected from the group consisting of CH and N;
R$_1$ and R$_2$ are independently selected from the group consisting of OR$_3$, SR$_5$, S(O)R$_5$, S(O)$_2$R$_5$, NR$_3$, NR$_3$C(O)R$_9$ or R$_3$, wherein R$_3$ is selected from the group consisting of H, C$_{1-6}$-alk(en/yn)yl and C$_{3-6}$-cycloalk(en)yl, wherein said C$_{1-6}$-alk(en/yn)yl and C$_{3-6}$-cycloalk(en)yl may be substituted with up to three substituents selected from the group consisting of —NR$_9$—CO—R$_{10}$, —N(R$_{10}$)$_2$—SO$_2$—R$_{12}$, —CO—NR$_9$R$_{10}$, —SO$_2$— NR$_9$R$_{10}$, —R$_{13}$—O— R$_{11}$, —NR$_9$R$_{10}$, —S(O)R$_{12}$, —S(O)$_2$R$_{12}$, cyano, —O—R$_{11}$, fluorinated C$_{1-3}$-alkyl, nitro and halo; or R$_1$ and R$_2$ are linked to form a C$_{3-6}$-cycloalk(en)yl or a halo-C$_{3-6}$-cycloalk(en)yl;
R$_4$ is selected from the group consisting of H, C$_{1-6}$-alk(en/yn)yl, C$_{3-6}$-cycloalk(en)yl, —NR$_9$—CO—R$_{10}$, —NR$_{10}$—SO$_2$—R$_{11}$, —CO—NR$_9$R$_{10}$, —SO$_2$— NR$_9$ R$_{10}$, —R$_{13}$—O—R$_{11}$, —NR$_9$R$_{10}$, cyano, O—R$_{11}$, fluorinated C$_{1-3}$, nitro and halo;
R$^5$ is selected from the group consisting of C$_{1-6}$-alk(en/yn)yl and C$_{3-6}$-cycloalk(en)yl, wherein said C$_{1-6}$-alk(en/yn)yl and C$_{3-6}$-cycloalk(en)yl may be substituted with up to three substituents selected from the group consisting of —NR$_9$—CO—R$_{10}$, —N(R$_{10}$)$_2$SO$_2$—R$_{12}$, —CO—NR$_9$ R$_{10}$, —SO$_2$—NR$_9$ R$_{10}$, —R$_{13}$— O—R$_{11}$, —NR$_9$R$_{10}$, —S(O)R$_{12}$, —S(O)$_2$R$_{12}$, cyano, —O—R$_{11}$, fluorinated C$_{1-3}$, nitro and halo; or R$_1$ and R$_2$ are linked to form a ring;
R$_9$, R$_{10}$, R$_{11}$ are independently selected from H or C$_{1-4}$-alk(en/yn)yl and C$_{3-6}$-cycloalk(en)yl;
R$_{12}$ is selected from C$_{1-4}$-alk(en/yn)yl and C$_{3-6}$-cycloalk(en)yl;
R$_{13}$ is selected from C$_{1-4}$-alk(an/en/yn)diyl and C$_{3-6}$-cycloalk(an/en)diyl;
for use in treating, ameliorating and/or preventing a neuromuscular disorder, and/or for use in reversing and/or ameliorating a neuromuscular blockade after surgery.

In one aspect the invention concerns a method of treating, preventing and/or ameliorating a neuromuscular disorder, said method comprising administering a therapeutically effective amount of the composition as defined herein to a person in need thereof.

In one aspect the invention concerns use of a composition as defined herein, for the manufacture of a medicament for the treatment, prevention and/or amelioration of a neuromuscular disorder, and/or for reversing and/or amelioration of a neuromuscular blockade after surgery.

In one aspect the invention concerns a method of reversing and/or ameliorating a neuromuscular blockade after surgery, said method comprising administering a therapeutically effective amount of the composition as defined herein to a person in need thereof.

In one aspect the invention concerns a method for recovery of neuromuscular transmission, said method comprising administering a therapeutically effective amount of the composition as defined herein to a person in need thereof.

In one aspect the invention concerns a composition as defined herein for use in recovery of neuromuscular transmission.

In one aspect, the invention concerns a compound of Formula (I.2):

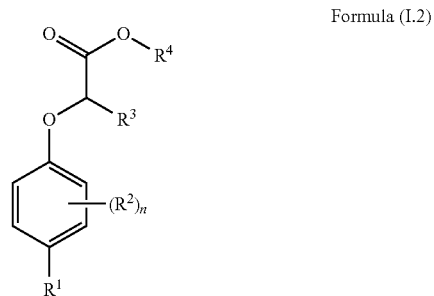

Formula (I.2)

wherein:
R$^1$ is selected from the group consisting of hydrogen, F, Cl, Br, I, —CN, —CF$_3$, C$_{1-4}$ alkyl, C$_{1-4}$ alkenyl, C$_{1-4}$ alkynyl, C$_4$ cycloalkyl and —S—CH$_3$;
R$^2$ is independently selected from the group consisting of hydrogen, deuterium, F, Cl, Br, I, —CN, —CF$_3$ and -oxime optionally substituted with C$_1$ alkyl;
R$^3$ is selected from the group consisting of C$_{1-5}$ alkyl, C$_{1-5}$ alkenyl, C$_{3-5}$ cycloalkyl and C$_5$ cycloalkenyl, each of which may be optionally substituted with one or more, identical or different, substituents R$^5$;
R$^4$ is selected from the group consisting of H or C$_{1-5}$ alkyl;
R$^5$ is independently selected from the group consisting of F and OH; and
n is an integer 0, 1 or 2;
or a pharmaceutically acceptable salt, hydrate, polymorph, tautomer, or solvate thereof;
for use in treating, ameliorating and/or preventing a neuromuscular disorder, and/or for use in reversing and/or ameliorating a neuromuscular blockade,
with the proviso that when R$^1$ is Cl, R$^4$ is H and n is 0, then R$^3$ is not methyl or ethyl.

In another aspect, the invention concerns a compound of Formula (I.2):

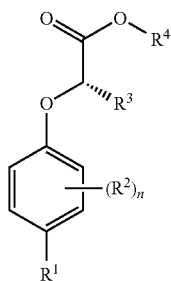

Formula (I.2)

wherein:
R$^1$ is selected from the group consisting of hydrogen, F, Cl, Br, I, —CN, —CF$_3$, C$_{1-4}$ alkyl, C$_{1-4}$ alkenyl, C$_{1-4}$ alkynyl, C$_4$ cycloalkyl and —S—CH$_3$;
R$^2$ is independently selected from the group consisting of hydrogen, deuterium, F, Cl, Br, I, —CN, —CF$_3$ and -oxime optionally substituted with C$_1$ alkyl;
R$^3$ is selected from the group consisting of C$_{1-5}$ alkyl, C$_{1-5}$ alkenyl, C$_{3-5}$ cycloalkyl and C$_5$ cycloalkenyl, each of which may be optionally substituted with one or more, identical or different, substituents R$^5$;
R$^4$ is selected from the group consisting of H or C$_{1-5}$ alkyl;
R$^5$ is independently selected from the group consisting of F and OH; and
n is an integer 0, 1 or 2;
or a pharmaceutically acceptable salt, hydrate, polymorph, tautomer, or solvate thereof;
with the proviso that when R$^1$ is Cl, R$^4$ is H and n is 0, then R$^3$ is not methyl or ethyl.

In yet another aspect, the invention concerns a composition comprising a compound as defined herein.

In one aspect the invention concerns use of a composition as defined herein for the manufacture of a medicament for the recovery of neuromuscular transmission.

DESCRIPTION OF DRAWINGS

In FIG. 1A, the muscle was stimulated to contract either directly using field stimulation with pulses of 0.2 ms duration or indirectly through stimulation of the nerve using a suction electrode. In FIG. 1B and FIG. 1C, muscles were stimulated directly as described above or indirectly via the nerve using field stimulation with short pulses of 0.02 ms. Two different methods of compromising neuromuscular transmission were applied: In FIG. 1A and FIG. 1B, a sub-maximal concentration of tubocurarine (0.2 μM) was used to inhibit ACh receptors in the post-synaptic muscle fiber membrane. In FIG. 1C, neuromuscular transmission was reduced by elevating extracellular Mg$^{2+}$ to 3.5 mM. In experiments were nerve-stimulation was conducted using a suction electrode, the electrical activity of the muscle could be recorded as M-waves (Inserts in FIG. 1A). The entire M-wave train is shown with the first and the last M-waves in the trains enlarged above.

FIG. 2A shows representative recordings of tetani from a soleus muscle from a 4-week-old animal that first contracted in control conditions, then during the pre-incubation with tubocurarine and, finally, in the presence of both tubocurarine and 9-AC. At the end of the experiment, tubocurarine was washed out to ensure full recovery of contractile force. M-wave recordings from the muscle have been included for the force responses indicated by i, ii and iii. The entire M-wave train is shown with the first and the last M-waves in the trains enlarged above. To depress any myotonia with the pronounced ClC-1 channel inhibition with 9-AC, 10 nM TTX was added together with tubocurarine. FIG. 2B shows representative recordings of tetani from a soleus muscle from a 4-week-old animal that first contracted in control conditions, then during the pre-incubation with 3.5 mM Mg$^{2+}$ and, finally, at 3.5 mM Mg$^{2+}$ in the presence of 9-AC. When returned to normal extracellular Mg$^{2+}$ of 1.2 mM, full contractile force ensued. M-wave recordings from the muscle have been included for the force responses indicated by i, ii and iii as described in A.

FIG. 3A shows force recordings from two muscles with the traces being overlaid to illustrate the effect of C8 clearly. Traces are shown before addition tubocurarine, after 40 min with tubocurarine, and after 110 min tubocurarine. After 40 min with tubocurarine, 50 μM C8 was added to the muscle that is presented by black traces. FIG. 3B shows average observations from 5 muscles treated with C8 and 5 control muscles exposed to only tubocurarine. Dotted lines indicate the recovery of nerve-stimulated force in the muscles treated with C8 compared to their force production after 40 min with tubocurarine. This recovery of force was used in Table 1.

FIG. 4A shows the voltage responses at three inter-electrode distances in a control muscle fiber, and in a fiber exposed to 10 μM C8. FIG. 4B to determine $G_m$ the steady state deflection of the membrane potential was measured at each of the three inter-electrode distances. The magnitude of these steady state deflections were next plotted against the inter-electrode distance, and the data was fitted to a two-parameter exponential function (lines). From these parameters the fiber length constant and input resistance were obtained enabling $G_m$ to be calculated. FIG. 4C shows $G_m$ at a range of C8 concentrations. By fitting a sigmoidal function to this data the concentration of C8 that reduced $G_m$ by 50% was obtained and this has been presented in Table 3.

FIGS. 5A-5E. Effect of C8 and neostigmine on the tubocurarine concentration required to reduce nerve-stimulated force in soleus muscles. Muscles from 4-week-old rats were stimulated to contract by activating the motor nerve with short duration pulses in field stimulation. Muscles contracted every 10 min for 2 s in response to 30 Hz stimulation. Four different experimental conditions were used. Thus, muscles were initially incubated for 30 min in either i) control conditions, ii) with 50 μM C8, iii) in the presence of 10 nM neostigmine, or iv) with the combination of neostigmine and C8. After this pre-incubation, increasing concentrations of tubocurarine were added to the bath solutions with 60 min (corresponding to six contractions) between each increase in tubocurarine. FIG. 5A shows representative recordings of force at different concentrations of tubocurarine in a control muscle. FIG. 5B similar to FIG. 5A but this muscle had been pre-incubated with C8. FIG. 5C similar to FIG. 5A but this muscle had been pre-incubated with neostigmine. FIG. 5D similar to FIG. 5A but this muscle had been pre-incubated with the combination of C8 and neostigmine. The force integral (AUC) was determined at each tubocurarine concentration. Such AUC determinations were plotted against tubocurarine concentration for each muscle. FIG. 5E shows such plots of AUC for muscles in FIG. 5A-FIG. 5D. The lines connecting the symbols are fits of the data to a sigmoidal function from which the tubocurarine concentration that was required to reduce AUC to 50% could be obtained ($Tub_{50}$). The averages of $Tub_{50}$ in the four groups of muscles are given in Table 4.

FIGS. 6A-6E. Effect of a C8 and 3,4-AP on the extracellular $Mg^{2+}$ concentration required to reduce nerve-stimulated force in soleus muscles. Muscles from 4-week-old rats were stimulated to contract by activating the motor nerve with short duration pulses in field stimulation. Muscles contracted every 10 min for 2 s in response to 30 Hz stimulation. Four different experimental conditions were used. Thus, muscles were initially incubated for 30 min in either i) control conditions, ii) with 50 μM C8, iii) in the presence of 10 μM 3,4-AP, or iv) with the combination of 3,4-AP and C8. After this pre-incubation, the extracellular $Mg^{2+}$ was progressively increased in the bath solutions every 60 min resulting in six contractions between each increase in extracellular $Mg^{2+}$. FIG. 6A shows representative recordings of force at different concentrations of $Mg^{2+}$ in a control muscle. FIG. 6B similar to FIG. 6A but this muscle had been pre-incubated with C8. C) similar to A) but this muscle had been pre-incubated with 3,4-AP. FIG. 6B similar to FIG. 6A but this muscle had been pre-incubated with the combination of C8 and 3,4-AP. The force integral (AUC) was determined at each extracellular $Mg^{2+}$ concentration. AUC was plotted against $Mg^{2+}$ concentration and the data was fitted to a sigmoidal function. This provided the extracellular $Mg^{2+}$ concentration that was required to reduce the nerve-stimulated force to 50% ($Mg_{50}$) under the four different conditions (see Table 5).

FIG. 7A shows representative EPPs under control conditions and with two concentrations of C8. FIG. 7B shows average EPP amplitudes in the fibers. *Indicates significantly different from control as evaluated using a student t-test.

FIG. 8A shows effect of adding 150 μM C8 on force in a muscle at elevated $K^+$ and with TTX. FIG. 8B shows the average force at elevated $K^+$ in the presence or absence of C8. *Indicates significant different as evaluated using a one-tailed student t-test.

FIG. 9A illustrates the design of the experiments. Prior to Day One the animals had been familiarized to the rotarod in three training sessions distributed over two days. FIG. 9B shows the distance covered by the rats on the two days 21-26 mins after injection of tubocurarine. FIG. 9C shows the increase in performance on Day Two when compared to performance on Day One. FIG. 9D shows the number of animals that on Day Two had an increased performance of more than 100% compared to performance on Day One.

FIG. 11A shows a schematic representation of the positioning of the three microelectrodes ($V_1$, $V_2$ and $V_3$) when inserted in a single skeletal muscle fibre for $G_m$ determination. Please note that the drawing illustrates only the impaled fibre although it is part of an intact muscle that contains many such fibres. All electrodes recorded the membrane potential of the fibre and the two peripheral electrodes were used to inject current (−30 nA, 50 ms). The electrodes were inserted with known inter-electrode distances ($X_1$, $X_2$ and $X_3$). After insertion, current was passed first via the $V_1$ electrode and then via the $V_3$ electrode. The resulting deflections in the membrane voltage were measured by the other electrodes. The steady state deflections in membrane potential were measured and divided by the magnitude of the injected current (−30 nA) to obtain transfer resistances. These were next plotted against inter-electrode distances, and fitted to an exponential function (FIG. 11B), from which $G_m$ could be calculated using linear cable theory. The approach described in FIGS. 11A and 11B, was repeated for several muscle fibres in the muscle during exposure at increasing concentrations of compound A-19, with approx. 10 fibres at each concentration. Average $G_m$ at each concentration was plotted as a function of compound concentration in FIG. 11C, and fitted to a 4-parameter sigmoidal function from which the $EC_{50}$ value for the compound was obtained (dashed line)

FIG. 12A shows representative force traces before and after exposure to compound A-19. Force traces from a representative muscle stimulated to contract in 1) control condition before addition of neuromuscular blocking agent, 2) the force response to stimulation after 90 minutes incubation with Tubocurarine. Here the muscle displays severe neuromuscular transmission impediment, and 3) The muscle force response after addition of 50 μM compound A-19. FIG. 12B shows average force (AUC) from 3 muscles relative to their initial force. The traces presented in FIG. 12A (1, 2, 3), correspond to the dotted lines in FIG. 12B, respectively. Thus, force is lost due to 90 min incubation in tubocurarine and is subsequently recovered when compound A-19 is added.

DETAILED DESCRIPTION

Definitions

Figure 1A:
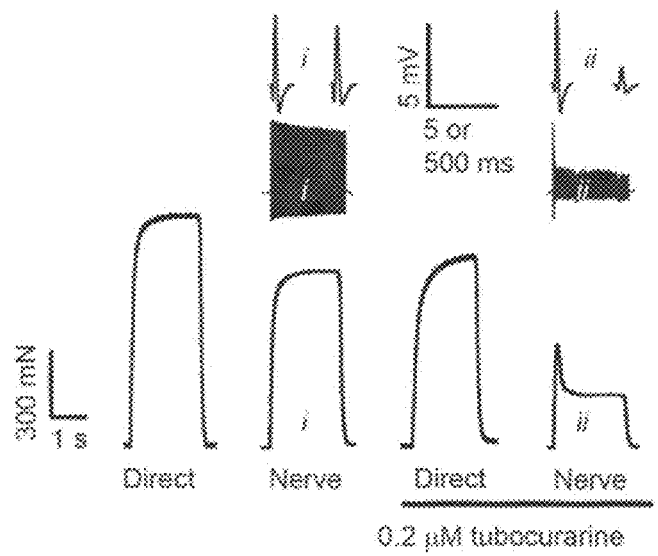
FIGS. 1A-1C: Experimental methods for compromising neuromuscular transmission and the approaches employed to selectively activate contractions either via stimulation of the motor nerve or by directly exciting the rat muscle fibers. Soleus muscles were stimulated to contract using three different methods.

The term "halogen" means fluoro, chloro, bromo or iodo. "Halo" means halogen.

The term "$C_{1-4}$-alkyl" refers to a branched or unbranched alkyl group having from one to four carbon atoms, including but not limited to methyl, ethyl, prop-1-yl, prop-2-yl, 2-methyl-prop-1-yl, 2-methyl-prop-2-yl, but-1-yl and but-2-yl.

The term "$C_{1-4}$-alkenyl" refers to a branched or unbranched alkenyl group having from one to four carbon atoms, two of which are connected by a double bond, including but not limited to ethenyl, propenyl, isopropenyl, butenyl and isobutenyl.

The term "$C_{1-4}$-alkynyl" refers to a branched or unbranched alkynyl group having from one to four carbon atoms, two of which are connected by a triple bond, including but not limited to ethynyl, propynyl and butynyl.

The term "$C_{3-4}$-cycloalkyl" refers to a group having three to four carbon atoms, including but not limited to cyclopropyl, cyclobutyl and cyclopropylmethyl.

The term "$C_{1-8}$-alk(en/yn)yl" means $C_{1-8}$-alkyl, $C_{2-8}$-alkenyl or $C_{2-6}$-alkynyl; wherein:

The term "$C_{1-8}$-alkyl" refers to a branched or unbranched alkyl group having from one to eight carbon atoms, including but not limited to methyl, ethyl, prop-1-yl, prop-2-yl, 2-methyl-prop-1-yl, 2-methyl-prop-2-yl, 2,2-dimethyl-prop-1-yl, but-1-yl, but-2-yl, 3-methyl-but-1-yl, 3-methyl-but-2-yl, pent-1-yl, pent-2-yl, pent-3-yl, hex-1-yl, hex-2-yl, hex-3-yl, 2-methyl-4,4-dimethyl-pent-1-yl and hept-1-yl;

The term "$C_{2-8}$-alkenyl" refers to a branched or unbranched alkenyl group having from two to eight carbon atoms and one double bond, including but not limited to ethenyl, propenyl, and butenyl; and The term "$C_{2-8}$-alkynyl" refers to a branched or unbranched alkynyl group having from two to eight carbon atoms and one triple bond, including but not limited to ethynyl, propynyl and butynyl.

The term "$C_{3-6}$-cycloalk(en)yl" means $C_{3-6}$-cycloalkyl or $C_{3-6}$-cycloalkenyl, wherein:

The term "$C_{3-6}$-cycloalkyl" refers to a group having three to six carbon atoms including a monocyclic or bicyclic carbocycle, including but not limited to cyclopropyl, cyclopentyl, cyclopropylmethyl and cyclohexyl;

The term "$C_{3-6}$-cycloalkenyl" refers to a group having three to six carbon atoms including a monocyclic or bicyclic carbocycle having three to six carbon atoms and at least one double bond, including but not limited to cyclobutenylmethyl, cyclopentenyl, cyclohexenyl The term "half-life" as used herein is the time it takes for the compound to lose one-half of its pharmacologic activity. The term "plasma half-life" is the time that it takes the compound to lose one-half of its pharmacologic activity in the blood plasma.

The term "treatment" refers to the combating of a disease or disorder. "Treatment" or "treating," as used herein, includes any desirable effect on the symptoms or pathology of a disease or condition as described herein, and may include even minimal changes or improvements in one or more measurable markers of the disease or condition being treated. "Treatment" or "treating" does not necessarily indicate complete eradication or cure of the disease or condition, or associated symptoms thereof.

The term "amelioration" refers to moderation in the severity of the symptoms of a disease or condition. Improvement in a patient's condition, or the activity of making an effort to correct, or at least make more acceptable, conditions that are difficult to endure related to patient's conditions is considered "ameliorative" treatment.

The term "prevent" or "preventing" refers to precluding, averting, obviating, forestalling, stopping, or hindering something from happening, especially by advance action.

The term "reversal" or "reversing" refers to the ability of a compound to restore nerve-stimulated force in skeletal muscle exposed either ex vivo or in vivo to a non-depolarizing neuromuscular blocking agent or another pharmaceutical that is able to depress neuromuscular transmission.

The term "ester hydrolysing reagent" refers to a chemical reagent which is capable of converting an ester functional group to a carboxylic acid with elimination of the alcohol moiety of the original ester, including but not limited to acid, base, a fluoride source, $PBrs$, $PCl_3$ and lipase enzymes.

The term "non-depolarizing blockers" refers to pharmaceutical agents that antagonize the activation of acetylcholine receptors at the post-synaptic muscle fibre membrane by blocking the acetylcholine binding site on the receptor. These agents are used to block neuromuscular transmission and induce muscle paralysis in connection with surgery.

The term "recovery of force in muscle with neuromuscular dysfunction" refers to the ability of a compound to recover contractile force in nerve-stimulated healthy rat muscle after exposure to submaximal concentration of (115 nM) tubocurarine for 90 mins. Recovery of force is quantified as the percentage of the force prior to tubocurarine that is recovered by the compound.

The term "total membrane conductance (Gm)" is the electrophysiological measure of the ability of ions to cross the muscle fibre surface membrane. It reflects the function of ion channels that are active in resting muscle fibres of which ClC-1 is known to contribute around 80% in most animal species.

Composition

It is within the scope of the present invention to provide a composition for use in treating, ameliorating and/or preventing neuromuscular disorders characterized in that the neuromuscular function is reduced. As disclosed herein, inhibition of ClC-1 surprisingly improves or restores neuromuscular function. The compositions of the present invention comprise compounds capable of inhibiting the ClC-1 channel thereby improving or restoring neuromuscular function.

In one aspect, the invention relates to a composition comprising a compound of Formula (I):

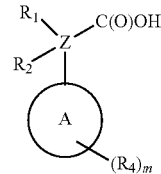

Formula (I)

or a pharmaceutically acceptable salt, solvate, polymorph, or tautomer thereof;
wherein
A is an aromatic or heteroaromatic ring selected from the group consisting of phenyl, naphthyl, biphenyl, quinolinyl, isoquinolinyl, imidazolyl, thiazolyl, thiadiazolyl, triazolyl, oxazolyl, pyridinyl, pyrimidinyl, pyrazyl, and pyridazinyl;
m is 0, 1, 2, 3, 4 or 5;
Z is a 2-5 atom chain comprising at least one carbon atom and optionally one heteroatom or substituted heteroatom, wherein the heteroatom or substituted heteroatom is selected from the group consisting of O, N, NC(O)$R_3$, S, S(O)$R_5$ and S(O)$_2R^5$, wherein each atom of said 2-5 atom chain is optionally substituted with $R_1$ and $R_2$; wherein $R_1$ and $R_2$ are independently selected from the group consisting of O$R_3$, S$R_5$, S(O)$R_5$, S(O)$_2R_5$, N$R_3$, N$R_3$C(O)$R_9$ or $R_3$, wherein $R_3$ is selected from the group consisting of H, $C_{1-8}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of —N$R_9$—CO—$R_{10}$, —N($R_{10}$)$_2$—SO$_2$—$R_{12}$, —CO—N$R_9R_{10}$, —SO$_2$—N$R_9$ $R_{10}$, —$R_{13}$—O—$R_{11}$, N$R_9$ $R_{10}$, —S(O)$R_{12}$, S(O)$_2R_{12}$, cyano, O—$R_{11}$, fluorinated $C_{1-3}$-alkyl, nitro and halo; or $R_1$ and $R_2$ are linked to form a ring;

$R_4$ is selected from the group consisting of H, $C_{1-6}$-alk(en/yn)yl, $C_{3-6}$-cycloalk(en)yl, —N$R_9$—CO—$R_{10}$, —N$R_{10}$—SO$_2$—$R_{12}$, —CO—N$R_9R_{10}$, —SO$_2$—N$R_9$ $R_{10}$, —$R_{13}$—O—$R_{11}$, N$R_9R_{10}$, cyano, O—$R^{11}$, fluorinated $C_{1-3}$, nitro and halo;

$R_5$ is selected from the group consisting of $C_{1-8}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of —N$R_9$—CO—$R_{10}$, —N($R_{10}$)$_2$SO$_2$—$R_{12}$, —CO—N$R_9R_{10}$, —SO$_2$—N$R_9$ $R_{10}$, —$R_{13}$—O—$R_{11}$, N$R_9R_{10}$, —S(O)$R_{12}$, S(O)$_2R_{12}$, cyano, O—$R_{11}$, fluorinated $C_{1-3}$, nitro and halo;

$R_9$, $R_{10}$, $R_{11}$, are independently selected from H or $C_{1-4}$-alk(en/yn)yl and $C_{3-6}$-cycloalk(en)yl;

$R_{12}$ is selected from $C_{1-4}$-alk(en/yn)yl and $C_{3-6}$-cycloalk(en)yl $R_{13}$ is selected from $C_{1-4}$-alk(an/en/yn)diyl and $C_{3-6}$-cycloalk(an/en)diyl for use in treating, ameliorating and/or preventing a neuromuscular disorder.

In one embodiment A is a monocyclic or bicyclic aromatic or heteroaromatic ring. A may for example be a monocyclic ring comprising 5 to 6 carbon atoms or a bicyclic ring comprising 8 to 10 C-atoms. In one embodiment A is five-membered or six-membered aromatic ring. A can also be a five-membered or six-membered heteroaromatic ring. In a preferred embodiment A is phenyl or naphthyl.

The heteroaromatic ring may for example comprise S, O or N atoms. In one embodiment A is a five or six-membered aromatic ring comprising at least one N. In one embodiment A is a five-membered heteroaromatic ring comprising an S and four C atoms. In another embodiment A is a five-membered heteroaromatic ring comprising an O and four C atoms.

In one aspect, the invention relates to a composition comprising a compound of Formula (I.2):

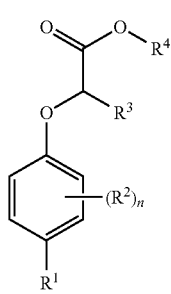

Formula (I.2)

wherein:

$R^1$ is selected from the group consisting of hydrogen, F, Cl, Br, I, —CN, —CF$_3$, $C_{1-4}$ alkyl, $C_{1-4}$ alkenyl, $C_{1-4}$ alkynyl, $C_4$ cycloalkyl and —S—CH$_3$;

$R^2$ is independently selected from the group consisting of hydrogen, deuterium, F, Cl, Br, I, —CN, —CF$_3$ and -oxime optionally substituted with $C_1$ alkyl;

$R^3$ is selected from the group consisting of $C_{1-5}$ alkyl, $C_{1-5}$ alkenyl, $C_{3-5}$ cycloalkyl and $C_5$ cycloalkenyl, each of which may be optionally substituted with one or more, identical or different, substituents $R^5$;

$R^4$ is selected from the group consisting of H or $C_{1-5}$ alkyl;

$R^5$ is independently selected from the group consisting of F and OH; and n is an integer 0, 1 or 2;

or a pharmaceutically acceptable salt, hydrate, polymorph, tautomer, or solvate thereof;

with the proviso that when $R^1$ is Cl, $R^4$ is H and n is 0, then $R^3$ is not methyl or ethyl.

In one embodiment, the invention relates to a composition comprising a compound of Formula (II):

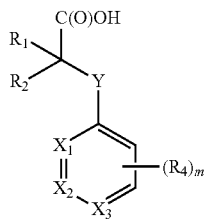

Formula (II)

or a pharmaceutically acceptable salt, solvate, polymorph, or tautomer thereof; wherein Y is selected from the group consisting of O, NH, N—CH$_3$, CH$_2$, CH$_2$—O, S and SO$_2$;

$X_1$, $X_2$ and $X_3$ are selected from the group consisting of, CH and N;

$R_1$ and $R_2$ are independently selected from the group consisting of O$R_3$, S$R_5$, S(O)$R_5$, S(O)$_2R^5$, N$R_3$, N$R_3$C(O)Ra or $R_3$, wherein $R_3$ is selected from the group consisting of H, $C_{1-8}$-alk(en/yn)yl and $C_{3-8}$-cycloalk(en)yl, wherein said $C_{1-8}$-alk(en/yn)yl and $C_{3-6}$-cycloalk(en)yl may be substituted with up to three substituents selected from the group consisting of —N$R_9$—CO—$R_{10}$, —N($R_{10}$)$_2$—SO$_2$—$R_{12}$, —CO—N$R_9R_{10}$, —SO$_2$—N$R_9$ $R_{10}$, —$R_{13}$—O—$R_{11}$, NRs $R_{10}$, —S(O)$R_{12}$, S(O)$_2R_{12}$, cyano, O—$R_{11}$, fluorinated $C_{1-3}$-alkyl, nitro and halo; or $R_1$ and $R_2$ are linked to form a $C_{3-6}$-cycloalk(en)yl or a halo-$C_{3-6}$-cycloalk(en)yl;

$R_4$ is as defined in embodiment 1 below;

m is as defined in embodiment 1 below;

$R_5$ is selected from the group consisting of $C_{1-8}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of —N$R_9$—CO—$R_{10}$, —N($R_{10}$)$_2$SO$_2$—$R_{12}$, —CO—N$R_9$ $R_{10}$, —SO$_2$—N$R_9$ $R_{10}$, —$R_{13}$—O—$R_{11}$, N$R_9R_{10}$, —S(O)$R_{12}$, S(O)$_2R_{12}$, cyano, O—$R_{11}$, fluorinated $C_{1-3}$, nitro and halo;

$R_9$, $R_{10}$ and $R_{11}$ are independently selected from H, $C_{1-4}$-alk(en/yn)yl and $C_{3-6}$-cycloalk(en)yl whereas $R_{12}$ is selected from $C_{1-4}$-alk(en/yn)yl and $C_{3-6}$-cycloalk(en)yl for use in treating, ameliorating and/or preventing a neuromuscular disorder.

Y is selected from the group consisting of O, NH, N—$CH_3$, $CH_2$, $CH_2$—O, S and $SO_2$. Thus Y may be O, NH, N—$CH_3$, $CH_2$, $CH_2$—O, S or $SO_2$. In one preferred embodiment Y is selected from the group consisting of O, NH, $CH_2$, S, and $SO_2$. In a particular embodiment Y is O.

$X_1$, $X_2$ and $X_3$ are selected from the group consisting of, CH and N. In one embodiment $X_1$ is N, $X_2$ is N or $X_3$ is N. In another preferred embodiment $X_1$ is N. In particular embodiment $X_2$ is N.

$R_4$ is selected from the group consisting of H, $C_{1-6}$-alk(en/yn)yl, $C_{3-6}$-cycloalk(en)yl, —$NR_9$—CO—$R_{10}$, —$NR_{10}$—$SO_2$—$R_{12}$, —CO—$NR_9R_{10}$, —$SO_2$—$NR_9$ $R_{10}$, —$R_{13}$—O—$R_{11}$, $NR_9R_{10}$, cyano, O—$R_{11}$, fluorinated $C_{1-3}$, nitro and halo, wherein $R_9$, $R_{10}$ and $R_{11}$ are independently selected from H, $C_{1-4}$-alk(en/yn)yl and $C_{3-6}$-cycloalk(en)yl whereas $R_{12}$ is selected from $C_{1-4}$-alk(en/yn)yl and $C_{3-6}$-cycloalk(en)yl In one embodiment $R_4$ is selected from the group consisting of H, $C_{1-6}$-alk(en/yn)yl and $C_{3-6}$-cycloalk(en)yl. In an embodiment thereof $R_4$ is selected from the group consisting of H, $C_{1-4}$-alk(en/yn)yl and $C_{3-6}$-cycloalk(en)yl, from the group consisting of H, $C_{1-4}$-alk(en)yl and $C_{3-6}$-cycloalk(en)yl or from the group consisting of H, $C_{1-4}$-alkyl and $C_{3-6}$-cycloalk(en)yl. In one embodiment $R_4$ is selected from the group consisting of H and $C_{1-4}$-alkyl.

In another embodiment $R_4$ is selected from the group consisting of $NR_9$—CO—$R_{10}$, —$NR_{10}$—$SO_2$—$R_{12}$, —CO—$NR_9R_{10}$, —$SO_2$—$NR_9$ $R_{10}$, —$R_{13}$—O—$R_{11}$, $NR_9R_{10}$ or O—$R_{11}$, wherein $R_9$, $R_{10}$ and $R_{11}$ are independently selected from H, $C_{1-4}$-alk(en/yn)yl and $C_{3-6}$-cycloalk(en)yl whereas $R_{12}$ is selected from $C_{1-4}$-alk(en/yn)yl and $C_{3-6}$-cycloalk(en)yl. $R_9$, $R_{10}$ and $R_{11}$ may for example be independently selected from H and $C_{1-4}$-alkyl or from the group consisting of H and $C_{1-3}$-alkyl. In one embodiment $R_9$, $R_{10}$ and $R_{11}$ are independently selected from H and —$CH_3$.

In another embodiment $R_4$ is selected from the group consisting of cyano, fluorinated $C_{1-3}$, nitro and halo. In one embodiment $R_4$ is selected from the group consisting of Cl, Br, I or F. In one embodiment $R_4$ is selected from the group consisting of Cl and Br.

$R_4$ can be located in either ortho-meta or para-position with respect to Y.

m can be 0, 1, 2, 3, 4 or 5. In one embodiment m is 0, 1, 2, 3 or 4, such as 0, 1, 2 or 3 or such as 0, 1 or 2. In another embodiment m is 0 or 1.

In one embodiment $R_1$ and $R_2$ are independently selected from the group consisting of $OR_3$, $SR_5$, $S(O)R_5$, $S(O)_2R_5$, $NR_3$, $NR_3C(O)R_9$, wherein $R_3$ is selected from the group consisting of H, $C_{1-8}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of —$NR_9$—CO—$R_{10}$, —$N(R_{10})_2$—$SO_2$—$R_{12}$, —CO—$NR_9R_{10}$, —$SO_2$—$NR_9$ $R_{10}$, —$R_{13}$—O—$R_{11}$ $NR_9$ $R_{10}$, —$S(O)R_{12}$, $S(O)_2R_{12}$, cyano, O—$R_{11}$, fluorinated $C_{1-3}$-alkyl, nitro and halo;

$R_5$ is selected from the group consisting of $C_{1-8}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of —$NR_9$—CO—$R_{10}$, —$N(R_{10})_2SO_2$—$R_{12}$, —CO—$NR_9$ $R_{10}$, —$SO_2$—$NR_9$ $R_{10}$, —$R_{13}$—O—$R_{11}$, $NR_9R_{10}$, —$S(O)R_{12}$, $S(O)_2R_{12}$, cyano, O—$R_{11}$, fluorinated $C_{1-3}$-alkyl, nitro and halo; and $R_9$, $R_{10}$ and $R_{11}$ are independently selected from H, $C_{1-4}$-alk(en/yn)yl and $C_{3-6}$-cycloalk(en)yl whereas $R_{12}$ is selected from $C_{1-4}$-alk(en/yn)yl and $C_{3-6}$-cycloalk(en)yl.

In one embodiment $R_3$ and/or $R_5$ is selected from the group consisting of H, $C_{1-8}$-alk(en/yn)yl and $C_{3-6}$-cycloalk(en)yl. In another embodiment $R_3$ is selected from the group consisting of H, $C_{1-6}$-alkyl and $C_{3-7}$-cycloalkyl. In yet another embodiment $R_3$ is selected from the group consisting of H, $C_{1-6}$-alkyl, such as from the group consisting of H and $C_{1-4}$-alkyl. In another embodiment $R_3$ is selected from the group consisting of H and $CH_3$.

In another embodiment $R_1$ and $R_2$ are independently selected from the group consisting of H, $C_{1-8}$-alk(en/yn)yl and $C_{3-6}$-cycloalk(en)yl. $C_{1-8}$-alk(en/yn)yl and $C_{3-6}$-cycloalk(en)yl may be substituted with up to three substituents selected from the group consisting of —$NR_9$—CO—$R_{10}$, —$N(R_{10})_2$—$SO_2$—$R_{12}$, —CO—$NR_9R_{10}$, —$SO_2$—$NR_9$ $R_{10}$, —$R_{13}$—O—$R_{11}$, $NR_9$ $R_{10}$, —$S(O)R_{12}$, $S(O)_2R_{12}$, cyano, O—$R_{11}$, fluorinated $C_{1-3}$-alkyl, nitro and halo.

$R_9$, $R_{10}$ and $R_{11}$ are independently selected from H, $C_{1-4}$-alk(en/yn)yl and $C_{3-6}$-cycloalk(en)yl whereas $R_{12}$ is selected from $C_{1-4}$-alk(en/yn)yl and $C_{3-6}$-cycloalk(en)yl It is appreciated that $R_1$ is different from $R_2$.

In a preferred embodiment $R_1$ is selected from the group consisting of H and —$CH_3$. In a more preferred embodiment $R_1$ is H.

In one embodiment $R_1$ is H and $R_2$ is selected from the group consisting of H, $C_{1-8}$-alk(en/yn)yl and $C_{3-6}$-cycloalk(en)yl. $C_{1-8}$-alk(en/yn)yl and $C_{3-6}$-cycloalk(en)yl may be substituted with up to three substituents selected from the group consisting of —$NR_9$—CO—$R_{10}$, —$N(R_{10})_2$—$SO_2$—$R_{12}$, —CO—$NR_9R_{10}$, —$SO_2$—$NR_9$ $R_{10}$, —$R_{13}$—O—$R_{11}$, $NR_9$ $R_{10}$, —$S(O)R_{12}$, $S(O)_2R_{12}$, cyano, O—$R_{11}$, fluorinated $C_{1-3}$-alkyl, nitro and halo, wherein $R_9$, $R_{10}$ and $R_{11}$ are independently selected from H, $C_{1-4}$-alk(en/yn)yl and $C_{3-6}$-cycloalk(en)yl whereas $R_{12}$ is selected from $C_{1-4}$-alk(en/yn)yl and $C_{3-6}$-cycloalk(en)yl.

In another embodiment $R_1$ is H and $R_2$ is selected from the group consisting of H, $C_{1-4}$-alk(en)yl, $C_{3-6}$-cycloalk(en)yl, wherein said $C_{1-4}$-alk(en/yn)yl and $C_{3-6}$-cycloalk(en)yl may be substituted with up to two substituents selected from the group consisting of —$NR_9$—CO—$R_{10}$, —$N(R_{10})_2$—$SO_2$—$R_{12}$, —CO—$NR_9R_{10}$, —$SO_2$—$NR_9$ $R_{10}$, —$R_{13}$—O—$R_{11}$, $NR_9$ $R_{10}$, —$S(O)R_{12}$, $S(O)_2R_{12}$, cyano, O—$R_{11}$, fluorinated $C_{1-3}$-alkyl, nitro and halo, wherein $R_9$, $R_{10}$ and $R_{11}$ are independently selected from H, $C_{1-4}$-alk(en/yn)yl and $C_{3-6}$-cycloalk(en)yl whereas $R_{12}$ is selected from $C_{1-4}$-alk(en/yn)yl and $C_{3-6}$-cycloalk(en)yl.

In yet another embodiment $R_1$ is H and $R_2$ is selected from the group consisting of H, $C_{1-4}$-alkyl, $C_{3-6}$-cycloalkyl and amino-$C_{1-4}$-alkyl, wherein said $C_{1-4}$-alkyl and $C_{3-6}$-cycloalkyl may be substituted with O—$R_{11}$, wherein $R_{11}$ is as defined above. In a specific embodiment $R_{11}$ is —$CH_3$.

In one embodiment $R_1$ and $R_2$ are independently selected from the group consisting of H and $CH_3$. In a preferred embodiment $R_1$ is H and $R_2$ is selected from the group consisting of H, $C_{1-6}$-alkyl and $C_{3-7}$-cycloalkyl. For example, $R_1$ is H and $R_2$ is selected from the group consisting of H, $C_{1-4}$-alkyl and $C_{3-5}$-cycloalkyl. In a further preferred embodiment $R_1$ is H and $R_2$ is selected from the group consisting of H, $C_{1-4}$-alkyl. In a particular embodiment, $R_1$ is H and $R_2$ is selected from the group consisting of H, —$CH_3$, —$CH(CH_3)_2$ and cyclopropyl. In an embodiment thereof $R_1$ is H and $R_2$ is —$CH(CH_3)_2$.

In a specific embodiment $R_2$ is —CH(CH$_3$)CH$_2$—O—CH$_3$. In particular, $R_1$ is H and $R_2$ is —CH(CH$_3$)CH$_2$—O—CH$_3$.

In a preferred embodiment the compound is the S-enantiomer with respect to the C-atom to which $R_2$ is bound.

$R_1$ and $R_2$ are in one embodiment linked to form a $C_{3-6}$-cycloalk(en)yl or a halo-$C_{3-6}$-cycloalk(en)yl. In one particular embodiment $R_1$ and $R_2$ are linked to form a $C_{3-5}$-cycloalk(en)yl or a halo-$C_{3-5}$-cycloalk(en)yl. In another embodiment $R_1$ and $R_2$ are linked to form a $C_{3-4}$-cycloalk(en)yl or a halo-$C_{3-4}$-cycloalk(en)yl. In a preferred embodiment $R_1$ and $R_2$ are linked to form a cyclopropyl or a halo-cyclopropyl. In a more preferred embodiment $R_1$ and $R_2$ are linked to form a cyclopropyl.

In one aspect, the invention relates to a composition comprising a compound of Formula (II.2):

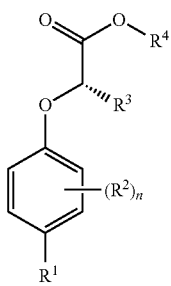

Formula (II.2)

wherein:
- $R^1$ is selected from the group consisting of F, Cl, Br, I, —CN, —CF$_3$, $C_{1-4}$ alkyl, $C_{1-4}$ alkenyl, $C_{1-4}$ alkynyl, $C_4$ cycloalkyl and —S—CH$_3$;
- $R^2$ is independently selected from the group consisting of hydrogen, deuterium, F, Cl, Br, I, —CN, —CF$_3$ and -oxime optionally substituted with $C_1$ alkyl;
- $R^3$ is selected from the group consisting of $C_{1-5}$ alkyl, $C_{1-5}$ alkenyl, $C_{3-5}$ cycloalkyl and $C_5$ cycloalkenyl, each of which may be optionally substituted with one or more, identical or different, substituents $R^5$;
- $R^4$ is selected from the group consisting of H and $C_{1-5}$ alkyl;
- $R^5$ is independently selected from the group consisting of F and OH; and
- n is an integer 0, 1 or 2;
- or a pharmaceutically acceptable salt, hydrate, polymorph, tautomer, or solvate thereof;
- with the proviso that when $R^1$ is Cl, $R^4$ is H and n is 0, then $R^3$ is not methyl or ethyl.

In a particular embodiment $R_1$ is H and $R_2$ is —CH(CH$_3$)$_2$ and wherein said compound is the S-enantiomer with respect to the C-atom to which $R_2$ is bound as shown in formula (III):

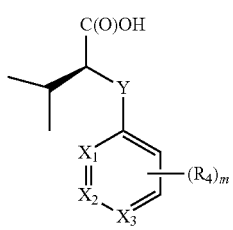

Formula (III)

or a pharmaceutically acceptable salt, solvate, polymorph, or tautomer thereof;

wherein, m, Y, $X_1$, $X_2$ and $X_3$ and $R_4$ are as defined above. For example $X_1$ is N, $X_2$ is N or $X_3$ is N. In another embodiment $X_1$, $X_2$ and $X_3$ is C. $R_4$ may for example be selected from the group consisting of H, halo, cyano, —CHO, $C_{1-4}$-alk(en)yl, halo-$C_{1-4}$-alk(en)yl, —O—$C_{1-4}$-alk(en)yl In a preferred embodiment m is 0, 1 or 2. In one embodiment m is 0 or 1. For example m is 1.

In one aspect, the invention relates to a compound of Formula (III.2):

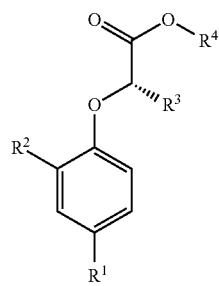

Formula (III.2)

wherein:
- $R^1$ is selected from the group consisting of Cl, Br, and I;
- $R^2$ is selected from the group consisting of deuterium, F, Cl, Br, I, and -oxime optionally substituted with $C_1$ alkyl;
- $R^3$ is selected from the group consisting of $C_{1-5}$ alkyl, $C_{1-5}$ alkenyl, $C_{3-5}$ cycloalkyl and $C_5$ cycloalkenyl, each of which may be optionally substituted with one or more F; and
- $R^4$ is selected from the group consisting of H or $C_{1-5}$ alkyl; preferably H;
- or a pharmaceutically acceptable salt, hydrate, polymorph, tautomer, or solvate thereof.

In an embodiment of the present invention the compound of Formula (I) is further defined by Formula (IV):

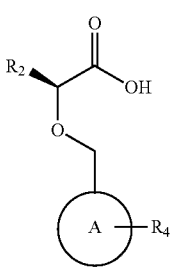

Formula (IV)

or a pharmaceutically acceptable salt, solvate, polymorph, or tautomer thereof; wherein A, $R_2$ and $R_4$ are as defined above. In one embodiment $R_2$ is $C_{1-6}$-alkyl or $C_{3-7}$-cycloalkyl. For example A is a monocyclic ring such as a phenyl. It is preferred that $R_4$ is in ortho- or meta position.

In one aspect, the invention relates to a compound of Formula (IV.2):

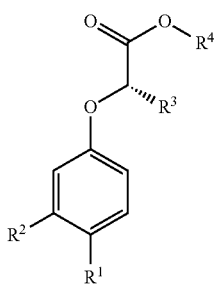

Formula (IV.2)

wherein:
- $R^1$ is selected from the group consisting of Cl, Br, and I;
- $R^2$ is selected from the group consisting of deuterium, F, Cl, Br, and I;
- $R^3$ is selected from the group consisting of $C_{1-5}$ alkyl, $C_{1-5}$ alkenyl, $C_{3-5}$ cycloalkyl and $C_5$ cycloalkenyl, each of which may be optionally substituted with one or more F; and
- $R^4$ is selected from the group consisting of H or $C_{1-5}$ alkyl; preferably H;
- or a pharmaceutically acceptable salt, hydrate, polymorph, tautomer, or solvate thereof.

Thus, in an embodiment thereof, the compound of Formula (IV) is further defined by Formula (V):

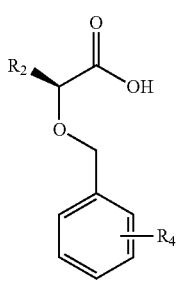

Formula (V)

wherein $R_2$ and $R_4$ are as defined above.

In one aspect, the invention relates to a compound of Formula (V.2):

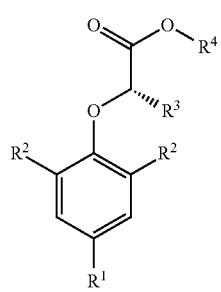

Formula (V.2)

wherein:
- $R^1$ is Br, Cl or I;
- $R^2$ is independently deuterium, F, Cl, Br, or I;
- $R^3$ is selected from the group consisting of $C_{1-5}$ alkyl, $C_{1-5}$ alkenyl, $C_{3-5}$ cycloalkyl and $C_5$ cycloalkenyl, each of which may be optionally substituted with one or more F; and
- $R^4$ is selected from the group consisting of H or $C_{1-5}$ alkyl; preferably H;
- or a pharmaceutically acceptable salt, hydrate, polymorph, tautomer, or solvate thereof.

In one embodiment thereof, the compound of Formula (V) is further defined by Formula (VI):

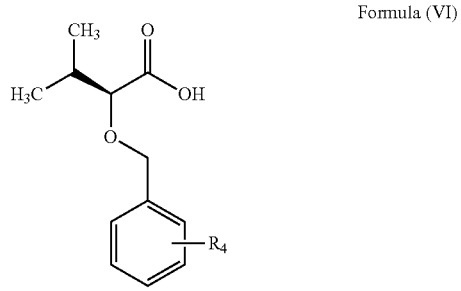

Formula (VI)

wherein $R_4$ is as defined above. It is preferred the $R_4$ is in ortho- or meta position.

In one aspect, the invention relates to a compound of Formula (VI.2):

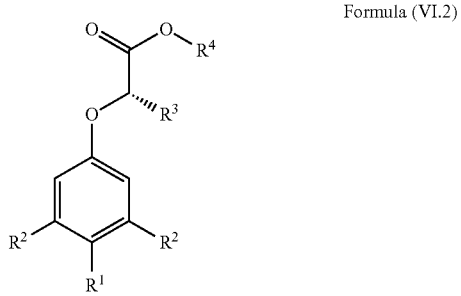

Formula (VI.2)

wherein:
- $R^1$ is Br, Cl or I;
- $R^2$ is independently deuterium, F, Cl, Br, or I;
- $R^3$ is selected from the group consisting of $C_{1-5}$ alkyl, $C_{1-5}$ alkenyl, $C_{3-5}$ cycloalkyl and $C_5$ cycloalkenyl, each of which may be optionally substituted with one or more F; and
- $R^4$ is selected from the group consisting of H or $C_{1-5}$ alkyl; preferably H;
- or a pharmaceutically acceptable salt, hydrate, polymorph, tautomer, or solvate thereof.

In another embodiment of the present invention the compound of Formula (I) is further defined by Formula (VII):

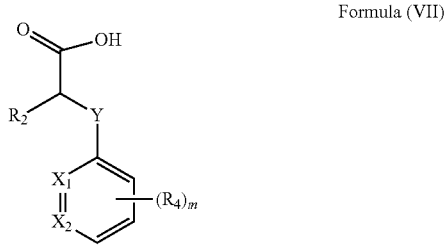

Formula (VII)

or a pharmaceutically acceptable salt, solvate, polymorph, or tautomer thereof; wherein m is 2 and $X_1$, $X_2$, Y, $R_2$ and $R_4$ are as defined above.

In one embodiment thereof Formula (VII) is further defined by Formula (VIII)

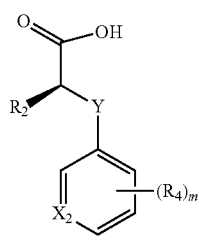

Formula (VIII)

or a pharmaceutically acceptable salt, solvate, polymorph, or tautomer thereof;

wherein m, $X_2$, Y, $R_2$ and $R_4$ are as defined above. For example, in a preferred embodiment Y is O. Further, it is preferred that $R_2$ is selected from the group consisting of H and $C_{1-4}$-alkyl. $R_4$ is in one embodiment selected from the group consisting of H, —$CH_3$ and halogen.

In a specific embodiment the compound of Formula (VIII) is further defined by Formula (IX):

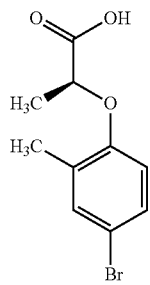

Formula (IX)

In one embodiment of the present invention the compound of Formula (VII) is further defined by Formula (X):

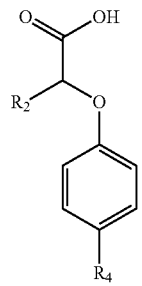

Formula (X)

or a pharmaceutically acceptable salt, solvate, polymorph, or tautomer thereof; wherein $R_2$ is selected from the group consisting of —$CH_3$, —$CH_2$—$CH_3$, —$CH(CH_3)_2$, —$C(CH_3)_3$, —$CH(CH_3)CH_2$—O—$CH_3$, —$CH_2$—$CH_2$—$CH_3$, —$CH_2$—$NH_2$, —$CH_2$—$CHF_2$, —$CH_2$—$CF_3$, —$CH_2$—NH—CO—$CH_3$ and —$CH_2$—NH—$SO_2$—$CH_3$ and cyclopropyl, and $R_4$ is selected from the group consisting of H, Br, Cl, F and I. In a preferred embodiment $R_2$ is —$CH_3$ or —$CH(CH_3)_2$; and $R_4$ is selected from the group consisting of H, Br, Cl, F and I. In particular, $R_2$ is —$CH(CH_3)_2$ and $R_4$ is selected from the group consisting of H, Br, Cl, F and I.

In specific embodiments Formula (VII) is further defined by any one of Formulas (XI) to (XXVIII):

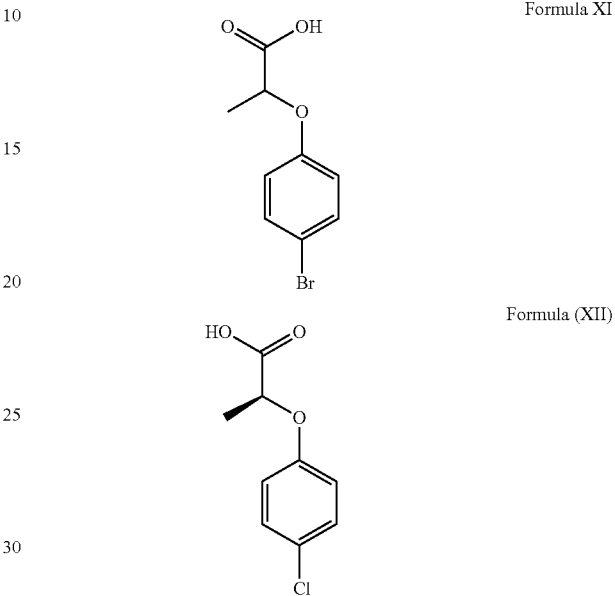

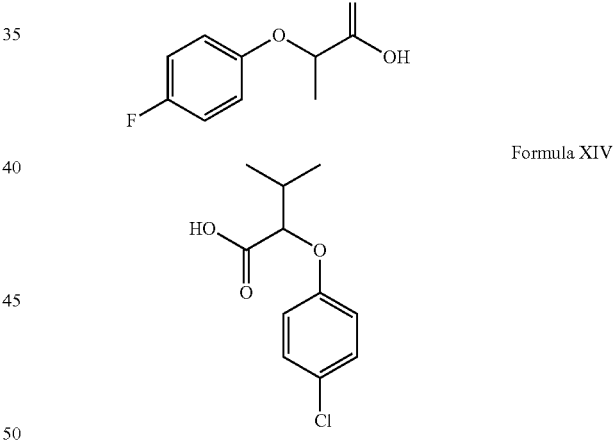

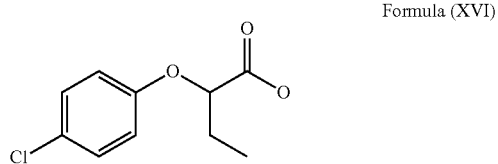

-continued
Formula (XVII)
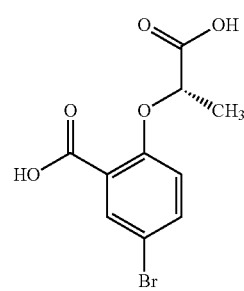
Formula (XVIII)
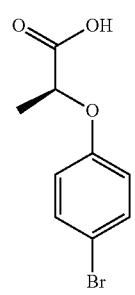
Formula (XIX)
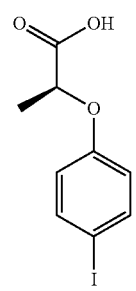
Formula (XX)
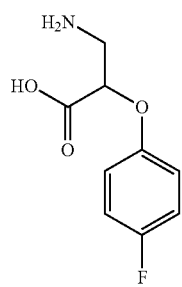
Formula XXI
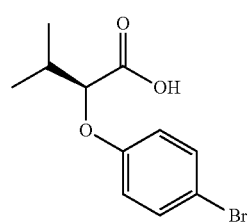
Formula (XXII)
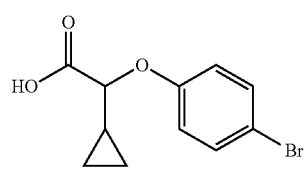
-continued
Formula (XXIII)
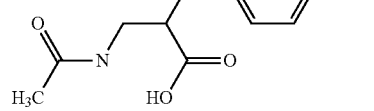
Formula (XXIV)
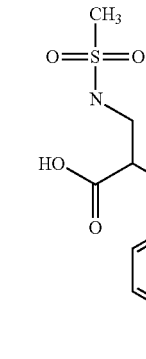
Formula (XXV)
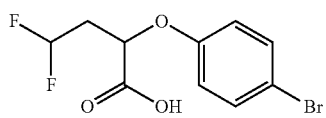
Formula (XXVI)
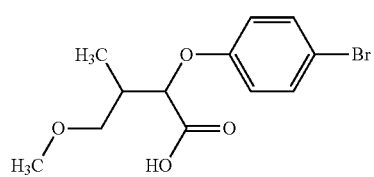
Formula (XXVII)
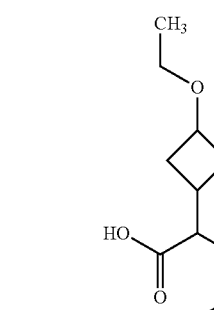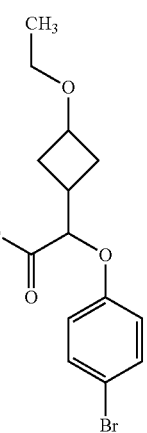
Formula (XXVIII)
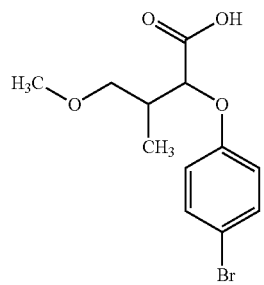

In another embodiment of the present invention the compound of Formula (VII) is further defined by Formula (XXIX):

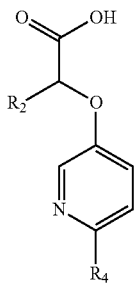
Formula (XXIX)

or a pharmaceutically acceptable salt, solvate, polymorph, or tautomer thereof; wherein $R_2$ is selected from the group consisting of —$CH_3$, —$CH_2$—$CH_3$, —$CH(CH_3)_2$, —$C(CH_3)_3$, —$CH_2$—$CH_2$—$CH_3$ and —$CH_2$—$NH_2$ and $R_4$ is selected from the group consisting of H, Br, Cl, F and I. In a preferred embodiment $R_2$ is —$CH_3$ or —$CH(CH_3)_2$; and $R_4$ is selected from the group consisting of H, Br, Cl, F and I. In another preferred embodiment $R_2$ is —$CH_3$ or —$CH(CH_3)_2$ and $R_4$ is selected from the group consisting of H, Br, Cl and F. It is further preferred that the compound of Formula (X) is the S-enantiomer with respect to the C-atom to which $R_2$ is bound. This embodiment is exemplified by Formulas (XXIII) and (XXIV), where $R_2$ is —$CH_3$ and $R_4$ is Cl or Br.

Thus, in one embodiment the compound of Formula (XXIX) is further defined by Formula (XXX):

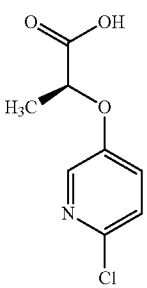
Formula (XXX)

In another specific embodiment the compound of Formula (VII) is further defined by Formula (XXXI):

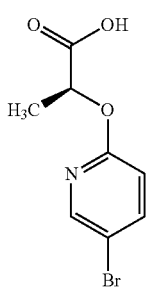
Formula (XXXI)

In one embodiment of the present invention Y is $SO_2$. In particular, the compound of Formula (VII) can be further defined by Formula (XXXII):

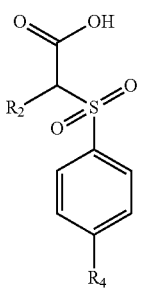
Formula (XXXII)

or a pharmaceutically acceptable salt, solvate, polymorph, or tautomer thereof; wherein $R_2$ is selected from the group consisting of —$CH_3$, —$CH_2$—$CH_3$, —$CH(CH_3)_2$, —$C(CH_3)_3$, —$CH_2$—$CH_2$—$CH_3$ and —$CH_2$—$NH_2$ and $R_4$ is selected from the group consisting of H, Br, Cl, F and I. In a preferred embodiment $R_2$ is —$CH_3$ or —$CH(CH_3)_2$; and $R_4$ is selected from the group consisting of H, Br, Cl, F and I. In another preferred embodiment $R_2$ is —$CH_3$ or —$CH(CH_3)_2$ and $R_4$ is selected from the group consisting of H, Br, Cl and F.

In a specific embodiment the compound of Formula (XXXII) is defined by Formula (XXXIII):

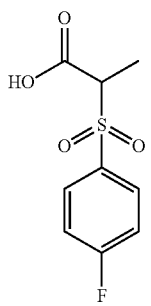
Formula (XXXIII)

As mentioned above, in one embodiment of the present A can be a naphthyl. In one embodiment Y is O. Thus, in a preferred embodiment of the present invention the compound of Formula (I) is further defined by Formula (XXXIV):

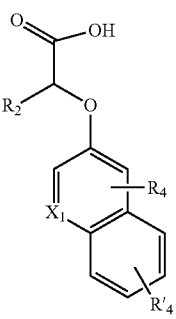
Formula (XXXIV)

or a salt or tautomer thereof;

wherein $R_2$ and $X_1$ are as defined above; and $R_4$ and $R'_4$ are independently selected from the group consisting of H, halo, cyano, hydroxy, —CHO, $C_{1-6}$-alk(en/yn)yl, halo-$C_{1-6}$-alk(en/yn)yl, O—$C_{1-6}$-alk(en/yn)yl. In a preferred embodiment $R_2$ is selected from the group consisting of —$CH_3$, —$CH_2$—$CH_3$, —$CH(CH_3)_2$, —$C(CH_3)_3$, —$CH_2$—$CH_2$—$CH_3$ and —$CH_2$—$NH_2$. Preferably $R_2$ is $CH_3$ or —$CH(CH_3)_2$. It is preferred that $R_4$ and $R'_4$ are individually selected from the group consisting of H, Br, Cl, F and I. In another preferred embodiment $R_4$ and/or $R'_4$ are H. It is further preferred that $X_1$ is N or C.

In a particular embodiment $R_2$ is selected from the group consisting of —$CH_3$, —$CH_2$—$CH_3$, —$CH(CH_3)_2$, —$C(CH_3)_3$, —$CH_2$—$CH_2$—$CH_3$ and —$CH_2$—$NH_2$; $X_1$ is N or C; and $R_4$ and $R'_4$ are individually selected from the group consisting of H, Br, Cl, F and I. In a particular embodiment Formula (XXXIV) is further defined by Formula (XXXV):

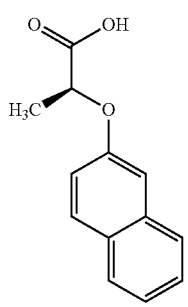

Formula (XXXV)

In specific embodiments of the present invention the compound of Formula (I) is further defined by any one of Formulas (XXXVI) to (LIX):

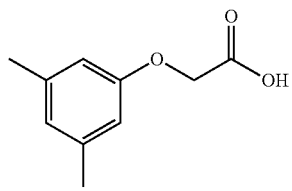

Formula (XXXVI)

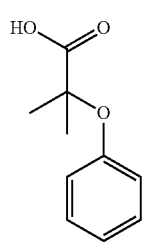

Formula (XXXVII)

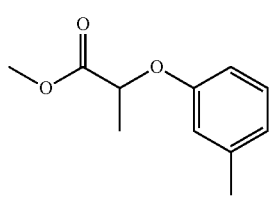

Formula (XXXVIII)

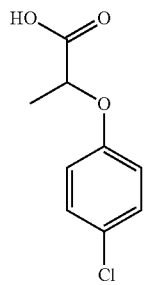

Formula (XXXIX)

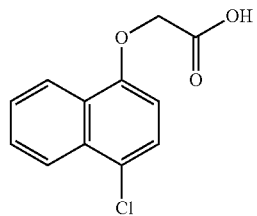

Formula (XL)

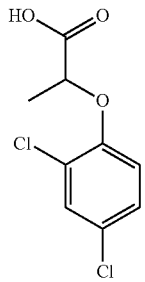

Formula (XLII)

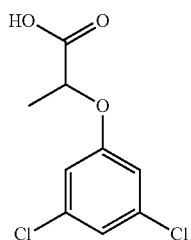

Formula (XLIII)

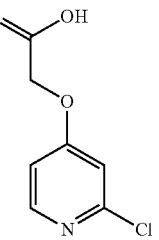

Formula (XLIV)

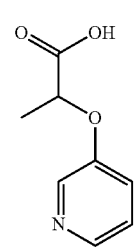

Formula (XLV)

Formula (XLVI)
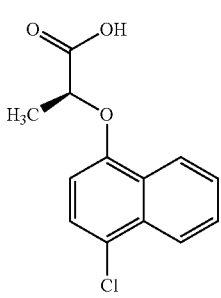
Formula (XLVII)
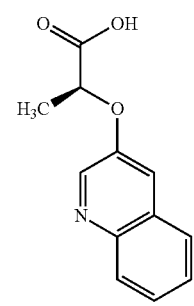
Formula (XLVIII)
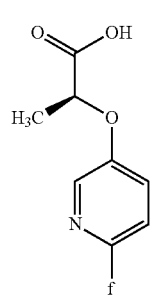
Formula (XLIX)
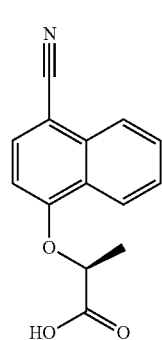
Formula (L)
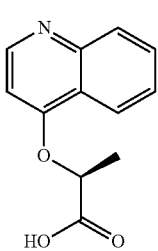
Formula (LI)
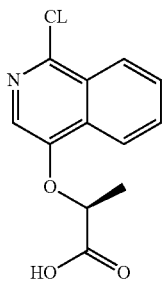
Formula (LII)
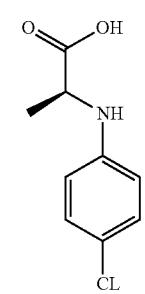
Formula (LIII)
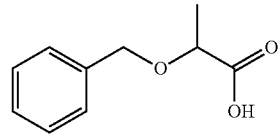
Formula (LIV)
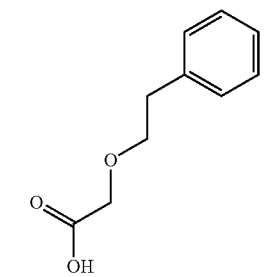
Formula (LV)
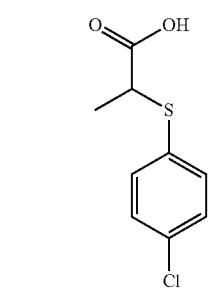
Formula (LVI)
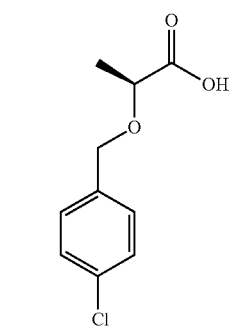

-continued
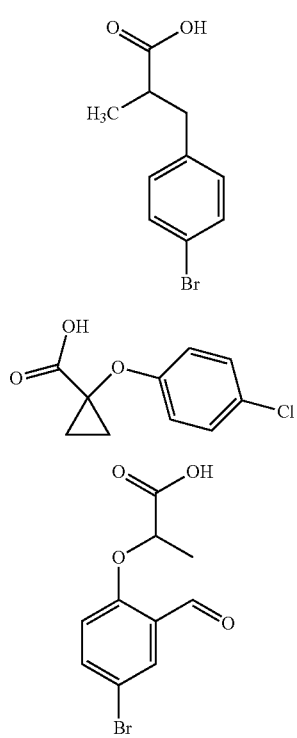
Formula (LVII)
Formula (LVIII)
Formula (LIX)
In a specific embodiment, the compound is selected from the group consisting of:
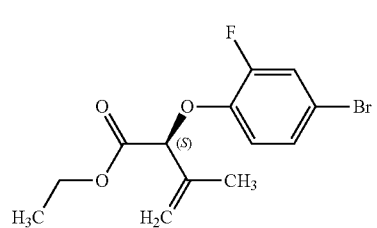
Compound A-1
Compound A-2
Compound A-3
-continued
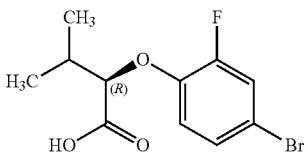
Compound A-4
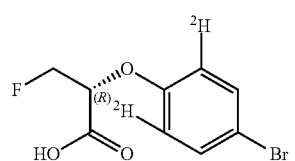
Compound A-5
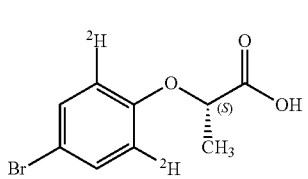
Compound A-6
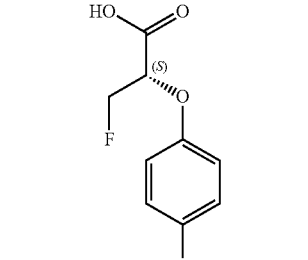
Compound A-7
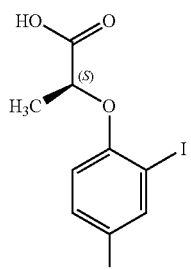
Compound A-8
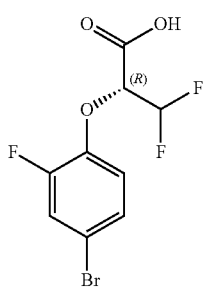
Compound A-9
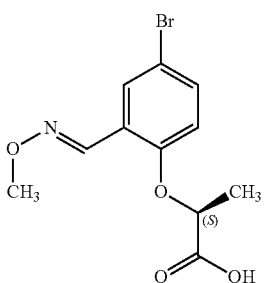
Compound A-10

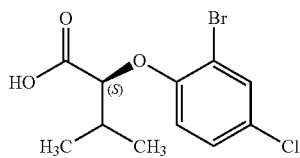
Compound A-11
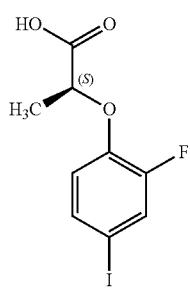
Compound A-12
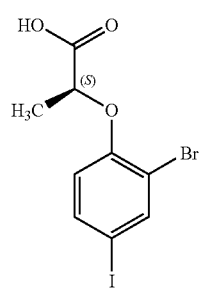
Compound A-13
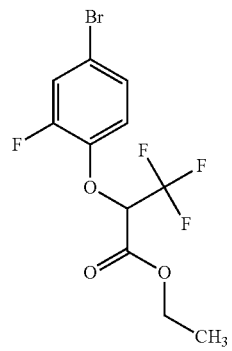
Compound A-14
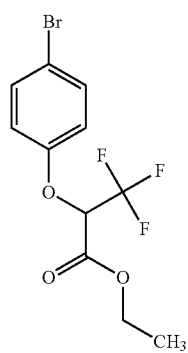
Compound A-15
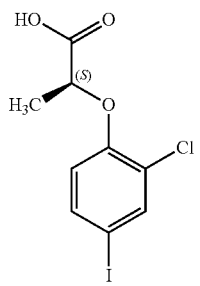
Compound A-16
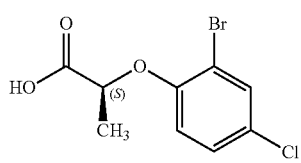
Compound A-17
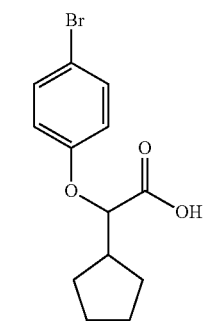
Compound A-18
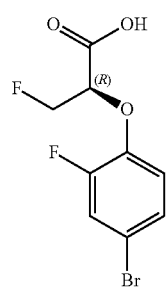
Compound A-19
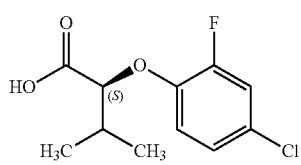
Compound A-20
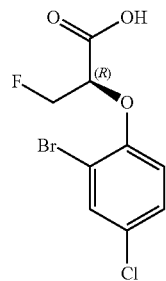
Compound A-21

-continued
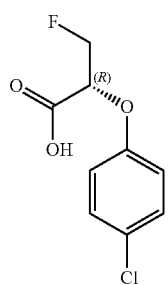
Compound A-22
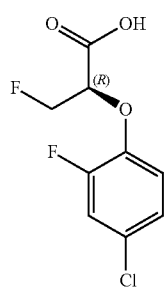
Compound A-23
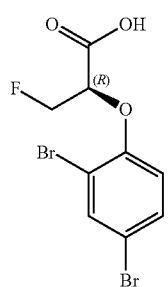
Compound A-24
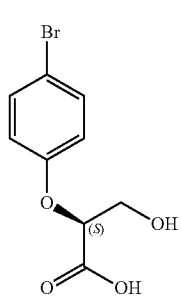
Compound A-25
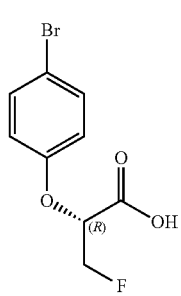
Compound A-26
-continued
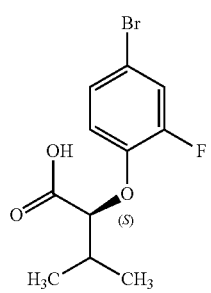
Compound A-27
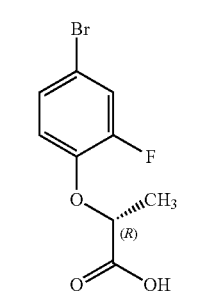
Compound A-28
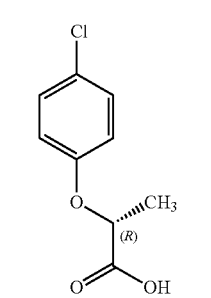
Compound A-29
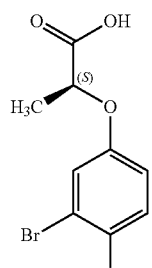
Compound A-30
Compound A-31

-continued

Compound A-32

Compound A-33

Compound A-34

Compound A-35

Compound A-36

Compound A-37

Compound A-38

-continued

Compound A-39

Compound A-40

Compound A-41

Compound A-42

Compound A-43

Compound A-44
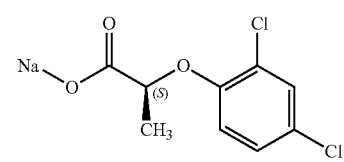
Compound A-45
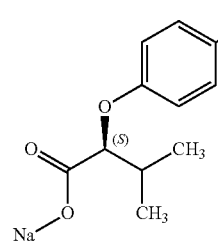
Compound A-46
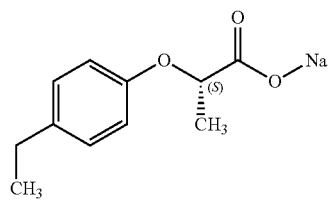
Compound A-47
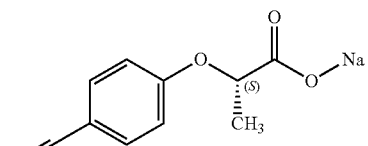
Compound A-48
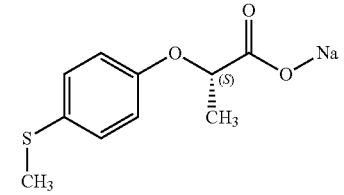
Compound A-49
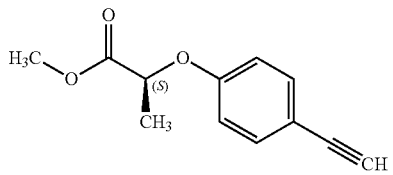
Compound A-50
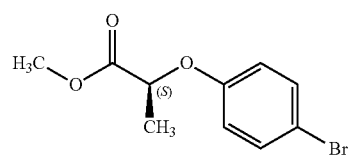
Compound A-51
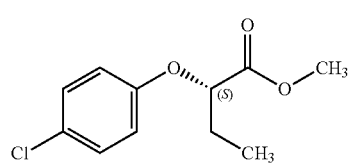
Compound A-52
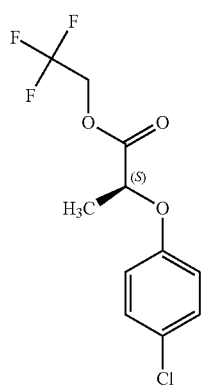
Compound A-53
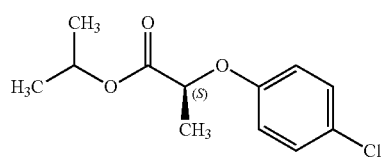
Compound A-54
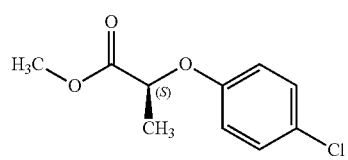
Compound A-55
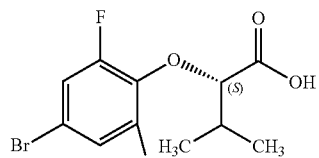
Compound A-56
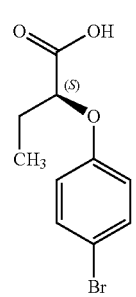
Compound A-57
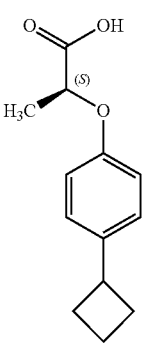

Compound A-58

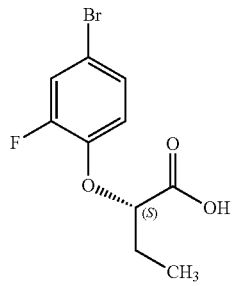

Compounds

In one aspect, the invention relates to the use of the following compounds in treating, ameliorating and/or preventing a neuromuscular disorder. In one aspect, the invention relates to the use of the following compounds in reversing and/or ameliorating a neuromuscular blockade.

Another aspect of the present invention relates to a compound of Formula (I):

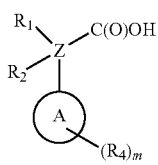

Formula (I)

or a pharmaceutically acceptable salt, solvate, polymorph, or tautomer thereof;
wherein
A is an aromatic or heteroaromatic ring selected from the group consisting of phenyl, naphthyl, biphenyl, quinolinyl, isoquinolinyl, imidazolyl, thiazolyl, thiadiazolyl, triazolyl, oxazolyl, pyridinyl, pyrimidinyl, pyrazyl, and pyridazinyl;
m is 0, 1, 2, 3, 4 or 5;
Z is a 2-5 atom chain comprising at least one carbon atom and optionally one heteroatom or substituted heteroatom, wherein the heteroatom or substituted heteroatom is selected from the group consisting of O, N, NC(O)$R_3$, S, S(O)$R_5$ and S(O)$_2R^5$, wherein each atom of said 2-5 atom chain is optionally substituted with $R_1$ and $R_2$; wherein
$R_1$ and $R_2$ are independently selected from the group consisting of O$R_3$, S$R_5$, S(O)$R_5$, S(O)$_2R^5$, N$R_3$, N$R_3$C(O)$R_9$ or $R_3$, wherein $R_3$ is selected from the group consisting of H, $C_{1-8}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of —N$R_9$—CO—$R_{10}$, —N($R_{10}$)$_2$—SO$_2$—$R_{12}$, —CO—N$R_9R_{10}$, —SO$_2$—N$R_9$ $R_{10}$, —$R_{13}$—O—$R_{11}$, N$R_9$ $R_{10}$, —S(O)$R_{12}$, S(O)$_2R_{12}$, cyano, O—$R_{11}$, fluorinated $C_{1-3}$-alkyl, nitro and halo; or $R_1$ and $R_2$ are linked to form a ring;
$R_4$ is selected from the group consisting of H, $C_{1-6}$-alk(en/yn)yl, $C_{3-6}$-cycloalk(en)yl, —N$R_9$—CO—$R_{10}$, —N$R_{10}$—SO$_2$—$R_{12}$, —CO—N$R_9R_{10}$, —SO$_2$—N$R_9$ $R_{10}$, —$R_{13}$—O—$R_{11}$, N$R_9R_{10}$, cyano, O—$R^{11}$, fluorinated $C_{1-3}$, nitro and halo;
$R_5$ is selected from the group consisting of $C_{1-3}$-alk(en/yn)yl and $C_{3-6}$-cycloalk(en)yl, wherein said $C_{1-3}$-alk(en/yn)yl and $C_{3-6}$-cycloalk(en)yl may be substituted with up to three substituents selected from the group consisting of —N$R_9$—CO—$R_{10}$, —N($R_{10}$)$_2$SO$_2$—$R_{12}$, —CO—N$R_9R_{10}$, —SO$_2$—N$R_9$ $R_{10}$, —$R_{13}$—O—$R_{11}$, N$R_9R_{10}$, —S(O)$R_{12}$, S(O)$_2R_{12}$, cyano, O—$R_{11}$, fluorinated $C_{1-3}$-alkyl, nitro and halo;
$R_9$, $R_{10}$, $R_{11}$ are independently selected from H or $C_{1-4}$-alk(en/yn)yl and $C_{3-6}$-cycloalk(en)yl;
$R_{12}$ is selected from $C_{1-4}$-alk(en/yn)yl and $C_{3-6}$-cycloalk(en)yl
$R_{13}$ is selected from $C_{1-4}$-alk(an/en/yn)diyl and $C_{3-6}$-cycloalk(an/en)diyl In one embodiment thereof, A is a monocyclic or bicyclic aromatic or heteroaromatic ring. For example, A can be a five-membered or six-membered aromatic ring. In one embodiment A is phenyl, or naphthyl.

in one aspect, the invention relates to a compound of Formula (I.2):

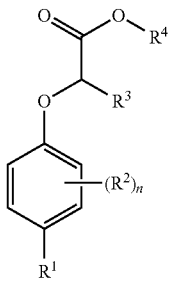

Formula (I.2)

wherein:
$R^1$ is selected from the group consisting of hydrogen, F, Cl, Br, I, —CN, —CF$_3$, $C_{1-4}$ alkyl, $C_{1-4}$ alkenyl, $C_{1-4}$ alkynyl, $C_4$ cycloalkyl and —S—CH$_3$;
$R^2$ is independently selected from the group consisting of hydrogen, deuterium, F, Cl, Br, I, —CN, —CF$_3$ and -oxime optionally substituted with $C_1$ alkyl;
$R^3$ is selected from the group consisting of $C_{1-5}$ alkyl, $C_{1-5}$ alkenyl, $C_{3-5}$ cycloalkyl and $C_5$ cycloalkenyl, each of which may be optionally substituted with one or more, identical or different, substituents $R^5$;
$R^4$ is selected from the group consisting of H or $C_{1-5}$ alkyl;
$R^5$ is independently selected from the group consisting of F and OH; and
n is an integer 0, 1 or 2;
with the proviso that when $R^1$ is Cl, $R^4$ is H and n is 0, then $R^3$ is not methyl or ethyl.

In another embodiment of the present invention, the compound of Formula (I) is further defined by Formula (II):

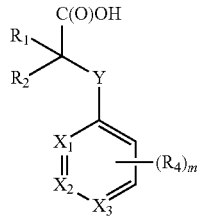

Formula (II)

or a pharmaceutically acceptable salt, solvate, polymorph, or tautomer thereof; wherein Y is selected from the group consisting of O, NH, N—CH$_3$, CH$_2$, CH$_2$—O, S and SO$_2$;

X$_1$, X$_2$ and X$_3$ are selected from the group consisting of, CH and N;

R$_1$ and R$_2$ are independently selected from the group consisting of OR$_3$, SR$_5$, S(O)R$_5$, S(O)$_2$R$^5$, NR$_3$, NR$_3$C(O)R$_a$ or R$_3$, wherein R$_3$ is selected from the group consisting of H, C$_{1-8}$-alk(en/yn)yl and C$_{3-6}$-cycloalk(en)yl, wherein said C$_{1-8}$-alk(en/yn)yl and C$_{3-5}$-cycloalk(en)yl may be substituted with up to three substituents selected from the group consisting of —NR$_9$—CO—R$_{10}$, —N(R$_{10}$)$_2$—SO$_2$—R$_{12}$, —CO—NR$_9$R$_{10}$, —SO$_2$—NR$_9$ R$_{10}$, —R$_{13}$—O—R$_{11}$, NR$_9$ R$_{10}$, —S(O)R$_{12}$, S(O)$_2$R$_{12}$, cyano, O—R$_{11}$, fluorinated C$_{1-3}$-alkyl, nitro and halo; or R$_1$ and R$_2$ are linked to form a C$_{3-6}$-cycloalk(en)yl or a halo-C$_{3-6}$-cycloalk(en)yl;

R$_4$ is as defined in embodiment 1 below;

m is as defined in embodiment 1 below;

R$^5$ is selected from the group consisting of C$_{1-8}$-alk(en/yn)yl and C$_{3-6}$-cycloalk(en)yl, wherein said C$_{1-8}$-alk(en/yn)yl and C$_{3-6}$-cycloalk(en)yl may be substituted with up to three substituents selected from the group consisting of —NR$_9$—CO—R$_{10}$, —N(R$_{10}$)$_2$SO$_2$—R$_{12}$, —CO—NR$_9$ R$_{10}$, —SO$_2$—NR$_9$ R$_{10}$, —R$_{13}$—O—R$_{11}$, NR$_9$R$_{10}$, —S(O)R$_{12}$, S(O)$_2$R$_{12}$, cyano, O—R$_{11}$, fluorinated C$_{1-3}$, nitro and halo; or R$_1$ and R$_2$ are linked to form a ring;

R$_9$, R$_{10}$ and R$_{11}$ are independently selected from H, C$_{1-4}$-alk(en/yn)yl and C$_{3-6}$-cycloalk(en)yl whereas R$_{12}$ is selected from C$_{1-4}$-alk(en/yn)yl and C$_{3-6}$-cycloalk(en)yl; for use in treating, ameliorating and/or preventing a neuromuscular disorder.

In a preferred embodiment R$_1$ is selected from the group consisting of H and —CH$_3$. In a particular embodiment R$_1$ is H.

Thus, in one embodiment R$_1$ is H and R$_2$ is selected from the group consisting of H, C$_{1-4}$-alk(en)yl, C$_{3-6}$-cycloalk(en)yl, wherein said C$_{1-4}$-alk(en/yn)yl and C$_{3-6}$-cycloalk(en)yl may be substituted with up to two substituents selected from the group consisting of —NR$_9$—CO—R$_{10}$, —N(R$_{10}$)$_2$—SO$_2$—R$_{12}$, —CO—NR$_9$R$_{10}$, —SO$_2$—NR$_9$ R$_{10}$, —R$_{13}$—O—R$_{11}$, NR$_9$ R$_{10}$, —S(O)R$_{12}$, S(O)$_2$R$_{12}$, cyano, O—R$_{11}$, fluorinated C$_{1-3}$-alkyl, nitro and halo, wherein R$_9$, R$_{10}$ and R$_{11}$ are independently selected from H, C$_{1-4}$-alk(en/yn)yl and C$_{3-6}$-cycloalk(en)yl whereas R$_{12}$ is selected from C$_{1-4}$-alk(en/yn)yl and C$_{3-6}$-cycloalk(en)yl Thus, in another embodiment R$^1$ is H and R$_2$ is selected from the group consisting of H, C$_{1-4}$-alkyl, C$_{3-6}$-cycloalkyl and amino-C$_{1-4}$-alkyl, wherein said C$_{1-4}$-alkyl and C$_{3-6}$-cycloalkyl may be substituted with O—R$_{11}$, wherein R$_1$, is as defined above. In one embodiment R$_{11}$ is —CH$_3$. In another embodiment R$_2$ is —CH(CH$_3$)CH$_2$—O—CH$_3$.

In a preferred embodiment of the present invention R$_1$ is H and R$_2$ is selected from the group consisting of H, C$_{1-6}$-alkyl and C$_{3-7}$-cycloalkyl. For example, R$_1$ is H and R$_2$ is selected from the group consisting of H, —CH$_3$, —CH(CH$_3$)$_2$ and cyclopropyl. In a particular embodiment, R$_1$ is H and R$_2$ is —CH(CH$_3$)$_2$.

It is preferred that R$_1$ is different from R$_2$.

It is appreciated that the compound as defined herein is the S-enantiomer with respect to the C-atom to which R$_2$ is bound.

In one aspect, the invention relates to a compound of Formula (II.2):

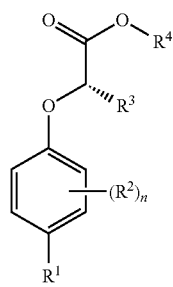

Formula (II.2)

wherein:

R$^1$ is selected from the group consisting of F, Cl, Br, I, —CN, —CF$_3$, C$_{1-4}$ alkyl, C$_{1-4}$ alkenyl, C$_{1-4}$ alkynyl, C$_4$ cycloalkyl and —S—CH$_3$;

R$^2$ is independently selected from the group consisting of hydrogen, deuterium, F, Cl, Br, I, —CN, —CF$_3$ and -oxime optionally substituted with C$_1$ alkyl;

R$^3$ is selected from the group consisting of C$_{1-5}$ alkyl, C$_{1-5}$ alkenyl, C$_{3-5}$ cycloalkyl and C$_5$ cycloalkenyl, each of which may be optionally substituted with one or more, identical or different, substituents R$^5$;

R$^4$ is selected from the group consisting of H and C$_{1-5}$ alkyl;

R$^5$ is independently selected from the group consisting of F and OH; and n is an integer 0, 1 or 2;

with the proviso that when R$^1$ is Cl, R$^4$ is H and n is 0, then R$^3$ is not methyl or ethyl.

In one embodiment thereof, R$_1$ is H and R$_2$ is C$_{1-6}$-alkyl or C$_{3-7}$-cycloalkyl and wherein said compound is the S-enantiomer with respect to the C-atom to which R$_2$ is bound as shown in Formula (III):

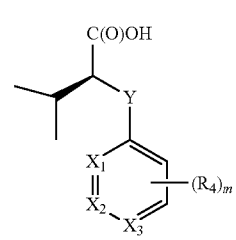

Formula (III)

or a pharmaceutically acceptable salt, solvate, polymorph, or tautomer thereof; wherein, Y, X$_1$, X$_2$ and X$_3$ and R$_4$ are as defined above.

In one preferred embodiment of the invention, R$_4$ is selected from the group consisting of H, halo, cyano, —CHO, C$_{1-4}$-alk(en)yl, halo-C$_{1-4}$-alk(en)yl, —O—C$_{1-4}$-alk(en)yl.

In one embodiment m is 0, 1 or 2. For example m is 1.

In one embodiment of the invention X$_1$ is N, X$_2$ is N or X$_3$ is N. In another embodiment X1, X$_2$ and X$_3$ is C.

In one aspect, the invention relates to a compound of Formula (III.2):

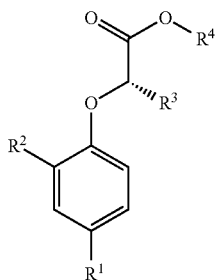

Formula (III.2)

wherein:
R$^1$ is selected from the group consisting of Cl, Br, and I;
R$^2$ is selected from the group consisting of deuterium, F, Cl, Br, I, and -oxime optionally substituted with C$_1$ alkyl;
R$^3$ is selected from the group consisting of C$_{1-5}$ alkyl, C$_{1-5}$ alkenyl, C$_{3-5}$ cycloalkyl and C$_5$ cycloalkenyl, each of which may be optionally substituted with one or more F; and
R$^4$ is selected from the group consisting of H or C$_{1-5}$ alkyl; preferably H.

The compound may in one embodiment be defined by Formula (I), which is further defined by Formula (IV):

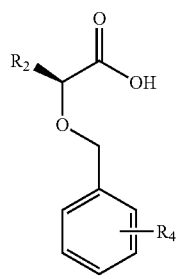

Formula (IV)

or a pharmaceutically acceptable salt, solvate, polymorph, or tautomer thereof; wherein A, R$_2$ and R$_4$ are as defined above.

In one aspect, the invention relates to a compound of Formula (IV.2):

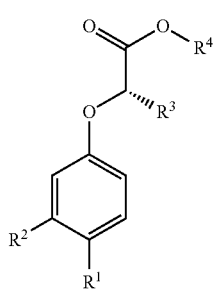

Formula (IV.2)

wherein:
R$^1$ is selected from the group consisting of Cl, Br, and I;
R$^2$ is selected from the group consisting of deuterium, F, Cl, Br, and I;
R$^3$ is selected from the group consisting of C$_{1-5}$ alkyl, C$_{1-5}$ alkenyl, C$_{3-5}$ cycloalkyl and C$_5$ cycloalkenyl, each of which may be optionally substituted with one or more F; and
R$^4$ is selected from the group consisting of H or C$_{1-5}$ alkyl; preferably H.

Also, the compound of Formula (IV) can be further defined by Formula (V):

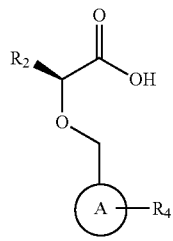

Formula (V)

wherein R$_2$ and R$_4$ are as defined above. It is preferred that R$_2$ is C$_{1-6}$-alkyl or C$_{3-7}$-cycloalkyl.

In one aspect, the invention relates to a compound of Formula (V.2):

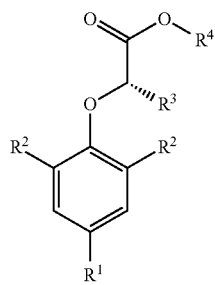

Formula (V.2)

wherein:
R$^1$ is Br, Cl or I;
R$^2$ is independently deuterium, F, Cl, Br, or I;
R$^3$ is selected from the group consisting of C$_{1-5}$ alkyl, C$_{1-5}$ alkenyl, C$_{3-5}$ cycloalkyl and C$_5$ cycloalkenyl, each of which may be optionally substituted with one or more F; and
R$^4$ is selected from the group consisting of H or C$_{1-5}$ alkyl; preferably H.

In one embodiment thereof, the compound of Formula (V) is further defined by Formula (VI):

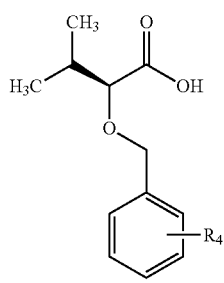

Formula (VI)

wherein R$_4$ is as defined above. Preferably, R$_4$ is in ortho- or meta position.

In one aspect, the invention relates to a compound of Formula (VI.2):

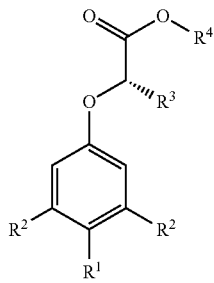

Formula (VI.2)

wherein:
$R^1$ is Br, Cl or I;
$R^2$ is independently deuterium, F, Cl, Br, or I;
$R^3$ is selected from the group consisting of $C_{1-5}$ alkyl, $C_{1-5}$ alkenyl, $C_{3-5}$ cycloalkyl and $C_5$ cycloalkenyl, each of which may be optionally substituted with one or more F; and
$R^4$ is selected from the group consisting of H or $C_{1-5}$ alkyl; preferably H.

In one embodiment of the present invention the compound of Formula (I) is further defined by Formula (VII):

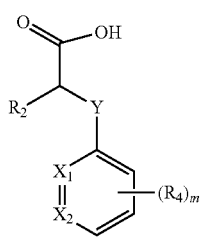

Formula (VII)

or a pharmaceutically acceptable salt, solvate, polymorph, or tautomer thereof;
wherein m is 2 and $X_1$, $X_2$, Y, $R_2$ and $R_4$ are as defined above.

In an embodiment thereof, the compound of Formula (VII) is further defined by Formula (VIII)

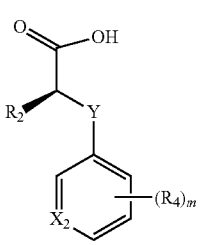

Formula (VIII)

or a pharmaceutically acceptable salt, solvate, polymorph, or tautomer thereof; wherein m, $X_2$, Y, $R_2$ and $R_4$ are as defined above.

In one preferred embodiment Y is O. It is further preferred that $R_2$ is selected from the group consisting of H and $C_{1-4}$-alkyl. Preferably, $R_4$ is selected from the group consisting of H, —$CH_3$ and halogen. Thus, in one embodiment the compound is further defined by Formula (IX):

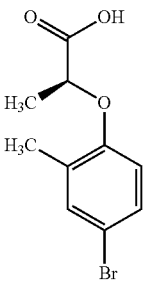

Formula (IX)

In one embodiment the compound of Formula (VII) is further defined by Formula (X):

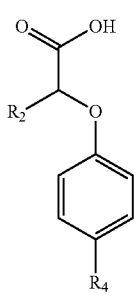

Formula (X)

or a pharmaceutically acceptable salt, solvate, polymorph, or tautomer thereof; wherein $R_2$ is selected from the group consisting of —$CH_3$, —$CH_2$—$CH_3$, —$CH(CH_3)_2$, —$C(CH_3)_3$, —$CH(CH_3)CH_2$—O—$CH_3$, —$CH_2$—$CH_2$—$CH_3$, —$CH_2$—$NH_2$, —$CH_2$—$CHF_2$, —$CH_2$—$CF_3$, —$CH_2$—NH—CO—$CH_3$ and —$CH_2$—NH—$SO_2$—$CH_3$ and cyclopropyl, and $R_4$ is selected from the group consisting of H, Br, Cl, F and I.

In specific embodiments, the compound of Formula (VII) is further defined by any one of Formulas (XI) to (XXVIII) as defined herein.

Another embodiment of the present invention relates to a compound of Formula (VII) that is further defined by Formula (XXIX):

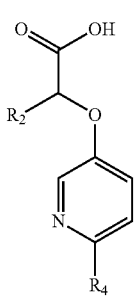

Formula (XXIX)

or a pharmaceutically acceptable salt, solvate, polymorph, or tautomer thereof; wherein $R_2$ is selected from the group consisting of —$CH_3$, —$CH_2$—$CH_3$, —$CH(CH_3)_2$, —$C(CH_3)_3$, —$CH_2$—$CH_2$—$CH_3$ and —$CH_2$—$NH_2$ and $R_4$ is selected from the group consisting of H, Br, Cl, F and I.

In particular, the compound of Formula (XXIX) is further defined by Formula (XXX):

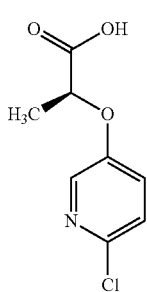

Formula (XXX)

In one embodiment, the compound of Formula (VII) is further defined by Formula (XXXI):

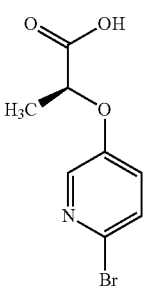

Formula (XXXI)

Also, the compound of Formula (VII) can be further defined by Formula (XXXII):

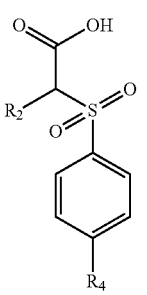

Formula (XXXII)

or a pharmaceutically acceptable salt, solvate, polymorph, or tautomer thereof; wherein $R_2$ is selected from the group consisting of —$CH_3$, —$CH_2$—$CH_3$, —$CH(CH_3)_2$, —$C(CH_3)_3$, —$CH_2$—$CH_2$—$CH_3$ and —$CH_2$—$NH_2$ and $R_4$ is selected from the group consisting of H, Br, Cl, F and I.

Preferably, the compound of Formula (XXXII) is further defined by Formula (XXXIII):

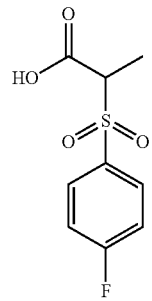

Formula (XXXIII)

In another embodiment of the present invention the compound of Formula (I) is further defined by Formula (XXXIV):

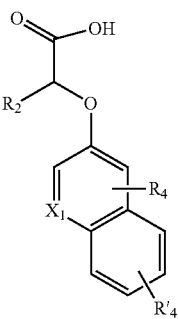

Formula (XXXIV)

or a pharmaceutically acceptable salt, solvate, polymorph, or tautomer thereof; wherein $R_2$ is selected from the group consisting of —$CH_3$, —$CH_2$—$CH_3$, —$CH(CH_3)_2$, —$C(CH_3)_3$, —$CH_2$—$CH_2$—$CH_3$ and —$CH_2$—$NH_2$; $X_1$ is N or C; and $R_4$ and $R'_4$ are individually selected from the group consisting of H, Br, Cl, F and I.

In particular, Formula (XXXIV) can be further defined by Formula (XXXV):

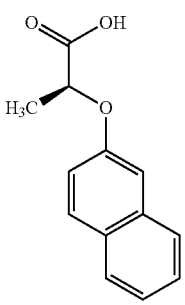

Formula (XXXV)

In specific embodiments of the present invention, the compound of Formula (I) is further defined by any one of Formulas (XXXVI) to (LIX)) and compounds A-1 to A-58 and for use in treating, ameliorating and/or preventing a neuromuscular disorder, and/or for use in reversing and/or ameliorating a neuromuscular blockade.

In one embodiment, the compound or the compound for use according to the present invention has been modified in order to increase its half-life when administered to a patient, in particular its plasma half-life.

In one embodiment, the compound or the compound for use according to the present invention further comprises a moiety conjugated to said compound, thus generating a moiety-conjugated compound. In one embodiment, said moiety-conjugated compound has a plasma and/or serum half-life being longer than the plasma and/or serum half-life of the non-moiety conjugated compound.

In one embodiment, the moiety conjugated to the compound or compound for use according to the present invention, is one or more type(s) of moieties selected from the group consisting of albumin, fatty acids, polyethylene glycol (PEG), acylation groups, antibodies and antibody fragments Neuromuscular Disorders The compositions and compounds of the present invention are used for treating, ameliorating and/or preventing a neuromuscular disorder, or reversing neuromuscular blockade caused by non-depolarizing neuromuscular blocker or antibiotic agent.

The inventors of the present invention have shown that inhibition of ClC-1 channels recovers neuromuscular transmission. ClC-1 function may therefore contribute to muscle weakness in conditions of compromised neuromuscular transmission.

Thus, in one embodiment of the present invention, the composition for use as described herein inhibits ClC-1 channels. Thus, it is appreciated that compounds of Formula (I) inhibit ClC-1 channels.

The neuromuscular disorder may also include neuromuscular dysfunctions.

Neuromuscular disorders include for example disorders with symptoms of muscle weakness and fatigue. Such disorders may include conditions with reduced neuromuscular transmission safety factor. In one embodiment the neuromuscular disorders are motor neuron disorders. Motor neuron disorders are disorders with reduced safety in the neuromuscular transmission. In one embodiment motor neuron disorders are selected from the group consisting of amyotrophic lateral sclerosis (ALS), spinal muscular atrophy (SMA), X-linked spinal and bulbar muscular atrophy, Kennedy's disorder, multifocal motor neuropathy, Guillain-Barre syndrome, poliomyelitis and post-polio syndrome.

Thus, in one preferred embodiment of the present invention the neuromuscular disorder is ALS. In another preferred embodiment the neuromuscular disorder is SMA. In another preferred embodiment the neuromuscular disorder is Charcot-Marie tooth disease (CMT). In another preferred embodiment the neuromuscular disorder is sarcopenia. In yet another preferred embodiment, the neuromuscular disorder is critical illness myopathy (CIM).

As stated above the neuromuscular disorders include for example disorders with symptoms of muscle weakness and fatigue. Such disorder may for example include diabetes.

In one embodiment the composition of the present invention is used to prevent neuromuscular disorder. The composition may for example be used prophylactically against nerve gas that is known to cause symptoms of muscle weakness and fatigue.

In another embodiment the neuromuscular disorders is chronic fatigue syndrome. Chronic fatigue syndrome (CFS) is the common name for a medical condition characterized by debilitating symptoms, including fatigue that lasts for a minimum of six months in adults. CFS may also be referred to as systemic exertion intolerance disorder (SEID), myalgic encephalomyelitis (ME), post-viral fatigue syndrome (PVFS), chronic fatigue immune dysfunction syndrome (CFIDS), or by several other terms. Symptoms of CFS include malaise after exertion; unrefreshing sleep, widespread muscle and joint pain, physical exhaustion, and muscle weakness.

In a further embodiment the neuromuscular disorder is a critical illness polyneuropathy or CIM. Critical illness polyneuropathy and CIM are overlapping syndromes of widespread muscle weakness and neurological dysfunction developing in critically ill patients.

The neuromuscular disorder may also include metabolic myopathy and mitochondrial myopathy. Metabolic myopathies result from defects in biochemical metabolism that primarily affects muscle. These may include glycogen storage disorders, lipid storage disorder and 3-phosphocreatine stores disorder. Mitochondrial myopathy is a type of myopathy associated with mitochondrial disorder. Symptoms of mitochondrial myopathies include muscular and neurological problems such as muscle weakness, exercise intolerance, hearing loss and trouble with balance and coordination.

In a preferred embodiment the neuromuscular disorder is a myasthenic condition. Myasthenic conditions are characterized by muscle weakness and neuromuscular transmission failure. Congenital myasthenia gravis is an inherited neuromuscular disorder caused by defects of several types at the neuromuscular junction.

Myasthenia gravis and Lambert-Eaton syndrome are also examples of myasthenic condition. Myasthenia gravis is either an autoimmune or congenital neuromuscular disorder that leads to fluctuating muscle weakness and fatigue. In the most common cases, muscle weakness is caused by circulating antibodies that block ACh receptors at the postsynaptic neuromuscular junction, inhibiting the excitatory effects of the neurotransmitter ACh on nicotinic Ach-receptors at neuromuscular junctions. Lambert-Eaton myasthenic syndrome (also known as LEMS, Lambert-Eaton syndrome, or Eaton-Lambert syndrome) is a rare autoimmune disorder that is characterized by muscle weakness of the limbs. It is the result of an autoimmune reaction in which antibodies are formed against presynaptic voltage-gated calcium channels, and likely other nerve terminal proteins, in the neuromuscular junction.

Thus, in one preferred embodiment of the present invention the neuromuscular disorder is myasthenia gravis. In another preferred embodiment the neuromuscular disorder is Lambert-Eaton syndrome.

Neuromuscular blockade is used in connection with surgery under general anaesthesia. Reversing agents are used for more rapid and safer recovery of muscle function after such blockade. Complications with excessive muscle weakness after blockade during surgery can result in delayed weaning from mechanical ventilation and respiratory complications after the surgery. Since such complications have pronounced effects on outcome of the surgery and future quality of life of patients, there is a need for improved reversing agents. Thus, in a preferred embodiment the neuromuscular disorder is muscle weakness caused by neuromuscular blockade after surgery. In another preferred embodiment of the present invention the composition is used for reversing and/or ameliorating neuromuscular blockade after surgery. Thus, one aspect of the present invention relates to a composition comprising a compound of Formula (I):

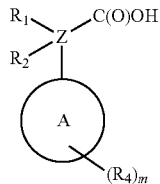

Formula (I)

or a pharmaceutically acceptable salt, solvate, polymorph, or tautomer thereof;

wherein

A is an aromatic or heteroaromatic ring selected from the group consisting of phenyl, naphthyl, biphenyl, quinolinyl, isoquinolinyl, imidazolyl, thiazolyl, thiadiazolyl, triazolyl, oxazolyl, pyridinyl, pyrimidinyl, pyrazyl, and pyridazinyl;

m is 0, 1, 2, 3, 4 or 5;

Z is a 2-5 atom chain comprising at least one carbon atom and optionally one heteroatom or substituted heteroatom, wherein the heteroatom or substituted heteroatom is selected from the group consisting of O, N, $NC(O)R_3$, S, $S(O)R_5$ and $S(O)_2R^5$, wherein each atom of said 2-5 atom chain is optionally substituted with $R_1$ and $R_2$; wherein $R_1$ and $R_2$ are independently selected from the group consisting of $OR_3$, $SR_5$, $S(O)R_5$, $S(O)_2R_5$, $NR_3$, $NR_3C(O)R_9$ or $R_3$, wherein $R_3$ is selected from the group consisting of H, $C_{1-8}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of —$NR_9$—CO—$R_{10}$, —$N(R_{10})_2$—$SO_2$—$R_{12}$, —CO—$NR_9R_{10}$, —$SO_2$—$NR_9$ $R_{10}$, —$R_{13}$—O—$R_{11}$, $NR_9$ $R_{10}$, —$S(O)R_{12}$, $S(O)_2R_{12}$, cyano, O—$R_{11}$, fluorinated $C_{1-3}$-alkyl, nitro and halo; or $R_1$ and $R_2$ are linked to form a ring;

$R_4$ is selected from the group consisting of H, $C_{1-6}$-alk(en/yn)yl, $C_{3-6}$-cycloalk(en)yl, —$NR_9$—CO—$R_{10}$, —$NR_{10}$—$SO_2$—$R_{12}$, —CO—$NR_9R_{10}$, —$SO_2$—$NR_9$ $R_{10}$, —$R_{13}$—O—$R^{11}$, $NR_9R_{10}$, cyano, O—$R^{11}$, fluorinated $C_{1-3}$, nitro and halo;

$R_5$ is selected from the group consisting of $C_{1-6}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of —$NR_9$—CO—$R_{10}$, —$N(R_{10})_2SO_2$—$R_{12}$, —CO—$NR_9R_{10}$, —$SO_2$—$NR_9$ $R_{10}$, —$R_{13}$—O—$R_{11}$, $NR_9R_{10}$, —$S(O)R_{12}$, $S(O)_2R_{12}$, cyano, O—$R_{11}$, fluorinated $C_{1-3}$-alkyl, nitro and halo;

$R_9$, $R_{10}$, $R_{11}$, are independently selected from H or $C_{1-4}$-alk(en/yn)yl and $C_{3-6}$-cycloalk(en)yl;

$R_{12}$ is selected from $C_{1-4}$-alk(en/yn)yl and $C_{3-6}$-cycloalk(en)yl $R_{13}$ is selected from $C_{1-4}$-alk(an/en/yn)diyl and $C_{3-6}$-cycloalk(an/en)diyl for use in reversing and/or ameliorating a neuromuscular blockade after surgery.

In one aspect, the invention relates to a compound of Formula (I.2):

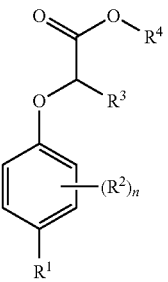

Formula (I.2)

wherein:

$R^1$ is selected from the group consisting of hydrogen, F, Cl, Br, I, —CN, —$CF_3$, $C_{1-4}$ alkyl, $C_{1-4}$ alkenyl, $C_{1-4}$alkynyl, $C_4$ cycloalkyl and —S—$CH_3$;

$R^2$ is independently selected from the group consisting of hydrogen, deuterium, F, Cl, Br, I, —CN, —$CF_3$ and -oxime optionally substituted with $C_1$ alkyl;

$R^3$ is selected from the group consisting of $C_{1-5}$ alkyl, $C_{1-5}$ alkenyl, $C_{3-5}$ cycloalkyl and $C_5$ cycloalkenyl, each of which may be optionally substituted with one or more, identical or different, substituents $R^5$;

$R^4$ is selected from the group consisting of H or $C_{1-5}$ alkyl;

$R^5$ is independently selected from the group consisting of F and OH; and n is an integer 0, 1 or 2;

or a pharmaceutically acceptable salt, hydrate, polymorph, tautomer, or solvate thereof, for use in treating, ameliorating and/or preventing a neuromuscular disorder, and/or for use in reversing and/or ameliorating a neuromuscular blockade;

with the proviso that when $R^1$ is Cl, $R^4$ is H and n is 0, then $R^3$ is not methyl or ethyl.

In one aspect, the invention relates to a compound of Formula (II.2):

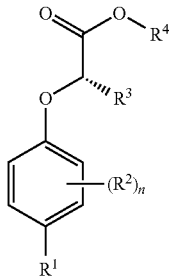

Formula (II.2)

wherein:

$R^1$ is selected from the group consisting of F, Cl, Br, I, —CN, —$CF_3$, $C_{1-4}$ alkyl, $C_{1-4}$ alkenyl, $C_{1-4}$ alkynyl, $C_4$ cycloalkyl and —S—$CH_3$;

$R^2$ is independently selected from the group consisting of hydrogen, deuterium, F, Cl, Br, I, —CN, —$CF_3$ and -oxime optionally substituted with $C_1$ alkyl;

$R^3$ is selected from the group consisting of $C_{1-5}$ alkyl, $C_{1-5}$ alkenyl, $C_{3-5}$ cycloalkyl and $C_5$ cycloalkenyl, each of which may be optionally substituted with one or more, identical or different, substituents $R^5$;

$R^4$ is selected from the group consisting of H and $C_{1-5}$ alkyl;

$R^5$ is independently selected from the group consisting of F and OH; and n is an integer 0, 1 or 2;

or a pharmaceutically acceptable salt, hydrate, polymorph, tautomer, or solvate thereof, for use in treating, ameliorating and/or preventing a neuromuscular disorder, and/or for use in reversing and/or ameliorating a neuromuscular blockade;

with the proviso that when $R^1$ is Cl, $R^4$ is H and n is 0, then $R^3$ is not methyl or ethyl.

In one aspect, the invention relates to a compound of Formula (III.2):

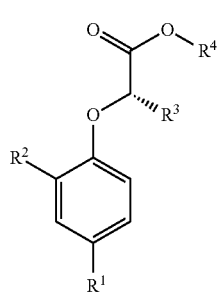

Formula (III.2)

wherein:
$R^1$ is selected from the group consisting of Cl, Br, and I;
$R^2$ is selected from the group consisting of deuterium, F, Cl, Br, I, and -oxime optionally substituted with $C_1$ alkyl;
$R^3$ is selected from the group consisting of $C_{1-5}$ alkyl, $C_{1-5}$ alkenyl, $C_{3-5}$ cycloalkyl and $C_5$ cycloalkenyl, each of which may be optionally substituted with one or more F; and
$R^4$ is selected from the group consisting of H or $C_{1-5}$ alkyl; preferably H;

or a pharmaceutically acceptable salt, hydrate, polymorph, tautomer, or solvate thereof, for use in treating, ameliorating and/or preventing a neuromuscular disorder, and/or for use in reversing and/or ameliorating a neuromuscular blockade.

In one aspect, the invention relates to a compound of Formula (IV.2):

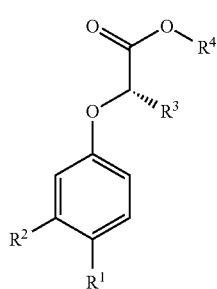

Formula (IV.2)

wherein:
$R^1$ is selected from the group consisting of Cl, Br, and I;
$R^2$ is selected from the group consisting of deuterium, F, Cl, Br, and I;
$R^3$ is selected from the group consisting of $C_{1-5}$ alkyl, $C_{1-5}$ alkenyl, $C_{3-5}$ cycloalkyl and $C_5$ cycloalkenyl, each of which may be optionally substituted with one or more F; and
$R^4$ is selected from the group consisting of H or $C_{1-5}$ alkyl; preferably H;

or a pharmaceutically acceptable salt, hydrate, polymorph, tautomer, or solvate thereof, for use in treating, ameliorating and/or preventing a neuromuscular disorder, and/or for use in reversing and/or ameliorating a neuromuscular blockade.

In one aspect, the invention relates to a compound of Formula (V.2):

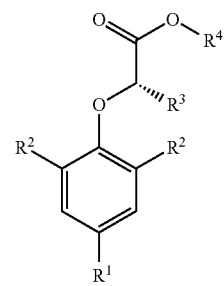

Formula (V.2)

wherein:
$R^1$ is Br, Cl or I;
$R^2$ is independently deuterium, F, Cl, Br, or I;
$R^3$ is selected from the group consisting of $C_{1-5}$ alkyl, $C_{1-5}$ alkenyl, $C_{3-5}$ cycloalkyl and $C_5$ cycloalkenyl, each of which may be optionally substituted with one or more F; and
$R^4$ is selected from the group consisting of H or $C_{1-5}$ alkyl; preferably H;

or a pharmaceutically acceptable salt, hydrate, polymorph, tautomer, or solvate thereof, for use in treating, ameliorating and/or preventing a neuromuscular disorder, and/or for use in reversing and/or ameliorating a neuromuscular blockade.

In one aspect, the invention relates to a compound of Formula (VI.2):

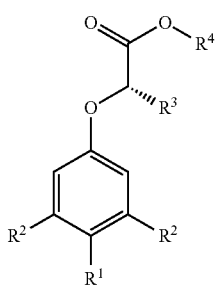

Formula (VI.2)

wherein:
$R^1$ is Br, Cl or I;
$R^2$ is independently deuterium, F, Cl, Br, or I;
$R^3$ is selected from the group consisting of $C_{1-5}$ alkyl, $C_{1-5}$ alkenyl, $C_{3-5}$ cycloalkyl and $C_5$ cycloalkenyl, each of which may be optionally substituted with one or more F; and
$R^4$ is selected from the group consisting of H or $C_{1-5}$ alkyl; preferably H;

or a pharmaceutically acceptable salt, hydrate, polymorph, tautomer, or solvate thereof, for use in treating, ameliorating and/or preventing a neuromuscular disorder, and/or for use in reversing and/or ameliorating a neuromuscular blockade.

In one embodiment, the compound for use in treating, ameliorating and/or preventing a neuromuscular disorder, and/or for use in reversing and/or ameliorating a neuromuscular blockade is selected from the group consisting of:

Compound A-1

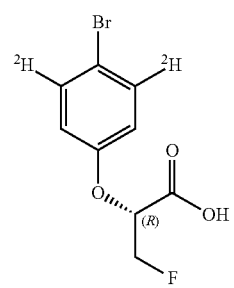

Compound A-2

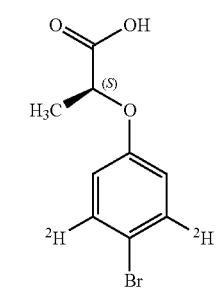

Compound A-3

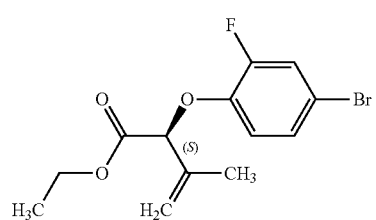

Compound A-4

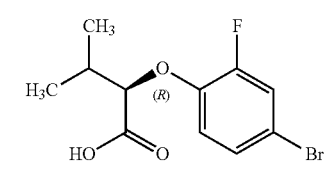

Compound A-5

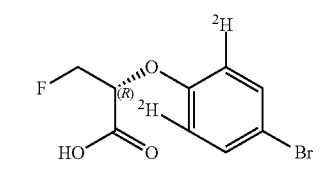

Compound A-6

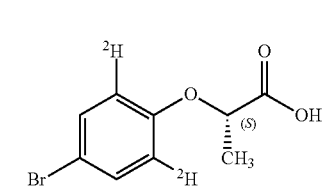

Compound A-7

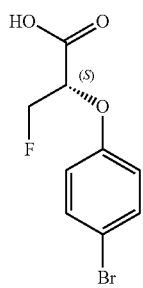

Compound A-8

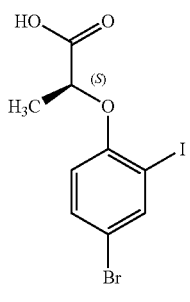

Compound A-9

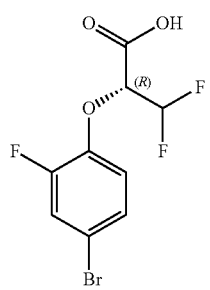

Compound A-10

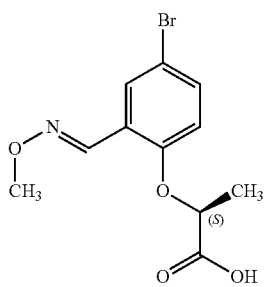

Compound A-11

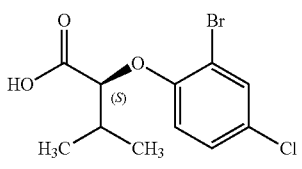

Compound A-12

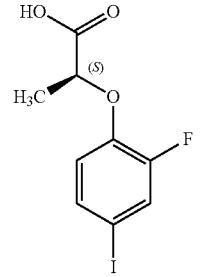

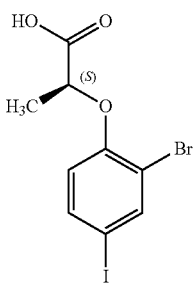
Compound A-13
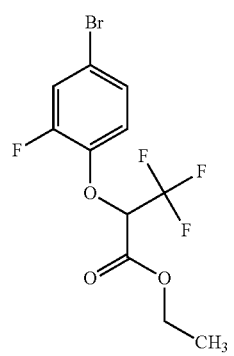
Compound A-14
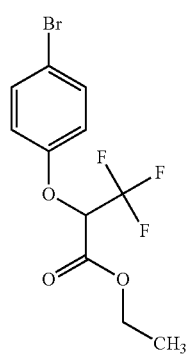
Compound A-15
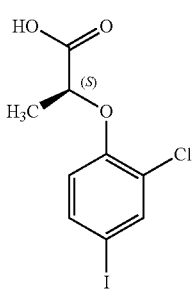
Compound A-16
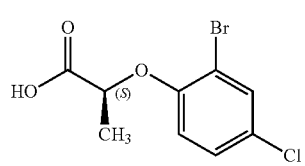
Compound A-17
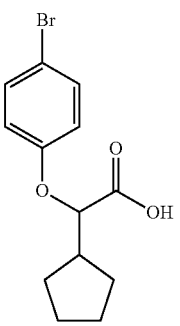
Compound A-18
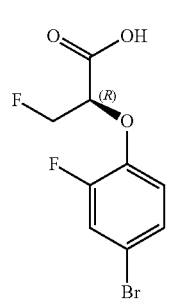
Compound A-19
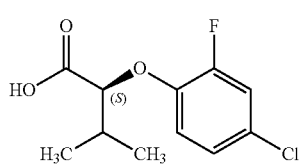
Compound A-20
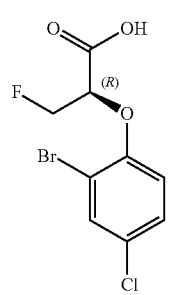
Compound A-21
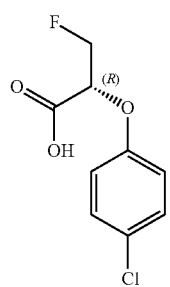
Compound A-22
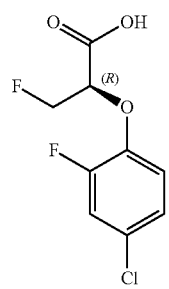
Compound A-23

Compound A-24
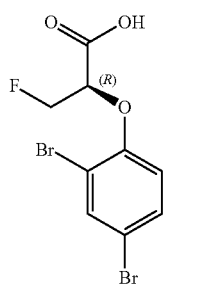
Compound A-25
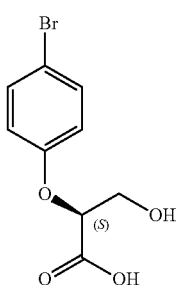
Compound A-26
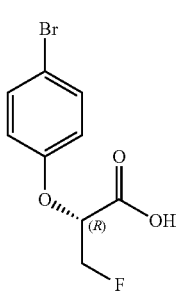
Compound A-27
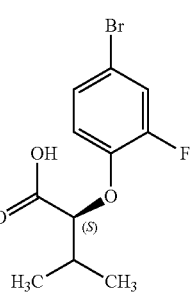
Compound A-28
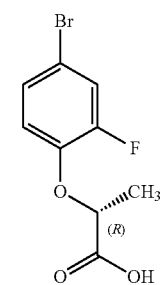
Compound A-29
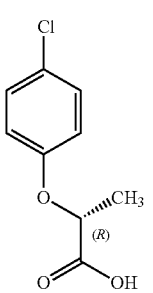
Compound A-30
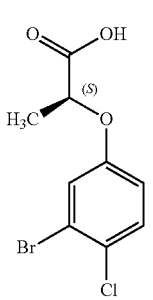
Compound A-31
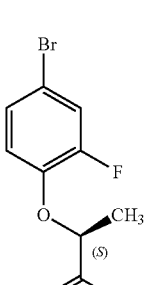
Compound A-32
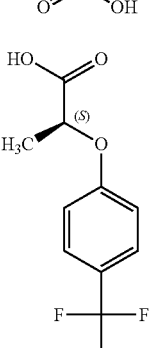
Compound A-33
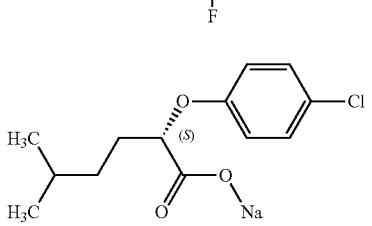
Compound A-34
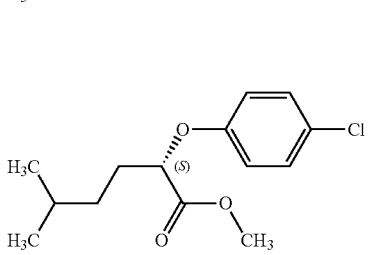

-continued
Compound A-35
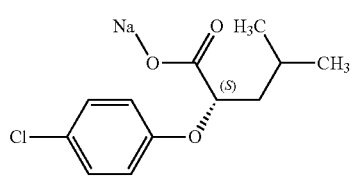
Compound A-36
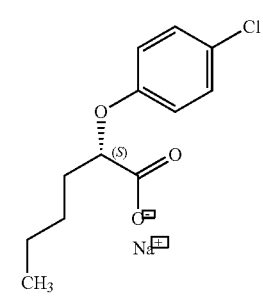
Compound A-37
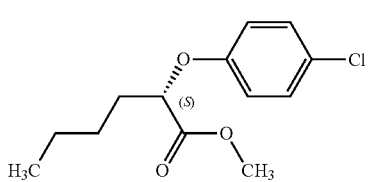
Compound A-38
Compound A-39
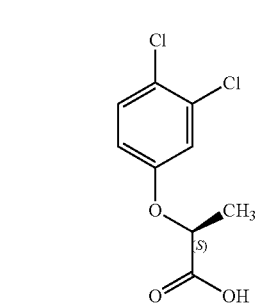
Compound A-40
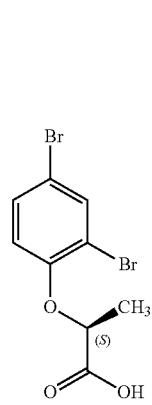
-continued
Compound A-41
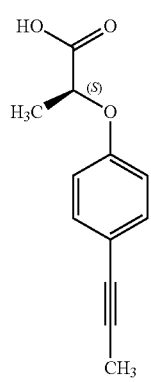
Compound A-42
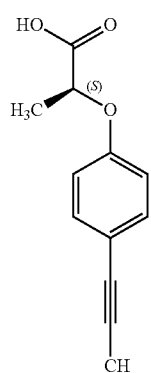
Compound A-43
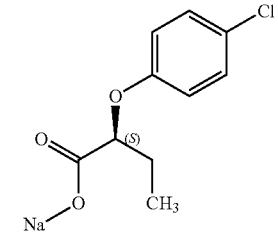
Compound A-44
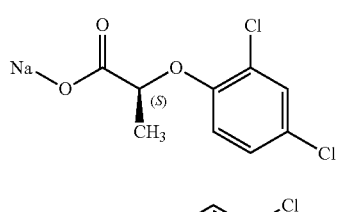
Compound A-45
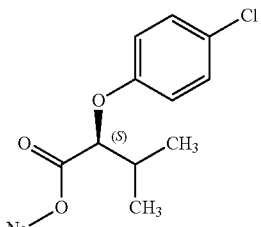
Compound A-46
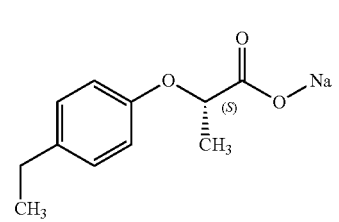

Compound A-47

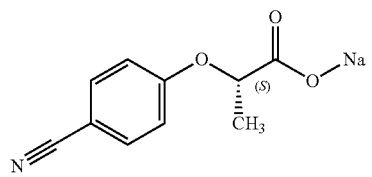

Compound A-48

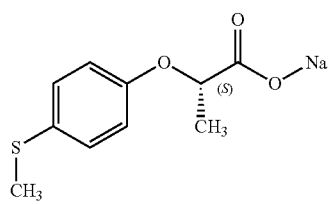

Compound A-49

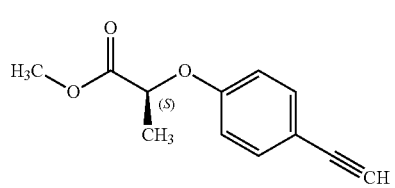

Compound A-50

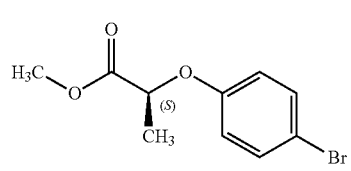

Compound A-51

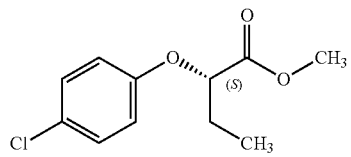

Compound A-52

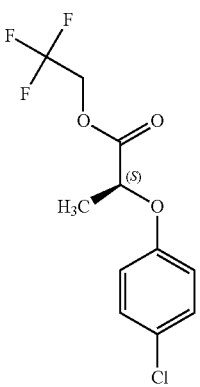

Compound A-53

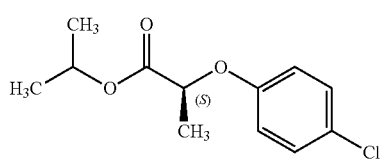

Compound A-54

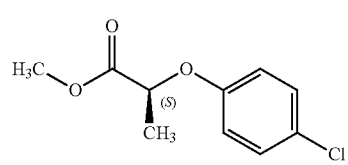

Compound A-55

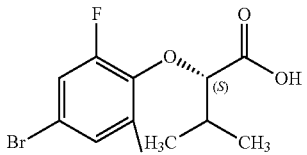

Compound A-56

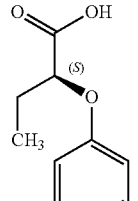

Compound A-57

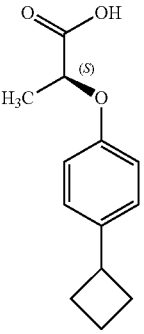

Compound A-58

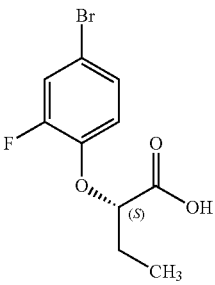

In one embodiment, the compound or the compound for use according to the present invention has been modified in order to increase its half-life when administered to a patient, in particular its plasma half-life.

In one embodiment, the compound or the compound for use according to the present invention further comprises a moiety conjugated to said compound, thus generating a moiety-conjugated compound. In one embodiment, said moiety-conjugated compound has a plasma and/or serum half-life being longer than the plasma and/or serum half-life of the non-moiety conjugated compound.

In one embodiment, the moiety conjugated to the compound or compound for use according to the present invention, is one or more type(s) of moieties selected from the group consisting of albumin, fatty acids, polyethylene glycol (PEG), acylation groups, antibodies and antibody fragments.

Another aspect of the invention relates to a method of reversing and/or ameliorating a neuromuscular blockade after surgery, said method comprising administering a therapeutically effective amount of the composition as defined in any one of the embodiments herein below to a person in need thereof.

In yet another aspect, the present invention relates to use of a composition as defined herein, for the manufacture of a medicament for reversing and/or amelioration of a neuromuscular blockade after surgery.

Combination Therapy

The composition of the present invention may comprise further active ingredients/agents or other components to increase the efficiency of the composition. Thus, in one embodiment the composition further comprises at least one further active agent. It is appreciated that the active agent is suitable for treating, preventing or ameliorating said neuromuscular disorder.

The active agent is in a preferred embodiment an acetylcholine esterase inhibitor. Said acetylcholine esterase inhibitor may for example be selected from the group consisting of delta-9-tetrahydrocannabinol, carbamates, physostigmine, neostigmine, pyridostigmine, ambenonium, demecarium, rivastigmine, phenanthrene derivatives, galantamine, caffeine—noncompetitive, piperidines, donepezil, tacrine, edrophonium, huperzine, ladostigil, ungeremine and lactucopicrin.

Preferably the acetylcholine esterase inhibitor is selected from the group consisting of neostigmine, physostigmine and pyridostigmine. It is preferred that the acetylcholine esterase inhibitor is neostigmine or pyridostigmine.

The active agent may also be an immunosuppressive drug. Immunosuppressive drugs are drugs that suppress or reduce the strength of the body's immune system. They are also known as anti-rejection drugs. Immunosuppressive drugs include but are not limited to glucocorticoids, corticosteroids, cytostatics, antibodies and drugs acting on immunophilins. In one embodiment the active agent is prednisone.

The active agent may also be an agent that is used in anti-myotonic treatment. Such agents include for example blockers of voltage gated $Na^+$ channels, and aminoglycosides.

The active agent may also be an agent for reversing a neuromuscular blockade after surgery. Such agents include for example neostigmine or suggammadex.

The active agent may also be an agent for increasing the $Ca^{2+}$ sensitivity of the contractile filaments in muscle. Such agent includes tirasemtiv.

The active agent may also be an agent for increasing ACh release by blocking voltage gated $K^+$ channels in the pre-synaptic terminal. Such agent includes 3,4-aminopyridine. As illustrated in example 5, combination therapy using C8 and 3,4-diaminopyridine resulted in an unexpected synergistic effect on recovery of neuromuscular transmission.

Pharmaceutical Formulations

In one embodiment, a composition comprising the compound or the compound for use, according to the present invention, is provided. The composition according to the present invention is used for treating, ameliorating and/or preventing a neuromuscular disorder, and/or for use in reversing and/or ameliorating a neuromuscular blockade. Thus, it is preferred that the compositions and compounds described herein are pharmaceutically acceptable. In one embodiment the composition as described herein is in the form of a pharmaceutical formulation. In one embodiment, the composition as described herein further comprises a pharmaceutically acceptable carrier. Accordingly, the present invention further provides a pharmaceutical formulation, which comprises a compound of as disclosed herein and a pharmaceutically acceptable salt or a pharmaceutically acceptable salt, solvate, polymorph, or tautomer thereof, as herein defined, and a pharmaceutically acceptable carrier.

Thus, in one embodiment the composition of the present invention further comprises a pharmaceutically acceptable carrier. The pharmaceutical formulations may be prepared by conventional techniques, e.g. as described in Remington: The Science and Practice of Pharmacy 2005, Lippincott, Williams & Wilkins.

The pharmaceutically acceptable carriers can be either solid or liquid. Solid form preparations include powders, tablets, pills, capsules, cachets, suppositories, and dispersible granules. A solid carrier can be one or more excipients which may also act as diluents, flavoring agents, solubilizers, lubricants, suspending agents, binders, preservatives, wetting agents, tablet disintegrating agents, or an encapsulating material.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The compositions of the present invention may be formulated for parenteral administration and may be presented in unit dose form in ampoules, pre-filled syringes, small volume infusion or in multi-dose containers, optionally with an added preservative. The compositions may take such forms as suspensions, solutions, or emulsions in oily or aqueous vehicles, for example solutions in aqueous polyethylene glycol. Examples of oily or non-aqueous carriers, diluents, solvents or vehicles include propylene glycol, polyethylene glycol, vegetable oils (e.g., olive oil), and injectable organic esters (e.g., ethyl oleate), and may contain agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

In a preferred embodiment the compositions of the present invention is formulated for oral administration. Oral administration forms include solid form preparations including powders, tablets, drops, capsules, cachets, lozenges, and dispersible granules. Other forms suitable for oral administration may include liquid form preparations including emulsions, syrups, elixirs, aqueous solutions, aqueous suspensions, toothpaste, gel dentrifrice, chewing gum, or solid form preparations which are intended to be converted shortly before use to liquid form preparations, such as solutions, suspensions, and emulsions. In powders, the carrier is a finely divided solid which is a mixture with the finely divided active component.

In a preferred embodiment the composition as described herein is formulated in a tablet or capsule. In tablets, the active component is mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent.

Suitable solvents for the preparation of an oily solution include glycerol, diluted alcohol and propylene glycol.

Emulsions may be prepared in solutions in aqueous propylene glycol solutions or may contain emulsifying agents such as lecithin, sorbitan monooleate, or acacia. Aqueous solutions can be prepared by dissolving the active component in water and adding suitable colorants, flavors, stabilizing and thickening agents. Aqueous suspensions can be prepared by dispersing the finely divided active component in water with viscous material, such as natural or synthetic gums, resins, methylcellulose, sodium carboxymethylcellulose, and other well-known suspending agents.

The compositions of the present invention may also be formulated in a wide variety of formulations for parenteral administration.

For injections and infusions the formulations may take such forms as suspensions, solutions, or emulsions in oily or aqueous vehicles, for example solutions in aqueous polyethylene glycol. Alternatively, the composition may be in powder form, obtained by aseptic isolation of sterile solid or by lyophilisation from solution for constitution before use with a suitable vehicle, e.g., sterile, pyrogen-free water. The formulations can be presented in unit-dose or multi-dose sealed containers, such as ampoules, vials, pre-filled syringes, infusion bags, or can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Examples of oily or non-aqueous carriers, diluents, solvents or vehicles include propylene glycol, polyethylene glycol, vegetable oils, and injectable organic esters, and may contain formulatory agents such as preserving, wetting, emulsifying or suspending, stabilizing and/or dispersing agents.

The formulations for injection will typically contain from about 0.5 to about 25% by weight of the active ingredient in solution.

Topical Delivery

The compounds may also be administered topically. Regions for topical administration include the skin surface and also mucous membrane tissues of the vagina, rectum, nose, mouth, and throat.

The topical composition will typically include a pharmaceutically acceptable carrier adapted for topical administration. Thus, the composition may take the form of a suspension, solution, ointment, lotion, sexual lubricant, cream, foam, aerosol, spray, suppository, implant, inhalant, tablet, capsule, dry powder, syrup, balm or lozenge, for example. Methods for preparing such compositions are well known in the pharmaceutical industry.

The compounds of the present invention may be formulated for topical administration to the epidermis as ointments, creams or lotions, or as a transdermal patch. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin or a fatty acid. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Lotions according to the present invention also include those suitable for application to the eye. An eye lotion may comprise a sterile aqueous solution optionally containing a bactericide.

Nasal, Pulmonary and Bronchial Administration

Formulations for use in nasal, pulmonary and/or bronchial administration are normally administered as aerosols in order to ensure that the aerosolized dose actually reaches the mucous membranes of the nasal passages, bronchial tract or the lung. The term "aerosol particle" is used herein to describe the liquid or solid particle suitable for nasal, bronchial or pulmonary administration, i.e., that will reach the mucous membranes.

Typically aerosols are administered by use of a mechanical devices designed for pulmonary and/or bronchial delivery, including but not limited to nebulizers, metered dose inhalers, and powder inhalers. With regard to construction of the delivery device, any form of aerosolization known in the art, including but not limited to spray bottles, nebulization, atomization or pump aerosolization of a liquid formulation, and aerosolization of a dry powder formulation, can be used.

Liquid Aerosol Formulations in general contain a compound of the present invention in a pharmaceutically acceptable diluent. Pharmaceutically acceptable diluents include but are not limited to sterile water, saline, buffered saline, dextrose solution, and the like.

Formulations for dispensing from a powder inhaler device will normally comprise a finely divided dry powder containing pharmaceutical composition of the present invention (or derivative) and may also include a bulking agent, such as lactose, sorbitol, sucrose, or mannitol in amounts which facilitate dispersal of the powder from the device. Dry powder formulations for inhalation may also be formulated using powder-filled capsules, in particularly capsules the material of which is selected from among the synthetic plastics.

The formulation is formulated to the type of device employed and may involve the use of an appropriate propellant material, in addition to the usual diluents, adjuvants and/or carriers useful in therapy and known to the person skilled in the art. The propellant may be any propellant generally used in the art. Specific non-limiting examples of such useful propellants are a chlorofluorocarbon, a hydrofluorocarbon, a hydrochlorofluorocarbon, or a hydrocarbon.

The formulations of the present embodiment may also include other agents useful for pH maintenance, solution stabilization, or for the regulation of osmotic pressure.

The formulations of the present embodiment may also include other agents useful for pH maintenance, solution stabilization, or for the regulation of osmotic pressure.

Transdermal Delivery

The pharmaceutical agent-chemical modifier complexes described herein can be administered transdermally. Transdermal administration typically involves the delivery of a pharmaceutical agent for percutaneous passage of the drug into the systemic circulation of the patient. The skin sites include anatomic regions for transdermally administering the drug and include the forearm, abdomen, chest, back, buttock, mastoidal area, and the like.

Transdermal delivery is accomplished by exposing a source of the complex to a patient's skin for an extended period of time. Transdermal patches have the added advantage of providing controlled delivery of a pharmaceutical agent-chemical modifier complex to the body. Such dosage forms can be made by dissolving, dispersing, or otherwise incorporating the pharmaceutical agent-chemical modifier complex in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel. For example, a simple adhesive patch can be prepared from a backing material and an acrylate adhesive.

Administration Forms

As described herein above administration forms include but are not limited to oral, parental, topical, enteral, rectal or buccal administration.

In one embodiment the composition is administered or adapted for administration enterally, topically, parenterally or as part of a sustained release implant.

The parenteral administration may for example be intravenous, subcutaneous, intramuscular, intracranial or intraperitoneal. In a preferred embodiment the parental administration is intramuscular. Enteral administration includes oral, rectal, or buccal administration. In one embodiment topical administration is dermal, epicutaneous, vaginal, intravesical, pulmonary, intranasal, intratracheal or as eye drops.

In another embodiment the composition is administered or adapted for administration subcutaneously or intravenously.

It is appreciated that the composition of the present invention comprises at least 30 wt. % compound, such as at least 25 wt. % compound, such as for example at least 20 wt. % compound, at least 15 wt. % compound, such as at least 25 wt. % compound, such as for example at least 20 wt. % compound, at least 15 wt. % compound, such as at least 10 wt. % compound, such as for example at least 8 wt. % compound, at least 5 wt. % compound, such as at least 4 wt. % compound, such as for example at least 3 wt. % compound, at least 2 wt. % compound, such as at least 1 wt. % compound, such as for example at least 0.5 wt. % compound or at least 0.5 wt. % compound. Wt. % is an abbreviation for weight percent.

The compound is any compound defined by Formula (I). Thus, the active ingredient can be any of the compounds defined by the formulas or embodiments presented herein.

In one embodiment the compound as described herein is to be administered in a dosage of from 1 µg/kg-30,000 µg/kg body weight, such as 1 µg/kg-7,500 µg/kg, such as 1 µg/kg-5,000 µg/kg, such as 1 µg/kg-2,000 µg/kg, such as 1 µg/kg-1,000 µg/kg, such as 1 µg/kg-700 µg/kg, such as 5 µg/kg-500 µg/kg, such as 10 µg/kg to 100 µg/kg bodyweight.

In another embodiment the compound as described herein is to be administered in a dosage of from 1 µg/kg-1,000 µg/kg body weight, such as 1 µg/kg-500 µg/kg, such as 1 µg/kg-250 µg/kg, such as 1 µg/kg-100 µg/kg, such as 1 µg/kg-50 µg/kg, such as 1 µg/kg to 10 µg/kg bodyweight.

In yet another embodiment the compound as described herein is to be administered in a dosage of from 10 µg/kg-30,000 µg/kg body weight, such as 10 µg/kg-7,500 µg/kg, such as 10 µg/kg-5,000 µg/kg, such as 10 µg/kg-2,000 µg/kg, such as 10 µg/kg-1,000 µg/kg, such as 10 µg/kg-700 µg/kg, such as 10 µg/kg-500 µg/kg, such as 10 µg/kg to 100 µg/kg bodyweight.

In one embodiment the administration of the composition as described herein is repeated at least 1, 2, 3, 4, 5 or 6 times weekly.

In another embodiment the administration is repeated at least 1-3 times weekly, such as 2-5 times weekly, such as 3-6 times weekly.

In a further embodiment the administration is repeated daily. The administration of the composition may for example be repeated 1, 2, 3, 4, 5, 6, 7 or 8 times daily. In one embodiment the administration is repeated 1 to 8 times daily, such as 2 to 5 times daily.

The compound as defined herein can be modified in order to increase its half-life when administered to a patient, in particular its plasma half-life.

The term "half-life" as used herein is the time it takes for the compound to lose one-half of its pharmacologic activity. The term "plasma half-life" is the time that it takes the compound to lose one-half of its pharmacologic activity in the blood plasma.

Modification of the compound to increase its half-life may for example include conjugation of a moiety that increases the half-life of the compound. Thus, in an embodiment the compound further comprises a moiety conjugated to said compound, thus generating a moiety-conjugated compound. It is preferred that the moiety-conjugated compound has a plasma and/or serum half-life being longer than the plasma and/or serum half-life of the non-moiety conjugated compound.

The moiety conjugated to the compound can for example be one or more type(s) of moieties selected from the group consisting of albumin, fatty acids, polyethylene glycol (PEG), acylation groups, antibodies and antibody fragments.

Methods

In one aspect the present invention relates to a method of treating, preventing and/or ameliorating a neuromuscular disorder, said method comprising administering a therapeutically effective amount of the compositions and compounds as defined herein to a person in need thereof.

In one aspect, the present invention relates to a method of reversing and/or ameliorating a neuromuscular blockade, said method comprising administering a therapeutically effective amount of the compound or the compound for use as defined herein to a person in need thereof.

In one aspect, the present invention relates to a method for recovery of neuromuscular transmission, said method comprising administering a therapeutically effective amount of the compound or the compound for use as defined herein to a person in need thereof.

The person in need thereof may be a person having a neuromuscular disorder or a person at risk of developing a neuromuscular disorder or a person having symptoms of muscle weakness and/or fatigue. In another embodiment the person in need thereof is a person with reduced neuromuscular transmission safety with prolonged recovery after neuromuscular blockade. Types of neuromuscular disorders are defined herein above. In a preferred embodiment the person has, amyotrophic lateral sclerosis, spinal muscular atrophy, myasthenia gravis or Lambert-Eaton syndrome.

A therapeutically effective amount is an amount that produces a therapeutic response or desired effect in the person taking it. Administration routes, formulations, forms and dosages are as defined herein above and throughout this specification.

The method of treatment may be combined with other methods that are known to treat, prevent and/or ameliorate neuromuscular disorders. The treatment method may for example be combined with administration of any of the agents mentioned herein above. In one embodiment the treatment is combined with administration of acetylcholine esterase inhibitor such as for example neostigmine or pyridostigmine.

Another aspect of the invention relates to use of a composition as defined herein, for the manufacture of a medicament for the treatment, prevention and/or amelioration of a neuromuscular disorder.

Another aspect relates to use of a composition as defined herein, for the manufacture of a medicament or a reversal agent for reversing and/or ameliorating a neuromuscular blockade after surgery.

Method of Manufacturing

In one aspect, the present invention relates to methods of manufacturing compounds or compounds for use according to formula (I).

One method for manufacturing the compounds or compounds for use according to the present invention comprises the steps of a. reacting a compound having formula (VIII)

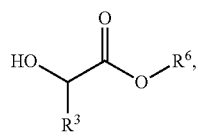

(VIII)

wherein $R^3$ is as defined herein and $R^6$ is a protecting group, such as selected from the group consisting of alkyl, alkenyl, akynyl, cycloalkyl, cycloalkenyl, aromatic ring, heteroaromatic ring and -alkylene-Si-alkyl, with first a reagent capable of converting the alcohol (OH) into a leaving group and secondly with a compound having formula (VII)

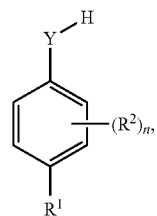

(VII)

wherein $R^1$, $R^2$, and n are as defined herein and Y is O to generate a compound having formula (IX)

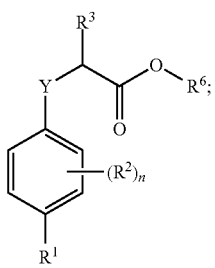

(IX)

and b. reacting the product compound of a) with an ester hydrolysing reagent thus generating a compound as defined herein.

A second method for manufacturing the compounds or compounds for use according to the present invention comprises the steps of a. reacting a compound having formula (XI)

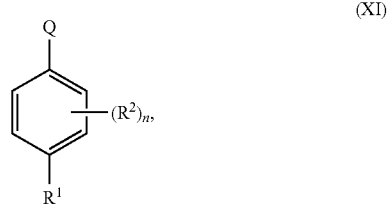

(XI)

wherein $R^1$, $R^2$ and n are as defined herein and Q is a leaving group, such as selected from the group consisting of fluorine and iodine, with a compound having formula (XII)

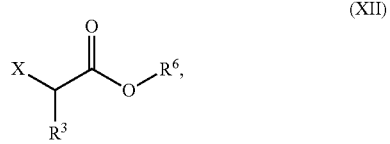

(XII)

wherein $R^3$ is as defined herein, and $R^6$ is a protecting group, such as selected from the group consisting of alkyl, alkenyl, akynyl, cycloalkyl, cycloalkenyl, aromatic ring, heteroaromatic ring and -alkylene-Si-alkyl to generate a compound having formula (X)

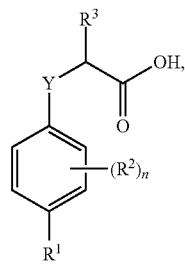

(X)

wherein Y is O; and b. reacting the product compound of a) with an ester hydrolysing reagent thus generating a compound as defined herein.

Yet a third method for manufacturing the compounds or compounds for use according to the present invention comprises the steps of a. reacting a compound having formula (XIII)

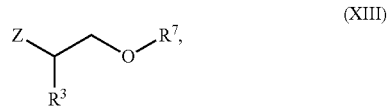

(XIII)

wherein $R^3$ is as defined herein, Z is OH and $R^7$ is a protecting group, such as an —Si-alkyl, with first a reagent capable of converting the alcohol (Z) into a leaving group and secondly with a compound having formula (VII)

(VII)

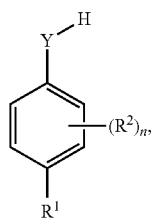

wherein $R^1$, $R^2$ and n are as defined herein, and Y is O to generate a compound having formula (XIV)

(XIV)

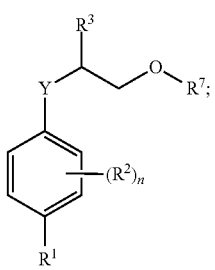

b. reacting the product compound of a) with an ether cleaving reagent to generate a compound having formula (XV)

(XV)

c. reacting the product compound of b) with an oxidising agent thus generating a compound as defined herein.

Prodrugs

The compounds of formula (I) may be administered as a prodrug to modify the distribution, duration of efficacy or other properties. Conversion of the carboxylic acid group of compounds of formula (I) to an ester using ethanol to form the ethyl ester is an example of such prodrug. Preferred alcohols include low molecular weight alcohols, phenols and other aromatic alcohols, and fluorinated alcohols. In some cases, it is preferable to use an enol as the alcohol, for example 4-hydroxy-pent-3-ene-2-one. Alternatively, the prodrug may be the corresponding aldehyde, or an imine thereof. Again, these precursors can be expected to transform to the carboxylic acid in vivo. The prodrugs are administered using the same formulations and in the same dosage ranges as the compounds of formula (I).

In one aspect, said prodrug is defined by Formula (LX):

Formula (LX)

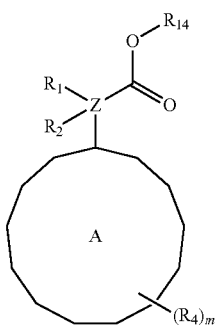

or a salt of tautomer thereof wherein m, A, Z, $R_1$, $R_2$ and $R_4$ are as defined above and wherein $R_{14}$ is an aromatic or heteroaromatic ring selected from the group consisting of phenyl, pyrimidyl, pyridinyl, thiazolyl, oxadiazolyl and quinolyl, all aromatic and heteroaromatic groups optionally substituted by one or more $R_4$ In one embodiment $R_{14}$ is a phenyl substituted with methoxy, nitro, cyano, Cl, Br, I and/or F.

In one embodiment Formula (LX) is further defined by Formula (LXI):

Formula (LXI)

In another embodiment of the present invention the prodrug is defined by Formula (LXII):

Formula (LXII)

or a pharmaceutically acceptable salt, solvate, polymorph, or tautomer thereof, wherein m, A, Z, $R_1$, $R_2$ and $R_4$ are as defined above.

The prodrug can also be defined by Formula (LXIII):

Formula (LXII)

wherein m, A, Z, $R_1$, $R_2$ and $R_4$ are as defined above, and B is a 5- to 7-membered heterocyclic.

Embodiments of the Invention

Embodiment 1 is a composition comprising a compound of Formula (I):

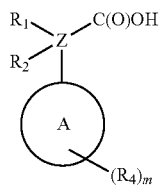

Formula (I)

or a pharmaceutically acceptable salt, solvate, polymorph, or tautomer thereof; wherein A is an aromatic or heteroaromatic ring selected from the group consisting of phenyl, naphthyl, biphenyl, quinolinyl, isoquinolinyl, imidazolyl, thiazolyl, thiadiazolyl, triazolyl, oxazolyl, pyridinyl, pyrimidinyl, pyrazyl, and pyridazinyl;

m is 0, 1, 2, 3, 4 or 5;

Z is a 2-5 atom chain comprising at least one carbon atom and optionally one heteroatom or substituted heteroatom, wherein the heteroatom or substituted heteroatom is selected from the group consisting of O, N, $NC(O)R_3$, S, $S(O)R_5$ and $S(O)_2R_5$, wherein each atom of said 2-5 atom chain is optionally substituted with $R_1$ and $R_2$; wherein $R_1$ and $R_2$ are independently selected from the group consisting of $OR_3$, $SR_5$, $S(O)R_5$, $S(O)_2R_5$, $NR_3$, $NR_3C(O)R_9$ or $R_3$, wherein $R_3$ is selected from the group consisting of H, $C_{1-8}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of —$NR_9$—CO—$R_{10}$, —$N(R_{10})_2$—$SO_2$—$R_{12}$, —CO—$NR_9R_{10}$, —$SO_2$—$NR_9$ $R_{10}$, —$R_{13}$—O—$R_{11}$, —$NR_9$ $R_{10}$, —$S(O)R_{12}$, —$S(O)_2R_{12}$, cyano, —O—$R_{11}$, fluorinated $C_{1-3}$-alkyl, nitro and halo; or $R_1$ and $R_2$ are linked to form a ring;

$R_4$ is selected from the group consisting of H, $C_{1-6}$-alk(en/yn)yl, $C_{3-6}$-cycloalk(en)yl, —$NR_9$—CO—$R_{10}$, —$NR_{10}$—$SO_2$—$R_{11}$, —CO—$NR_9R_{10}$, —$SO_2$—$NR_9$ $R_{10}$, —$R_{13}$—O—$R_{11}$, —$NR_9R_{10}$, cyano, O—$R^{11}$, fluorinated $C_{1-3}$, nitro and halo;

$R_5$ is selected from the group consisting of $C_{1-8}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of —$NR_9$—CO—$R_{10}$, —$N(R_{10})_2SO_2$—$R_{12}$, —CO—$NR_9R_{10}$, —$SO_2$—$NR_9$ $R_{10}$, —$R_{13}$—O—$R_{11}$, —$NR_9R_{10}$, —$S(O)R_{12}$, —$S(O)_2R_{12}$, cyano, —O—$R_{11}$, fluorinated $C_{1-3}$-alkyl, nitro and halo;

$R_9$, $R_{10}$, $R_{11}$ are independently selected from H or $C_{1-4}$-alk(en/yn)yl and $C_{3-6}$-cycloalk(en)yl;

$R_{12}$ is selected from $C_{1-4}$-alk(en/yn)yl and $C_{3-6}$-cycloalk(en)yl $R_{13}$ is selected from $C_{1-4}$-alk(an/en/yn)diyl and $C_{3-6}$-cycloalk(an/en)diyl for use in treating, ameliorating and/or preventing a neuromuscular disorder.

Embodiment 2 is a composition according to embodiment 1, wherein A is a monocyclic or bicyclic aromatic or heteroaromatic ring.

Embodiment 3 composition according to embodiments 1 and 2, wherein A is five-membered or six-membered aromatic ring.

Embodiment 4 composition according to embodiment 1 to 3, wherein A is phenyl, or naphthyl.

Embodiment 5 composition according to any of the preceding embodiments, wherein said compound is a compound of Formula (II):

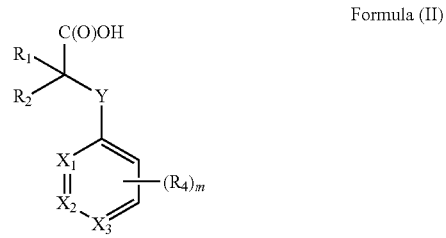

Formula (II)

or a pharmaceutically acceptable salt, solvate, polymorph, or tautomer thereof; wherein m is 0, 1, 2, 3, 4 or 5;

Y is selected from the group consisting of O, NH, N—$CH_3$, $CH_2$, $CH_2$—O, S and $SO_2$;

$X_1$, $X_2$ and $X_3$ are independently selected from the group consisting of CH and N;

$R_1$ and $R_2$ are independently selected from the group consisting of $OR_3$, $SR_5$, $S(O)R_5$, $S(O)_2R_5$, $NR_3$, $NR_3C(O)R_5$ or $R_3$, wherein $R_3$ is selected from the group consisting of H, $C_{1-8}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of —$NR_9$—CO—$R_{10}$, —$N(R_{10})_2$—$SO_2$—$R_{12}$, —CO—$NR_9R_{10}$, —$SO_2$—$NR_9$ $R_{10}$, —$R_{13}$—O—$R_{11}$, —$NR_9$ $R_{10}$, —$S(O)R_{12}$, —$S(O)_2R_{12}$, cyano, —O—$R_{11}$, fluorinated $C_{1-3}$-alkyl, nitro and halo; or $R_1$ and $R_2$ are linked to form a $C_{3-6}$-cycloalk(en)yl or a halo-$C_{3-6}$-cycloalk(en)yl;

$R_4$ is selected from the group consisting of H, $C_{1-6}$-alk(en/yn)yl, $C_{3-6}$-cycloalk(en)yl, —$NR_9$—CO—$R_{10}$, —$NR_{10}$—$SO_2$—$R_{11}$, —CO—$NR_9R_{10}$, —$SO_2$—$NR_9$ $R_{10}$, —$R_{13}$—O—$R_{11}$, —$NR_9R_{10}$, cyano, O—$R^{11}$, fluorinated $C_{1-3}$, nitro and halo;

$R^5$ is selected from the group consisting of $C_{1-8}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of —$NR_9$—CO—$R_{10}$, —$N(R_{10})_2SO_2$—$R_{12}$, —CO—$NR_9$ $R_{10}$, —$SO_2$—$NR_9$ $R_{10}$, —$R_{13}$—O—$R_{11}$, —$NR_9R_{10}$, —$S(O)R_{12}$, —$S(O)_2R_{12}$, cyano, —O—$R_{11}$, fluorinated $C_{1-3}$, nitro and halo; or $R_1$ and $R_2$ are linked to form a ring;

$R_9$, $R_{10}$, $R_{11}$ are independently selected from H or $C_{1-4}$-alk(en/yn)yl and $C_{3-6}$-cycloalk(en)yl;

$R_{12}$ is selected from $C_{1-4}$-alk(en/yn)yl and $C_{3-6}$-cycloalk(en)yl;

$R_{13}$ is selected from $C_{1-4}$-alk(an/en/yn)diyl and $C_{3-6}$-cycloalk(an/en)diyl;

for use in treating, ameliorating and/or preventing a neuromuscular disorder.

Embodiment 6 is a composition for use according to any one of the preceding embodiments, wherein $R_1$ is selected from the group consisting of H and —$CH_3$.

Embodiment 7 is a composition according to any one of the preceding embodiments, wherein $R_1$ is H.

Embodiment 8 is a composition for use according to any of the preceding embodiments, wherein $R_1$ is H and $R_2$ is selected from the group consisting of H, $C_{1-4}$-alk(en)yl, $C_{3-6}$-cycloalk(en)yl, wherein said $C_{1-4}$-alk(en/yn)yl and $C_{3-6}$-cycloalk(en)yl may be substituted with up to two substituents selected from the group consisting of —$NR_9$—CO—$R_{10}$, —$N(R_{10})_2$—$SO_2$—$R_{12}$, —CO—$NR_9R_{10}$, —$SO_2$—$NR_9 R_{10}$, —$R_{13}$—O—$R_{11}$, —$NR_9 R_{10}$, —$S(O)R_{12}$, —$S(O)_2R_{12}$, cyano, —O—$R_{11}$, fluorinated $C_{1-3}$-alkyl, nitro and halo, wherein $R_9$, $R_{10}$, and $R_{11}$ are independently selected from H, $C_{1-4}$-alk(en/yn)yl and $C_{3-6}$-cycloalk(en)yl, whereas $R_{12}$ is selected from $C_{1-4}$-alk(en/yn)yl and $C_{3-6}$-cycloalk(en)yl.

Embodiment 9 is a composition for use according to any of the preceding embodiments, wherein $R_1$ is H and $R_2$ is selected from the group consisting of H, $C_{1-4}$-alkyl, $C_{3-6}$-cycloalkyl and amino-$C_{1-4}$-alkyl, wherein said $C_{1-4}$-alkyl and $C_{3-6}$-cycloalkyl may be substituted with O—$R_{11}$, wherein $R_{11}$ is selected from H, $C_{1-4}$-alk(en/yn)yl and $C_{3-6}$-cycloalk(en)yl.

Embodiment 10 is a composition for use according to embodiment 9, wherein $R_{11}$ is —$CH_3$.

Embodiment 11 is a composition for use according to embodiment 9, wherein $R_2$ is —$CH(CH_3)CH_2$—O—$CH_3$.

Embodiment 12 is a composition for use according to any of embodiments 1 to 7, wherein $R_1$ is H and $R_2$ is selected from the group consisting of H, $C_{1-6}$-alkyl and $C_{3-7}$-cycloalkyl.

Embodiment 13 is a composition for use according to any of the preceding embodiments, wherein $R_1$ is H and $R_2$ is selected from the group consisting of H, —$CH_3$, —CH$(CH_3)_2$ and cyclopropyl.

Embodiment 14 is a composition for use according to any of the preceding embodiments, wherein $R_1$ is H and $R_2$ is —CH$(CH_3)_2$.

Embodiment 15 is composition for use according to any one of the preceding embodiments, wherein $R_1$ is different from $R_2$.

Embodiment 16 is a composition for use according to any one of the preceding embodiments, wherein said compound is an S-enantiomer with respect to the C-atom to which $R_2$ is bound.

Embodiment 17 is a composition for use according to any embodiments 1 to 16, wherein $R_1$ is H and $R_2$ is $C_{1-6}$-alkyl or $C_{3-4}$-cycloalkyl and wherein said compound is an S-enantiomer with respect to the C-atom to which $R_2$ is bound as shown in Formula (III):

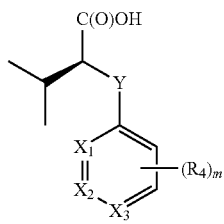

Formula (III)

or a pharmaceutically acceptable salt, solvate, polymorph, or tautomer thereof;

wherein Y is selected from the group consisting of O, NH, N—$CH_3$, $CH_2$, $CH_2$—O, S and $SO_2$;

$X_1$, $X_2$ and $X_3$ are selected from the group consisting of, CH and N;

$R_4$ is selected from the group consisting of H, $C_{1-6}$-alk(en/yn)yl, $C_{3-6}$-cycloalk(en)yl, —$NR_9$—CO—$R_{10}$, —$NR_{10}$—$SO_2$—$R_{11}$, —CO—$NR_9R_{10}$, —$SO_2$—$NR_9$ $R_{10}$, —$R_{13}$—O—$R_{11}$, —$NR_9R_{10}$, cyano, O—$R^{11}$, fluorinated $C_{1-3}$, nitro and halo.

Embodiment 18 is a composition for use according to any one of the preceding embodiments wherein $R_4$ is selected from the group consisting of H, halo, cyano, —CHO, $C_{1-4}$-alk(en)yl, halo-$C_{1-4}$-alk(en)yl, —O—$C_{1-4}$-alk(en)yl.

Embodiment 19 is a composition for use according to any one of the preceding embodiments wherein m is 0, 1 or 2.

Embodiment 20 is a composition for use according to any one of the preceding embodiments wherein m is 1.

Embodiment 21 is a composition for use according to any embodiments, wherein $X_1$ is N, $X_2$ is N or $X_3$ is N.

Embodiment 22 is a composition for use according to any one of embodiments 5 to 20, wherein $X_1$, $X_2$ and $X_3$ is C.

Embodiment 23 is a composition for use according to any one of embodiments 1 to 4, wherein the compound of Formula (I) is further defined by Formula (IV):

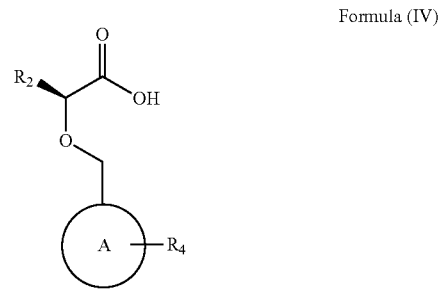

Formula (IV)

or a pharmaceutically acceptable salt, solvate, polymorph, or tautomer thereof;

wherein A is an aromatic or heteroaromatic ring selected from the group consisting of phenyl, naphthyl, biphenyl, quinolinyl, isoquinolinyl, imidazolyl, thiazolyl, thiadiazolyl, triazolyl, oxazolyl, pyridinyl, pyrimidinyl, pyrazyl, and pyridazinyl;

$R_2$ is selected from the group consisting of $OR_3$, $SR_5$, $S(O)R_5$, $S(O)_2R_5$, $NR_3$, $NR_3C(O)R_9$ or $R_3$, wherein $R_3$ is selected from the group consisting of H, $C_{1-8}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of —$NR_9$—CO—$R_{10}$, —$N(R_{10})_2$—$SO_2$—$R_{12}$, —CO—$NR_9R_{10}$, —$SO_2$—$NR_9$ $R_{10}$, —$R_{13}$—O—$R_{11}$, —$NR_9$ $R_{10}$, —$S(O)R_{12}$, —$S(O)_2R_{12}$, cyano, —O—$R_{11}$, fluorinated $C_{1-3}$-alkyl, nitro and halo; or $R_1$ and $R_2$ are linked to form a ring;

$R_4$ is selected from the group consisting of H, $C_{1-6}$-alk(en/yn)yl, $C_{3-6}$-cycloalk(en)yl, —$NR_9$—CO—$R_{10}$, —$NR_{10}$—$SO_2$—$R_{11}$, —CO—$NR_9R_{10}$, —$SO_2$—$NR_9$ $R_{10}$, —$R_{13}$—O—$R_{11}$, —$NR_9R_{10}$, cyano, O—$R^{11}$, fluorinated $C_{1-3}$, nitro and halo.

$R_5$ is selected from the group consisting of $C_{1-8}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of —$NR_9$—CO—$R_{10}$, —$N(R_{10})_2SO_2$—$R_{12}$, —CO—NR$_9$R$_{10}$, —SO$_2$—NR$_9$ R$_{10}$, —R$_{13}$—O—R$_{11}$, —NR$_9$R$_{10}$, —S(O)R$_{12}$, —S(O)$_2$R$_{12}$, cyano, —O—R$_{11}$, fluorinated C$_{1-3}$-alkyl, nitro and halo;

R$_9$, R$_{10}$, R$_{11}$, are independently selected from H or C$_{1-4}$-alk(en/yn)yl and C$_{3-6}$-cycloalk(en)yl;

R$_{12}$ is selected from C$_{1-4}$-alk(en/yn)yl and C$_{3-6}$-cycloalk(en)yl

R$_{13}$ is selected from C$_{1-4}$-alk(an/en/yn)diyl and C$_{3-6}$-cycloalk(an/en)diyl.

Embodiment 24 is a composition for use according to embodiment 23, wherein the compound of Formula (IV) is further defined by Formula (V):

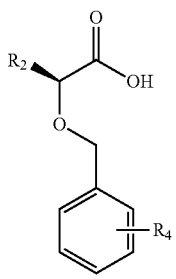

Formula (V)

wherein

R$_2$ is selected from the group consisting of OR$_3$, SR$_5$, S(O)R$_5$, S(O)$_2$R$^5$, NR$_3$, NR$_3$C(O)R$_9$ or R$_3$, wherein R$_3$ is selected from the group consisting of H, C$_{1-8}$-alk(en/yn)yl and C$_{3-6}$-cycloalk(en)yl, wherein said C$_{1-8}$-alk(en/yn)yl and C$_{3-6}$-cycloalk(en)yl may be substituted with up to three substituents selected from the group consisting of —NR$_9$—CO—R$_{10}$, —N(R$_{10}$)$_2$—SO$_2$—R$_{12}$, —CO—NR$_9$R$_{10}$, —SO$_2$—NR$_9$ R$_{10}$, —R$_{13}$—O—R$_{11}$, —NR$_9$ R$_{10}$, —S(O)R$_{12}$, —S(O)$_2$R$_{12}$, cyano, —O—R$_{11}$, fluorinated C$_{1-3}$-alkyl, nitro and halo; or R$_1$ and R$_2$ are linked to form a ring;

R$_4$ is selected from the group consisting of H, C$_{1-6}$-alk(en/yn)yl, C$_{3-6}$-cycloalk(en)yl, —NR$_9$—CO—R$_{10}$, —NR$_{10}$—SO$_2$—R$_{11}$, —CO—NR$_9$R$_{10}$, —SO$_2$—NR$_9$ R$_{10}$, —R$_{13}$—O—R$_{11}$, —NR$_9$R$_{10}$, cyano, O—R$^{11}$, fluorinated C$_{1-3}$, nitro and halo;

R$_5$ is selected from the group consisting of C$_{1-8}$-alk(en/yn)yl and C$_{3-6}$-cycloalk(en)yl, wherein said C$_{1-8}$-alk(en/yn)yl and C$_{3-6}$-cycloalk(en)yl may be substituted with up to three substituents selected from the group consisting of —NR$_9$—CO—R$_{10}$, —N(R$_{10}$)$_2$SO$_2$—R$_{12}$, —CO—NR$_9$R$_{10}$, —SO$_2$—NR$_9$ R$_{10}$, —R$_{13}$—O—R$_{11}$, —NR$_9$R$_{10}$, —S(O)R$_{12}$, —S(O)$_2$R$_{12}$, cyano, —O—R$_{11}$, fluorinated C$_{1-3}$-alkyl, nitro and halo;

R$_9$, R$_{10}$, R$_{11}$ are independently selected from H or C$_{1-4}$-alk(en/yn)yl and C$_{3-6}$-cycloalk(en)yl;

R$_{12}$ is selected from C$_{1-4}$-alk(en/yn)yl and C$_{3-6}$-cycloalk(en)yl

R$_{13}$ is selected from C$_{1-4}$-alk(an/en/yn)diyl and C$_{3-6}$-cycloalk(an/en)diyl.

Embodiment 25 is a composition for use according to embodiments 23, wherein R$_2$ is C$_{1-6}$-alkyl or C$_{3-7}$-cycloalkyl.

Embodiment 26 is a composition for use according embodiment 25, wherein the compound of Formula (V) is further defined by Formula (VI):

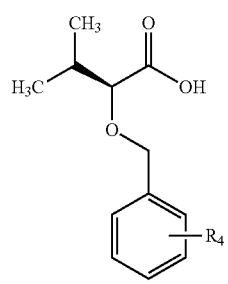

Formula (VI)

wherein R$_4$ is selected from the group consisting of H, C$_{1-6}$-alk(en/yn)yl, C$_{3-6}$-cycloalk(en)yl, —NR$_9$—CO—R$_{10}$, —NR$_{10}$—SO$_2$—R$_{11}$, —CO—NR$_9$R$_{10}$, —SO$_2$—NR$_9$ R$_{10}$, —R$_{13}$—O—R$_{11}$, —NR$_9$R$_{10}$, cyano, O—R$^{11}$, fluorinated C$_{1-3}$, nitro and halo;

R$_9$, R$_{10}$, R$_{11}$ are independently selected from H or C$_{1-4}$-alk(en/yn)yl and C$_{3-6}$-cycloalk(en)yl;

R$_{12}$ is selected from C$_{1-4}$-alk(en/yn)yl and C$_{3-6}$-cycloalk(en)yl

R$_{13}$ is selected from C$_{1-4}$-alk(an/en/yn)diyl and C$_{3-6}$-cycloalk(an/en)diyl.

Embodiment 27 is a composition for use according to any one of embodiments 24 to 26, wherein R$_4$ is in ortho- or meta position.

Embodiment 28 is a composition for use according to embodiment 1, wherein the compound of Formula (I) is further defined by Formula (VII):

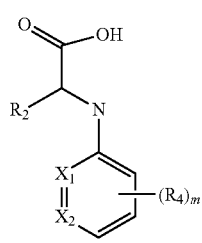

Formula (VII)

or a pharmaceutically acceptable salt, solvate, polymorph, or tautomer thereof; wherein m is 2;

Y is selected from the group consisting of O, NH, N—CH$_3$, CH$_2$, CH$_2$—O, S and SO$_2$;

X$_1$ and X$_2$ are independently selected from the group consisting of CH and N;

R$_2$ is selected from the group consisting of —OR$_3$, —SR$_5$, —S(O)R$_5$, —S(O)$_2$R$^5$, —NR$_3$, —NR$_3$C(O)Ra or —R$_3$, wherein R$_3$ is selected from the group consisting of H, C$_{1-3}$-alk(en/yn)yl and C$_{3-6}$-cycloalk(en)yl, wherein said C$_{1-8}$-alk(en/yn)yl and C$_{3-6}$-cycloalk(en)yl may be substituted with up to three substituents selected from the group consisting of —NR$_9$—CO—R$_{10}$, —N(R$_{10}$)$_2$—SO$_2$—R$_{12}$, —CO—NR$_9$R$_{10}$, —SO$_2$—NR$_9$ R$_{10}$, —R$_{13}$—O—R$_{11}$, —NR$_9$ R$_{10}$, —S(O)R$_{12}$, —S(O)$_2$R$_{12}$, cyano, —O—R$_{11}$, fluorinated C$_{1-3}$-alkyl, nitro and halo; or R$_1$ and R$_2$ are linked to form a ring;

$R_4$ is selected from the group consisting of H, $C_{1-6}$-alk(en/yn)yl, $C_{3-6}$-cycloalk(en)yl, $-NR_9-CO-R_{10}$, $-NR_{10}-SO_2-R_{11}$, $-CO-NR_9R_{10}$, $-SO_2-NR_9R_{10}$, $-R_{13}-O-R_{11}$, $-NR_9R_{10}$, cyano, $O-R^{11}$, fluorinated $C_{1-3}$, nitro and halo; $R_2$ is selected from the group consisting of $OR_3$, $SR_5$, $S(O)R_5$, $S(O)_2R_5$, $NR_3$, $NR_3C(O)R_9$ or $R_3$, wherein $R_3$ is selected from the group consisting of H, $C_{1-8}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of $-NR_9-CO-R_{10}$, $-N(R_{10})_2-SO_2-R_{12}$, $-CO-NR_9R_{10}$, $-SO_2-NR_9R_{10}$, $-R_{13}-O-R_{11}$, $-NR_9R_{10}$, $-S(O)R_{12}$, $-S(O)_2R_{12}$, cyano, $-O-R_{11}$, fluorinated $C_{1-3}$-alkyl, nitro and halo; or $R_1$ and $R_2$ are linked to form a ring;

$R_5$ is selected from the group consisting of $C_{1-8}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of $-NR_9-CO-R_{10}$, $-N(R_{10})_2SO_2-R_{12}$, $-CO-NR_9R_{10}$, $-SO_2-NR_9R_{10}$, $-R_{13}-O-R_{11}$, $-NR_9R_{10}$, $-S(O)R_{12}$, $-S(O)_2R_{12}$, cyano, $-O-R_{11}$, fluorinated $C_{1-3}$-alkyl, nitro and halo;

$R_9$, $R_{10}$, $R_{11}$ are independently selected from H or $C_{1-4}$-alk(en/yn)yl and $C_{3-6}$-cycloalk(en)yl;

$R_{12}$ is selected from $C_{1-4}$-alk(en/yn)yl and $C_{3-6}$-cycloalk(en)yl $R_{13}$ is selected from $C_{1-4}$-alk(an/en/yn)diyl and $C_{3-6}$-cycloalk(an/en)diyl.

Embodiment 29 is a composition for use according to embodiment 28, wherein the compound of Formula (VII) is further defined by Formula (VIII)

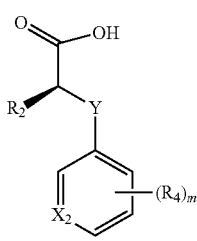

Formula (VIII)

or a pharmaceutically acceptable salt solvate, polymorph, or tautomer thereof;
wherein
m is 2;
Y is selected from the group consisting of O, NH, N—$CH_3$, $CH_2$, $CH_2$—O, S and $SO_2$;
$X_2$ is selected from the group consisting of, CH and N;
$R_2$ is selected from the group consisting of —$OR_3$, —$SR_5$, —$S(O)R_5$, —$S(O)_2R_5$, —$NR_3$, —$NR_3C(O)R_9$ or —$R_3$, wherein $R_3$ is selected from the group consisting of H, $C_{1-8}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of $-NR_9-CO-R_{10}$, $-N(R_{10})_2-SO_2-R_{12}$, $-CO-NR_9R_{10}$, $-SO_2-NR_9R_{10}$, $-R_{13}-O-R_{11}$, $-NR_9R_{10}$, $-S(O)R_{12}$, $-S(O)_2R_{12}$, cyano, $-O-R_{11}$, fluorinated $C_{1-3}$-alkyl, nitro and halo; or $R_1$ and $R_2$ are linked to form a ring;

$R_4$ is selected from the group consisting of H, $C_{1-8}$-alk(en/yn)yl, $C_{3-6}$-cycloalk(en)yl, $-NR_9-CO-R_{10}$, $-NR_{10}-SO_2-R_{11}$, $-CO-NR_9R_{10}$, $-SO_2-NR_9R_{10}$, $-R_{13}-O-R_{11}$, $-NR_9R_{10}$, cyano, $O-R^{11}$, fluorinated $C_{1-3}$, nitro and halo; $R_2$ is selected from the group consisting of $OR_3$, $SR_5$, $S(O)R_5$, $S(O)_2R^5$, $NR_3$, $NR_3C(O)R_9$ or $R_3$, wherein $R_3$ is selected from the group consisting of H, $C_{1-8}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of $-NR_9-CO-R_{10}$, $-N(R_{10})_2-SO_2-R_{12}$, $-CO-NR_9R_{10}$, $-SO_2-NR_9R_{10}$, $-R_{13}-O-R_{11}$, $-NR_9R_{10}$, $-S(O)R_{12}$, $-S(O)_2R_{12}$, cyano, $-O-R_{11}$, fluorinated $C_{1-3}$-alkyl, nitro and halo; or $R_1$ and $R_2$ are linked to form a ring;

$R_5$ is selected from the group consisting of $C_{1-8}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of $-NR_9-CO-R_{10}$, $-N(R_{10})_2SO_2-R_{12}$, $-CO-NR_9R_{10}$, $-SO_2-NR_9R_{10}$, $-R_{13}-O-R_{11}$, $-NR_9R_{10}$, $-S(O)R_{12}$, $-S(O)_2R_{12}$, cyano, $-O-R_{11}$, fluorinated $C_{1-3}$-alkyl, nitro and halo;

$R_9$, $R_{10}$, $R_{11}$ are independently selected from H or $C_{1-4}$-alk(en/yn)yl and $C_{3-6}$-cycloalk(en)yl;

$R_{12}$ is selected from $C_{1-4}$-alk(en/yn)yl and $C_{3-6}$-cycloalk(en)yl $R_{13}$ is selected from $C_{1-4}$-alk(an/en/yn)diyl and $C_{3-6}$-cycloalk(an/en)diyl.

Embodiment 30 is a composition for use according to any one of embodiment 5 to 29, wherein Y is O.

Embodiment 31 is a composition for use according to any one of embodiments 28 to 30, wherein $R_2$ is selected from the group consisting of H and $C_{1-4}$-alkyl.

Embodiment 32 is a composition for use according to any one of embodiments 28 to 31, wherein $R_4$ is selected from the group consisting of H, —$CH_3$ and halogen.

Embodiment 33 is a composition for use according to embodiment 32, wherein said compound is further defined by Formula (IX):

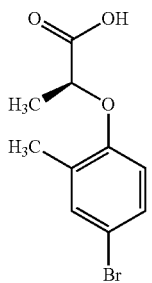

Formula (IX)

Embodiment 34 is a composition for use according to embodiment 28, wherein the compound of Formula (VII) is further defined by Formula (X):

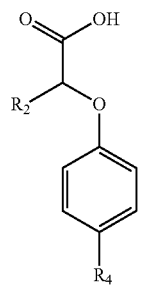

Formula (X)

or a pharmaceutically acceptable salt, solvate, polymorph, or tautomer thereof; wherein $R_2$ is selected from the group consisting of —$CH_3$, —$CH_2$—$CH_3$, —$CH(CH_3)_2$, —$C(CH_3)_3$, —$CH(CH_3)CH_2$—O—$CH_3$, —$CH_2$—$CH_2$—$CH_3$, —$CH_2$—$NH_2$, —$CH_2$—$CHF_2$, —$CH_2$—$CF_3$, —$CH_2$—NH—CO—$CH_3$ and —$CH_2$—NH—$SO_2$—$CH_3$ and cyclopropyl, and $R_4$ is selected from the group consisting of H, Br, Cl, F and I.

Embodiment 35 is a composition for use according to embodiment 28, wherein the compound of Formula (VII) is further defined by any one of Formulas (XI) to (XXVIII):

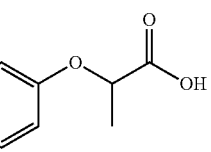

Formula (XI)

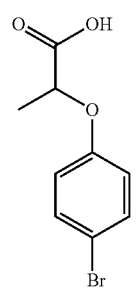

Formula (XII)

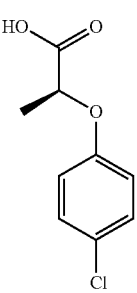

Formula (XIII)

-continued

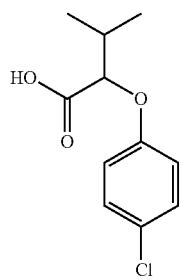

Formula (XIV)

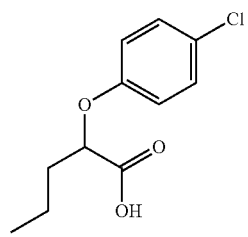

Formula (XV)

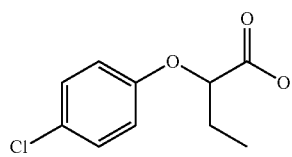

Formula (XVI)

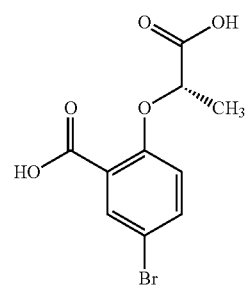

Formula (XVII)

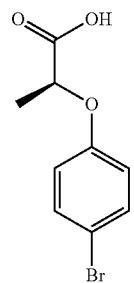

Formula (XVIII)

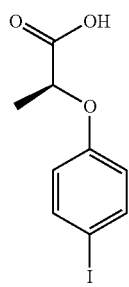

Formula (XIX)

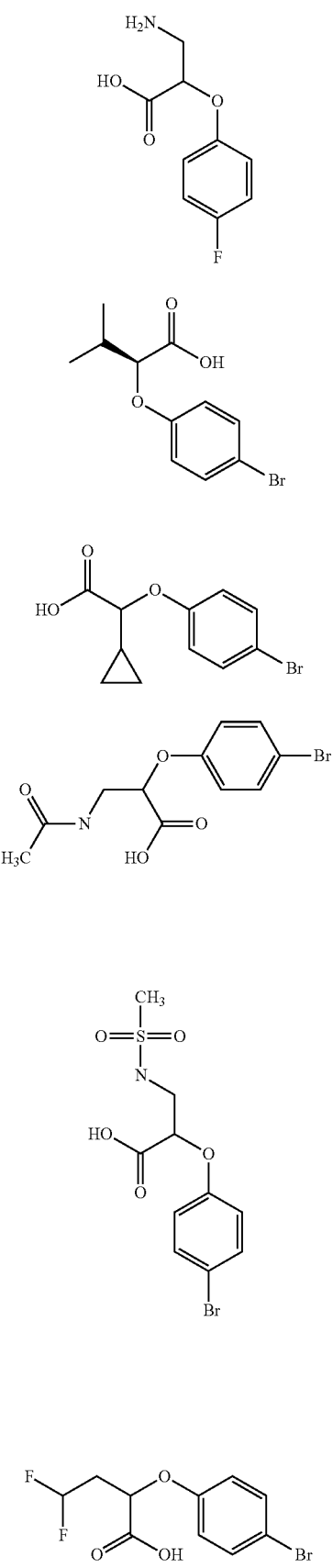

Formula (XX)

Formula XXI

Formula (XXII)

Formula (XXIII)

Formula (XXIV)

Formula (XXV)

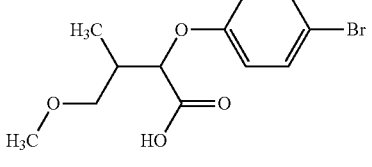

Formula (XXVI)

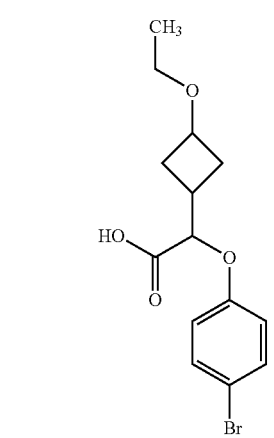

Formula (XXVII)

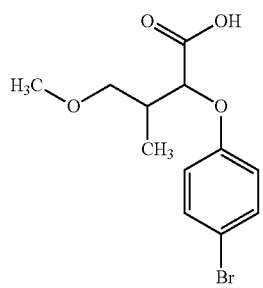

Formula (XXVIII)

Embodiment 36 is a composition for use according to embodiment 28, wherein the compound of Formula (VII) is further defined by Formula (XXIX):

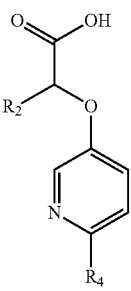

Formula (XXIX)

or a pharmaceutically acceptable salt, solvate, polymorph, or tautomer thereof; wherein $R_2$ is selected from the group consisting of —$CH_3$, —$CH_2$—$CH_3$, —$CH(CH_3)_2$, —$C(CH_3)_3$, —$CH_2$—$CH_2$—$CH_3$ and —$CH_2$—$NH_2$ and $R_4$ is selected from the group consisting of H, Br, Cl, F and I.

Embodiment 37 is a composition for use according to embodiment 36, wherein the compound of Formula (XXIX) is further defined by Formula (XXX):

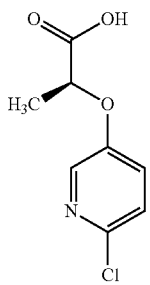

Formula (XXX)

Embodiment 38 is a composition for use according to embodiment 28, wherein the compound of Formula (VII) is further defined by Formula (XXXI):

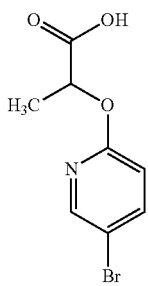

Formula (XXXI)

Embodiment 39 is a composition for use according to embodiment 28, wherein the compound of Formula (VII) is further defined by Formula (XXXII):

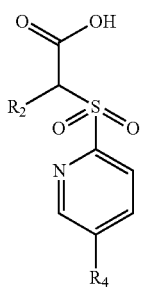

Formula (XXXII)

or a pharmaceutically acceptable salt, solvate, polymorph, or tautomer thereof; wherein $R_2$ is selected from the group consisting of —$CH_3$, —$CH_2$—$CH_3$, —$CH(CH_3)_2$, —$C(CH_3)_3$, —$CH_2$—$CH_2$—$CH_3$ and —$CH_2$—$NH_2$ and $R_4$ is selected from the group consisting of H, Br, Cl, F and I.

Embodiment 40 is a composition for use according to embodiment 39, wherein the compound of Formula (XXXII) is further defined by Formula (XXXIII):

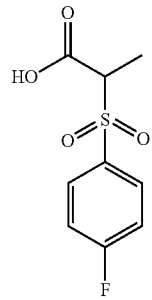

Formula (XXXIII)

Embodiment 41 is a composition for use according to embodiment 1, wherein the compound of Formula (I) is further defined by Formula (XXXIV):

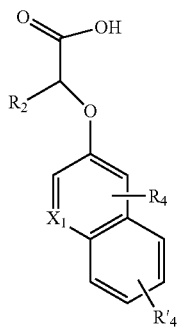

Formula (XXXIV)

or a pharmaceutically acceptable salt, solvate, polymorph, or tautomer thereof; wherein $R_2$ is selected from the group consisting of —$CH_3$, —$CH_2$—$CH_3$, —$CH(CH_3)_2$, —$C(CH_3)_3$, —$CH_2$—$CH_2$—$CH_3$ and —$CH_2$—$NH_2$; $X_1$ is N or C; and $R_4$ and $R'_4$ are independently selected from the group consisting of H, Br, Cl, F and I.

Embodiment 42 is a composition for use according to embodiment 41, wherein Formula (XXXIV) is further defined by Formula (XXXV):

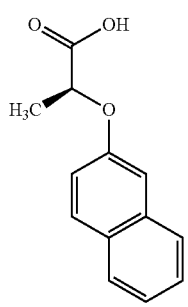

Formula (XXXV)

Embodiment 43 is a composition for use according to embodiment 1, wherein the compound of Formula (I) is further defined by any one of Formulas (XXXVI) to (LIX)

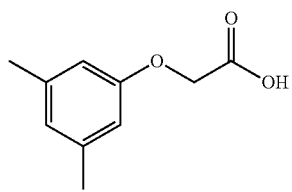
Formula (XXXVI)
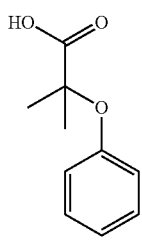
Formula (XXXVII)
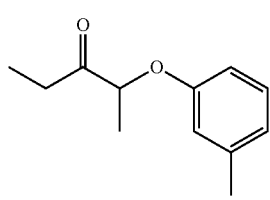
Formula (XXXVIII)
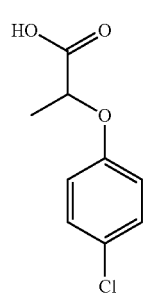
Formula (XXXIX)
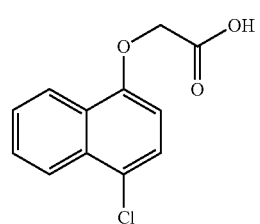
Formula XL
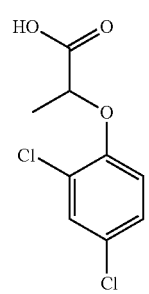
Formula XLII
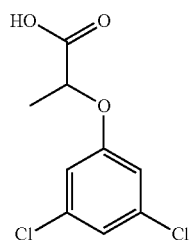
Formula XLIII
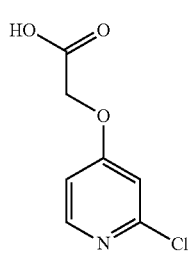
Formula XLIV
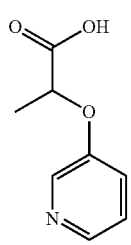
Formula (XLV)
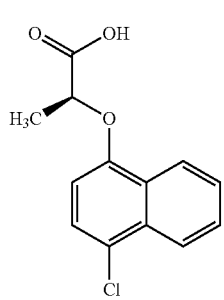
Formula XLVI
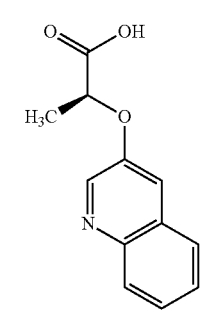
Formula XLVII
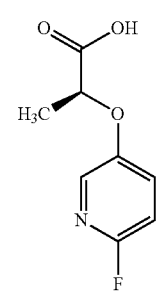
Formula (XLVIII)

-continued

Formula (XLIX)
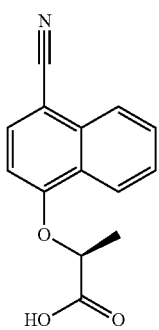

Formula (L)
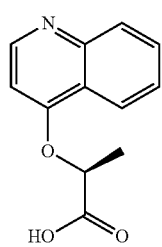

Formula (LI)
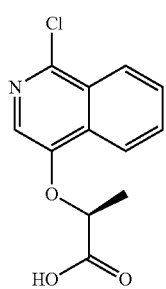

Formula (LII)
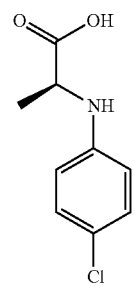

Formula (LIII)
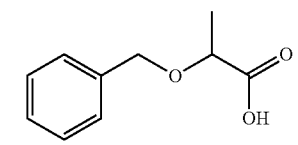

Formula (LIV)
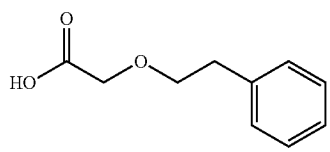

-continued

Formula (LV)
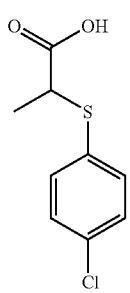

Formula LVI
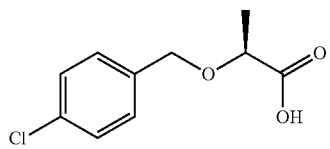

Formula (LVII)
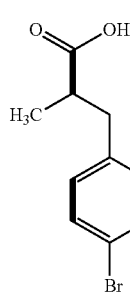

Formula (LVIII)
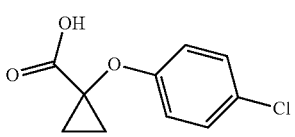

Formula LIX
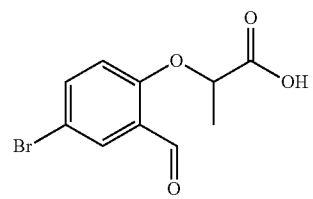

Embodiment 44 is a composition for use according to any one of the preceding embodiments wherein said prodrug is defined by Formula (LX):

Formula (LX)
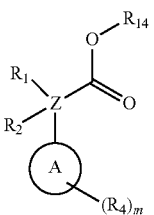

or a pharmaceutically acceptable salt, solvate, polymorph, or tautomer thereof; wherein
A is an aromatic or heteroaromatic ring selected from the group consisting of phenyl, naphthyl, biphenyl, quinolinyl, isoquinolinyl, imidazolyl, thiazolyl, thiadiazolyl, triazolyl, oxazolyl, pyridinyl, pyrimidinyl, pyrazyl, and pyridazinyl;

m is 0, 1, 2, 3, 4 or 5;

Z is a 2-5 atom chain comprising at least one carbon atom and optionally one heteroatom or substituted heteroatom, wherein the heteroatom or substituted heteroatom is selected from the group consisting of O, N, NC(O)R$_3$, S, S(O)R$_5$ and S(O)$_2$R$_5$, wherein each atom of said 2-5 atom chain is optionally substituted with R$_1$ and R$_2$;

R$_1$ and R$_2$ are independently selected from the group consisting of OR$_3$, SR$_5$, S(O)R$_5$, S(O)$_2$R$_5$, NR$_3$, NR$_3$C(O)R$_9$ or R$_3$, wherein R$_3$ is selected from the group consisting of H, C$_{1-8}$-alk(en/yn)yl and C$_{3-6}$-cycloalk(en)yl, wherein said C$_{1-8}$-alk(en/yn)yl and C$_{3-6}$-cycloalk(en)yl may be substituted with up to three substituents selected from the group consisting of —NR$_9$—CO—R$_{10}$, —N(R$_{10}$)$_2$—SO$_2$—R$_{12}$, —CO—NR$_9$R$_{10}$, —SO$_2$—NR$_9$ R$_{10}$, —R$_{13}$—O—R$_{11}$, —NR$_9$ R$_{10}$, —S(O)R$_{12}$, —S(O)$_2$R$_{12}$, cyano, —O—R$_{11}$, fluorinated C$_{1-3}$-alkyl, nitro and halo; or R$^1$ and R$_2$ are linked to form a ring;

R$_4$ is selected from the group consisting of H, C$_{1-6}$-alk(en/yn)yl, C$_{3-6}$-cycloalk(en)yl, —NR$_9$—CO—R$_{10}$, —NR$_{10}$—SO$_2$—R$_{11}$, —CO—NR$_9$R$_{10}$, —SO$_2$—NR$_9$ R$_{10}$, —R$_{13}$—O—R$_{11}$, —NR$_9$R$_{10}$, cyano, O—R$^{11}$, fluorinated C$_{1-3}$, nitro and halo; R$_2$ is selected from the group consisting of OR$_3$, SR$_5$, S(O)R$_5$, S(O)$_2$R$_5$, NR$_3$, NR$_3$C(O)R$_9$ or R$_3$, wherein R$_3$ is selected from the group consisting of H, C$_{1-8}$-alk(en/yn)yl and C$_{3-6}$-cycloalk(en)yl, wherein said C$_{1-8}$-alk(en/yn)yl and C$_{3-6}$-cycloalk(en)yl may be substituted with up to three substituents selected from the group consisting of —NR$_9$—CO—R$_{10}$, —N(R$_{10}$)$_2$—SO$_2$—R$_{12}$, —CO—NR$_9$R$_{10}$, —SO$_2$—NR$_9$ R$_{10}$, —R$_{13}$—O—R$_{11}$, —NR$_9$ R$_{10}$, —S(O)R$_{12}$, —S(O)$_2$R$_{12}$, cyano, —O—R$_{11}$, fluorinated C$_{1-3}$-alkyl, nitro and halo; or R$^1$ and R$_2$ are linked to form a ring;

R$_4$ is selected from the group consisting of H, C$_{1-6}$-alk(en/yn)yl, C$_{3-6}$-cycloalk(en)yl, —NR$_9$—CO—R$_{10}$, —NR$_{10}$—SO$_2$—R$_{11}$, —CO—NR$_9$R$_{10}$, —SO$_2$—NR$_9$ R$_{10}$, —R$_{13}$—O—R$_{11}$, —NR$_9$R$_{10}$, cyano, O—R$^{11}$, fluorinated C$_{1-3}$, nitro and halo.

R$_5$ is selected from the group consisting of C$_{1-8}$-alk(en/yn)yl and C$_{3-6}$-cycloalk(en)yl, wherein said C$_{1-8}$-alk(en/yn)yl and C$_{3-6}$-cycloalk(en)yl may be substituted with up to three substituents selected from the group consisting of —NR$_9$—CO—R$_{10}$, —N(R$_{10}$)$_2$SO$_2$—R$_{12}$, —CO—NR$_9$R$_{10}$, —SO$_2$—NR$_9$ R$_{10}$, —R$_{13}$—O—R$_{11}$, —NR$_9$R$_{10}$, —S(O)R$_{12}$, —S(O)$_2$R$_{12}$, cyano, —O—R$_{11}$, fluorinated C$_{1-3}$-alkyl, nitro and halo;

R$_9$, R$_{10}$, R$_{11}$ are independently selected from H or C$_{1-4}$-alk(en/yn)yl and C$_{3-6}$-cycloalk(en)yl;

R$_{12}$ is selected from C$_{1-4}$-alk(en/yn)yl and C$_{3-6}$-cycloalk(en)yl

R$_{13}$ is selected from C$_{1-4}$-alk(an/en/yn)diyl and C$_{3-6}$-cycloalk(an/en)diyl.

R$_{14}$ is an aromatic or heteroaromatic ring selected from the group consisting of phenyl, pyrimidyl, pyridinyl, thiazolyl, oxadiazolyl and quinolyl, all aromatic and heteroaromatic groups optionally substituted by one or more R$_4$.

Embodiment 45 is a prodrug according to embodiment 44, wherein R$_{14}$ is a phenyl substituted with methoxy, nitro, cyano, Cl, Br, I and/or F.

Embodiment 46 is a prodrug according to embodiment 44, wherein Formula (LX) is further defined by Formula (LXI):

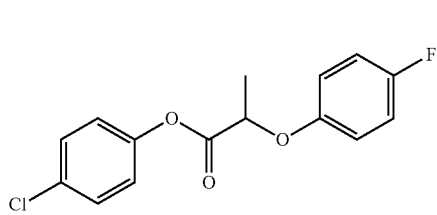

Formula LXI

Embodiment 47 is a composition for use according to any one of embodiments 1 to 43, wherein said prodrug is defined by Formula (LXII):

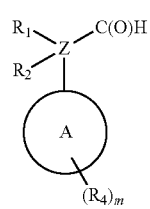

Formula (LXII)

or a pharmaceutically acceptable salt, solvate, polymorph, or tautomer thereof, wherein A is an aromatic or heteroaromatic ring selected from the group consisting of phenyl, naphthyl, biphenyl, quinolinyl, isoquinolinyl, imidazolyl, thiazolyl, thiadiazolyl, triazolyl, oxazolyl, pyridinyl, pyrimidinyl, pyrazyl, and pyridazinyl;

m is 0, 1, 2, 3, 4 or 5;

Z is a 2-5 atom chain comprising at least one carbon atom and optionally one heteroatom or substituted heteroatom, wherein the heteroatom or substituted heteroatom is selected from the group consisting of O, N, NC(O)R$_3$, S, S(O)R$_5$ and S(O)$_2$R$^5$, wherein each atom of said 2-5 atom chain is optionally substituted with R$_1$ and R$_2$;

R$_1$ and R$_2$ are independently selected from the group consisting of OR$_3$, SR$_5$, S(O)R$_5$, S(O)$_2$R$_5$, NR$_3$, NR$_3$C(O)R$_9$ or R$_3$, wherein R$_3$ is selected from the group consisting of H, C$_{1-8}$-alk(en/yn)yl and C$_{3-6}$-cycloalk(en)yl, wherein said C$_{1-8}$-alk(en/yn)yl and C$_{3-6}$-cycloalk(en)yl may be substituted with up to three substituents selected from the group consisting of —NR$_9$—CO—R$_{10}$, —N(R$_{10}$)$_2$—SO$_2$—R$_{12}$, —CO—NR$_9$R$_{10}$, —SO$_2$—NR$_9$ R$_{10}$, —R$_{13}$—O—R$_{11}$, —NR$_9$ R$_{10}$, —S(O)R$_{12}$, —S(O)$_2$R$_{12}$, cyano, —O—R$_{11}$, fluorinated C$_{1-3}$-alkyl, nitro and halo; or R$_1$ and R$_2$ are linked to form a ring;

R$_4$ is selected from the group consisting of H, C$_{1-6}$-alk(en/yn)yl, C$_{3-6}$-cycloalk(en)yl, —NR$_9$—CO—R$_{10}$, —NR$_{10}$—SO$_2$—R$_{11}$, —CO—NR$_9$R$_{10}$, —SO$_2$—NR$_9$ R$_{10}$, —R$_{13}$—O—R$_{11}$, —NR$_9$R$_{10}$, cyano, O—R$^{11}$, fluorinated C$_{1-3}$, nitro and halo.

Embodiment 48 is a composition for use according to any one of embodiments 1 to 43, wherein said prodrug is defined by Formula (LXIII):

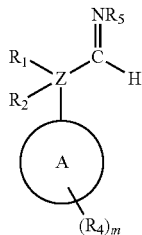

Formula (LXIII)

wherein
A is an aromatic or heteroaromatic ring selected from the group consisting of phenyl, naphthyl, biphenyl, quinolinyl, isoquinolinyl, imidazolyl, thiazolyl, thiadiazolyl, triazolyl, oxazolyl, pyridinyl, pyrimidinyl, pyrazyl, and pyridazinyl;

m is 0, 1, 2, 3, 4 or 5;

Z is a 2-5 atom chain comprising at least one carbon atom and optionally one heteroatom or substituted heteroatom, wherein the heteroatom or substituted heteroatom is selected from the group consisting of O, N, NC(O)$R_3$, S, S(O)$R_5$ and S(O)$_2R^5$, wherein each atom of said 2-5 atom chain is optionally substituted with $R_1$ and $R_2$;

$R_1$ and $R_2$ are independently selected from the group consisting of O$R_3$, S$R_5$, S(O)$R_5$, S(O)$_2R^5$, N$R_3$, N$R_3$C(O)$R_9$ or $R^3$, wherein $R_3$ is selected from the group consisting of H, $C_{1-8}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of —N$R_9$—CO—$R_{10}$, —N($R_{10}$)$_2$—SO$_2$—$R_{12}$, —CO—N$R_9R_{10}$, —SO$_2$—N$R_9$ $R_{10}$, —$R_{13}$—O—$R_{11}$, —N$R_9$ $R_{10}$, —S(O)$R_{12}$, —S(O)$_2R_{12}$, cyano, —O—$R_{11}$, fluorinated $C_{1-3}$-alkyl, nitro and halo; or $R_1$ and $R_2$ are linked to form a ring;

$R_4$ is selected from the group consisting of H, $C_{1-6}$-alk(en/yn)yl, $C_{3-6}$-cycloalk(en)yl, —N$R_9$—CO—$R_{10}$, —N$R_{10}$—SO$_2$—$R_{11}$, —CO—N$R_9R_{10}$, —SO$_2$—N$R_9$ $R_{10}$, —$R_{13}$—O—$R^{11}$, —N$R_9R_{10}$, cyano, O—$R^{11}$, fluorinated $C_{1-3}$, nitro and halo;

$R_5$ is selected from the group consisting of $C_{1-8}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of —N$R_9$—CO—$R_{10}$, —N($R_{10}$)$_2$SO$_2$—$R_{12}$, —CO—N$R_9R_{10}$, —SO$_2$—N$R_9$ $R_{10}$, —$R_{13}$—O—$R_{11}$, —N$R_9R_{10}$, —S(O)$R_{12}$, —S(O)$_2R_{12}$, cyano, —O—$R_{11}$, fluorinated $C_{1-3}$-alkyl, nitro and halo;

$R_9$, $R_{10}$, $R_{11}$ are independently selected from H or $C_{1-4}$-alk(en/yn)yl and $C_{3-6}$-cycloalk(en)yl;

$R_{12}$ is selected from $C_{1-4}$-alk(en/yn)yl and $C_{3-6}$-cycloalk(en)yl $R_{13}$ is selected from $C_{1-4}$-alk(an/en/yn)diyl and $C_{3-6}$-cycloalk(an/en)diyl Embodiment 49 is a composition for use according to any one of embodiments 1 to 43, wherein said prodrug is defined by Formula (LXIV):

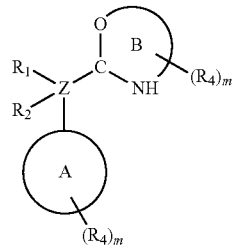

Formula (LXIV)

wherein
A is an aromatic or heteroaromatic ring selected from the group consisting of phenyl, naphthyl, biphenyl, quinolinyl, isoquinolinyl, imidazolyl, thiazolyl, thiadiazolyl, triazolyl, oxazolyl, pyridinyl, pyrimidinyl, pyrazyl, and pyridazinyl;

m is 0, 1, 2, 3, 4 or 5;

Z is a 2-5 atom chain comprising at least one carbon atom and optionally one heteroatom or substituted heteroatom, wherein the heteroatom or substituted heteroatom is selected from the group consisting of O, N, NC(O)$R_3$, S, S(O)$R_5$ and S(O)$_2R^5$, wherein each atom of said 2-5 atom chain is optionally substituted with $R_1$ and $R_2$;

$R_1$ and $R_2$ are independently selected from the group consisting of O$R_3$, S$R_5$, S(O)$R_5$, S(O)$_2R_5$, N$R_3$, N$R_3$C(O)$R_9$ or $R_3$, wherein $R_3$ is selected from the group consisting of H, $C_{1-8}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of —N$R_9$—CO—$R_{10}$, —N($R_{10}$)$_2$—SO$_2$—$R_{12}$, —CO—N$R_9R_{10}$, —SO$_2$—N$R_9$ $R_{10}$, —$R_{13}$—O—$R_{11}$, —N$R_9$ $R_{10}$, —S(O)$R_{12}$, —S(O)$_2R_{12}$, cyano, —O—$R_{11}$, fluorinated $C_{1-3}$-alkyl, nitro and halo; or $R_1$ and $R_2$ are linked to form a ring;

$R_4$ is selected from the group consisting of H, $C_{1-6}$-alk(en/yn)yl, $C_{3-6}$-cycloalk(en)yl, —N$R_9$—CO—$R_{10}$, —N$R_{10}$—SO$_2$—$R_{11}$, —CO—N$R_9R_{10}$, —SO$_2$—N$R_9$ $R_{10}$, —$R_{13}$—O—$R_{11}$, —N$R_9R_{10}$, cyano, O—$R^{11}$, fluorinated $C_{1-3}$, nitro and halo;

B is a 5- to 7-membered heterocyclic.

Embodiment 50 is a composition for use according to any one of the preceding embodiments wherein the neuromuscular disorder is myasthenia gravis.

Embodiment 51 is a composition for use according to any one of the preceding embodiments wherein the neuromuscular disorder is autoimmune myasthenia gravis.

Embodiment 52 is a composition for use according to any one of the preceding embodiments wherein the neuromuscular disorder is congenital myasthenia gravis.

Embodiment 53 is a composition for use according to any one of the preceding embodiments wherein the neuromuscular disorder is Lambert-Eaton Syndrome.

Embodiment 54 is a composition for use according to any one of the preceding embodiments wherein the neuromuscular disorder is critical illness myopathy.

Embodiment 55 is a composition for use according to any one of the preceding embodiments wherein the neuromuscular disorder is amyotrophic lateral sclerosis (ALS).

Embodiment 56 is a composition for use according to any one of the preceding embodiments wherein the neuromuscular disorder is spinal muscular atrophy (SMA).

Embodiment 57 is a composition for use according to any one of the preceding embodiments wherein the neuromuscular disorder is critical illness myopathy (CIM).

Embodiment 58 is a composition for use according to any one of the preceding embodiments wherein the neuromuscular disorder is reversal diabetic polyneuropathy.

Embodiment 59 is a composition for use according to any one of the preceding embodiments wherein the neuromuscular disorder is selected from the group consisting of Guillain-Barré syndrome, poliomyelitis, post-polio syndrome, chronic fatigue syndrome, and critical illness polyneuropathy.

Embodiment 60 is a composition for use according to any one of the preceding embodiments, wherein the composition is for use in the treatment of symptoms of an indication selected from the group consisting of myasthenia gravis (such as autoimmune and congenital myasthenia gravis), Lambert-Eaton Syndrome, critical illness myopathy, amyotrophic lateral sclerosis (ALS), spinal muscular atrophy (SMA), critical illness myopathy (CIM), reversal diabetic polyneuropathy, Guillain-Barre syndrome, poliomyelitis, post-polio syndrome, chronic fatigue syndrome, and critical illness polyneuropathy.

Embodiment 61 is a composition for use according to any one of the preceding embodiments wherein the neuromuscular disorder has been induced by a neuromuscular blocking agent.

Embodiment 62 is a composition for use according to any one of the preceding embodiments further comprising a pharmaceutically acceptable carrier.

Embodiment 63 is a composition for use according to any one of the preceding embodiments further comprising at least one further active agent.

Embodiment 64 is a composition for use according to any one of the preceding embodiments wherein said further active agent is suitable for treating, preventing or ameliorating said neuromuscular disorder.

Embodiment 65 is a composition for use according to any one of the preceding embodiments, wherein said further active agent is an acetylcholine esterase inhibitor.

Embodiment 66 is a composition for use according to embodiment 65, wherein said acetylcholine esterase inhibitor is selected from the group consisting of delta-9-tetrahydrocannabinol, carbamates, physostigmine, neostigmine, pyridostigmine, ambenonium, demecarium, rivastigmine, phenanthrene derivatives, galantamine, caffeine—noncompetitive, piperidines, donepezil, tacrine, edrophonium, huperzine, ladostigil, ungeremine and lactucopicrin.

Embodiment 67 is a composition for use according embodiment 65, wherein said acetylcholine esterase inhibitor is neostigmine or pyridostigmine.

Embodiment 68 is a composition for use according to any one of the preceding embodiments, wherein said further active agent is suggamadex.

Embodiment 69 is a composition for use according to any one of the preceding embodiments, wherein said further active agent is tirasemtiv.

Embodiment 70 is a composition for use according to any one of the preceding embodiments, wherein said further active agent is 3,4-aminopyridine.

Embodiment 71 is a composition for use according to any one of the preceding embodiments, wherein the composition is administered or adapted for administration enterally, topically, parenterally or as part of a sustained release implant.

Embodiment 72 is a composition for use according to any one of the preceding embodiments, wherein the parenteral administration is intravenous, subcutaneous, intramuscular, intracranial or intraperitoneal.

Embodiment 73 is a composition for use according to any one of the preceding embodiments, wherein the enteral administration is oral, rectal, or buccal.

Embodiment 74 is a composition for use according to any one of the preceding embodiments, wherein the topical administration is dermal, epicutaneous, vaginal, intravesical, pulmonary, intranasal, intratracheal or as eye drops.

Embodiment 75 is a composition for use according to any one of the preceding embodiments, wherein the composition is administered or adapted for administration subcutaneously or intravenously.

Embodiment 76 is a composition for use according to any one of the preceding embodiments, wherein the composition is formulated for oral administration.

Embodiment 77 is a composition for use according to any one of the preceding embodiments, wherein the composition is formulated in a tablet or capsule.

Embodiment 78 is a composition for use according to any one of the preceding embodiments, wherein said composition is to be administered in a dosage of from 1 µg/kg-10,000 µg/kg body weight, such as 1 µg/kg-7,500 µg/kg, such as 1 µg/kg-5,000 µg/kg, such as 1 µg/kg-2,000 µg/kg, such as 1 µg/kg-1,000 µg/kg, such as 1 µg/kg-700 µg/kg, such as 5 µg/kg-500 µg/kg, such as 10 µg/kg to 100 µg/kg bodyweight.

Embodiment 79 is a composition for use according to any one of the preceding embodiments, wherein said administration is repeated daily.

Embodiment 80 is a composition for use according to any one of the preceding embodiments, wherein said administration is repeated at least 1-3 times weekly, such as 2-5 times weekly, such as 3-6 times weekly.

Embodiment 81 is a composition for use according to any one of the preceding embodiments, wherein said administration is repeated 1 to 8 times daily, such as 2 to 5 times daily.

Embodiment 82 is a composition for use according to any one of the preceding embodiments, wherein said compound further has been modified in order to increase its half-life when administered to a patient, in particular its plasma half-life.

Embodiment 83 is a composition for use according to any one of the preceding embodiments, wherein said compound further comprises a moiety conjugated to said compound, thus generating a moiety-conjugated compound.

Embodiment 84 is a composition for use according to any one of the preceding embodiments, wherein the moiety-conjugated compound has a plasma and/or serum half-life being longer than the plasma and/or serum half-life of the non-moiety conjugated compound.

Embodiment 85 is a composition for use according to any one of the preceding embodiments, wherein the moiety conjugated to the compound is one or more type(s) of moieties selected from the group consisting of albumin, fatty acids, polyethylene glycol (PEG), acylation groups, antibodies and antibody fragments.

Embodiment 86 is a method of treating, preventing and/or ameliorating a neuromuscular disorder, said method comprising administering a therapeutically effective amount of the composition as defined in any one of the preceding embodiment to a person in need thereof.

Embodiment 87 is a method of using a composition as defined in any one of embodiments 1 to 85, for the manufacture of a medicament for the treatment, prevention and/or amelioration of a neuromuscular disorder.

Embodiment 88 is a composition comprising a compound of Formula (I):

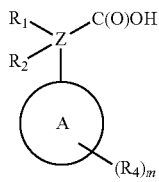

or a pharmaceutically acceptable salt, solvate, polymorph, or tautomer thereof; wherein A is an aromatic or heteroaromatic ring selected from the group consisting of phenyl, naphthyl, biphenyl, quinolinyl, isoquinolinyl, imidazolyl, thiazolyl, thiadiazolyl, triazolyl, oxazolyl, pyridinyl, pyrimidinyl, pyrazyl, and pyridazinyl;

m is 0, 1, 2, 3, 4 or 5;

Z is a 2-5 atom chain comprising at least one carbon atom and optionally one heteroatom or substituted heteroatom, wherein the heteroatom or substituted heteroatom is selected from the group consisting of O, N, NC(O)$R_3$, S, S(O)$R_5$ and S(O)$_2R_5$, wherein each atom of said 2-5 atom chain is optionally substituted with $R_1$ and $R_2$; wherein $R_1$ and $R_2$ are independently selected from the group consisting of —O$R_3$, —S$R_5$, —S(O)$R_5$, —S(O)$_2R_5$, —N$R_3$, —N$R_3$C(O)$R_9$ or —$R_3$, wherein $R_3$ is selected from the group consisting of —H, $C_{1-8}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of —N$R_9$—CO—$R_{10}$, —N($R_{10}$)$_2$—SO$_2$—$R_{12}$, —CO—N$R_9R_{10}$, —SO$_2$—N$R_9$ $R_{10}$, —$R_{13}$—O—$R_{11}$, —N$R_9$ $R_{10}$, —S(O)$R_{12}$, —S(O)$_2R_{12}$, cyano, —O—$R_{11}$, fluorinated $C_{1-3}$-alkyl, nitro and halo; or $R_1$ and $R_2$ are linked to form a ring;

$R_4$ is selected from the group consisting of —H, $C_{1-6}$-alk(en/yn)yl, $C_{3-6}$-cycloalk(en)yl, —N$R_9$—CO—$R_{10}$, —N$R_{10}$—SO$_2$—$R_{11}$, —CO—N$R_9R_{10}$, —SO$_2$—N$R_9$ $R_{10}$, —$R_{13}$—O—$R_{11}$, —N$R_9R_{10}$, cyano, —O—$R^{11}$, fluorinated $C_{1-3}$, nitro and halo;

$R_5$ is selected from the group consisting of $C_{1-3}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of —N$R_9$—CO—$R_{10}$, —N($R_{10}$)$_2$SO$_2$—$R_{12}$, —CO—N$R_9R_{10}$, —SO$_2$—N$R_9$ $R_{10}$, —$R_{13}$—O—$R_{11}$, —N$R_9R_{10}$, —S(O)$R_{12}$, —S(O)$_2R_{12}$, cyano, —O—$R_{11}$, fluorinated $C_{1-3}$-alkyl, nitro and halo;

$R_9$, $R_{10}$, $R_{11}$ are independently selected from —H or $C_{1-4}$-alk(en/yn)yl and $C_{3-6}$-cycloalk(en)yl;

$R_{12}$ is selected from $C_{1-4}$-alk(en/yn)yl and $C_{3-6}$-cycloalk(en)yl $R_{13}$ is selected from $C_{1-4}$-alk(an/en/yn)diyl and $C_{3-6}$-cycloalk(an/en)diyl for use in reversing and/or ameliorating a neuromuscular blockade after surgery.

Embodiment 89 is a method of reversing and/or ameliorating a neuromuscular blockade after surgery, said method comprising administering a therapeutically effective amount of the composition as defined in embodiment 88 to a person in need thereof.

Embodiment 90 is a method for recovery of neuromuscular transmission, said method comprising administering a therapeutically effective amount of the composition as defined in embodiment 88 to a person in need thereof.

Embodiment 91 is a method of using a composition as defined in embodiment 88, for the manufacture of a medicament for recovery of neuromuscular transmission.

Embodiment 92 is a compound of Formula (I):

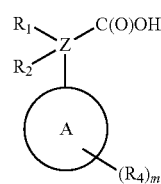

or a pharmaceutically acceptable salt, solvate, polymorph, or tautomer thereof; wherein A is an aromatic or heteroaromatic ring selected from the group consisting of phenyl, naphthyl, biphenyl, quinolinyl, isoquinolinyl, imidazolyl, thiazolyl, thiadiazolyl, triazolyl, oxazolyl, pyridinyl, pyrimidinyl, pyrazyl, and pyridazinyl;

m is 0, 1, 2, 3, 4 or 5;

Z is a 2-5 atom chain comprising at least one carbon atom and optionally one heteroatom or substituted heteroatom, wherein the heteroatom or substituted heteroatom is selected from the group consisting of O, N, NC(O)$R_3$, S, S(O)$R_5$ and S(O)$_2R_5$, wherein each atom of said 2-5 atom chain is optionally substituted with $R_1$ and $R_2$; wherein $R_1$ and $R_2$ are independently selected from the group consisting of O$R_3$, S$R_5$, S(O)$R_5$, S(O)$_2R_5$, N$R_3$, N$R_3$C(O)$R_9$ or $R_3$, wherein $R_3$ is selected from the group consisting of H, $C_{1-8}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of —N$R_9$—CO—$R_{10}$, —N($R_{10}$)$_2$—SO$_2$—$R_{12}$, —CO—N$R_9R_{10}$, —SO$_2$—N$R_9$ $R_{10}$, —$R_{13}$—O—$R_{11}$, N$R_9$ $R_{10}$, —S(O)$R_{12}$, —S(O)$_2R_{12}$, cyano, —O—$R^{11}$, fluorinated $C_{1-3}$-alkyl, nitro and halo; or $R_1$ and $R_2$ are linked to form a ring;

$R_4$ is selected from the group consisting of H, $C_{1-6}$-alk(en/yn)yl, $C_{3-6}$-cycloalk(en)yl, —N$R_9$—CO—$R_{10}$, —N$R_{10}$—SO$_2$—$R_{11}$, —CO—N$R_9R_{10}$, —SO$_2$—N$R_9$ $R_{10}$, —$R_{13}$—O—$R_{11}$, —N$R_9R_{10}$, cyano, —O—$R^{11}$, fluorinated $C_{1-3}$, nitro and halo;

$R_5$ is selected from the group consisting of $C_{1-3}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of —N$R_9$—CO—$R_{10}$, —N($R_{10}$)$_2$SO$_2$—$R_{12}$, —CO—N$R_9R_{10}$, —SO$_2$—N$R_9$ $R_{10}$, —$R_{13}$—O—$R_{11}$, —N$R_9R_{10}$, —S(O)$R_{12}$, —S(O)$_2R_{12}$, cyano, O—$R_{11}$, fluorinated $C_{1-3}$-alkyl, nitro and halo;

$R_9$, $R_{10}$, $R_{11}$ are independently selected from H or $C_{1-4}$-alk(en/yn)yl and $C_{3-6}$-cycloalk(en)yl;

$R_{12}$ is selected from $C_{1-4}$-alk(en/yn)yl and $C_{3-6}$-cycloalk(en)yl;

$R_{13}$ is selected from $C_{1-4}$-alk(an/en/yn)diyl and $C_{3-6}$-cycloalk(an/en)diyl.

Embodiment 93 is a compound according to embodiment 92, wherein A is a monocyclic or bicyclic aromatic or heteroaromatic ring.

Embodiment 94 is a compound according to any of embodiments 92 and 93, wherein A is five-membered or six-membered aromatic ring.

Embodiment 95 is a compound according to any one of embodiments 92 to 93, wherein A is phenyl, or naphthyl.

Embodiment 96 is a compound according to any of embodiments 92 to 95, wherein said compound is a compound of Formula (II):

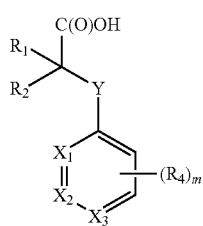

Formula (II)

or a pharmaceutically acceptable salt, solvate, polymorph, or tautomer thereof; wherein m is 0, 1, 2, 3, 4 or 5;

Y is selected from the group consisting of O, NH, N—$CH_3$, $CH_2$, $CH_2$—O, S and $SO_2$;

$X_1$, $X_2$ and $X_3$ are independently selected from the group consisting of CH and N;

$R_1$ and $R_2$ are independently selected from the group consisting of $OR_3$, $SR_5$, $S(O)R_5$, $S(O)_2R^5$, $NR_3$, $NR_3C(O)R_9$ or $R_3$, wherein $R_3$ is selected from the group consisting of H, $C_{1-8}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of —$NR_9$—CO—$R_{10}$, —$N(R_{10})_2$—$SO_2$—$R_{12}$, —CO—$NR_9R_{10}$, —$SO_2$—$NR_a$ $R_{10}$, —$R_{13}$—O—$R_{11}$, —$NR_9$ $R_{10}$, —$S(O)R_{12}$, —$S(O)_2R_{12}$, cyano, —O—$R_{11}$, fluorinated $C_{1-3}$-alkyl, nitro and halo; or $R_1$ and $R_2$ are linked to form a $C_{3-6}$-cycloalk(en)yl or a halo-$C_{3-6}$-cycloalk(en)yl;

$R_4$ is selected from the group consisting of H, $C_{1-6}$-alk(en/yn)yl, $C_{3-6}$-cycloalk(en)yl, —$NR_9$—CO—$R_{10}$, —$NR_{10}$—$SO_2$—$R_{11}$, —CO—$NR_9R_{10}$, —$SO_2$—$NR_9$ $R_{10}$, —$R_{13}$—O—$R_{11}$, —$NR_9R_{10}$, cyano, O—$R^{11}$, fluorinated $C_{1-3}$, nitro and halo;

$R^5$ is selected from the group consisting of $C_{1-8}$-alk(en/yn)yl and $C_{3-6}$-cycloalk(en)yl, wherein said $C_{1-8}$-alk(en/yn)yl and $C_{3-6}$-cycloalk(en)yl may be substituted with up to three substituents selected from the group consisting of —$NR_9$—CO—$R_{10}$, —$N(R_{10})_2SO_2$—$R_{12}$, —CO—$NR_9$ $R_{10}$, —$SO_2$—$NR_9$ $R_{10}$, —$R_{13}$—O—$R_{11}$, —$NR_9R_{10}$, —$S(O)R_{12}$, —$S(O)_2R_{12}$, cyano, —O—$R_{11}$, fluorinated $C_{1-3}$, nitro and halo; or $R_1$ and $R_2$ are linked to form a ring;

$R_9$, $R_{10}$, $R_{11}$ are independently selected from H or $C_{1-4}$-alk(en/yn)yl and $C_{3-6}$-cycloalk(en)yl;

$R_{12}$ is selected from $C_{1-4}$-alk(en/yn)yl and $C_{3-6}$-cycloalk(en)yl;

$R_{13}$ is selected from $C_{1-4}$-alk(an/en/yn)diyl and $C_{3-6}$-cycloalk(an/en)diyl.

Embodiment 97 is a compound according to any one of embodiments 92 to 96, wherein $R_1$ is selected from the group consisting of —H and —$CH_3$.

Embodiment 98 is a compound according to any one of embodiments 92 to 96, wherein $R_1$ is H.

Embodiment 99 is a compound according to any of embodiments 92 to 98, wherein $R_1$ is H and $R_2$ is selected from the group consisting of H, $C_{1-4}$-alk(en)yl, $C_{3-6}$-cycloalk(en)yl, wherein said $C_{1-4}$-alk(en/yn)yl and $C_{3-6}$-cycloalk(en)yl may be substituted with up to two substituents selected from the group consisting of —$NR_9$—CO—$R_{10}$, —$N(R_{10})_2$—$SO_2$—$R_{12}$, —CO—$NR_9R_{10}$, —$SO_2$—$NR_9$ $R_{10}$, —$R_{13}$—O—$R_{11}$, —$NR_9$ $R_{10}$, —$S(O)R_{12}$, $S(O)_2R_{12}$, cyano, —O—$R_{11}$, fluorinated $C_{1-3}$-alkyl, nitro and halo, wherein $R_9$, $R_{10}$, and $R_{11}$ are independently selected from H, $C_{1-4}$-alk(en/yn)yl and $C_{3-6}$-cycloalk(en)yl, whereas $R_{12}$ is selected from $C_{1-4}$-alk(en/yn)yl and $C_{3-6}$-cycloalk(en)yl.

Embodiment 100 is a compound according to any of embodiments 92 to 98, wherein $R_1$ is H and $R_2$ is selected from the group consisting of H, $C_{1-4}$-alkyl, $C_{3-6}$-cycloalkyl and amino-$C_{1-4}$-alkyl, wherein said $C_{1-4}$-alkyl and $C_{3-6}$-cycloalkyl may be substituted with O—$R_{11}$, wherein $R_{11}$ is selected from H or $C_{1-4}$-alk(en/yn)yl and $C_{3-6}$-cycloalk(en)yl.

Embodiment 101 is a compound according to embodiment 100, wherein $R_{11}$ is —$CH_3$.

Embodiment 102 is a compound according to embodiment 100, wherein $R_2$ is —$CH(CH_3)CH_2$—O—$CH_3$.

Embodiment 103 is a compound according to any of embodiments 92 to 102, wherein $R^1$ is H and $R_2$ is selected from the group consisting of H, $C_{1-6}$-alkyl and $C_{3-7}$-cycloalkyl.

Embodiment 104 is a compound according to any of embodiments 92 to 102, wherein $R_1$ is H and $R_2$ is selected from the group consisting of H, —$CH_3$, —$CH(CH_3)_2$ and cyclopropyl.

Embodiment 105 is a compound according to any one of embodiments 92 to 104, wherein $R_1$ is H and $R_2$ is —$CH(CH_3)_2$.

Embodiment 106 is a compound according to any one of embodiments 92 to 105, wherein $R_1$ is different from $R_2$.

Embodiment 107 is a compound according to any one of embodiments 92 to 106, wherein said compound is an S-enantiomer with respect to the C-atom to which $R_2$ is bound.

Embodiment 108 is a compound according to any embodiments 92 to 107, wherein $R_1$ is H and $R_2$ is $C_{1-6}$-alkyl or $C_{3-7}$-cycloalkyl and wherein said compound is an S-enantiomer with respect to the C-atom to which $R_2$ is bound as shown in Formula (III):

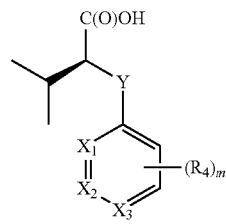

Formula (III)

or a pharmaceutically acceptable salt, solvate, polymorph, or tautomer thereof; wherein m is 0, 1, 2, 3, 4 or 5

Y is selected from the group consisting of O, NH, N—$CH_3$, $CH_2$, $CH_2$—O, S and $SO_2$;

$X_1$, $X_2$ and $X_3$ are independently selected from the group consisting of CH and N;

R$_4$ is selected from the group consisting of H, C$_{1-6}$-alk(en/yn)yl, C$_{3-6}$-cycloalk(en)yl, —NR$_9$—CO—R$_{10}$, —NR$_{10}$—SO$_2$—R$_{11}$, —CO—NR$_9$R$_{10}$, —SO$_2$—NR$_9$ R$_{10}$, —R$_{13}$—O—R$_{11}$, —NR$_9$R$_{10}$, cyano, O—R$^{11}$, fluorinated C$_{1-3}$, nitro and halo, wherein R$_9$, R$_{10}$, R$_{11}$ are independently selected from H or C$_{1-4}$-alk(en/yn)yl and C$_{3-6}$-cycloalk(en)yl; R$_{12}$ is selected from C$_{1-4}$-alk(en/yn)yl and C$_{3-6}$-cycloalk(en)yl and R$_{13}$ is selected from C$_{1-4}$-alk(an/en/yn)diyl and C$_{3-6}$-cycloalk(an/en)diyl;

R$^5$ is selected from the group consisting of C$_{1-8}$-alk(en/yn)yl and C$_{3-8}$-cycloalk(en)yl, wherein said C$_{1-8}$-alk(en/yn)yl and C$_{3-6}$-cycloalk(en)yl may be substituted with up to three substituents selected from the group consisting of —NR$_9$—CO—R$_{10}$, —N(R$_{10}$)$_2$SO$_2$—R$_{12}$, —CO—NR$_9$ R$_{10}$, —SO$_2$—NR$_9$ R$_{10}$, —R$_{13}$—O—R$_{11}$, —NR$_9$R$_{10}$, —S(O)R$_{12}$, —S(O)$_2$R$_{12}$, cyano, —O—R$_{11}$, fluorinated C$_{1-3}$, nitro and halo; or R$_1$ and R$_2$ are linked to form a ring;

R$_9$, R$_{10}$, R$_{11}$ are independently selected from H or C$_{1-4}$-alk(en/yn)yl and C$_{3-6}$-cycloalk(en)yl;

R$_{12}$ is selected from C$_{1-4}$-alk(en/yn)yl and C$_{3-6}$-cycloalk(en)yl;

R$_{13}$ is selected from C$_{1-4}$-alk(an/en/yn)diyl and C$_{3-6}$-cycloalk(an/en)diyl.

Embodiment 109 is a compound according to any one of embodiments 92 to 108, wherein R$_4$ is selected from the group consisting of H, halo, cyano, —CHO, C$_{1-4}$-alk(en)yl, halo-C$_{1-4}$-alk(en)yl, —O—C$_{1-4}$-alk(en)yl.

Embodiment 110 is a compound according to any one of embodiments 92 to 109, wherein m is 0, 1 or 2.

Embodiment 111 is a compound according to any one of embodiments 92 to 110, wherein m is 1.

Embodiment 112 is a compound according to any one of embodiments 92 to 111, wherein X$_1$ is N, X$_2$ is N or X$_3$ is N.

Embodiment 113 is a compound according to any one of embodiments 92 to 111, wherein X$_1$, X$_2$ and X$_3$ is C.

Embodiment 114 is a compound according to any one of embodiments 92 to 113, wherein the compound of Formula (I) is further defined by Formula (IV):

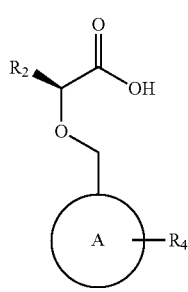

Formula (IV)

or a pharmaceutically acceptable salt, solvate, polymorph, or tautomer thereof; wherein A is an aromatic or heteroaromatic ring selected from the group consisting of phenyl, naphthyl, biphenyl, quinolinyl, isoquinolinyl, imidazolyl, thiazolyl, thiadiazolyl, triazolyl, oxazolyl, pyridinyl, pyrimidinyl, pyrazyl, and pyridazinyl;

R$_2$ is selected from the group consisting of OR$_3$, SR$_5$, S(O)R$_5$, S(O)$_2$R$_5$, NR$_3$, NR$_3$C(O)R$_9$ or R$_3$, wherein R$_3$ is selected from the group consisting of H, C$_{1-8}$-alk(en/yn)yl and C$_{3-6}$-cycloalk(en)yl, wherein said C$_{1-8}$-alk(en/yn)yl and C$_{3-6}$-cycloalk(en)yl may be substituted with up to three substituents selected from the group consisting of —NR$_9$-CO—R$_{10}$, —N(R$_{10}$)$_2$—SO$_2$—R$_{12}$, —CO—NR$_9$R$_{10}$, —SO$_2$—NR$_9$ R$_{10}$, —R$_{13}$—O—R$_{11}$, —NR$_9$ R$_{10}$, —S(O)R$_{12}$, —S(O)$_2$R$_{12}$, cyano, —O—R$_{11}$, fluorinated C$_{1-3}$-alkyl, nitro and halo; or R$_1$ and R$_2$ are linked to form a ring;

R$_4$ is selected from the group consisting of H, C$_{1-6}$-alk(en/yn)yl, C$_{3-6}$-cycloalk(en)yl, —NR$_9$—CO—R$_{10}$, —NR$_{10}$—SO$_2$—R$_{11}$, —CO—NR$_9$R$_{10}$, —SO$_2$—NR$_9$ R$_{10}$, —R$_{13}$—O—R$_{11}$, —NR$_9$R$_{10}$, cyano, O—R$^{11}$, fluorinated C$_{1-3}$, nitro and halo, wherein R$_9$, R$_{10}$, R$_{11}$ are independently selected from H or C$_{1-4}$-alk(en/yn)yl and C$_{3-5}$-cycloalk(en)yl; R$_{12}$ is selected from C$_{1-4}$-alk(en/yn)yl and C$_{3-5}$-cycloalk(en)yl and R$_{13}$ is selected from C$_{1-4}$-alk(an/en/yn)diyl and C$_{3-5}$-cycloalk(an/en)diyl;

R$^5$ is selected from the group consisting of C$_{1-8}$-alk(en/yn)yl and C$_{3-6}$-cycloalk(en)yl, wherein said C$_{1-8}$-alk(en/yn)yl and C$_{3-6}$-cycloalk(en)yl may be substituted with up to three substituents selected from the group consisting of —NR$_9$—CO—R$_{10}$, —N(R$_{10}$)$_2$SO$_2$—R$_{12}$, —CO—NR$_9$ R$_{10}$, —SO$_2$—NR$_9$ R$_{10}$, —R$_{13}$—O—R$_{11}$, —NR$_9$R$_{10}$, —S(O)R$_{12}$, —S(O)$_2$R$_{12}$, cyano, —O—R$_{11}$, fluorinated C$_{1-3}$, nitro and halo; or R$_1$ and R$_2$ are linked to form a ring;

R$_9$, R$_{10}$, R$_{11}$ are independently selected from H or C$_{1-4}$-alk(en/yn)yl and C$_{3-6}$-cycloalk(en)yl;

R$_{12}$ is selected from C$_{1-4}$-alk(en/yn)yl and C$_{3-6}$-cycloalk(en)yl;

R$_{13}$ is selected from C$_{1-4}$-alk(an/en/yn)diyl and C$_{3-6}$-cycloalk(an/en)diyl.

Embodiment 115 is a compound according to embodiment 114, wherein the compound of Formula (IV) is further defined by Formula (V):

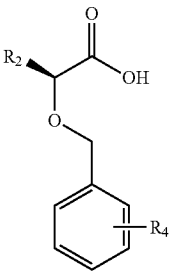

Formula (V)

wherein R$_2$ and R$_4$ are as defined above.

Embodiment 116 is a compound according to embodiment 114 or embodiment 115, wherein R$_2$ is C$_{1-6}$-alkyl or C$_{3-7}$-cycloalkyl.

Embodiment 117 is a compound according embodiment 115, wherein the compound of Formula (V) is further defined by Formula (VI):

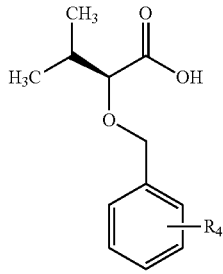

Formula (VI)

wherein R₄ is as defined above

Embodiment 118 is a compound according to any one of embodiments 115 to 117, wherein R₄ is in ortho- or meta position.

Embodiment 119 is a compound according to embodiment 92, wherein the compound of Formula (I) is further defined by Formula (VII):

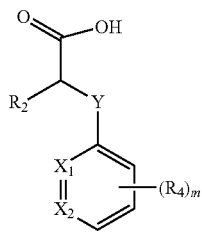

Formula (VII)

or a pharmaceutically acceptable salt, solvate, polymorph, or tautomer thereof; wherein m is 2 and $X_1$, $X_2$, Y, $R_2$ and $R_4$ are as defined above.

Embodiment 120 is a compound according to embodiment 119, wherein the compound of Formula (VII) is further defined by Formula (VIII)

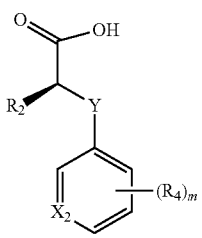

Formula (VIII)

or a pharmaceutically acceptable salt, solvate, polymorph, or tautomer thereof; wherein m, $X_2$, Y, $R_2$ and $R_4$ are as defined above.

Embodiment 121 is a compound according to any one of embodiments 92 to 120, wherein Y is O.

Embodiment 122 is a compound according to any one of embodiments 92 to 121, wherein $R_2$ is selected from the group consisting of H and $C_{1-4}$-alkyl.

Embodiment 123 is a compound according to any one of embodiments 92 to 122, wherein $R_4$ is selected from the group consisting of H, —$CH_3$ and halogen.

Embodiment 124 is a compound according to any one of embodiments 92 to 123, wherein said compound is further defined by Formula (IX):

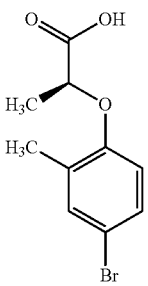

Formula (IX)

Embodiment 125 is a compound according to embodiment 119, wherein the compound of Formula (VII) is further defined by Formula (X):

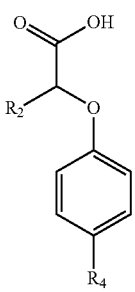

Formula (X)

or a pharmaceutically acceptable salt, solvate, polymorph, or tautomer thereof; wherein $R_2$ is selected from the group consisting of —$CH_3$, —$CH_2$—$CH_3$, —$CH(CH_3)_2$, —$C(CH_3)_3$, —$CH(CH_3)CH_2$—O—$CH_3$, —$CH_2$—$CH_2$—$CH_3$, —$CH_2$—$NH_2$, —$CH_2$—$CHF_2$, —$CH_2$—$CF_3$, —$CH_2$—NH—CO—$CH_3$ and —$CH_2$—NH—$SO_2$—$CH_3$ and cyclopropyl, and $R_4$ is selected from the group consisting of H, Br, Cl, F and I.

Embodiment 126 is a compound se according to embodiment 119, wherein the compound of Formula (VII) is further defined by any one of Formulas (XI) to (XXVIII) as defined in embodiment 35.

Embodiment 127 is a compound according to embodiment 119, wherein the compound of Formula (VII) is further defined by Formula (XXIX):

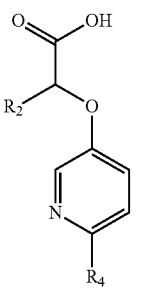

Formula (XXIX)

or a pharmaceutically acceptable salt, solvate, polymorph, or tautomer thereof; wherein $R_2$ is selected from the group consisting of —CH$_3$, —CH$_2$—CH$_3$, —CH(CH$_3$)$_2$, —C(CH$_3$)$_3$, —CH$_2$—CH$_2$—CH$_3$ and —CH$_2$—NH$_2$ and R$_4$ is selected from the group consisting of H, Br, Cl, F and I.

Embodiment 128 is a compound according to embodiment 127, wherein the compound of Formula (XXIX) is further defined by Formula (XXX):

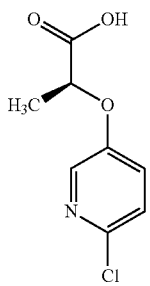

Formula (XXX)

Embodiment 129 is a compound according to embodiment 119, wherein the compound of Formula (VII) is further defined by Formula (XXXI):

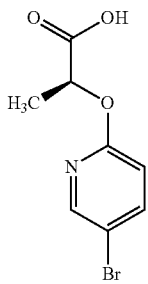

Formula (XXXI)

Embodiment 130 is a compound according to embodiment 119, wherein the compound of Formula (VII) is further defined by Formula (XXXII):

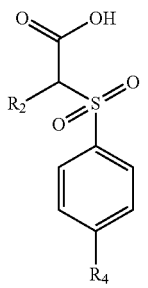

Formula (XXXII)

or a pharmaceutically acceptable salt, solvate, polymorph, or tautomer thereof; wherein R$_2$ is selected from the group consisting of —CH$_3$, —CH$_2$—CH$_3$, —CH(CH$_3$)$_2$, —C(CH$_3$)$_3$, —CH$_2$—CH$_2$—CH$_3$ and —CH$_2$—NH$_2$ and R$_4$ is selected from the group consisting of H, Br, Cl, F and I.

Embodiment 131 is a compound according to embodiment 130, wherein the compound of Formula (XXXII) is further defined by Formula (XXXIII):

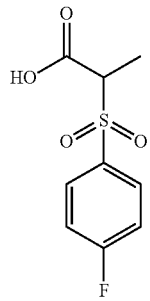

Formula (XXXIII)

Embodiment 132 is a compound according to embodiment 92, wherein the compound of Formula (I) is further defined by Formula (XXXIV):

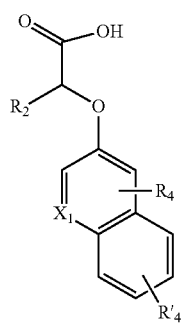

Formula (XXXIV)

or a pharmaceutically acceptable salt, solvate, polymorph, or tautomer thereof; wherein R$_2$ is selected from the group consisting of —CH$_3$, —CH$_2$—CH$_3$, —CH(CH$_3$)$_2$, —C(CH$_3$)$_3$, —CH$_2$—CH$_2$—CH$_3$ and —CH$_2$—NH$_2$; X$_1$ is N or C; and R$_4$ and R'$_4$ are independently selected from the group consisting of H, Br, Cl, F and I.

Embodiment 133 is a compound according to embodiment 132, wherein Formula (XXXIV) is further defined by Formula (XXXV):

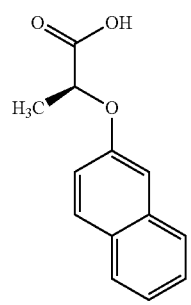

Formula (XXXV)

Embodiment 134 is a compound according to embodiment 92, wherein the compound of Formula (I) is further defined by any one of Formulas (XXXVI) to (LIX) as defined in embodiment 43.

Embodiment 135 is a compound of Formula (I.2):

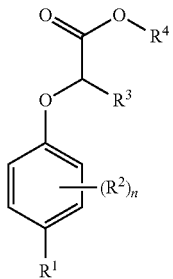

Formula (I.2)

wherein:
- $R^1$ is selected from the group consisting of F, Cl, Br, I, —CN, —$CF_3$, $C_{1-4}$ alkyl, $C_{1-4}$ alkenyl, $C_{1-4}$ alkynyl, $C_4$ cycloalkyl and —S—$CH_3$;
- $R^2$ is independently selected from the group consisting of hydrogen, deuterium, F, Cl, Br, I, —CN, —$CF_3$ and -oxime optionally substituted with $C_1$ alkyl;
- $R^3$ is selected from the group consisting of $C_{1-5}$ alkyl, $C_{1-5}$ alkenyl, $C_{3-5}$ cycloalkyl and $C_5$ cycloalkenyl, each of which may be optionally substituted with one or more, identical or different, substituents $R^5$;
- $R^4$ is selected from the group consisting of H or $C_{1-5}$ alkyl;
- $R^5$ is independently selected from the group consisting of F and OH; and
- n is an integer 0, 1 or 2;
- or a pharmaceutically acceptable salt, hydrate, polymorph, tautomer, or solvate thereof;
- with the proviso that when $R^1$ is Cl, $R^4$ is H and n is 0, then $R^3$ is not methyl or ethyl.

Embodiment 136 is a compound according to embodiment 035, wherein the compound is of Formula (II.2):

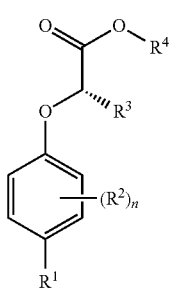

Formula (II)

wherein:
- $R^1$ is selected from the group consisting of F, Cl, Br, I, —CN, —$CF_3$, $C_{1-4}$ alkyl, $C_{1-4}$ alkenyl, $C_{1-4}$ alkynyl, $C_4$ cycloalkyl and —S—$CH_3$;
- $R^2$ is independently selected from the group consisting of hydrogen, deuterium, F, Cl, Br, I, —CN, —$CF_3$ and -oxime optionally substituted with $C_1$ alkyl;
- $R^3$ is selected from the group consisting of $C_{1-5}$ alkyl, $C_{1-5}$ alkenyl, $C_{3-5}$ cycloalkyl and $C_5$ cycloalkenyl, each of which may be optionally substituted with one or more, identical or different, substituents $R^5$;
- $R^4$ is selected from the group consisting of H and $C_{1-5}$ alkyl;
- $R^5$ is independently selected from the group consisting of F and OH; and
- n is an integer 0, 1 or 2;
- or a pharmaceutically acceptable salt, hydrate, polymorph, tautomer, or solvate thereof;
- with the proviso that when $R^1$ is Cl, $R^4$ is H and n is 0, then $R^3$ is not methyl or ethyl.

Embodiment 137 is a compound according to any one of the preceding embodiments, wherein $R^4$ is H.

Embodiment 138 is a compound according to any one of the preceding embodiments, wherein $R^4$ is the sodium counterion.

Embodiment 139 is a compound according to any one of the preceding embodiments, wherein n is 0.

Embodiment 140 is a compound according to any one of the preceding embodiments, wherein
- $R^1$ is selected from the group consisting of F, Cl, Br, I, —CN, —$CF_3$, $C_{1-4}$ alkyl, $C_{1-4}$ alkenyl, $C_{1-4}$ alkynyl, $C_4$ cycloalkyl and —S—$CH_3$;
- $R^3$ is is selected from the group consisting of $C_{1-5}$ alkyl, $C_{1-5}$ alkenyl, $C_{3-5}$ cycloalkyl and $C_5$ cycloalkenyl, each of which may be optionally substituted with one or more F; and
- $R^4$ is selected from the group consisting of H and $C_{1-5}$ alkyl, preferably H;
- n is 0;
- or a pharmaceutically acceptable salt, hydrate, polymorph, tautomer, or solvate thereof.

Embodiment 141 is a compound according to embodiment 140, wherein $R^3$ is selected from the group consisting of methyl, ethyl, n-propyl or isopropyl optionally substituted with one or more, identical or different, substituents $R^5$.

Embodiment 142 is a compound according to any one of the preceding embodiments, wherein $R^3$ is methyl.

Embodiment 143 is a compound according to any one of the preceding embodiments, wherein $R^3$ is ethyl Embodiment 144 is a compound according to any one of the preceding embodiments, wherein $R^3$ is n-propyl or isopropyl.

Embodiment 145 is a compound according to any one of the preceding embodiments, wherein $R^3$ is $C_{1-5}$ alkyl substituted with one or more F.

Embodiment 146 is a compound according to any one of the preceding embodiments, wherein $R^3$ is selected from the group consisting of —$CH_2F$, —$CHF_2$, —$CF_3$, —$CH_2CH_2F$, —$CH_2CHF_2$ and —$CH_2CF_3$, preferably —$CH_2F$.

Embodiment 147 is a compound according to any one of the preceding embodiments, wherein $R^3$ is $C_{2-5}$ alkenyl, optionally substituted with one or more, identical or different, substituents $R^5$.

Embodiment 148 is a compound according to any one of the preceding embodiments, wherein $R^3$ is selected from the group consisting of ethenyl, propenyl, isopropenyl, butenyl, isobutenyl and pentenyl, optionally substituted with one or more F.

Embodiment 149 is a compound according to any one of the preceding embodiments, wherein $R^3$ is $C_{3-5}$ cycloalkyl, optionally substituted with one or more F.

Embodiment 150 is a compound according to any one of the preceding embodiments, wherein $R^3$ is selected from the group consisting of cyclopropyl, cyclobutyl, cyclopentyl, cyclopropylmethyl, cyclopropylethyl and cyclobutylmethyl, optionally substituted with one or more F.

Embodiment 151 is a compound according to any one of the preceding embodiments, wherein $R^3$ is cycloalkenyl, optionally substituted with one or more F.

Embodiment 152 is a compound according to any one of the preceding embodiments, wherein $R^2$ is deuterium.

Embodiment 153 is a compound according to any one of the preceding embodiments, wherein the compound is of Formula (III.2):

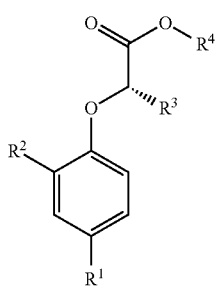

Formula (III.2)

wherein:
- $R^1$ is selected from the group consisting of Cl, Br, and I;
- $R^2$ is selected from the group consisting of deuterium, F, Cl, Br, I, and -oxime optionally substituted with $C_1$ alkyl;
- $R^3$ is selected from the group consisting of $C_{1-5}$ alkyl, $C_{1-5}$ alkenyl, $C_{3-5}$ cycloalkyl and $C_5$ cycloalkenyl, each of which may be optionally substituted with one or more F; and
- $R^4$ is selected from the group consisting of H or $C_{1-5}$ alkyl; preferably H.

or a pharmaceutically acceptable salt, hydrate, polymorph, tautomer, or solvate thereof.

Embodiment 154 is a compound according to any one of the preceding embodiments, wherein $R^3$ is selected from the group consisting of methyl, ethyl, n-propyl or isopropyl optionally substituted with one or more, identical or different, substituents $R^5$.

Embodiment 155 is a compound according to any one of the preceding embodiments, wherein $R^3$ is methyl.

Embodiment 156 is a compound according to any one of the preceding embodiments, wherein $R^3$ is ethyl Embodiment 157 is a compound according to any one of the preceding embodiments, wherein $R^3$ is n-propyl or isopropyl.

Embodiment 158 is a compound according to any one of the preceding embodiments, wherein $R^3$ is $C_{1-5}$ alkyl substituted with one or more F.

Embodiment 159 is a compound according to any one of the preceding embodiments, wherein $R^3$ is selected from the group consisting of —$CH_2F$, —$CHF_2$, —$CF_3$, —$CH_2CH_2F$, —$CH_2CHF_2$ and —$CH_2CF_3$, preferably —$CH_2F$.

Embodiment 160 is a compound according to any one of the preceding embodiments, wherein $R^3$ is $C_{2-5}$ alkenyl, optionally substituted with one or more, identical or different, substituents $R^5$.

Embodiment 161 is a compound according to any one of the preceding embodiments, wherein $R^3$ is selected from the group consisting of ethenyl, propenyl, isopropenyl, butenyl, isobutenyl and pentenyl, optionally substituted with one or more F.

Embodiment 162 is a compound according to any one of the preceding embodiments, wherein $R^3$ is $C_{3-5}$ cycloalkyl, optionally substituted with one or more F.

Embodiment 163 is a compound according to any one of the preceding embodiments, wherein $R^3$ is selected from the group consisting of cyclopropyl, cyclobutyl, cyclopentyl, cyclopropylmethyl, cyclopropylethyl and cyclobutylmethyl, optionally substituted with one or more F.

Embodiment 164 is a compound according to any one of the preceding embodiments, wherein $R^3$ is cycloalkenyl, optionally substituted with one or more F.

Embodiment 165 is a compound according to any one of any one of the preceding embodiments, wherein $R^1$ is different from $R^2$.

Embodiment 166 is a compound according to any one of the preceding embodiments, wherein the compound is of Formula (IV.2):

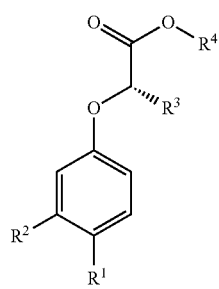

Formula (IV.2)

wherein:
- $R^1$ is selected from the group consisting of Cl, Br, and I;
- $R^2$ is selected from the group consisting of deuterium, F, Cl, Br, and I;
- $R^3$ is selected from the group consisting of $C_{1-5}$ alkyl, $C_{1-5}$ alkenyl, $C_{3-5}$ cycloalkyl and $C_5$ cycloalkenyl, each of which may be optionally substituted with one or more F; and
- $R^4$ is selected from the group consisting of H or $C_{1-5}$ alkyl; preferably H.

or a pharmaceutically acceptable salt, hydrate, polymorph, tautomer, or solvate thereof.

Embodiment 167 is a compound according to any one of the preceding embodiments, wherein $R^3$ is selected from the group consisting of methyl, ethyl, n-propyl or isopropyl optionally substituted with one or more, identical or different, substituents $R^5$.

Embodiment 168 is a compound according to any one of the preceding embodiments, wherein $R^3$ is methyl.

Embodiment 169 is a compound according to any one of the preceding embodiments, wherein $R^3$ is ethyl Embodiment 170 is a compound according to any one of the preceding embodiments, wherein $R^3$ is n-propyl or isopropyl.

Embodiment 171 is a compound according to any one of the preceding embodiments, wherein $R^3$ is $C_{1-5}$ alkyl substituted with one or more F.

Embodiment 172 is a compound according to any one of the preceding embodiments, wherein $R^3$ is selected from the group consisting of —$CH_2F$, —$CHF_2$, —$CF_3$, —$CH_2CH_2F$, —$CH_2CHF_2$ and —$CH_2CF_3$, preferably —$CH_2F$.

Embodiment 173 is a compound according to any one of the preceding embodiments, wherein $R^3$ is $C_{2-5}$ alkenyl, optionally substituted with one or more, identical or different, substituents $R^5$.

Embodiment 174 is a compound according to any one of the preceding embodiments, wherein $R^3$ is selected from the group consisting of ethenyl, propenyl, isopropenyl, butenyl, isobutenyl and pentenyl, optionally substituted with one or more F.

Embodiment 175 is a compound according to any one of the preceding embodiments, wherein $R^3$ is $C_{3-5}$ cycloalkyl, optionally substituted with one or more F.

Embodiment 176 is a compound according to any one of the preceding embodiments, wherein $R^3$ is selected from the group consisting of cyclopropyl, cyclobutyl, cyclopentyl, cyclopropylmethyl, cyclopropylethyl and cyclobutylmethyl, optionally substituted with one or more F.

Embodiment 177 is a compound according to any one of the preceding embodiments, wherein $R^3$ is cycloalkenyl, optionally substituted with one or more F.

Embodiment 178 is a compound according to any one of the preceding embodiments, wherein $R^1$ is different from $R^2$.

Embodiment 179 is a compound according to any one of the preceding embodiments, wherein n is 2.

Embodiment 180 is a compound according to any one of the preceding embodiments, wherein the compound is of Formula (V) or (VI):

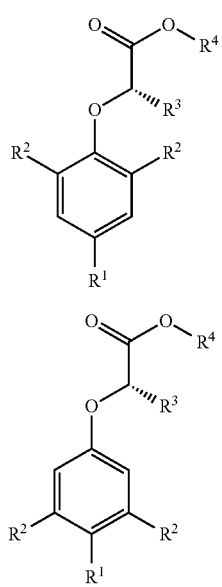

Formula (V)

Formula (VI)

wherein:
$R^1$ is Br, Cl or I;
$R^2$ is independently deuterium, F, Cl, Br, or I;
$R^3$ is selected from the group consisting of $C_{1-5}$ alkyl, $C_{1-5}$ alkenyl, $C_{3-5}$ cycloalkyl and $C_5$ cycloalkenyl, each of which may be optionally substituted with one or more F; and
$R^4$ is selected from the group consisting of H or $C_{1-5}$ alkyl; preferably H;
or a pharmaceutically acceptable salt, hydrate, polymorph, tautomer, or solvate thereof.

Embodiment 181 is a compound according to any one of the preceding embodiments, wherein $R^3$ is selected from the group consisting of methyl, ethyl, n-propyl or isopropyl optionally substituted with one or more, identical or different, substituents $R^5$.

Embodiment 182 is a compound according to any one of the preceding embodiments, wherein $R^3$ is methyl.

Embodiment 183 is a compound according to any one of the preceding embodiments, wherein $R^3$ is ethyl Embodiment 184 is a compound according to any one of the preceding embodiments, wherein $R^3$ is n-propyl or isopropyl.

Embodiment 185 is a compound according to any one of the preceding embodiments, wherein $R^3$ is $C_{1-5}$ alkyl substituted with one or more F.

Embodiment 186 is a compound according to any one of the preceding embodiments, wherein $R^3$ is selected from the group consisting of —$CH_2F$, —$CHF_2$, —$CF_3$, —$CH_2CH_2F$, —$CH_2CHF_2$ and —$CH_2CF_3$, preferably —$CH_2F$.

Embodiment 187 is a compound according to any one of the preceding embodiments, wherein $R^3$ is $C_{2-5}$ alkenyl, optionally substituted with one or more, identical or different, substituents $R^5$.

Embodiment 188 is a compound according to any one of the preceding embodiments, wherein $R^3$ is selected from the group consisting of ethenyl, propenyl, isopropenyl, butenyl, isobutenyl and pentenyl, optionally substituted with one or more F.

Embodiment 189 is a compound according to any one of the preceding embodiments, wherein $R^3$ is $C_{3-5}$ cycloalkyl, optionally substituted with one or more F.

Embodiment 190 is a compound according to any one of the preceding embodiments, wherein $R^3$ is selected from the group consisting of cyclopropyl, cyclobutyl, cyclopentyl, cyclopropylmethyl, cyclopropylethyl and cyclobutylmethyl, optionally substituted with one or more F.

Embodiment 191 is a compound according to any one of the preceding embodiments, wherein $R^3$ is cycloalkenyl, optionally substituted with one or more F.

Embodiment 192 is a compound according to any one of the preceding embodiments, wherein $R^1$ is different from $R^2$.

Embodiment 193 is a compound according to any one of the preceding embodiments, wherein $R^1$ is Br.

Embodiment 194 is a compound according to any one of the preceding embodiments, wherein $R^2$ is deuterium or F.

Embodiment 195 is a compound according to any one of the preceding embodiments, wherein the oxime is an aldoxime.

Embodiment 196 is a compound according to any one of the preceding embodiments, wherein the -oxime optionally substituted with $C_1$ alkyl is

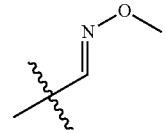 [SMILES: */C=N/OC]

Embodiment 197 is a compound according to any one of the preceding embodiments, wherein, the compound is selected from the group consisting of:

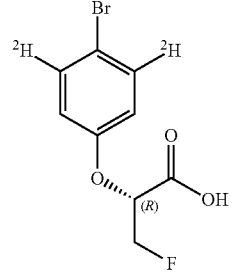

Compound A-1

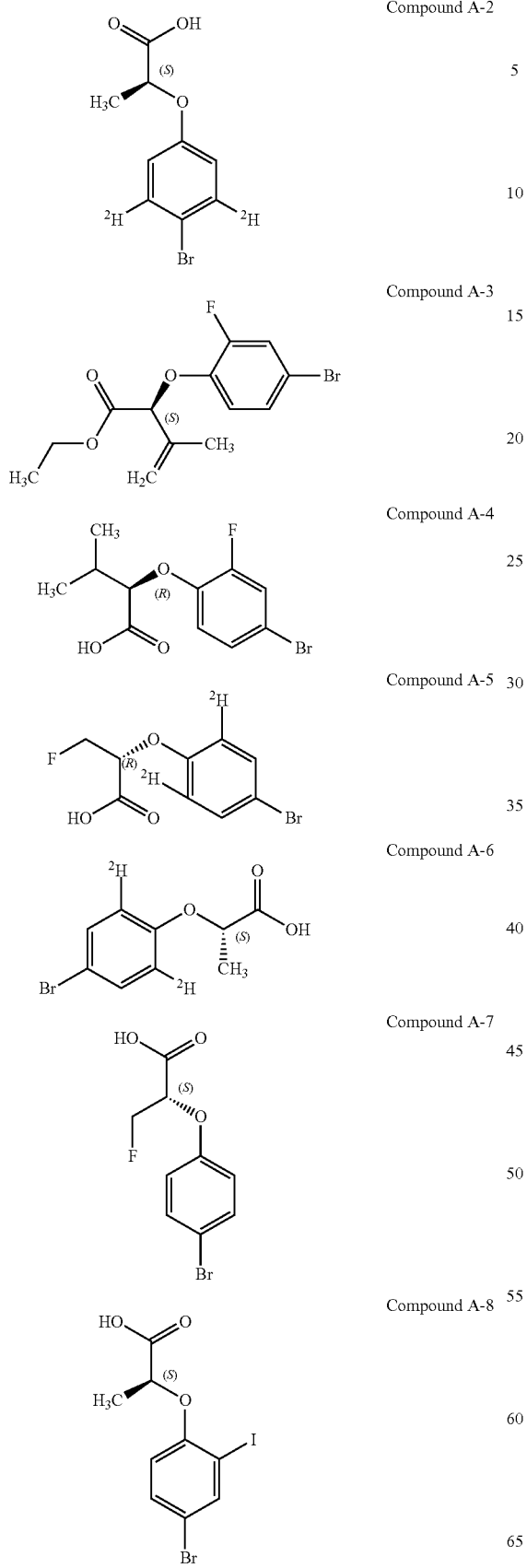
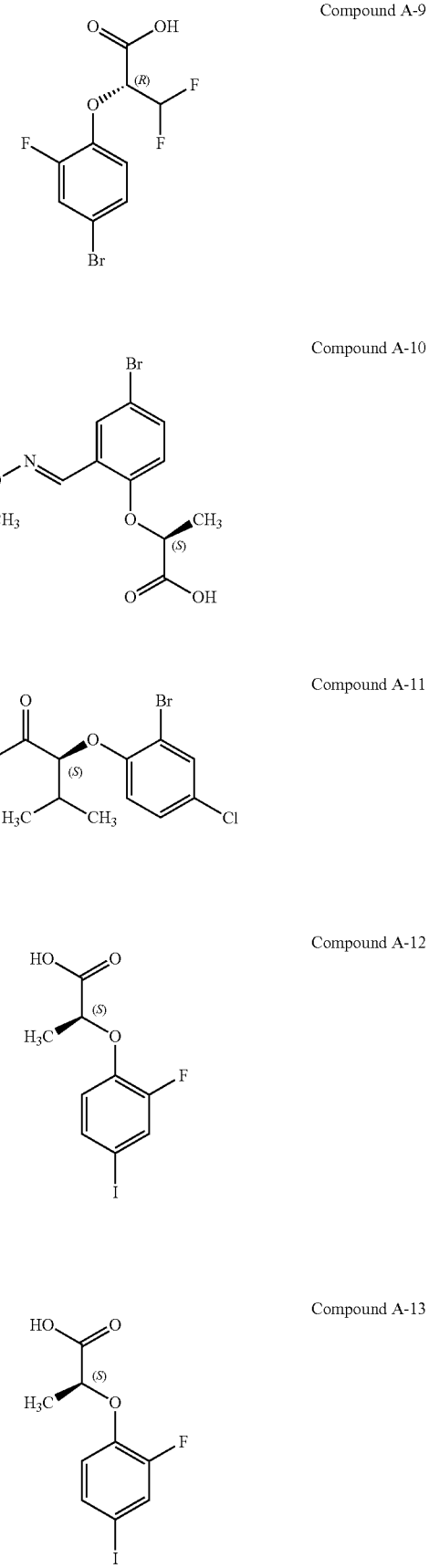

Compound A-14
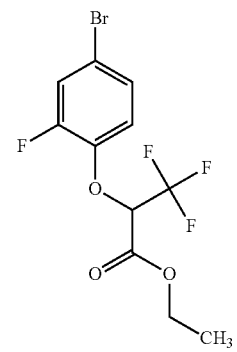
Compound A-15
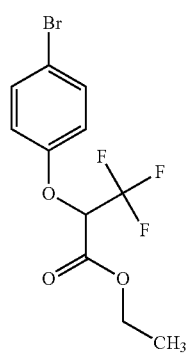
Compound A-16
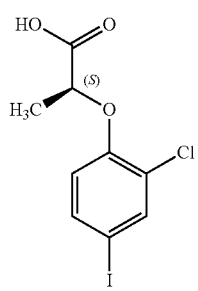
Compound A-17
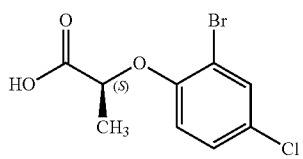
Compound A-18
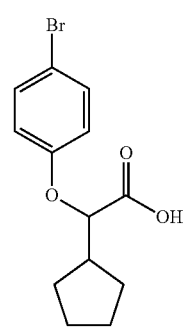
Compound A-19
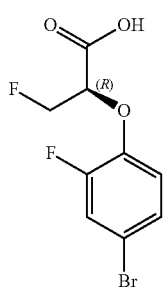
Compound A-20
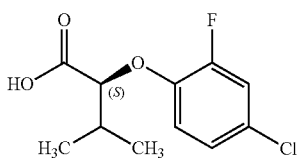
Compound A-21
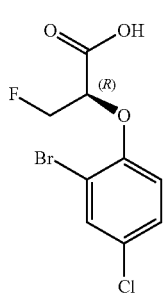
Compound A-22
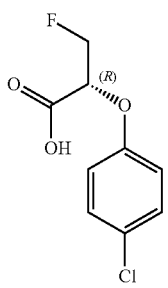
Compound A-23
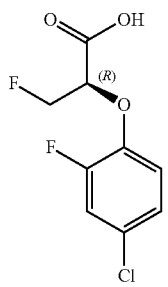
Compound A-24
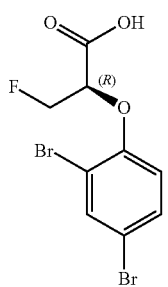

-continued
Compound A-25
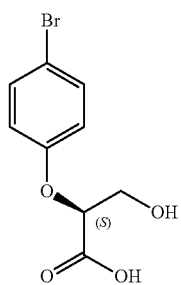
Compound A-26
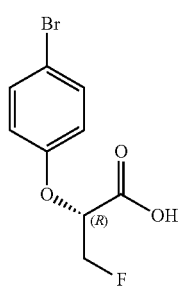
Compound A-27
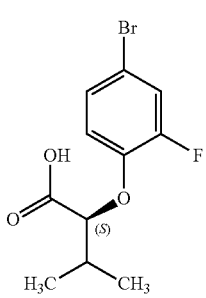
Compound A-28
Compound A-29
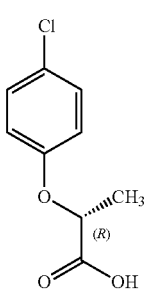
-continued
Compound A-30
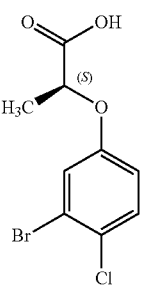
Compound A-31
Compound A-32
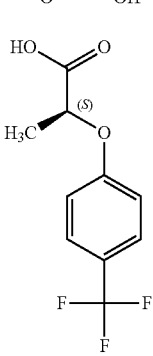
Compound A-33
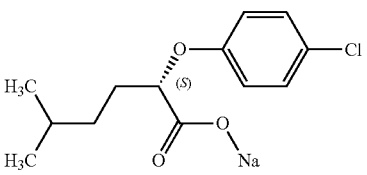
Compound A-34
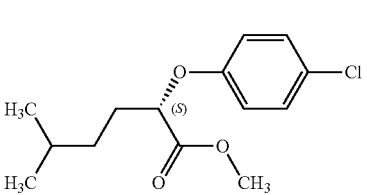
Compound A-35
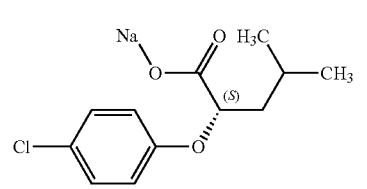

-continued
Compound A-36
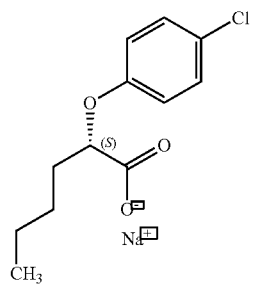
Compound A-37
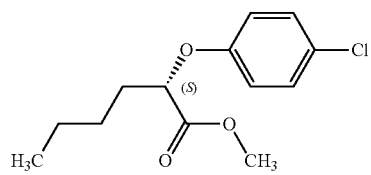
Compound A-38
Compound A-39
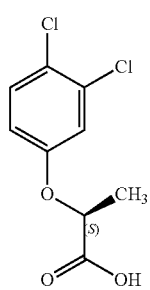
Compound A-40
-continued
Compound A-41
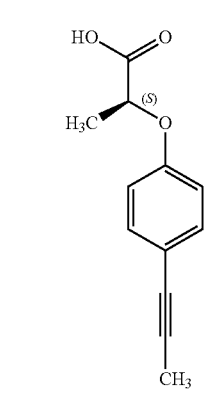
Compound A-42
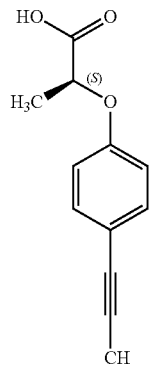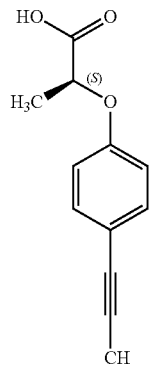
Compound A-43
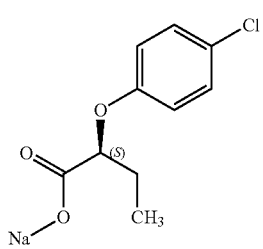
Compound A-44
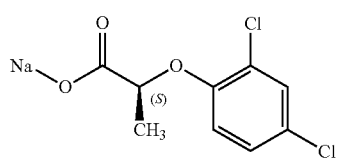
Compound A-45
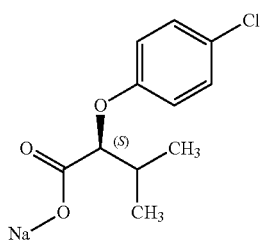
Compound A-46
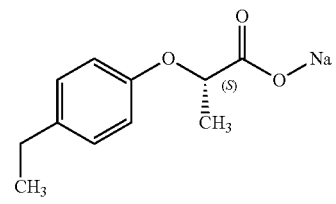

Compound A-47

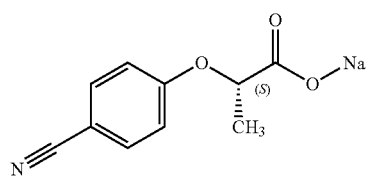

Compound A-48

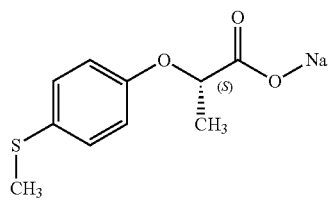

Compound A-49

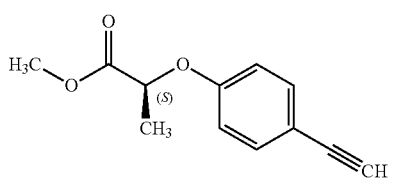

Compound A-50

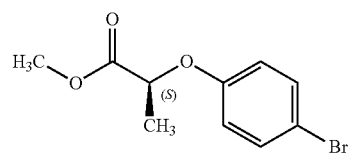

Compound A-51

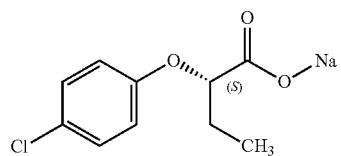

Compound A-52

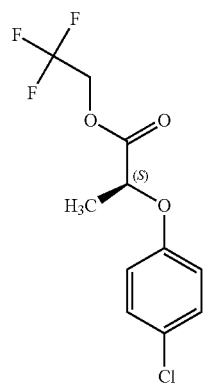

Compound A-53

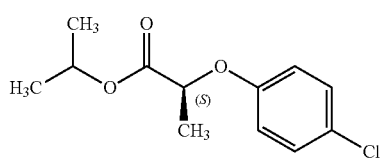

Compound A-54

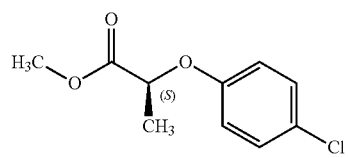

Compound A-55

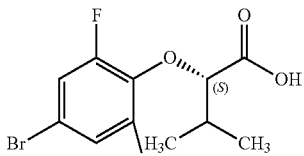

Compound A-56

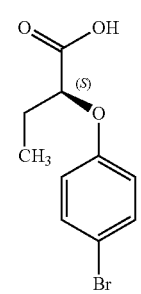

Compound A-57

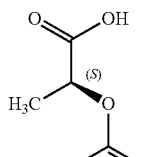

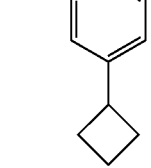

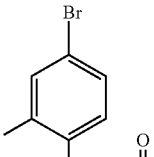

Compound A-58

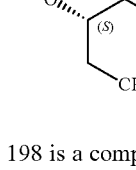

Embodiment 198 is a compound according to any one of the proceeding embodiments, wherein the compound is selected from the group consisting of:
(2R)-2-[4-bromo(3,5-$^2$H$_2$)phenoxy]-3-fluoropropanoic acid;
(2S)-2-[4-bromo(3,5-$^2$H$_2$)phenoxy]propanoic acid;
ethyl (2S)-2-(4-bromo-2-fluorophenoxy)-3-methylbut-3-enoate;
(2R)-2-(4-bromo-2-fluorophenoxy)-3-methylbutanoic acid;
(2R)-2-[4-bromo(2,6-$^2$H$_2$)phenoxy]-3-fluoropropanoic acid;
(2S)-2-[4-bromo(2,6-$^2$H$_2$)phenoxy]propanoic acid;
(2S)-2-(4-bromophenoxy)-3-fluoropropanoic acid;
(2S)-2-(4-bromo-2-iodophenoxy)propanoic acid;
(2R)-2-(4-bromo-2-fluorophenoxy)-3,3-difluoropropanoic acid;

(2S)-2-{4-bromo-2-[(1E)-(methoxyimino)methyl]phenoxy}propanoic acid;
(2S)-2-(2-bromo-4-chlorophenoxy)-3-methylbutanoic acid;
(2S)-2-(2-fluoro-4-iodophenoxy)propanoic acid;
(2S)-2-(2-bromo-4-iodophenoxy)propanoic acid;
ethyl 2-(4-bromo-2-fluorophenoxy)-3,3,3-trifluoropropanoate;
ethyl 2-(4-bromophenoxy)-3,3,3-trifluoropropanoate;
(2S)-2-(2-chloro-4-iodophenoxy)propanoic acid;
(2S)-2-(2-bromo-4-chlorophenoxy)propanoic acid;
2-(4-bromophenoxy)-2-cyclopentylacetic acid;
(2R)-2-(4-bromo-2-fluorophenoxy)-3-fluoropropanoic acid;
(2S)-2-(4-chloro-2-fluorophenoxy)-3-methylbutanoic acid;
(2R)-2-(2-bromo-4-chlorophenoxy)-3-fluoropropanoic acid;
(2R)-2-(4-chlorophenoxy)-3-fluoropropanoic acid;
(2R)-2-(4-chloro-2-fluorophenoxy)-3-fluoropropanoic acid;
(2R)-2-(2,4-dibromophenoxy)-3-fluoropropanoic acid;
(2S)-2-(4-bromophenoxy)-3-hydroxypropanoic acid;
(2R)-2-(4-bromophenoxy)-3-fluoropropanoic acid;
(2S)-2-(4-bromo-2-fluorophenoxy)-3-methylbutanoic acid;
(2R)-2-(4-bromo-2-fluorophenoxy)propanoic acid;
(2R)-2-(4-chlorophenoxy)propanoic acid;
(2S)-2-(3-bromo-4-chlorophenoxy)propanoic acid;
(2S)-2-(4-bromo-2-fluorophenoxy)propanoic acid;
(2S)-2-[4-(trifluoromethyl)phenoxy]propanoic acid;
sodium (2S)-2-(4-chlorophenoxy)-5-methylhexanoate;
methyl (2S)-2-(4-chlorophenoxy)-5-methylhexanoate;
sodium (2S)-2-(4-chlorophenoxy)-4-methylpentanoate;
sodium (2S)-2-(4-chlorophenoxy)hexanoic acid;
methyl (2S)-2-(4-chlorophenoxy)hexanoate;
(2S)-2-(4-chloro-2-fluorophenoxy)propanoic acid;
(2S)-2-(3,4-dichlorophenoxy)propanoic acid;
(2S)-2-(2,4-dibromophenoxy)propanoic acid;
(2S)-2-[4-(prop-1-yn-1-yl)phenoxy]propanoic acid;
(2S)-2-(4-ethynylphenoxy)propanoic acid;
sodium (2S)-2-(4-chlorophenoxy)butanoate;
sodium (2S)-2-(2,4-dichlorophenoxy)propanoate;
sodium (2S)-2-(4-chlorophenoxy)-3-methylbutanoate;
sodium (2S)-2-(4-ethylphenoxy)propanoate;
sodium (2S)-2-(4-cyanophenoxy)propanoate;
sodium (2S)-2-[4-(methylsulfanyl)phenoxy]propanoate;
methyl (2S)-2-(4-ethynylphenoxy)propanoate;
methyl (2S)-2-(4-bromophenoxy)propanoate;
methyl (2S)-2-(4-chlorophenoxy)butanoate;
2,2,2-trifluoroethyl (2S)-2-(4-chlorophenoxy)propanoate;
propan-2-yl (2S)-2-(4-chlorophenoxy)propanoate;
methyl (2S)-2-(4-chlorophenoxy)propanoate;
(2S)-2-(4-bromo-2,6-difluorophenoxy)-3-methylbutanoic acid;
(2S)-2-(4-bromophenoxy)butanoic acid;
(2S)-2-(4-cyclobutylphenoxy)propanoic acid; and
(2S)-2-(4-bromo-2-fluorophenoxy)butanoic acid.

Embodiment 199 is a compound according to any one of the preceding embodiments, wherein the compound has activity on ClC-1 receptor.

Embodiment 200 is a compound according to any one of the preceding embodiments, wherein the compound is an inhibitor of the ClC-1 ion channel.

Embodiment 201 is a compound according to any one of the preceding embodiments, wherein the $EC_{50}$<50 µM, preferably <40 µM, more preferably <30 µM, more preferably <20 µM, more preferably <15 µM, even more preferably <10 µM and most preferably <5 µM.

Embodiment 202 is a compound according to any one of the preceding embodiments, wherein the recovery of force in muscles with neuromuscular dysfunction is >5%, preferably >10%, more preferably >15%, more preferably >20%, more preferably >25%, even more preferably >30% and most preferably >35%.

Embodiment 203 is a compound according to any one of the preceding embodiments, wherein the compound improves the recovered force in isolated rat soleus muscles after exposure to tubocurarine.

Embodiment 204 is a composition comprising the compound of any one of the preceding embodiments.

Embodiment 205 is a composition according to any one of the preceding embodiments, wherein the composition is a pharmaceutical composition.

Embodiment 206 is a compound according to any one of the preceding embodiments, or the composition according to any one of embodiments 204 to 205, for use as a medicament.

Embodiment 207 is a composition according to any one of embodiments 204 to 206, wherein the composition further comprises a pharmaceutically acceptable carrier.

Embodiment 208 is a composition according to any one of embodiments 204 to 207 wherein the composition further comprises at least one further active agent.

Embodiment 209 is a composition according to embodiments 208, wherein said further active agent is suitable for treating, preventing or ameliorating said neuromuscular disorder.

Embodiment 210 is a composition according to any one of embodiments 208 to 209, wherein said further active agent is an acetylcholine esterase inhibitor.

Embodiment 211 is a composition according to embodiment 210, wherein said acetylcholine esterase inhibitor is selected from the group consisting of delta-9-tetrahydrocannabinol, carbamates, physostigmine, neostigmine, pyridostigmine, ambenonium, demecarium, rivastigmine, phenanthrene derivatives, galantamine, piperidines, donepezil, tacrine, edrophonium, huperzine, ladostigil, ungeremine and lactucopicrin.

Embodiment 212 is a composition according to embodiment 210, wherein said acetylcholine esterase inhibitor is neostigmine or pyridostigmine.

Embodiment 213 is a composition according to any one of embodiments 208 to 209, wherein said further active agent is suggamadex.

Embodiment 214 is a composition according to any one of embodiments 208 to 209, wherein said further active agent is tirasemtiv or CK-2127107.

Embodiment 215 is a composition according to any one of embodiments 208 to 209, wherein said further active agent is 3,4-aminopyridine.

Embodiment 216 is a method for manufacturing the compound according to any one of embodiments 135 to 198, the method comprising the steps of
a. reacting a compound having a formula of

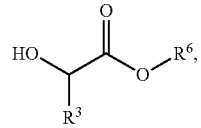

(VIII)

wherein $R^3$ is as defined in any one of embodiments 135 to 198 and $R^6$ is selected from the group consisting of alkyl, alkenyl, akynyl, cycloalkyl, cycloalkenyl, aromatic ring, heteroaromatic ring and -alkylene-Si-alkyl, with first a reagent capable of converting the alcohol (OH) into a leaving group and secondly with a compound having a formula of

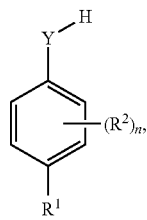
(VII)

wherein $R^1$, $R^2$ and n are as defined in any one of embodiments 135 to 198 and Y is O to generate a compound having a formula of

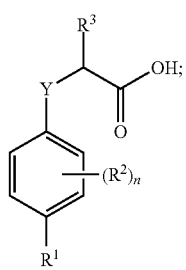
(X)

and b. reacting the product compound of a) with an ester hydrolysing reagent thus generating a compound according to any one of embodiments 135 to 198.

Embodiment 217 is a method for manufacturing the compound according to any one of embodiments 135 to 198, the method comprising the steps of b. reacting a compound having a formula of

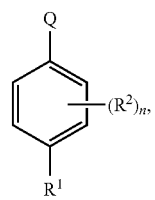
(XI)

wherein $R^1$, $R^2$ and n are as defined in any one of items v and Q is a leaving group selected from the group consisting of fluorine and iodine, with a compound having a formula of

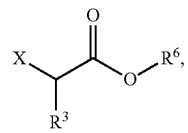
(XII)

wherein $R^3$ is as defined in any one of embodiments 135 to 198 and $R^6$ is selected from the group consisting of alkyl, alkenyl, akynyl, cycloalkyl, cycloalkenyl, aromatic ring, heteroaromatic ring and -alkylene-Si-alkyl to generate a compound having a formula of

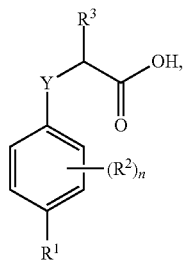
(X)

wherein Y is O; and c. reacting the product compound of a) with an ester hydrolysing reagent thus generating a compound according to any one of embodiments 135 to 198.

Embodiment 218 is a method for manufacturing the compound according to any one of embodiments 135 to 198, the method comprising the steps of c. reacting a compound having a formula of

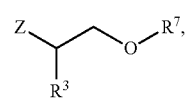
(XIII)

wherein $R^3$ is as defined in any one of embodiments 135 to 198, Z is OH and $R^7$ is selected from the group consisting of —Si-alkyl, with first a reagent capable of converting the alcohol (Z) into a leaving group and secondly with a compound having a formula of

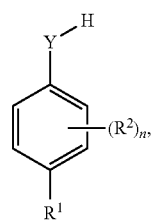
(VII)

wherein $R^1$, $R^2$ and n are as defined in any one of embodiments 135 to 198 and Y is O to generate a compound having a formula of

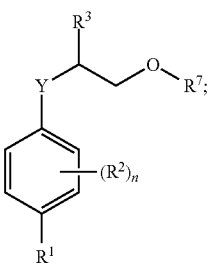
(XIV)

c. reacting the product compound of a) with an ether cleaving reagent to generate a compound having a formula of

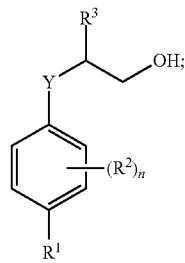

(XV)

and d. reacting the product compound of b) with an oxidising agent thus generating a compound according to any one of embodiments 135 to 198.

Embodiment 219 is a compound according to any one of embodiments 135 to 198 for use in treating, ameliorating and/or preventing a neuromuscular disorder, and/or for use in reversing and/or ameliorating a neuromuscular blockade.

Embodiment 220 is a compound for use according to any one of the preceding embodiments, wherein the compound improves the recovered force in isolated rat soleus muscles after exposure to tubocurarine.

Embodiment 221 is a compound for use according to any one of the preceding embodiments wherein the neuromuscular disorder is myasthenia gravis.

Embodiment 222 is a compound for use according to any one of the preceding embodiments wherein the neuromuscular disorder is autoimmune myasthenia gravis.

Embodiment 223 is a compound for use according to any one of the preceding embodiments wherein the neuromuscular disorder is congenital myasthenia gravis.

Embodiment 224 is a compound for use according to any one of the preceding embodiments wherein the neuromuscular disorder is Lambert-Eaton Syndrome.

Embodiment 225 is a compound for use according to any one of the preceding embodiments wherein the neuromuscular disorder is critical illness myopathy.

Embodiment 226 is a compound for use according to any one of the preceding embodiments wherein the neuromuscular disorder is amyotrophic lateral sclerosis (ALS).

Embodiment 227 is a compound for use according to any one of the preceding embodiments wherein the neuromuscular disorder is spinal muscular atrophy (SMA).

Embodiment 228 is a compound for use according to any one of the preceding embodiments wherein the neuromuscular disorder is critical illness myopathy (CIM).

Embodiment 229 is a compound for use according to any one of the preceding embodiments wherein the neuromuscular disorder is Charcot-Marie tooth disease (CMT).

Embodiment 230 is a compound for use according to any one of the preceding embodiments wherein the neuromuscular disorder is sarcopenia.

Embodiment 231 is a compound for use according to any one of the preceding embodiments wherein the neuromuscular disorder is reversal diabetic polyneuropathy.

Embodiment 232 is a compound for use according to any one of the preceding embodiments wherein the neuromuscular disorder is selected from the group consisting of Guillain-Barre syndrome, poliomyelitis, post-polio syndrome, chronic fatigue syndrome, and critical illness polyneuropathy.

Embodiment 233 is a compound for use according to any one of the preceding embodiments, wherein the compound is for use in the treatment of symptoms of an indication selected from the group consisting of myasthenia gravis (such as autoimmune and congenital myasthenia gravis), Lambert-Eaton Syndrome, critical illness myopathy, amyotrophic lateral sclerosis (ALS), spinal muscular atrophy (SMA), critical illness myopathy (CIM), reversal diabetic polyneuropathy, Guillain-Barre syndrome, poliomyelitis, post-polio syndrome, chronic fatigue syndrome, and critical illness polyneuropathy.

Embodiment 234 is a compound for use according to any one of the preceding embodiments wherein the neuromuscular disorder has been induced by a neuromuscular blocking agent.

Embodiment 235 is a compound for use according to any one of the preceding embodiments, wherein the neuromuscular blockade is neuromuscular blockade after surgery.

Embodiment 236 is a compound for use according to any one of the preceding embodiments, wherein the neuromuscular blockade is drug induced.

Embodiment 237 is a compound for use according to embodiment 215, wherein the drug is an antibiotic.

Embodiment 238 is a compound for use according to embodiment 215, wherein the drug is a non-depolarizing neuromuscular blocker.

Embodiment 239 is a compound for use according to any one of the preceding embodiments, wherein said compound further has been modified in order to increase its half-life when administered to a patient, in particular its plasma half-life.

Embodiment 240 is a compound for use according to any one of the preceding embodiments, wherein said compound further comprises a moiety conjugated to said compound, thus generating a moiety-conjugated compound.

Embodiment 241 is a compound for use according to any one of the preceding embodiments, wherein the moiety-conjugated compound has a plasma and/or serum half-life being longer than the plasma and/or serum half-life of the non-moiety conjugated compound.

Embodiment 242 is a compound for use according to any one of the preceding embodiments, wherein the moiety conjugated to the compound is one or more type(s) of moieties selected from the group consisting of albumin, fatty acids, polyethylene glycol (PEG), acylation groups, antibodies and antibody fragments.

Embodiment 243 is a compound for use according to any one of the preceding embodiments, wherein said compound is comprised in a composition.

Embodiment 244 is a compound for use according to any one of the preceding embodiments, wherein the composition is a pharmaceutical composition.

Embodiment 245 is a compound for use according to any one of the preceding embodiments, wherein the composition further comprises a pharmaceutically acceptable carrier.

Embodiment 246 is a compound for use according to any one of the preceding embodiments, wherein the composition further comprises at least one further active agent.

Embodiment 247 is a compound for use according to any one of the preceding embodiments, wherein said further active agent is suitable for treating, preventing or ameliorating said neuromuscular disorder.

Embodiment 248 is a compound for use according to any one of the preceding embodiments, wherein said further active agent is an acetylcholine esterase inhibitor.

Embodiment 249 is a compound for use according to any one of the preceding embodiments, wherein said acetylcholine esterase inhibitor is selected from the group consisting of Delta9-tetrahydrocannabinol, carbamates, physostigmine, neostigmine, pyridostigmine, ambenonium, demecarium, rivastigmine, phenanthrene derivatives, galantamine, piperidines, donepezil, tacrine, edrophonium, huperzine, ladostigil, ungeremine and lactucopicrin.

Embodiment 250 is a compound for use according to any one of the preceding embodiments, wherein said acetylcholine esterase inhibitor is neostigmine or pyridostigmine.

Embodiment 251 is a compound for use according to any one of the preceding embodiments, wherein said further active agent is suggamadex.

Embodiment 252 is a compound for use according to any one of the preceding embodiments, wherein said further active agent is tirasemtiv or CK-2127107.

Embodiment 253 is a compound for use according to any one of the preceding embodiments, wherein said further active agent is 3,4-aminopyridine.

Embodiment 254 is a method of treating, preventing and/or ameliorating a neuromuscular disorder, said method comprising administering a therapeutically effective amount of the compound as defined in any one of the preceding embodiments to a person in need thereof.

Embodiment 255 is a method of using of a compound as defined in any one of embodiments 135 to 198, for the manufacture of a medicament for the treatment, prevention and/or amelioration of a neuromuscular disorder, and/or for reversing and/or ameliorating of a neuromuscular blockade.

Embodiment 256 is a method of reversing and/or ameliorating a neuromuscular blockade, said method comprising administering a therapeutically effective amount of the compound as defined in any one of the preceding embodiments to a person in need thereof.

Embodiment 257 is a method for recovery of neuromuscular transmission, said method comprising administering a therapeutically effective amount of the compound as defined in any one of the preceding embodiments to a person in need thereof.

Embodiment 258 is a method for recovering neuromuscular transmission, the method comprising administering a compound as defined in any one of the preceding embodiments to an individual in need thereof.

EXAMPLES

Materials and Methods
Chemicals

Compounds for testing were obtained from different suppliers including Enamine, Vitas, and CanAm Bioresearch. For synthesis of particular compounds please see below.

General Synthetic Strategies

Compounds of Formula (I.2) may be synthesized by the following synthetic strategies, general methods I-K:

NMR Spectra $^1$H-NMR spectra were recorded on a Bruker AM-300 spectrometer and were calibrated using residual nondeuterated solvent as internal reference. Spectra were processed using Spinworks version 4.0 (developed by Dr. Kirk Marat, Department of Chemistry, University of Manitoba).

HPLC Method 1

The product was analysed by Waters 2695 HPLC consisting of a Waters 996 photodiode array detector, Kromasil Eternity C18, 5 μm, 4.6×150 mm column. Flow rate: 1 mL/minute, run time 20 minutes. Solvent A: methanol; solvent B: 0.1% formic acid in water. Gradient 0-100% Solvent B over 15 minutes with monitoring at 280 nm.

HPLC Method 2

Waters Acquity UPLC, X-Select; column: Waters X-Select UPLC C18, 1.7 μm, 2.1×30 mm. Solvent A: 0.1% formic acid in water; solvent B: 0.1% formic acid in MeCN. Gradient 5-95% Solvent B over 10 minutes; detector: diode array.

Statistics

Figure 4A:
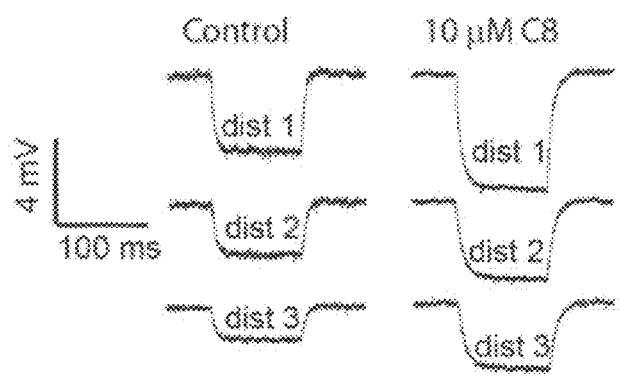
FIGS. 4A-4C. A three-electrode technique was used to determine the effect of clofibric acid derivatives on the resting membrane conductance, Gm. Three electrodes were inserted into the same muscle fiber enabling recordings of the membrane potential response to the injection of square current pulses at three inter-electrode distances (dist1<dist2<dist3).
Figure 6E:
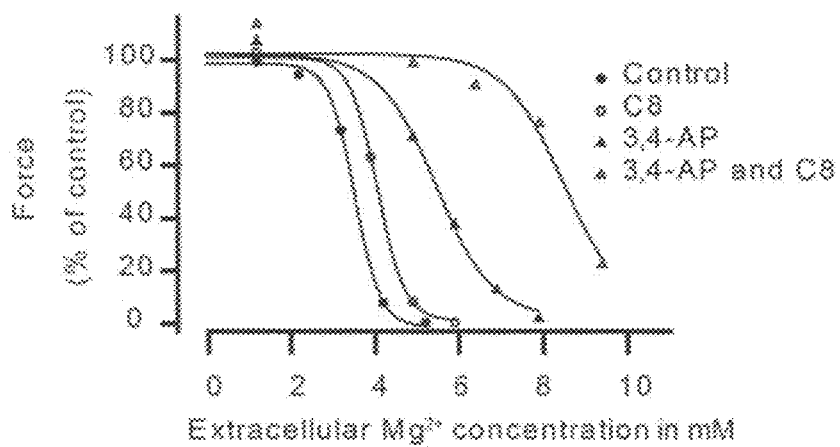

All data are expressed as mean with SEM. Significant difference between groups was ascertained using a Students t-test (paired for contra-lateral muscles). Statistical analysis was performed using Sigmaplot 12.0 including fitting of data (FIG. 4C, FIG. 5E, FIG. 6E) to a four parameter sigmoidal function to get Kd values for Tables 3-5. Categorical data was tested using Fishers Exact test. Groups were considered significantly different for P-values<0.05.

Synthetic Method a, Mitsunobu Coupling, Exemplified by (2S)-2-[(4-chloronaphthalen-1-yl)oxy]propanoic Acid

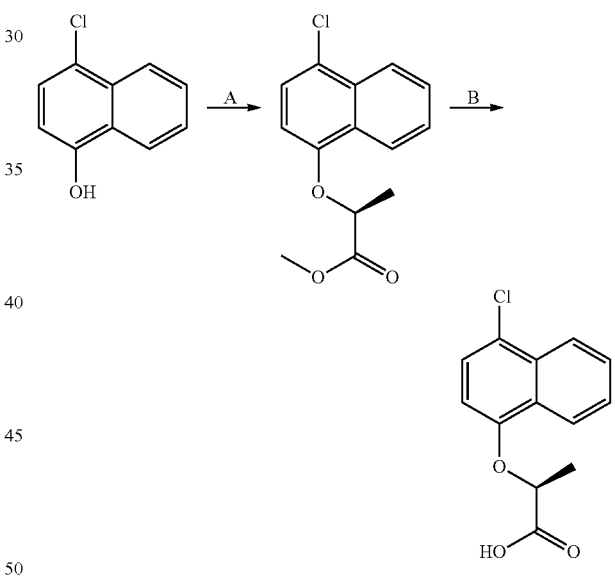

Procedure for Step A

To a solution of starting compound, Ph$_3$P, and ((R)-methyl 2-hydroxypropanoate in a solvent like DCM was added DEAD at 0° C. After stirring for 1 to 24 h at room temperature, the reaction completion was observed by NMR testing of a sample. Aqueous workup was performed. The compound was purified by chromatography.

Procedure for Step C

To a solution of the product of Step A in ethanol was added an aqueous solution of an alkali like KOH. The resulting mixture was refluxed for 1-12 h, and reaction was monitored by TLC. At the end of reaction, the mixture was subjected to an aqueous/acidic work up using a solvent like DCM or an ether. The compound was purified by chromatography if necessary.

Synthetic Method B, Displacement Coupling, Exemplified by (2S)-2-[(4-chlorophenyl)amino]propanoic Acid

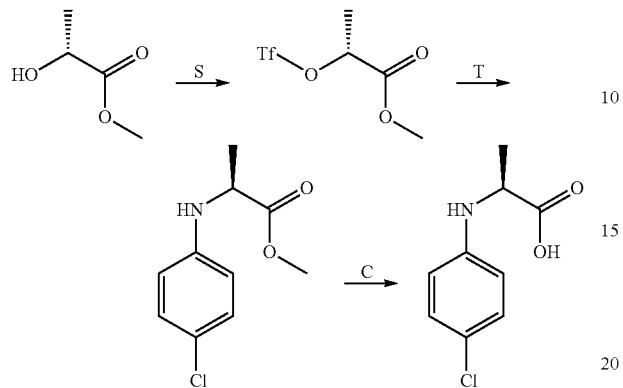

Procedure for Step S

To a cold solution of pyridine in a solvent like DCM was added trifluoromethanesulfonic anhydride at below 0° C. After stirring for 5-60 min, (R)-methyl 2-hydroxypropanoate was added. The mixture was stirred for 1-10 h at room temperature, filtered, and the filtrate was partially evaporated.

Procedure for Step T

To a mixture of 4-chloroaniline, a base like TEA and a solvent like DCM or DMF was added freshly prepared compound of step S at 0-5° C. The resulting mixture was stirred at 35° C. for 4 h, diluted with water, and extracted with DCM when the phases do not separate. Removal of the solvent yields the compound.

Procedure for Step C

See Step C in Synthetic Method A above.

Synthetic Method C, SNA, Displacement Coupling, Exemplified by (2S)-2-(4-bromophenoxy)-3-methylbutanoic Acid

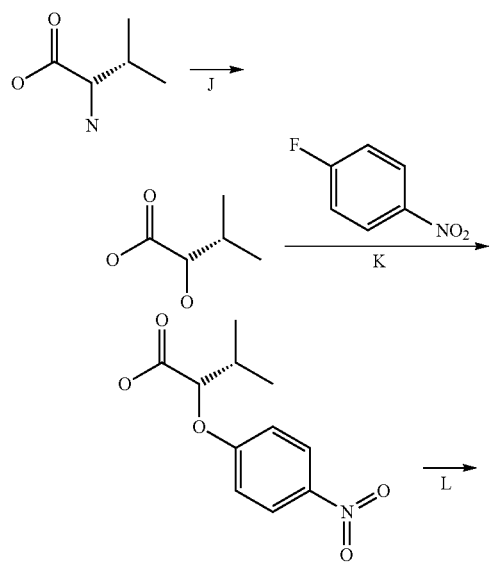

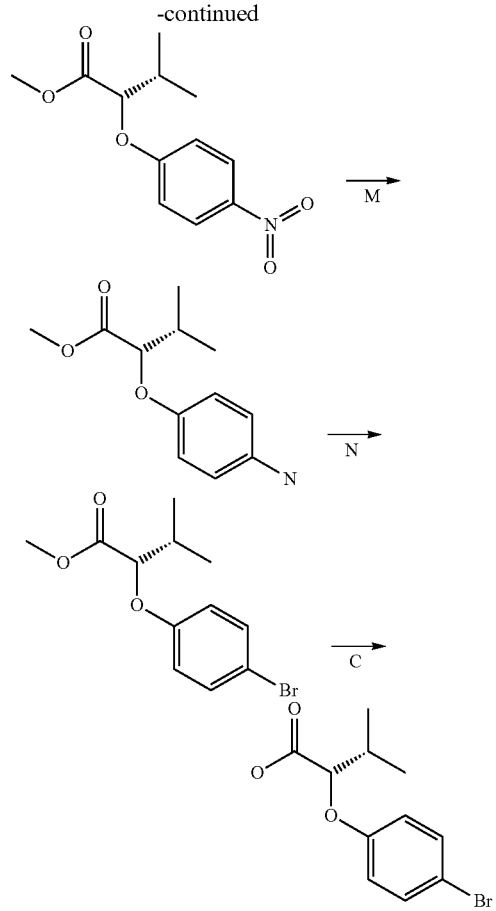

Procedure for Step J

To a solution of acid amino acid in 1N $H_2SO_4$, a solution of $NaNO_2$ in minimal quantity of water was added under cooling. The resulted mixture was stirred at room temperature for 1-3 days, saturated with $Na_2SO_4$, and extracted with a solvent like methyl-tert-butyl ether or DCM. The organic layer was evaporated.

Procedure for Step K

To a suspension of NaH in DMF a solution of the product of step J in DMF was added. After stirring, p-fluoronitrobenzene or the desired electrophile was added and stirring continued at 100° C. for 3-48 h. The mixture was diluted a solution of $NH_4Cl$ and $K_2CO_3$ at room temperature, and extracted with a solvent like methyl-tert-butyl ether or ethyl acetate. The water layer was acidified with 3N HCl and extracted with methyl-tert-butyl ether or ethyl acetate. The organic layer was evaporated.

Procedure for Step L

To a 0° C. solution of the product of step K in methanol, a catalytic amount of acetyl chloride was added. The mixture was heated under reflux for 3-9 h and the solvent was evaporated. The residue was extracted with a solvent like methyl-tert-butyl ether or DCM. The organic layer was evaporated.

Procedure for Step M

To a solution of the product of step L in methanol, 10% Pd/C was added and hydrogenated under ambient pressure for 24 h. The mixture was filtered through silica gel and evaporated.

Procedure for Step N

To a solution of t-BuNO₂ in acetonitrile, CuBr₂ was added. To the reaction mixture the product of step M in acetonitrile was added and the mixture was heated under reflux for 2-9 h. To the room temperature mixture, 20% aq. HCl was added and then extracted with a suitable solvent like methyl-tert-butyl ether or ethyl acetate. The organic layer was washed with water and evaporated. The oily residue was chromatographed.

Procedure for Step C

See Step C in Synthetic Method A above.

Synthesis Method D, Exemplified by 2-(4-fluorobenzenesulfonyl)propanoic Acid

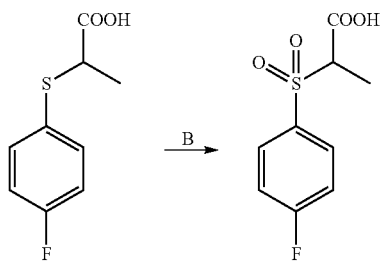

Procedure for Step B

The thioether obtained by Method A or B in a suitable solvent like DCM or ethyl acetate is treated with m-CPBA or another peracid at room temperature for 1-48 h and the reaction is monitored by TLC. After aqueous workup, the product is purified by chromatography.

Synthesis Method E, Exemplified by 3-amino-2-(4-fluorophenoxy)propanoic Acid Hydrochloride

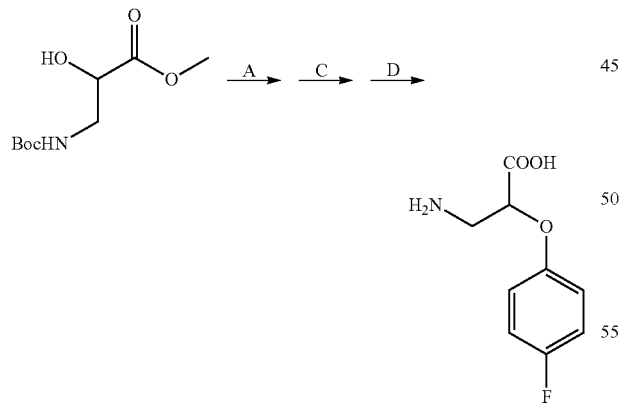

Procedure for Step A

See Step A in Synthetic Method A above.

Procedure for Step C

See Step C in Synthetic Method A above.

Procedure for Step D

The protected compound obtained from Step C in a suitable solvent like DCM is treated with TFA at room temperature for 1-18 h. After evaporation, the product is purified by reversed-phase chromatography with an HCl containing eluent.

Synthesis Method F, Exemplified by 4-nitrophenyl (2S)-2-(4-chlorophenoxy) Propanoate

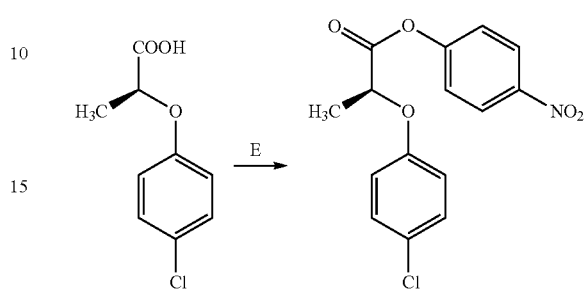

Procedure for Step E

The acid obtained by the previous methods in a suitable solvent like DCM or acetonitrile is treated DCC and the desired phenol, like p-nitrophenol, with a suitable catalyst like DMAP at room temperature for 1-48 h. After aqueous workup at acidic pH, the product is purified by rapid chromatography.

Synthesis Method G, Exemplified by (2S)-2-(4-chlorophenoxy)propanal

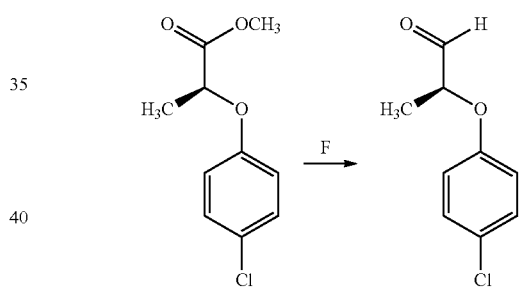

Procedure for Step F

The ester obtained by the previous methods in a suitable solvent like toluene is treated DIBAL-H at −78° C. for 1 h. After aqueous workup, the product is purified by rapid chromatography.

Synthesis Method H, Exemplified by [[(2S)-2-(4 chlorophenoxy)propylidene]amino]ethan-1-ol

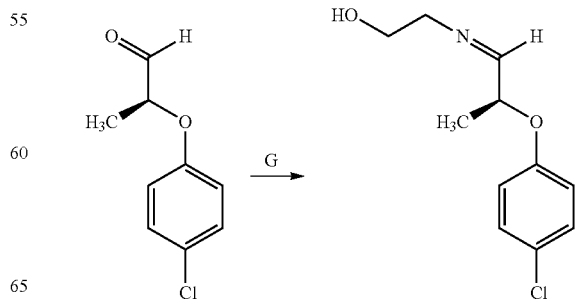

Procedure for Step G

The aldehyde obtained by the step F in a suitable solvent like DCM is treated at room temperature with the desired primary amine like 2-aminoethanol. Evaporation, redilution with DCM and re-evaporation yielded the desired product.

Compounds of Formula (I.2) May be Synthesized by the Following Synthetic Strategies, General Methods I-K General Method I

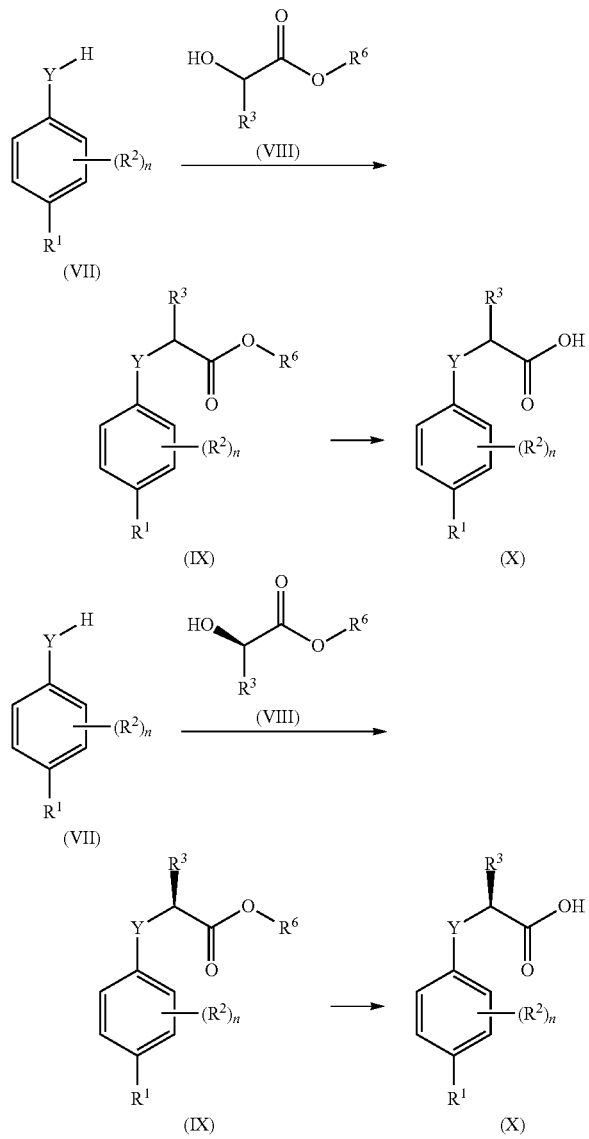

Method A involves the synthesis of Formula (X) (which is the same as Formula (I) in which $R^4$ is H), which is an ether structure when Y=oxygen, and —$R^1$, —$R^2$ and —$R^3$ are as defined in Formula (I) above. Compound (VII), in the case where Y=O is a phenol, is available either commercially or synthetically, and can be converted into an ether (IX) by methods which include Mitsunobu reaction conditions and compounds of Formula (VIII). This ether contains an ester functionality —$CO_2R^6$, which can be hydrolysed under a range of standard conditions, involving acid or base, to provide the carboxylic acid structure (X), Y=O. These standard conditions can also for example involve an enzymic hydrolysis, employing for example an esterase or lipase. If an ester molecule (IX) includes for example a $(CH_3)_3SiCH_2CH_2O$— group as —$OR^6$, then a fluoride ion source such as tetra-n-butylammonium fluoride can be employed to convert (IX) into the corresponding carboxylic acid (X). Some compounds can optionally be tested without hydrolysis of the ester group, and in this case $R^6$ is equivalent to $R^4$ as defined in Formula (I) above.

Substituted phenols of general formula (VII), Y=O, can be prepared by a variety of standard methods, for example by an ester rearrangement in the Fries rearrangement, by a rearrangement of N-phenylhydroxylamines in the Bamberger rearrangement, by hydrolysis of phenolic esters or ethers, by reduction of quinones, by replacement of an aromatic amine or by a hydroxyl group with water and sodium bisulfide in the Bucherer reaction. Other methods include hydrolysis of diazonium salts, by rearrangement reaction of dienones in the dienone phenol rearrangement, by the oxidation of aryl silanes, by the Hock process.

If a salt form of the product carboxylic acid is required, and alkali metal salt, e.g. a sodium salt can be prepared utilizing for example one equivalent of sodium hydroxide or sodium bicarbonate in aqueous solvent. This procedure also applies to General Methods B and C.

General Method J

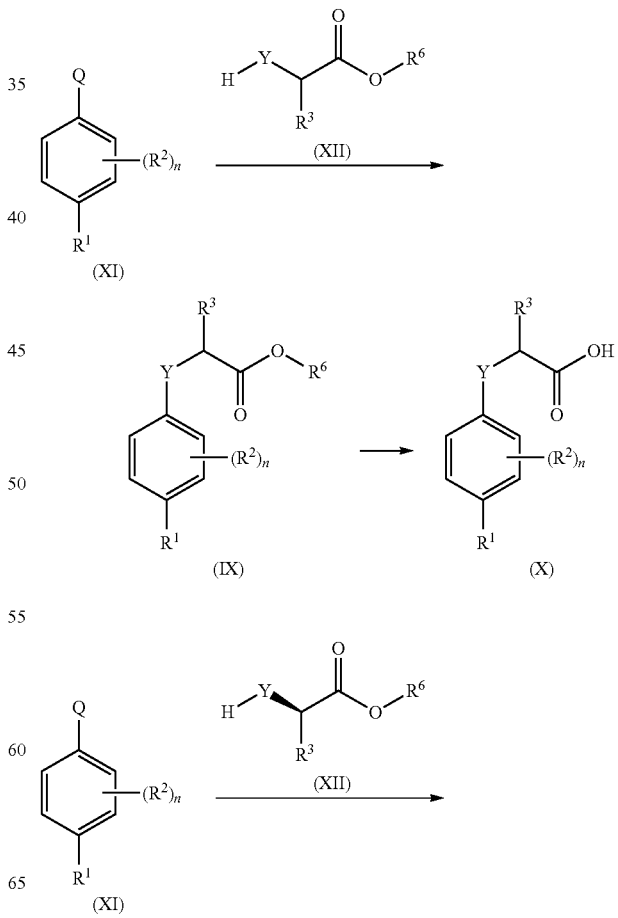

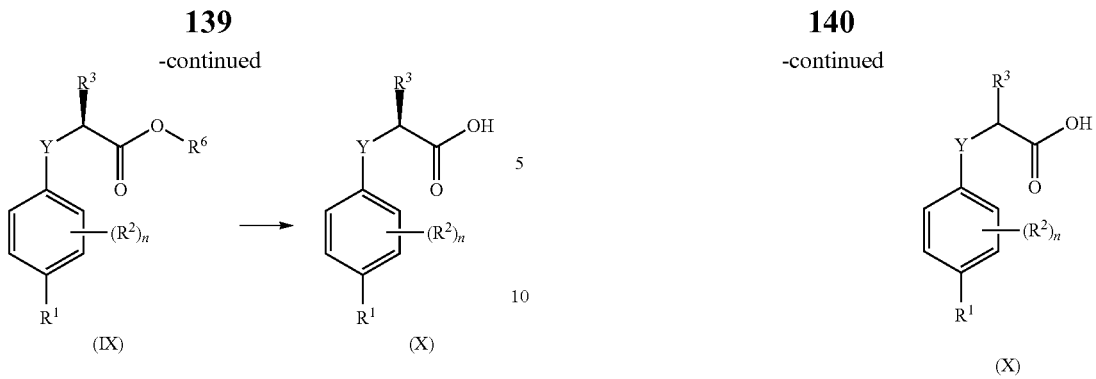

Carboxylic acids of Formula (X) (which is the same as Formula (I) in which $R^4$ is H), can also be prepared by the procedure illustrated as General Method B. A phenolic ether of Formula (IX) can be prepared by displacement of a suitable leaving group Q in (XI). Q can for example be a halogen such as fluorine or iodine, and the ether product of formula (IX) can be converted into the carboxylic acid derivative (X) by one of a range of methods outlined in Method A, involving hydrolysis of the ester functionality. Some compounds can optionally be tested without hydrolysis of the ester group, and in this case $R^6$ is equivalent to $R^4$ as defined in Formula (I) above.

General Method K

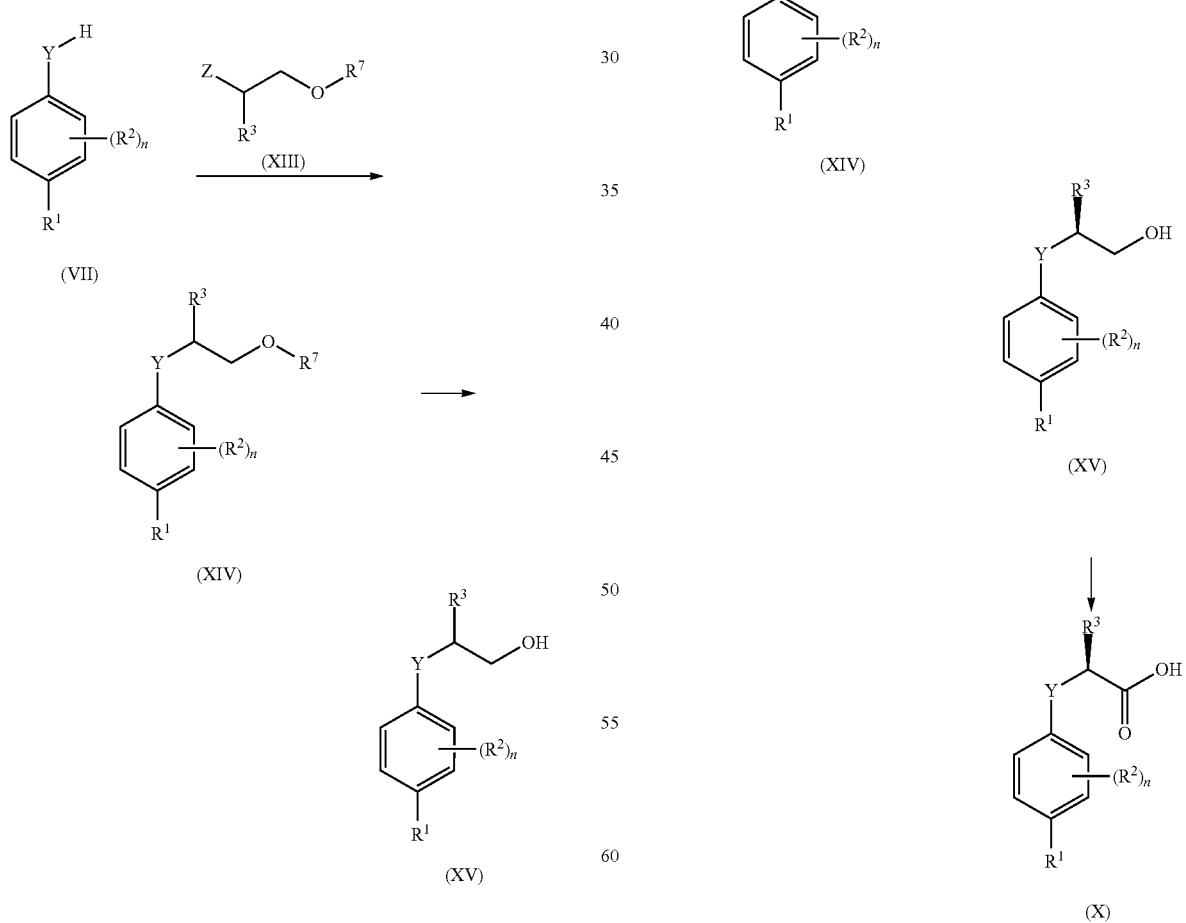

Carboxylic acids of Formula (X) (which is the same as Formula (I) in which $R^4$ is H), can be prepared by the procedure illustrated as General Method C. A phenolic ether of formula (XIV) can be prepared by utilising e.g. Mitsunobu conditions when (VII) is a phenol structure, i.e. Y=O, and XIII is a suitable secondary alcohol, i.e. Z=OH, and —R[7] is a suitable protecting group, such as a silyl-containing moiety. On removal of the protecting group —R[6] the primary alcohol (XV) can be oxidised to a carboxylic acid under standard conditions involving potassium permanganate, Jones oxidation conditions, the Heyns oxidation, ruthenium tetroxide or TEMPO.

Table B below illustrates Example compounds defined by the general Formula (I). In table B, the HPLC System is one of the methods as defined in the Materials and methods section.

Specific Examples of Syntheses

Example 1: Synthesis of (2R)-2-(4-bromophenoxy)-3-fluoropropanoic Acid; Following the Synthetic Strategy of General Method C

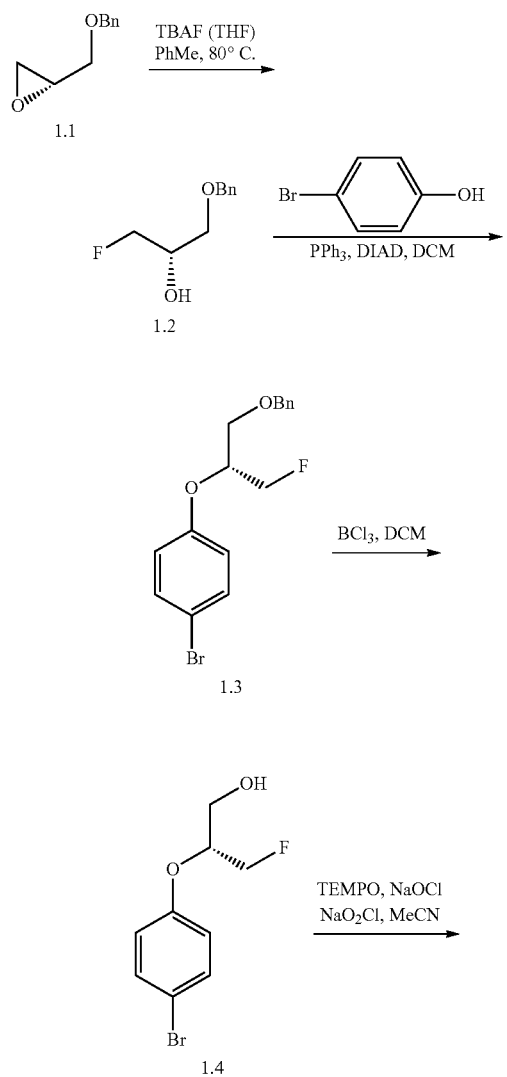

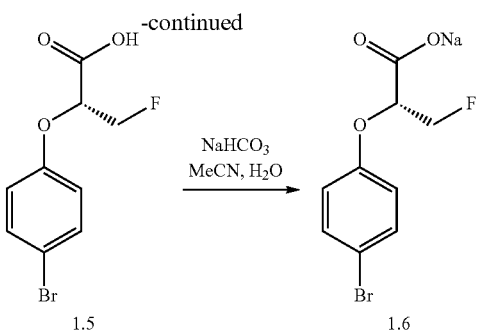

(S)-1-(Benzyloxy)-3-fluoropropan-2-ol (1.2)

Tetrabutylammonium fluoride, 1M solution in THF (114 mL, 114 mmol) was added to a solution of (R)-2-((benzyloxy)methyl)oxirane (1.1) (15.56 g, 95 mmol) in anhydrous toluene (300 mL, 95 mmol) and the mixture stirred at 80° C. under nitrogen for 24 h. The mixture was cooled to room temp., diluted with water and extracted with ethyl acetate. The organic phase was washed with brine, dried over $MgSO_4$ and evaporated in vacuo to afford a crude oil. The material was adsorbed onto silica then purified by chromatography on silica gel (220 g column, 0-100% EtOAc/isohexane) to afford (S)-1-(benzyloxy)-3-fluoropropan-2-ol (1.2) (6.419 g, 31.4 mmol, 33% yield) as a pale yellow oil. The product was analysed by LCMS (Waters Acquity UPLC, C18, Waters X-Bridge UPLC C18, 1.7 µm, 2.1×30 mm, Acidic (0.1% Formic acid) 3 min method, 5-95% MeCN/water) 0.978 min, 91% purity @ 254 nm; $^1$H NMR (400 MHz, CDCl3) δ 7.43-7.30 (m, 5H); 4.59 (s, 2H); 4.58-4.49 (m, 1H); 4.43 (qd, J=9.6, 4.9 Hz, 1H); 4.12-3.96 (m, 1H); 3.67-3.54 (m, 2H); 2.52 (d, J=4.7 Hz, 1H).

(R)-1-((1-(Benzyloxy)-3-fluoropropan-2-yl)oxy)-4-bromobenzene (1.3)

To a solution of (S)-1-(benzyloxy)-3-fluoropropan-2-ol (1.2) (1.725 g, 9.36 mmol), 4-bromophenol (1.62 g, 9.36 mmol) and triphenylphosphine (3.44 g, 13.11 mmol) in anhydrous THF (90 mL, 1098 mmol) at 0° C. was added DIAD (2.55 mL, 13.11 mmol). The solution was allowed to warm to room temperature and stirred for 4 hours. After the allotted time, MeOH was added and volatiles removed in vacuo. The crude product was purified by chromatography on silica gel (40 g column, 0-30% EtOAc/isohexane) to afford (R)-1-((1-(benzyloxy)-3-fluoropropan-2-yl)oxy)-4-bromobenzene (1.3) (998 mg, 2.80 mmol, 30% yield) as a clear colourless oil. The product was analysed by LCMS (Waters Acquity UPLC, C18, Waters X-Bridge UPLC C18, 1.7 µm, 2.1×30 mm, Acidic (0.1% Formic acid) 3 min method, 5-95% MeCN/water): m/z 339.822 (M+H)+ (ES+) at 1.858 min, 99% purity @ 254 nm. $^4$H NMR (400 MHz, DMSO-d$^6$) δ 7.45 (d, J=9.0 Hz, 2H); 7.37-7.25 (m, 5H); 7.00 (d, J=9.0 Hz, 2H); 4.89-4.67 (m, 2H); 4.61 (qd, J=10.4, 4.1 Hz, 1H), 4.53 (s, 2H); 3.73-3.62 (m, 2H).

(R)-2-(4-Bromophenoxy)-3-fluoropropan-1-ol (1.4)

Trichloroborane, 1M solution in dichloromethane (3.24 mL, 3.24 mmol) was added to a stirred solution of (R)-1-((1-(benzyloxy)-3-fluoropropan-2-yl)oxy)-4-bromobenzene (1.3) (998 mg, 2.94 mmol) in anhydrous dichloromethane (45 mL, 699 mmol) under nitrogen at 0° C. After 2 hours the

(2R)-2-(4-Bromophenoxy)-3-fluoropropanoic acid (1.5)

Sodium chlorite (1.342 g, 14.84 mmol) was dissolved in 1M sodium phosphate buffer pH6 (60 mL, 60.0 mmol) and added to a solution of (R)-2-(4-bromophenoxy)-3-fluoropropan-1-ol (2.843 g, 7.42 mmol) (1.4) in acetonitrile (60 mL), followed by aqueous sodium hypochlorite solution (0.087 mL, 0.074 mmol) and TEMPO (0.041 g, 0.260 mmol). The resulting 2-phase mixture was stirred at room temp for 1 hour. Further aqueous sodium hypochlorite solution (0.087 mL, 0.074 mmol) and TEMPO (0.041 g, 0.260 mmol) were added and the mixture was stirred overnight at room temperature. Further aqueous sodium hypochlorite solution (0.27 mL, 0.222 mmol) and TEMPO (0.123 g, 0.780 mmol) were added and the reaction stirred for a further 3 h.

To the mixture was added saturated sodium metabisulfite solution (40 mL) and the mixture was diluted with water, acidified by addition of conc. hydrochloric acid and extracted with ethyl acetate. The organic phase was extracted with aq. sodium hydroxide solution (1 M). The aqueous phase was acidified to pH 2, by addition of conc. hydrochloric acid, then extracted with ethyl acetate. The combined organic extracts were dried over $MgSO_4$ and volatiles removed in vacuo. The material was adsorbed onto silica then purified by chromatography on silica gel (80 g column, 0-50% EtOAc/isohexane) to afford (R)-2-(4-bromophenoxy)-3-fluoropropanoic acid (1.5) (1.307 g, 4.72 mmol, 63% yield) as a colourless solid. The product was analysed by LCMS (Agilent Infinity, X-Select, Waters X-Select C18, 2.5 μm, 4.6×30 mm, Acidic (0.1% Formic acid) 15 min method, 5-95% MeCN/water): (M+H)+ (ES+); 260.900 (M−H)− (ES−), at 4.166 min, 95% purity @ 254 nm. (Note: product has poor absorption at 254 nm). $^1$H NMR (400 MHz, DMSO-$d^6$) δ 13.53 (s, 1H); 7.46 (d, J=9.0 Hz, 2H); 6.93 (d, J=9.0 Hz, 2H); 5.20 (ddd, J=29.1, 3.9, 2.5 Hz, 1H); 4.97-4.71 (m, 2H).

To a solution of (R)-2-(4-bromophenoxy)-3-fluoropropanoic acid (1.5) (867 mg, 3.30 mmol) in acetonitrile (23 mL) was added sodium bicarbonate (277 mg, 3.30 mmol) in $H_2O$ (8 mL) and the reaction stirred at ambient temperature for 30 min. After the allotted time, volatiles were removed in vacuo and excess water removed by co-evaporation with toluene, resulting in a clear oil. Dichloromethane was added and removed resulting in a colourless solid. The solid was triturated with further dichloromethane and dried in a dessicator overnight to afford sodium (R)-2-(4-bromophenoxy)-3-fluoro-propanoate (1.6) (0.496 g, 1.65 mmol, 50%). The colourless solid product was analysed by LCMS (Agilent Infinity, X-Select, Waters X-Select C18, 2.5 μm, 4.6×30 mm, Acidic (0.1% Formic acid) 15 min method, 5-95% MeCN/water): (ES+); 260.976 (M-Na)− (ES−), at 1.476 min, 95% purity @ 254 nm. $^1$H NMR (400 MHz, DMSO-$d^6$) δ 7.36 (d, J=9.0 Hz, 2H); 6.78 (d, J=9.0 Hz, 2H); 4.86-4.53 (m, 2H); 4.47 (ddd, J=23.5, 7.5, 2.2 Hz, 1H).

Example 2: (2S)-2-(4-bromo-2-fluorophenoxy)-3-methylbutanoic Acid, Adapted from General Method A

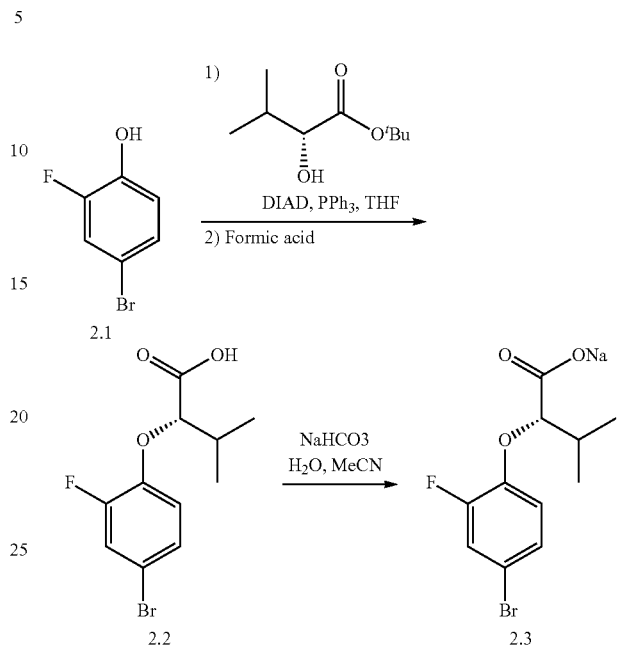

(S)-2-(4-bromo-2-fluorophenoxy)-3-methyl)butanoic Acid (2.2)

DIAD (2.343 mL, 12.05 mmol) was added to a stirred solution of (R)-tert-butyl 2-hydroxy-3-methylbutanoate (2.1) (1.5 g, 8.61 mmol), 4-bromo-2-fluorophenol (1.037 mL, 9.47 mmol) and triphenylphosphine (3.16 g, 12.05 mmol) in anhydrous tetrahydrofuran (50.6 mL, 8.61 mmol) at 0° C. and stirred for 30 min before being allowed to warm to room temperature. After 16 hours, the mixture was evaporated in vacuo to a syrup which was re-dissolved in formic acid (33.0 mL, 861 mmol) and heated to 70° C. for 1 hour. MeOH (20 mL) was added and the resulting solution was evaporated in vacuo and the residue co-evaporated with toluene (2×30 mL). The residue was dissolved in ethyl acetate (100 mL) and extracted with 0.5M sodium hydroxide solution (100 mL). The aqueous phase was washed with ethyl acetate (2×100 mL) then acidified to pH 2-3 by dropwise addition of c. hydrochloric acid. The resulting cloudy solution was extracted with ethyl acetate (3×100 mL). Organic extracts were filtered through a phase separating funnel. The residue was purified by column chromatography (40 g Grace silica cartridge) with 0-40% ethyl acetate in isohexane gradient elution to give an oil which was dried in vacuo at 40° C. overnight to give (S)-2-(4-bromo-2-fluorophenoxy)-3-methylbutanoic acid (2.2) (1.6436 g, 5.53 mmol, 64.3% yield) as a white waxy solid.

The product was analysed by LCMS (Waters Acquity UPLC, X-Select, Waters X-Select UPLC C18, 1.7 μm, 2.1×30 mm, Acidic (0.1% Formic acid) 10 min method, 5-95% MeCN/water): m/z 289-291 (M−H)− (ES−), at 4.352 min, 97.6% purity @ 254 nm; $^1$H NMR (400 MHz, DMSO-$d^6$) δ 13.16 (s, 1H), 7.53 (dd, J=10.9, 2.4 Hz, 1H), 7.34-7.27 (m, 1H), 6.97 (t, J=9.0 Hz, 1H), 4.61 (d, J=4.6 Hz, 1H), 2.31-2.18 (m, 1H), 1.01 (dd, J=6.5 Hz, 6H).

To (S)-2-(4-bromo-2-fluorophenoxy)-3-methylbutanoic acid (2.2) (0.8254 g, 2.77 mmol) in MeCN (27 mL) was added NaHCO$_3$ (0.232 g, 2.77 mmol) in H$_2$O (9 mL) and the mixture was stirred at room temperature for 30 min. The aqueous solvent was removed under reduced pressure to give a white solid which was dissolved in H$_2$O (30 mL) and washed with DCM (3×30 mL). The water was removed under reduced pressure and the residue dried at 45° C. in vacuo for 72 hours to give sodium (S)-2-(4-bromo-2-fluorophenoxy)-3-methylbutanoate (2.3) (0.866 g, 2.63 mmol, 95% yield) as a white solid. The product was analysed by LCMS (Waters Acquity UPLC, X-Select, Waters X-Select UPLC C18, 1.7 μm, 2.1×30 mm, Acidic (0.1% Formic acid) 10 min method, 5-95% MeCN/water): m/z 288.915, 290.966 (M−H)− (ES−), 89% purity @ 254 nm. 100% purity @ 210-400 nm. (Poor absorbance @254). 1H NMR (400 MHz, DMSO-d6) δ 7.39 (dd, J=11.0, 2.4 Hz, 1H), 7.18 (ddd, J=8.8, 2.5, 1.5 Hz, 1H), 6.86 (t, J=9.0 Hz, 1H), 3.92 (d, J=5.0 Hz, 1H), 2.21-2.08 (m, 1H), 0.95 (d, J=6.7 Hz, 6H).

In conclusions, this example demonstrates that compound 4.4 can be prepared using the synthetic strategy herein.

TABLE A

Synthesis of compounds
Compounds of formula (I) may be synthesized by one of Synthetic Methods A to H, as shown in the below.

| Example number | IUPAC name | Preparation method | NMR |
|---|---|---|---|
| C1 | (2S)-2-(4-chlorophenoxy)propanoic acid | A | 1H-NMR (400 MHz, DMSO-d6): δ 13.2 (s, 1H), 7.35 (m, 2H), 6.9 (m, 2H), 4.85 (q, 1H), 1.45 (d, 3H). |
| C2 | (2S)-2-[(4-chlorophenyl)amino]propanoic acid | B | 1H-NMR (500 MHz, DMSO-d6): δ 7.15 (m, 2H), 6.58 (m, 2H), 3.95 (q, 1H), 1.35 (d, 3H). |
| C3 | 2-(benzyloxy)propanoic acid | B | 1H-NMR (400 MHz, CDCl$_3$): δ 9.8 (s, 1H), 7.35 (m, 5H), 4.7 (d, 1H), 4.5 (d, 1H), 4.05 (q, 1H), 1.47 (d, 3H). |
| C4 | 2-(4-fluorophenoxy)propanoic acid | A | 1H-NMR (400 MHz, DMSO-d6): δ 12.68 (s, 1H), 6.9 (m, 4H), 4.68 (q, 1H), 1.62 (d, 3H). |
| C5 | (2S)-2-(benzyloxy)propanoic acid | B | 1H-NMR (400 MHz, CDCl$_3$): δ 11.3 (bs, 1H), 7.4 (m, 5H), 4.71 (d, 1H), 4.52 (d, 1H), 4.08 (q, 1H), 1.47 (d, 3H). |
| C6 | 2-(4-fluorobenzenesulfonyl)propanoic acid | D | 1H-NMR (500 MHz, DMSO-d6): δ 13.4 (s, 1H), 7.96 (m, 2H), 7.51 (m, 2H), 4.38 (q, 1H), 1.35 (d, 3H). |
| C7 | 2-(4-chlorophenoxy)butanoic acid | A | 1H-NMR (400 MHz, DMSO-d6): δ 12.72 (bs, 1H), 7.23 (m, 2H), 6.83 (m, 2H), 4.52 (m, 1H), 1.9 (m, 2H), 1.05 (m, 3H). |
| C8 | (2S)-2-(4-bromophenoxy)propanoic acid | A | 1H-NMR (300 MHz, CDCl$_3$): δ 8.42 (bs, 1H), 7.35 (m, 2H), 6.78 (m, 2H), 4.71 (q, 1H), 1.62 (d, 3H). |
| C9 | 3-amino-2-(4-fluorophenoxy) propanoic acid hydrochloride | E | 1H-NMR (400 MHz, DMSO-d6): δ 13.7 (bs, 1H), 8.25 (s, 2H), 7.18 (m, 2H), 7.02 (m, 2H), 5.05 (q, 1H), 3.15 (bs, 2H). |
| C10 | (2S)-2-[(4-chloronaphthalen-1-yl)oxy]propanoic acid | A | 1H-NMR (400 MHz, DMSO-d6): δ 13.2 (bs, 1H), 8.25 (d, 1H), 8.0 (d, 1H), 7.6 (m, 3H), 6.90 (d, 1H), 4.98 (q, 1H), 1.58 (d, 3H). |
| C11 | 4-chlorophenyl 2-(4-chlorophenoxy)propanoate | F | 1H-NMR (300 MHz, DMSO/CCl$_4$): δ 7.41 (m, 2H), 7.08 (m, 6H), 5.14 (m, 1H), 1.71 (d, 3H). |
| C12 | (2S)-2-(5-bromopyrimidin-2-yl)-3-methylbutanoic acid | C | 1H-NMR (300 MHz, CDCl$_3$): δ 9.65 (bs, 1H), 8.42 (m, 2H), 5.05 (dd, 1H), 2.44 (m, 1H), 1.2 (m, 6H). |
| C13 | 2-[(1S)-1-(4-chlorophenoxy)ethyl]-1,3-oxazolidine | H | 1H-NMR (300 MHz, CDCl$_3$): δ 7.24 (m, 2H), 6.9 (m, 2H), 4.62 (m, 1H), 4.41 (m, 1H), 3.8 (m, 2H), 3.3 (m, 1H), 3.1 (m, 1H), 1.4 (m, 3H). |
| C14 | 2-(4-bromophenoxy)-2-cyclopropylactic acid | B | 1H-NMR (500 MHz, DMSO-d6): δ 13.1 (s, 1H), 7.48 (m, 2H), 6.8 (m, 2H), 4.08 (d, 1H), 1.12 (m, 1H), 0.5 (m, 4H). |
| C15 | 2-(4-bromophenoxy)-3acetamidopropanoic acid | B | 1H-NMR (500 MHz, DMSO-d6): δ 13.3 (s, 1H), 8.15 (s, 1H), 7.48 (m, 2H), 6.85 (m, 2H), 4.70 (q, 1H), 3.61 (m, 1H), 3.31 (m, 1H), 1.72 (s, 3H). |
| C16 | 2-(4-bromophenoxy)-3-methanesulfonamidopropanoic acid | B | 1H-NMR (500 MHz, DMSO-d6): δ 13.4 (bs, 1H), 7.5 (m, 3H), 6.92 (m, 2H), 4.85 (m, 1H), 3.52 (m, 1H), 3.35 (m, 1H) 2.9 (s, 3H). |
| C17 | (2S)-2-(4-chlorophenoxy) propanal | G | 1H-NMR (300 MHz, CDCl$_3$): δ 9.7 (d, 1H), 7.25 (m, 2H), 6.81 (m, 2H), 4.61 (q, 1H), 1.45 (m, 3H). |
| C18 | 4-nitrophenyl (2S)-2-(4-chlorophenoxy)propanoate | F | 1H-NMR (300 MHz, CDCl$_3$): δ 8.28 (m, 2H), 7.25 (m, 4H), 6.84 (m, 2H), 5.02 (m, 1H), 1.82 (m, 3H). |
| C19 | 4-methoxyphenyl (2S)-2-(4-chlorophenoxy)propanoate | F | 1H-NMR (300 MHz, CDCl$_3$): δ 7.3 (m, 2H), 6.92 (m, 6H), 4.9 (q, 1H), 3.81 (s, 3H), 1.78 (dd, 3H). |
| C20 | 2-(4-bromophenoxy)-2-(3-ethoxycyclobutyl)acetic acid | B | 1H-NMR (400 MHz, DMSO-d6): δ 13.1 (bs, 1H), 7.42 (m, 2H), 6.81 (m, 2H), 4.65 (dd, 1H), 3.44 (m, 1H), 3.30 (m, 1H), 3.24 (m, 3H), 2.36 (m, 1H), 0.9 (dd, 3H). |

TABLE A-continued

Synthesis of compounds
Compounds of formula (I) may be synthesized by one of
Synthetic Methods A to H, as shown in the below.

| Example number | IUPAC name | Preparation method | NMR |
|---|---|---|---|
| C21 | 2-(4-bromophenoxy)-4-methoxy-3-methyl-butanoic acid | B | 1H-NMR (400 MHz, DMSO-d6): δ 13.1 (s, 1H), 7.42 (m, 2H), 6.82 (m, 2H), 4.61 (d, 1H), 3.80 (m, 1H), 3.28 (m, 2H), 2.31 (m , 3H), 1.80 (m, 2H ), 1.05 (t, 3H). |
| C22 | (2S)-2-(4-bromo-phenoxy)-3methyl-butanoic acid | A | 1H-NMR (500 MHz, CDCl$_3$): δ 7.41 (m, 2H), 6.78 (m, 2H), 4.41 (d, 1H), 2.38 (q, 1H), 1.11 (d, 6H). |

Table B below illustrates Example compounds defined by the general Formula (I.3.4). In table B, the HPLC System is one of the methods as defined in the Materials and methods section.

TABLE B

Illustrative Examples of the Invention

| Compound Number | IUPAC name | $^1$H NMR | HPLC retention time | Synthesis method |
|---|---|---|---|---|
| A-1 | (2R)-2-[4-bromo(3,5-$^2$H$_2$)phenoxy]-3-fluoropropanoic acid | 1H NMR (500 MHz, DMSO-d6) δ 13.53 (s, 1H), 6.92 (s, 2H), 5.19 (ddd, J = 29.2, 4.1, 2.4 Hz, 1H), 4.95-4.74 (m, 2H). | 2.911 | K |
| A-2 | (2S)-2-[4-bromo(3,5-$^2$H$_2$)phenoxy]propanoic acid | 1H NMR (500 MHz, DMSO-d6) δ 13.08 (s, 1H), 6.85 (s, 2H), 4.84 (q, J = 6.8 Hz, 1H), 1.50 (d, J = 6.8 Hz, 3H). | 3.036 | I |
| A-3 | ethyl (2S)-2-(4-bromo-2-fluorophenoxy)-3-methylbut-3-enoate | 1H NMR (300 MHz, CDCl3) δ 7.29-7.13 (m, 2H), 5.21 (d, 1H), 5.04 (s, 1H), 1.88 (s, 3H), 1.28 (t, 3H). | 13.499 | I |
| A-4 | (2R)-2-(4-bromo-2-fluorophenoxy)-3-methylbutanoic acid | 1H NMR (500 MHz, DMSO-d6) δ 13.15 (s, 1H), 7.54 (dd, J = 10.9, 2.4 Hz, 1H), 7.31 (ddd, J = 8.8, 2.4, 1.5 Hz, 1H), 6.98 (t, J = 9.0 Hz, 1H), 4.62 (d, J = 4.6 Hz, 1H), 2.25 (pd, J = 6.8, 4.5 Hz, 1H), 1.03 (d, J = 6.9 Hz, 3H), 1.01 (d, J = 6.8 Hz, 3H). | 4.358 | I |
| A-5 | (2R)-2-[4-bromo(2,6-$^2$H$_2$)phenoxy]-3-fluoropropanoic acid | 1H NMR (500 MHz, DMSO-d6) δ 13.54 (s, 1H), 7.46 (s, 2H), 5.17 (d, J = 28.7 Hz, 1H), 4.96-4.75 (m, 2H). | 2.852 | K |
| A-6 | (2S)-2-[4-bromo(2,6-$^2$H$_2$)phenoxy]propanoic acid | 1H NMR (400 MHz, DMSO-d6) δ 13.17 (s, 1H), 7.44 (s, 2H), 4.88-4.76 (m, 1H), 1.49 (d, J = 6.8 Hz, 3H). | 3.028 | I |
| A-7 | (2S)-2-(4-bromophenoxy)-3-fluoropropanoic acid | 1H NMR (400 MHz, DMSO-d6) δ 13.53 (s, 1H), 7.51-7.41 (m, 2H), 6.97-6.88 (m, 2H), 5.20 (ddd, J = 29.2, 4.0, 2.5 Hz, 1H), 4.96-4.72 (m, 2H). | 2.970 | K |
| A-8 | (2S)-2-(4-bromo-2-iodophenoxy)propanoic acid | $^1$H NMR (300 MHz, CDCl$_3$) δ 10.38-9.28 (br, 1H); 7.93 (d, 1H); 7.39 (dd, 1H); 6.63 (d, 1H); 4.78 (q, 1H); 1.75 (d, 3H). | 14.547 | I |

TABLE B-continued

Illustrative Examples of the Invention

| Compound Number | IUPAC name | $^1$H NMR | HPLC retention time | Synthesis method |
|---|---|---|---|---|
| A-9 | (2R)-2-(4-bromo-2-fluorophenoxy)-3,3-difluoropropanoic acid | 1H NMR (400 MHz, DMSO-d6) δ 7.58 (dd, J = 10.8, 2.4 Hz, 1H), 7.36-7.29 (m, 1H), 7.13 (t, J = 9.0 Hz, 1H), 6.51 (td, J = 53.1, 2.1 Hz, 1H), 5.30 (dd, J = 20.1, 7.9 Hz, 1H). | 3.424 | K |
| A-10 | (2S)-2-{4-bromo-2-[(1E)-(methoxyimino)methyl]phenoxy}propanoic acid | 1H NMR (300 MHz, CDCl3) δ 7.40 (d, 1H), 4.80 (q, 1H), 3.99 (s, 3H), 1.69 (d, 3H). | 14.473 | I |
| A-11 | (2S)-2-(2-bromo-4-chlorophenoxy)-3-methylbutanoic acid | 1H NMR (300 MHz, CDCl3) δ 6.68 (d, 1H), 4.48 (d, 1H), 2.41 (m, 1H), 1.18 (d, 3H), 1.16 (d, 3H); | 15.404 | I |
| A-12 | (2S)-2-(2-fluoro-4-iodophenoxy)propanoic acid | 1H-NMR (300 MHz, CDCl3): 10.50-10.12 (br, 1H), 7.40 (dd, 2H), 4.79 (q, 1H), 1.69 (d, 3H). | 13.629 | I |
| A-13 | (2S)-2-(2-bromo-4-iodophenoxy)propanoic acid | 1H-NMR (300 MHz, CDCl3): δ 10.48-10.09 (br, 1H), 7.88 (s, 1H), 4.79 (q, 1H), 1.73 (d, 3H). | 14.713 | I |
| A-14 | ethyl 2-(4-bromo-2-fluorophenoxy)-3,3,3-trifluoropropanoate | 1H NMR (300 MHz, CDCl3) δ 6.99 (t, 1H), 4.94 (q, 1H), 4.41-4.29 (m, 2H), 1.32 (t, 3H). | 18.077 | I |
| A-15 | ethyl 2-(4-bromophenoxy)-3,3,3-trifluoropropanoate | 1H NMR (300 MHz, CDCl3) δ 7.48-7.40 (m, 2H), 4.93 (q, 1H), 4.40-4.30 (m, 2H), 1.31 (t, 3H). | 17.92 | I |
| A-16 | (2S)-2-(2-chloro-4-iodophenoxy)propanoic acid | 1H-NMR (300 MHz, CDCl3): δ 10.38-10.19 (br, 1H), 7.72 (s, 1H), 4.79 (q, 1H), 1.73 (d, 3H). | 14.528 | I |
| A-17 | (2S)-2-(2-bromo-4-chlorophenoxy)propanoic acid | 1H NMR (300 MHz, MeOD) δ 6.90 (d, 1H), 4.85 (m, 1H), 1.64 (d, 3H); | 14.188 | I |
| A-18 | 2-(4-bromophenoxy)-2-cyclopentylacetic acid | $^1$H NMR (300 MHz, CDCl$_3$) δ 9.93-9.27 (br, 1H); 7.38 (d, 2H); 6.79 (d, 2H); 4.47 (d, 1H); 2.58-2.40 (m, 1H); 1.94-1.44 (m, 8H). | 15.452 | I |
| A-19 | (2R)-2-(4-bromo-2-fluorophenoxy)-3-fluoropropanoic acid | 1H NMR (400 MHz, DMSO-d6) δ 7.58 (dd, J = 10.9, 2.4 Hz, 1H), 7.33 (ddd, J = 8.8, 2.4, 1.5 Hz, 1H), 7.11 (t, J = 9.0 Hz, 1H), 5.30 (ddd, J = 29.3, 3.9, 2.4 Hz, 1H), 5.02-4.77 (m, 2H). | 3.109 | K |
| A-20 | (2S)-2-(4-chloro-2-fluorophenoxy)-3-methylbutanoic acid | 1H NMR (400 MHz, DMSO-d6) δ 13.19 (s, 1H), 7.44 (dd, J = 11.1, 2.6 Hz, 1H), 7.19 (ddd, J = 8.9, 2.6, 1.6 Hz, 1H), 7.03 (t, J = 9.0 Hz, 1H), 4.62 (d, J = 4.6 Hz, 1H), 2.25 (pd, J = 6.9, 4.6 Hz, 1H), 1.02 (app dd, J = 6.8, 6.0 Hz, 6H). | 4.148 | I |
| A-21 | (2R)-2-(2-bromo-4-chlorophenoxy)-3-fluoropropanoic acid | 1H NMR (400 MHz, DMSO-d6) δ 13.71 (s, 1H), 7.73 (d, J = 2.6 Hz, 1H), 7.40 (dd, J = 8.9, 2.6 Hz, 1H), 7.07 (d, J = 8.9 Hz, 1H), 5.32 (ddd, J = 29.1, 4.0, 2.4 Hz, 1H), 5.00-4.77 (m, 2H). | 1.936 | K |

TABLE B-continued

Illustrative Examples of the Invention

| Compound Number | IUPAC name | ¹H NMR | HPLC retention time | Synthesis method |
|---|---|---|---|---|
| A-22 | (2R)-2-(4-chlorophenoxy)-3-fluoropropanoic acid | 1H NMR (400 MHz, DMSO-d6) δ 13.47 (s, 1H), 7.38-7.30 (m, 2H), 7.02-6.93 (m, 2H), 5.20 (ddd, J = 29.1, 3.9, 2.5 Hz, 1H), 4.97-4.72 (m, 2H). | 1.088 | K |
| A-23 | (2R)-2-(4-chloro-2-fluorophenoxy)-3-fluoropropanoic acid | 1H NMR (400 MHz, DMSO-d6) δ 13.60 (s, 1H), 7.47 (dd, J = 11.2, 2.4 Hz, 1H), 7.21 (ddd, J = 8.9, 2.4, 1.0 Hz, 1H), 7.16 (t, J = 8.8 Hz, 1H), 5.30 (ddd, J = 29.3, 3.9, 2.4 Hz, 1H), 5.03-4.70 (m, 2H). | 1.188 | K |
| A-24 | (2R)-2-(2,4-dibromophenoxy)-3-fluoropropanoic acid | 1H NMR (400 MHz, DMSO-d6) δ 13.63 (s, 1H), 7.83 (d, J = 2.4 Hz, 1H), 7.52 (dd, J = 8.8, 2.4 Hz, 1H), 7.01 (d, J = 8.9 Hz, 1H), 5.32 (ddd, J = 29.0, 3.9, 2.4 Hz, 1H), 5.02-4.76 (m, 2H). | 2.041 | K |
| A-25 | (2S)-2-(4-bromophenoxy)-3-hydroxypropanoic acid | 1H NMR (400 MHz, DMSO-d6) δ 7.47-7.41 (m, 2H), 6.90-6.83 (m, 2H), 4.74 (dd, J = 5.1, 3.8 Hz, 1H), 3.86-3.78 (m, 2H). | 0.942 | I |
| A-26 | (2R)-2-(4-bromophenoxy)-3-fluoropropanoic acid | 1H NMR (400 MHz, DMSO-d6) δ 13.51 (s, 1H), 7.49-7.43 (m, 2H), 6.96-6.89 (m, 2H), 5.24-5.12 (m, 1H), 4.95-4.75 (m, 2H). | 2.913 | K |
| A-27 | (2S)-2-(4-bromo-2-fluorophenoxy)-3-methylbutanoic acid | 1H NMR (400 MHz, DMSO-d6) δ 13.19 (s, 1H), 7.54 (dd, J = 10.9, 2.4 Hz, 1H), 7.31 (ddd, J = 8.9, 2.4, 1.5 Hz, 1H), 6.98 (t, J = 9.0 Hz, 1H), 4.61 (d, J = 4.5 Hz, 1H), 2.31-2.20 (m, 1H), 1.02 (app dd, J = 6.9, 6.0 Hz, 6H). | 4.343 | I |
| A-28 | (2R)-2-(4-bromo-2-fluorophenoxy)propanoic acid | 1H NMR (400 MHz, DMSO-d6) δ 13.21 (s, 1H), 7.55 (dd, J = 10.9, 2.4 Hz, 1H), 7.31 (ddd, J = 8.8, 2.4, 1.5 Hz, 1H), 7.00 (t, J = 9.0 Hz, 1H), 4.95 (q, J = 6.8 Hz, 1H), 1.53 (d, J = 6.8 Hz, 3H). | 3.207 | I |
| A-29 | (2R)-2-(4-chlorophenoxy)propanoic acid | 1H NMR (400 MHz, DMSO-d6) δ 13.10 (s, 1H), 7.38-7.26 (m, 2H), 6.94-6.84 (m, 2H), 4.84 (q, J = 6.8 Hz, 1H), 1.50 (d, J = 6.8 Hz, 3H). | 2.825 | I |
| A-30 | (2S)-2-(3-bromo-4-chlorophenoxy)propanoic acid | 1H NMR (400 MHz, DMSO-d6) δ 13.16 (s, 1H), 7.52 (d, J = 8.9 Hz, 1H), 7.29 (d, J = 3.0 Hz, 1H), 6.95 (dd, J = 8.9, 3.0 Hz, 1H), 4.96 (q, J = 6.7 Hz, 1H), 1.50 (d, J = 6.8 Hz, 3H). | 3.683 | I |

TABLE B-continued

Illustrative Examples of the Invention

| Compound Number | IUPAC name | ¹H NMR | HPLC retention time | Synthesis method |
|---|---|---|---|---|
| A-31 | (2S)-2-(4-bromo-2-fluorophenoxy)propanoic acid | 1H NMR (Chloroform-d, 400 MHz) δ 7.29 (0.5H, d, J = 2.3 Hz), 7.26 (0.5H, d, J = 2.3 Hz), 7.19 (0.5H, dd, J = 2.3, 1.6 Hz), 7.17 (0.5H, dd, J = 2.3, 1.6 Hz), 6.85 (1H, t, J = 8.7 Hz), 4.78 (1H, q, J = 6.9 Hz), 1.69 (3H, d, J = 6.9 Hz) | 1.283 (3 minute method) | I |
| A-32 | (2S)-2-[4-(trifluoromethyl)phenoxy]propanoic acid | 1H NMR (400 MHz, CDCl₃) δ 7.56 (2H, d, J = 8.5 Hz), 6.96 (2H, d, J = 8.5 Hz), 4.86 (1H, q, J = 6.9 Hz), 1.70 (3H, d, J = 6.9 Hz) | 1.302 (3 minute method) | I |
| A-33 | sodium (2S)-2-(4-chlorophenoxy)-5-methylhexanoate | 1H-NMR (300 MHz, CD₃OD): δ 7.18 (d, 2H), 4.29 (t, 1H), 1.97-1.84 (m, 2H), 0.93 (d, 6H). | 15.797 | I |
| A-34 | methyl (2S)-2-(4-chlorophenoxy)-5-methylhexanoate | 1H-NMR (300 MHz, CDCl3): δ 7.23 (d, 2H), 4.56 (t, 1H), 3.76 (s, 3H), 1.68-1.51 (m, 1H), 1.49-1.26 (m, 2H), 0.93 (d, 6H). | 16.382 | I |
| A-35 | sodium (2S)-2-(4-chlorophenoxy)-4-methylpentanoate | 1H NMR (300 MHz, CDCl3) δ 6.84 (d, 2H), 4.68-4.59 (m, 1H), 1.01 (d, 3H), 0.95 (d, 3H); | 15.306 | I |
| A-36 | sodium (2S)-2-(4-chlorophenoxy)hexanoic acid | 1H NMR (300 MHz, CD3OD) δ 7.17 (d, 2H), 4.31 (t, 1H), 1.88 (q, 2H), 1.60-1.30 (m, 4H), 0.92 (t, 3H). | 15.39 | I |
| A-37 | methyl (2S)-2-(4-chlorophenoxy)hexanoate | 1H NMR (300 MHz, CDCl3) δ 6.82 (d, 2H), 4.57 (t, 1H), 3.75 (s, 3H), 1.95 (m, 2H), 0.93 (t, 3H). | 16.07 | I |
| A-38 | (2S)-2-(4-chloro-2-fluorophenoxy)propanoic acid | 1H NMR (400 MHz, DMSO-d6) δ 13.15 (s, 1H), 7.45 (dd, J = 11.2, 2.6 Hz, 1H), 7.19 (ddd, J = 8.8, 2.5, 1.5 Hz, 1H), 7.06 (t, J = 9.0 Hz, 1H), 4.95 (q, J = 6.8 Hz, 1H), 1.53 (d, J = 6.8 Hz, 3H). | 3.04 | I |
| A-39 | (2S)-2-(3,4-dichlorophenoxy)propanoic acid | 1H NMR (400 MHz, DMSO-d6) δ 13.16 (s, 1H), 7.53 (d, J = 9.0 Hz, 1H), 7.18 (d, J = 2.9 Hz, 1H), 6.92 (dd, J = 9.0, 2.9 Hz, 1H), 4.96 (q, J = 6.8 Hz, 1H), 1.50 (d, J = 6.8 Hz, 3H). | 7.59 | I |
| A-40 | (2S)-2-(2,4-dibromophenoxy)propanoic acid | 1H NMR (400 MHz, CDCl₃) δ 7.71 (1H, d, J = 2.4 Hz), 7.36 (1H, dd, J = 8.7, 2.4 Hz), 6.75 (1H, d, J = 8.8 Hz), 4.78 (1H, q, J = 6.9 Hz), 1.72 (3H, d, J = 6.9 Hz) | 1.451 (3 minute method) | I |
| A-41 | (2S)-2-[4-(prop-1-yn-1-yl)phenoxy]propanoic acid | 1H NMR (300 MHz, CD₃OD) δ 7.25 (d, 2H), 4.77 (q, 1H), 1.98 (s, 3H), 1.57 (d, 3H). | 12.97 | I |
| A-42 | (2S)-2-(4-ethynylphenoxy)propanoic acid | 1H-NMR (300 MHz, CD3OD): δ 7.31 (d, 2H), 4.49 (q, 1H), 1.52 (d, 3H). | 11.175 | I |
| A-43 | sodium (2S)-2-(4-chlorophenoxy)butanoate | 1H NMR (300 MHz, CD3OD) δ 6.87 (d, 2H), 4.28 (t, 1H), 1.07 (t, 3H); | 13.299 | I |
| A-44 | sodium (2S)-2-(2,4-dichlorophenoxy)propanoate | 1H-NMR (300 MHz, CD3OD): δ 7.35 (s, 1H), 6.86 (d, 1H), 4.44 (q, 1H), 1.58 (d, 3H). | 13.564 | I |

TABLE B-continued

Illustrative Examples of the Invention

| Compound Number | IUPAC name | $^1$H NMR | HPLC retention time | Synthesis method |
|---|---|---|---|---|
| A-45 | sodium (2S)-2-(4-chlorophenoxy)-3-methylbutanoate | 1H-NMR (300 MHz, CD3OD): δ 7.16 (d, 2H), 4.05 (q, 1H), 2.26-2.09 (m, 1H), 1.04 (dd, 6H). | 9.686 | I |
| A-46 | sodium (2S)-2-(4-ethylphenoxy)propanoate | 1H NMR (300 MHz, CD3OD) δ 6.81 (d, 2H), 4.47 (q, 1H), 2.54 (q, 2H), 1.51 (d, 3H), 1.17 (t, 3H); | 12.937 | I |
| A-47 | sodium (2S)-2-(4-cyanophenoxy)propanoate | 1H NMR (300 MHz, CD3OD) δ 7.00 (d, 2H), 4.58 (q, 1H), 1.57 (d, 3H); | 10.35 | I |
| A-48 | sodium (2S)-2-[4-(methylsulfanyl)phenoxy]propanoate | 1H NMR (300 MHz, CD3OD) δ 6.85 (d, 2H), 4.47, (q, 1H), 2.39 (s, 3H), 1.52 (d, 3H); | 5.858 | I |
| A-49 | methyl (2S)-2-(4-ethynylphenoxy)propanoate | 1H NMR (300 MHz, CDCl3) δ 7.42 (d, 2H), 4.78 (q, 1H), 3.76 (s, 3H), 3.01 (s, 1H), 1.67 (d, 3H). | 11.73 | I |
| A-50 | methyl (2S)-2-(4-bromophenoxy)propanoate | 1H NMR (300 MHz, CDCl3) δ 7.38 (d, 2H), 4.73 (q, 1H), 3.76 (s, 3H), 1.63 (d, 3H). | 15.11 | I |
| A-51 | methyl (2S)-2-(4-chlorophenoxy)butanoate | 1H NMR (300 MHz, CDCl3) δ 7.24 (d, 2H), 4.54 (t, 1H), 3.76 (s, 3H), 1.99 (m, 2H), 1.07 (t, 3H). | 12.98 | I |
| A-52 | 2,2,2-trifluoroethyl (2S)-2-(4-chlorophenoxy)propanoate | 1H NMR (300 MHz, CDCl3) δ 7.25 (m, 2H), 4.84 (q, 1H), 4.56 (q, 2H), 1.67 (d, 3H). | 13.279 | I |
| A-53 | propan-2-yl (2S)-2-(4-chlorophenoxy)propanoate | 1H NMR (300 MHz, CDCl3) δ 7.23 (m, 2H), 5.07 (m, 1H), 4.67 (q, 1H), 1.61 (d, 3H), 1.27 (d, 3H). | 13.595 | I |
| A-54 | methyl (2S)-2-(4-chlorophenoxy)propanoate | 1H NMR (300 MHz, CDCl3) δ 7.20 (d, 2H), 4.70 (q, 1H), 3.78 (s, 3H), 1.65 (d, 3H). | 14.969 | I |
| A-55 | (2S)-2-(4-bromo-2,6-difluorophenoxy)-3-methylbutanoic acid | 1H NMR (400 MHz, DMSO-d6) δ 13.11 (s, 1H), 7.55-7.42 (m, 2H), 4.58 (dt, J = 4.5, 1.2 Hz, 1H), 2.21 (pd, J = 6.8, 4.5 Hz, 1H), 1.03 (d, J = 6.8 Hz, 3H), 1.01 (d, J = 6.9 Hz, 3H). | 4.444 | I |
| A-56 | (2S)-2-(4-bromophenoxy)butanoic acid | $^1$H NMR (300 MHz, CDCl$_3$) δ 10.21-9.28 (br, 1H); 7.39 (d, 2H); 6.79 (d, 2H); 4.58 (t, 1H); 2.03 (q, 2H); 1.11 (t, 3H). | 14.016 | I |
| A-57 | (2S)-2-(4-cyclobutylphenoxy)propanoic acid | 1H NMR (300 MHz, CDCl3) δ 11.19 (br s, 1H), 7.16 (d, 2H), 4.78 (q, 1H), 3.57-3.43 (m, 1H), 1.67 (d, 3H). | 14.623 | I |
| A-58 | (2S)-2-(4-bromo-2-fluorophenoxy)butanoic acid | 1H NMR (300 MHz, CDCl3) δ 10.68 (br s, 1H), 6.85 (t, 1H), 4.61 (m, 1H), 2.06 (m, 2H), 1.13 (t, 3H). | 14.177 | I |

Description of Pharmacological Methods and Drawings

Isolation of Muscles from Rats and Human, Ethical Approval, Dissection of Muscles, Solutions, and Chemicals Experiments were performed using rat soleus muscles from either young (4-wk-old) or adult Wistar rats (12-14-week-old). Animal handling, killing and isolation of muscle is described elsewhere All experiments were performed using normal Krebs-Ringer bicarbonate solution (NKR). In solutions with elevated $Mg^{2+}$, $MgCl_2$ was added to NKR-solution causing minor increases in osmolarity and ionic strength. In solutions with elevated $K^+$, 4 mM NaCl was replaced by 4 mM KCl in the NKR.

For experiments conducted using human abdominal muscle, details on patients, approval and the approaches for isolation, transportation, and experimentation are available elsewhere Electrical Stimulation, Contractile Force and M-Waves In all contraction experiments, isometric force production was determined and force produced during contractions was quantified by measuring the integral of the force response (AUC). Stimulation and force recordings have been described elsewhere. Briefly, muscles were stimulated to contract in three different ways (FIG. 1): i) When using field stimulation (25-30 V/cm) and pulses with a duration of 0.2 ms, the muscles could be stimulated directly without requirements of a functional motor nerve. ii) If the duration of the pulses used in the field stimulation was only 0.02 ms, the contractile force could be completely suppressed by the nicotinic ACh receptor antagonist tubocurarine. This shows that stimulation with short pulses activates the muscles indirectly through stimulation of the attached motor nerve. iii) Stimulation could be isolated to the motor nerve after it had been sucked into a glass capillary. In these latter experiments, extracellular recordings of action potentials (M-waves) could be measured without temporal overlap with stimulation artefacts.

Cable Properties and Endplate Potentials

Isolated soleus muscles from adult rats or human abdominal muscles preparations were placed in a chamber and the resting membrane conductance (Gm) was measured in individual fibers using electrophysiological techniques described in detail elsewhere (FIG. 4). $G_m$ reflects function of ion channels that are open at the resting membrane potential. In skeletal muscle, $G_m$ is dominated by ClC-1 $Cl^-$ channels and for this reason an effect of a compound on Gm predominantly reflects alterations in ClC-1 function. To ensure that the compound indeed affected ClC-1 function, recordings were in some cases repeated in the presence of the ClC-1 inhibitor 9-AC (100 μM) to quantify for effects of the compounds on $K^+$ channels. To determine affinity of ClC-1 channels for a particular compound, $G_m$ was plotted against compound concentration and a Boltzmann sigmoidal function was fitted to the data to obtain Kd of the compound (Table 3).

To measure endplate potentials (EPPs), soleus muscles from adult rats were placed in a chamber and the motor nerve was stimulated. To only measure EPPs, 1 μM of p-conotoxin GiiiB was added to solution. All recordings were corrected for variation in resting membrane potential using −80 mV as the standard Pharmacokinetic Analysis and Test of C8 in Rat Models of Myasthenia Gravis The pharmacokinetic analysis of a single, intraperitoneal (I. P.) dose of C8 (10 mg/kg) was studied in young (4 weeks old) Sprague-Dawley rats. This part of the study was performed by Pipeline Biotech A/S (Sporring, Denmark). 24 animals were injected with C8 and three animals were sacrificed at times 15 min, 30 min, 1 hr, 2 hr, 4 hr, 6 hr, 8 hr, 24 hr after injection and plasma concentrations of C8 was determined using Liquid Chromatography Mass Spectrometry (LC-MS). Plasma concentrations (free and bound) were determined by OnTarget Chemistry (Uppsala, Sweden, Project No.: PB243-001).

Two sets of in vivo experiments were performed with C8: In the first series of experiments I.P. tubocurarine at (0.13 mg/kg) was used to induce a myasthenia like phenotype while in the second series of experiments a passive immunization model of myasthenia gravis was used in which rats were injected I.P. with a monoclonal antibody against the acetylcholine receptors at the neuromuscular endplate (MAB35, GTX14187, Genetex, 0.4-0.6 mg/kg). In both series of experiments, running performance was tested on a rotarod using a protocol where the rod was accelerated gradually over a 5 min period, and the running time and covered distance before falling off the rod were measured. To accustom the animals to the rotarod, the animals were tested three times on two consecutive days and animals that failed to complete the 5 min of running on the last day of familiarization period were not used in experiments. Experiments with tubocurarine were carried out over two days, and on each day the effect of tubocurarine on running performance was tested. On the first day only tubocurarine was injected. Animals that failed to respond to tubocurarine were not used on the next day of experimentation. On the second day, the animals were first allowed to run on the rotarod, and all animals performed normally. This shows that effects of the tubocurarine that had been injected on the day before had completely disappeared. Animals were then divided into two groups: One group was injected with 20 mg/kg C8 while the other group received sham treatment. 2 hrs after the C8 or sham injection, the second injection of tubocurarine was administered and the animals running performance on the rotarod was tested. The allocation of the animals into the two groups (C8 or sham) was random and unknown to the experimenter (blinded experimental design).

In experiments with MAB35, animals were first familiarized with the rotarod over two consecutive days and then injected I.P. with MAB35. After injection, rotarod performance was then again monitored regularly over the consecutive two days. Performance generally started to decline within 21-43 hrs after MAB35 injection, and if a stable reduction in performance was obtained, the animals were administered either C8 or sham. A considerable number of animals, however, became moribund failing to walk and they had altered ventilation (rapid) and pronounced ptosis. These animals were not included in experiments. Animals with a stable reduction in performance were injected with C8 (20 or 30 mg/kg) or sham treated and their performance were again monitored 2, 4, and 6 hrs after C8 or sham injection.

Example 5: Experimental Approach for Testing Compounds

The aim was to find compounds that by inhibition of CIC-1 channels can recover nerve-stimulated force under conditions of fatigue including conditions where fatigue is caused by compromised neuromuscular transmission. Neuromuscular transmission dysfunction can develop because of both pre- and/or post-synaptic complications in connection with a disorder or as part of neuromuscular blockade during/after surgery. In the initial series of drug testing, experiments were performed with isolated muscles in the presence of sub-maximal ACh receptor antagonist tubocurarine. Since the inclusion of tubocurarine caused a partial loss of neuromuscular transmission this experiment mimics the conditions in myasthenia gravis and neuromuscular blockade. To mimic conditions with pre-synaptic complication (Lambert Eaton syndrome, motor neuron disorder, polyneuropathy) the intact nerve-muscle preparations were incubated at elevated extracellular $Mg^{2+}$, which is known to suppress release of ACh from nerve terminals of motor neurons.

Figure 1B:
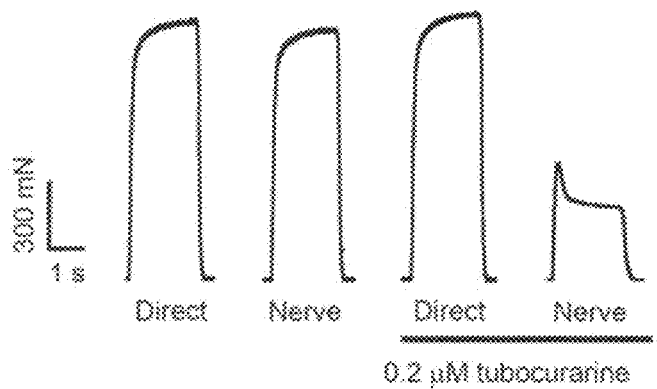
Figure 1C:
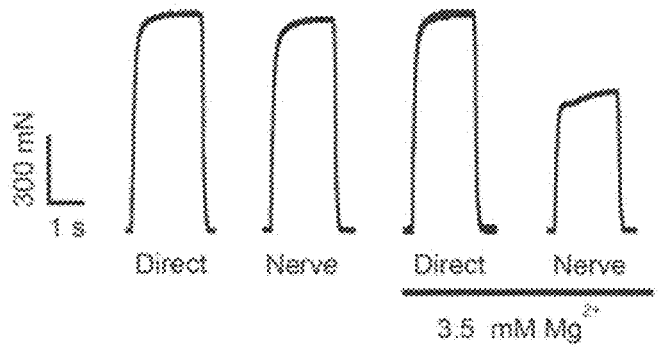

Experiments shown in FIG. 1 were performed to confirm that tubocurarine and elevated extracellular $Mg^{2+}$ specifically suppressed neuromuscular transmission without affecting the capacity of the muscle fibers to generate force. The experiments also illustrate that field stimulation of the entire nerve-muscle preparation selectively activates the motor nerve when short-duration pulses (0.02 vs 0.2 ms) were used. In FIG. 1A the preparation was stimulated either via field stimulation or via nerve-stimulation using a suction electrode. With the suction electrode only the nerve could be stimulated. When exposed to a submaximal concentration of the ACh receptor antagonist tubocurarine (0.2 µM) a clear drop in peak force and a further decline (or fade) in force during the stimulation developed. This drop in force clearly reflected compromised neuromuscular transmission, as the decline in peak force and fading were not seen with direct stimulation of the muscle. Recordings of M-waves in the muscle in FIG. 1A show that tubocurarine caused marked decline in M-wave signal during the stimulation (compare inserts i and ii in FIG. 1A). Thus, loss of M-wave and force with tubocurarine reflected partial blockade of neuromuscular function. Such fading of force and M-waves during stimulation represent clinical hallmarks of both myasthenia gravis and neuromuscular blockade in connection with surgery. In FIG. 1B, observations with normal (0.2 ms) and short-duration (0.02 ms) pulses have been compared. It can be seen that only with short-duration pulses did tubocurarine cause a decline in peak force and fading (FIG. 1B). This confirms that short-duration pulses in field stimulation could be used as specific nerve-stimulation. FIG. 1C shows that also elevated extracellular $Mg^{2+}$ primarily affected nerve-stimulated force while it did not affect force when the muscle was stimulated directly. Elevated extracellular $Mg^{2+}$ could thus be used to partially block neuromuscular transmission and thus be used as a model of conditions with compromised pre-synaptic function (Lambert Eaton syndrome, amyotrophic lateral sclerosis, spinal muscular atrophy).

Example 6: Proof-of-Concept that CIC-1 Inhibition can Overcome Loss of Neuromuscular Transmission in Conditions Mimicking Neuromuscular Disorders To initially confirm that inhibition of CIC-1 ion channels can be used to recover contractile force in muscle with reduced neuromuscular transmission, isolated nerve-muscle preparations were first exposed to either tubocurarine (FIG. 2A) or elevated $Mg^{2+}$ (FIG. 2B) and then a specific CIC-1 inhibitor (9-AC) was added. It can be seen that CIC-1 inhibition caused a marked recovery of both force and M-wave signal in both conditions. This demonstrates the novel concept that CIC-1 channel inhibition can alleviate loss of force induced by compromised neuromuscular transmission. Similar observations were seen in EDL and diaphragm muscles from both young and adult rats (data not shown). 9-AC does not have the potential to be used as a pharmaceutical.

Example 7: Identification of Useful Compounds for Improving Neuromuscular Transmission To identify CIC-1 inhibitors that could be used for treatment of neuromuscular disorders we repeated the experiment shown in FIG. 2A but instead of adding 9-AC we added the compounds of interest in different concentrations within the range from 10 to 500 µM. The starting point for finding CIC-1 inhibitors was derivatives of clofibrate that have been shown to have CIC-1 inhibiting actions (Table 1). FIG. 3A shows representative nerve-stimulated force in two muscles during such an experiment before and during exposure to tubocurarine. In one of the muscles (black trace), 50 µM of a test compound (C8) was added after 40 mins in tubocurarine. For comparison with the muscle only exposed to tubocurarine (grey trace), the two traces have been overlaid. It can be seen that while tubocurarine affected the two muscles equally before C8 addition (middle traces), the muscle receiving C8 recovered markedly when compared to its force before C8 addition and especially when compared to the other muscle that did not get C8 (right traces). To quantify the recovery of force with compounds such as C8, the force integrals (AUC) were determined for each contraction during an experiment and these AUC values were related to AUC before addition of tubocurarine. FIG. 3B shows average AUC observations of force during experiments in which muscles at tubocurarine were exposed to C8. For comparison, muscles only exposed to tubocurarine have been included. The dotted line indicates the recovery of force with C8 when compared to the force production before its addition. This value was used in Table 1 for evaluation of the efficacy of the different compounds in recovering force. Please note that force produced by the muscles only exposed to tubocurarine continued to fall after C8 had been added to the other group of muscles. This shows that C8 is able to recover force despite a progressively stronger suppressive action of tubocurarine.

TABLE 1

Recovery of nerve-stimulated force by some compounds in isolated rat soleus muscles exposed to sub-maximal tubocurarine concentration. AUC force was first determined after 40 min in tubocurarine (column 3) and related to nerve-stimulated force prior to addition of tubocurarine. The AUC at the different concentrations of compounds (columns 4-6) is the % change in AUC compared to the AUC before addition (column 3).

| | IUPAC | Force before addition of compound % of control | 50 µM % change after addition | 150 µM % change after addition | 500 µM % change after addition | n |
|---|---|---|---|---|---|---|
| C5 | (2S)-2-(benzyloxy)propanoic acid | 24 | −7 | 1 | 42 | 2 |
| C6 | 2-(4-fluorobenzenesulfonyl)propanoic acid | 39 | −11 | −8 | 9 | 5 |
| C7 | 2-(4-chlorophenoxy)butanoic acid | 41 | −12 | 0 | 40 | 2 |
| C8 | (2S)-2-(4-bromophenoxy)propanoic acid | 36 | 16 | 23 | NT | 10 |
| C9 | 3-amino-2-(4-fluorophenoxy)propanoic acid hydrochloride | 57 | −14 | −13 | 5 | 2 |
| C11 | 4-chlorophenyl 2-(4-fluorophenoxy)propanoate | 38 | 46 | 54 | NT | 4 |
| C21 | 2-(4-bromophenoxy)-4-methoxy-3-methylbutanoic acid | 54 | −3 | 7 | 36 | 2 |
| C22 | (2S)-2-(4-bromophenoxy)-3methylbutanoic acid | 42 | 16 | NT | NT | 2 |

NT: Not Tested

In a separate series of experiments with 8 isolated rat soleus muscles, ACh receptors were inhibited using 2 µM rocuronium, which is a clinically used neuromuscular blocking agent. Under these conditions the nerve-stimulated force was reduced to 51±5% of force before rocuronium. When 50 µM C8 was subsequently added nerve-stimulated contractile force was significantly recovered to 81±4% of force before rocuronium (p<0.01). This illustrates the potential of these compounds to be used as reversal agents.

The next series of experiments determined whether the compounds that recovered nerve-stimulated force in the presence of tubocurarine could also recover nerve-stimulated force at elevated extracellular $Mg^{2+}$. To do this the experiment depicted in FIG. 2B was repeated with C8. As in FIG. 3, AUC was quantified for each contraction and the capacity of C8 to recover force at elevated $Mg^{2+}$ was evaluated from the recovery of AUC compared to AUC immediately before application of the compound (Table 2).

TABLE 2

Recovery of nerve-stimulated force with compounds in isolated rat soleus muscles exposed to 3.5 mM $Mg^{2+}$. AUC force was first determined after 70 min at elevated extracellular $Mg^{2+}$ (column 3) and related to nerve-stimulated force prior to addition of additional $Mg^{2+}$. The AUC at the different concentrations of compounds (columns 4 and 5) is the % change in AUC compared to the AUC before $Mg^{2+}$ elevation (column 3). As in experiments with tubocurarine, please note that force kept dropping in muscles only exposed to elevated $Mg^{2+}$.

| | IUPAC | Force before addition of compound % of control | 50 µM % change after addition | 100 µM % change after addition | n |
|---|---|---|---|---|---|
| C8 | (2S)-2-(4-bromophenoxy)propanoic acid | 38 ± 6 | 13 ± 4 | 26 ± 5 | 2 |

Example 7: Effect of Compounds on ClC-1 Channels—Target Validation

Figure 4B:
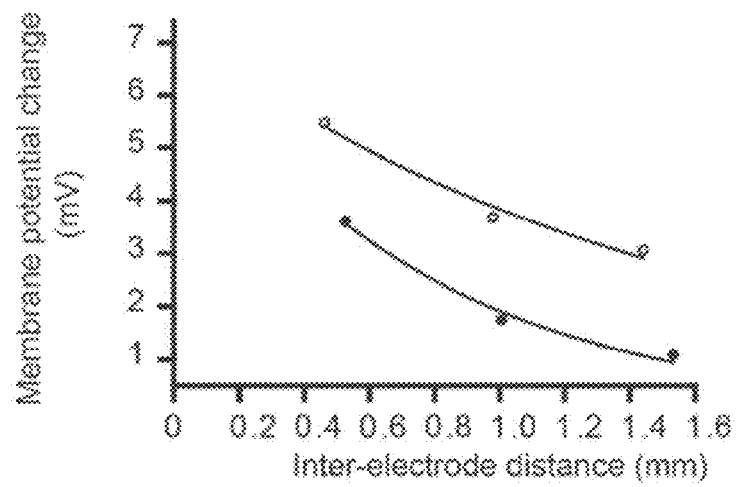
Figure 4C:
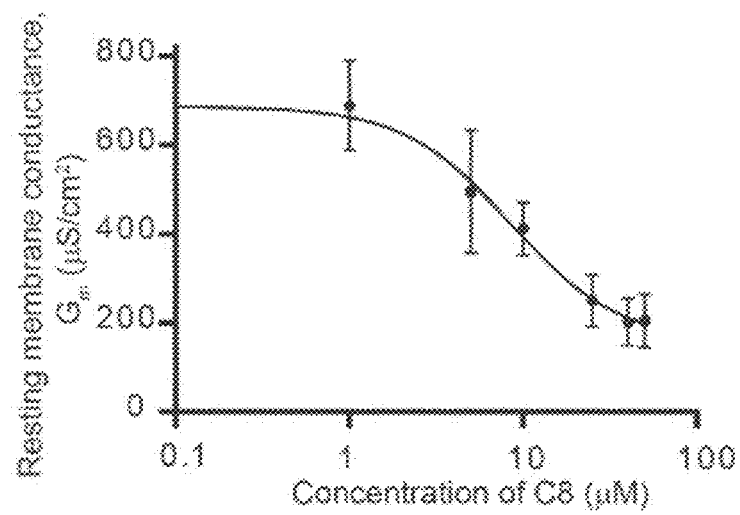

The effect of compounds on ClC-1 ion channels was determined in muscle from adult rats using electrophysiological techniques described elsewhere. With this technique, three electrodes were placed in the same muscle fiber and by injecting small current pulses through two electrodes it was possible to obtain the voltage responses to this current injection at three inter-electrode distances. Examples of voltage responses at the three inter-electrode distances in a control fiber and in a fiber at 10 µM C8 are presented in FIG. 4A. By plotting the steady state deflection of the voltage responses against inter-electrode distance, $G_m$ can be determined from fits of the data to a two-parameter exponential function (FIG. 4B). The lines connecting data points in FIG. 4B show fits of data to the two-parameter exponential function. Such recordings were performed for relevant compounds for a range of compound concentrations, and in FIG. 4C the observations of $G_m$ at the different concentrations of C8 have been plotted. A Kd for a particular compound was obtained by fitting the data of Gm in FIG. 4C to a sigmoidal function (line in FIG. 4C). Such Kd values have been included in Table 3 for relevant compounds. The observations in Table 3 show that compounds that were particular effective in recovering nerve-stimulated force in muscle with compromised neuromuscular transmission (Tables 1 and 2) were also potent inhibitors of $G_m$ (Table 3).

Also included are Kd values for compounds when tested in human muscle using an approach identical to that in rat muscle.

TABLE 3

Effect of different compounds on $G_m$ in isolated rat and human muscles.

| | $G_m$ No Compound | Kd for ClC-1 inhibition |
|---|---|---|
| C8 Rat | 642 ± 25, n = 33 | 9 µM |
| C8 Human | 430 ± 41, n = 5 | 5.5 µM |
| C22 rat | 642 ± 25, n = 33 | 4.1 µM |

Example 8: Combination Treatments

ClC-1 is a novel target in treatment of neuromuscular complications and it was therefore explored whether this approach for symptomatic treatment could be used in combination with existing symptomatic treatment approaches. In myasthenia gravis, which in isolated muscles was mimicked by tubocurarine, the symptoms of muscle fatigue are most commonly treated with inhibitors of acethylcholineesterase of which neostigmine and pyridostigmine are examples. Also, neostigmine is the most commonly used reversal agent of neuromuscular blocked after surgery. To test if ClC-1 inhibitors and neostigmine or pyridsostigmine can be used in combination, the concentration of tubocurarine that was required to depress nerve-stimulated force by 50% (Kd,tub) was determined in four experimental conditions: i) control conditions, ii) with ClC-1 inhibitor alone, ii) with neostigmine or pyridostigmine alone, and iv) with neostigmine or pyridostigmine and ClC-1 inhibitor together. FIG. 5A-D show recordings of nerve-stimulated force production at different tubocurarine concentrations when tested under the four experimental conditions. It can be seen that C8 (FIG. 5B) and neostigmine (FIG. 5C) both resulted in elevated nerve-stimulated force when compared to control (FIG. 5A). The force was, however, best maintained when both neostigmine and C8 were used (FIG. 5D). To quantify the effect of compounds on tubocurarine sensitivity, the force at the different tubocurarine concentrations was determined. In plots of nerve-stimulated force against tubocurarine concentration (FIG. 5E) Kd,tub was determined by fitting four parameter sigmoidal functions to the data and the Kd,tub for the different compounds have been collected in Table 4.

TABLE 4

Effect of neostigmine, pyridostigmine, ClC-1 inhibitor, and combination of neostigmine or pyridostigmine and ClC-1 inhibitor on Kd, tub.

| Compound | Control | Neostigmine (10 nM) | Pyridostigmine (100 nM) | Compound (50 µM) | Compound (50 µM) + Neostigmine (10 nM) | Compound (50 µM) + Pyridostigmine (100 nM) |
|---|---|---|---|---|---|---|
| C8 | 118 ± 5 nM | 166 ± 13 nM*,** | | 177 ± 7 nM*,** | 218 ± 18 nM* | |
| C8 | 118 ± 5 nM | | 127 ± 15 nM | 177 ± 7 nM*,** | | 186 ± 5 nM* |

*Indicates significantly different from control.
**Significantly different from the combination of neostigmine and compound.

While the use of tubocurarine mimics conditions with reduced neuromuscular transmission due to post-synaptic dysfunction (myasthenia gravis, neuromuscular blockade), the experiments with elevated extracellular $Mg^{2+}$ mimics conditions with pre-synaptic dysfunction akin to a range of neuromuscular disorders including Lambert Eaton syndrome, motor neuron disorders and polyneuropathy. Patients with Lambert Eaton syndrome are commonly treated with inhibitors of voltage gated $K^+$ channels such as 3,4-diaminopyridine (3,4-AP). Based on this it was determined whether recovery of nerve-stimulated force at elevated extracellular $Mg^{2+}$ with ClC-1 inhibiting compounds could be added to force recovery with 3,4-AP. This was done by determining the concentration of $Mg^{2+}$ that was required to depress nerve-stimulated force by 50% (Kd,$Mg^{2+}$) in four experimental conditions: 1) in control conditions, ii) with 3,4-AP alone, iii) with C8 alone, and iv) with 3,4-AP and C8 together. FIG. 6A-D show recordings of nerve-stimulated force production at different $Mg^{2+}$ concentrations when tested under these four experimental conditions. It can be seen that with both 3,4-AP and ClC-1 inhibitor did the nerve-stimulated force at elevated $Mg^{2+}$ remain elevated when compared to control. The force was, however, best maintained when the combination of both 3,4-AP and ClC-1 inhibitor was used. To quantify the effect of compounds on $Mg^{2+}$ sensitivity the force at the different $Mg^{2+}$ concentrations was determined. In plots of nerve-stimulated force against $Mg^{2+}$ concentration (FIG. 6E) the Kd,$Mg^{2+}$ was determined by fitting four parameter sigmoidal function to the data. Kd, $Mg^{2+}$ for the different compounds have been collected in Table 5.

TABLE 5

Effect of 3,4-AP, ClC-1 inhibitor and combination of 3,4-AP and ClC-1 inhibitor on Kd, $Mg^{2+}$

| Compound | IUPAC | Control | 3,4-AP (10 μM) | Compound (50 μM) | Compound (50 μM) + 3,4-AP (10 μM) |
|---|---|---|---|---|---|
| C8 | (2S)-2-(4-bromophenoxy)propanoic acid | 3.5 ± 0.1 mM n = 6 | 5.8 ± 0.3 mM*,** n = 3 | 4.0 ± 0.1 mM*,** n = 7 | 7.8 ± 0.5 mM* n = 4 |

*Indicates significantly different from control.
**Significantly different from the combination of 3,4-AP and compound.

As illustrated in table 5, combination therapy using C8 and 3,4-diaminopyridine results in an unexpected synergistic effect on recovery of neuromuscular transmission.

Example 9: Effect of ClC-1 Inhibitor on Endplate Potentials (EPPs)

Figure 7A:
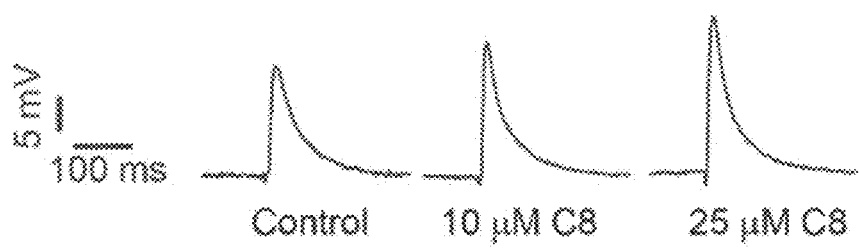
FIGS. 7A-7B. Effects of C8 on EPP amplitude in rat soleus muscle. Intracellular electrodes were inserted near visible nerve branches in the muscle. The solution contained 1 μM μ-conotoxin GiiiB to block NaV1.4. Under these conditions nerve-stimulation only resulted in EPP formation in the fibers and it did not trigger muscle fiber action potentials.
Figure 7B:
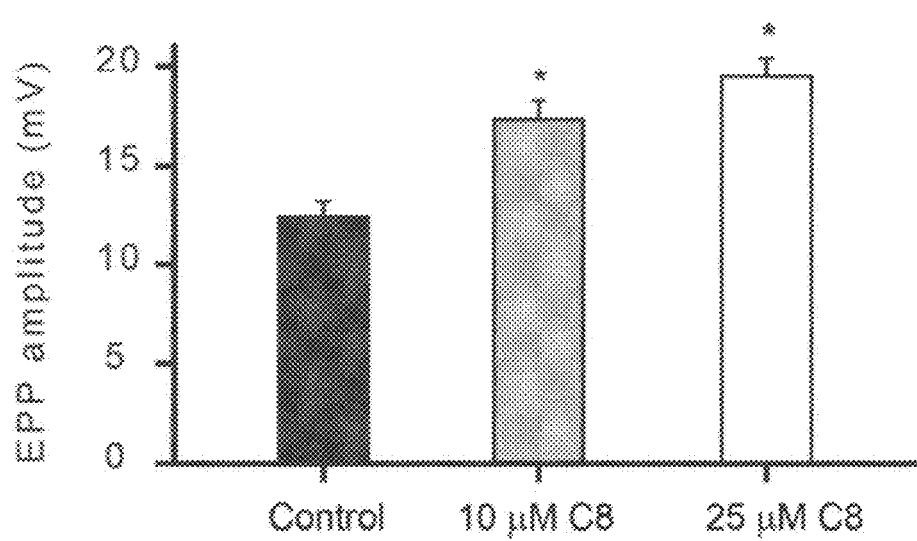

Experiments with intracellular electrodes inserted near visible nerves in rat soleus muscles enabled recordings of EPPs upon nerve stimulation. To prevent action potential initiation upon nerve stimulation, μ-conotoxin GiiiB (1 μM) was included in the incubation solution to inhibit voltage gated $Na^+$ channels in the muscle fibers (NaV1.4). As shown by representative recordings in FIG. 7A the EPP amplitude became larger when C8 was used to inhibit ClC-1 channels. FIG. 7B show summarized data from all fibers. Both 10 and 25 μM C8 caused significantly larger EPPs when compared to control conditions.

Figure 8A:
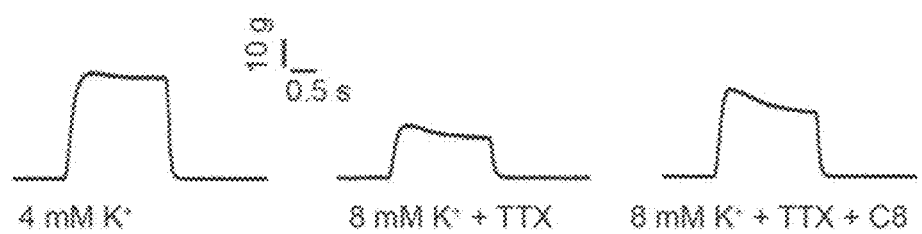
FIGS. 8A-8B. Effects of C8 on contractile force in human muscles depressed by elevated extracellular $K^+$ and low dose of TTX.
Figure 8B:
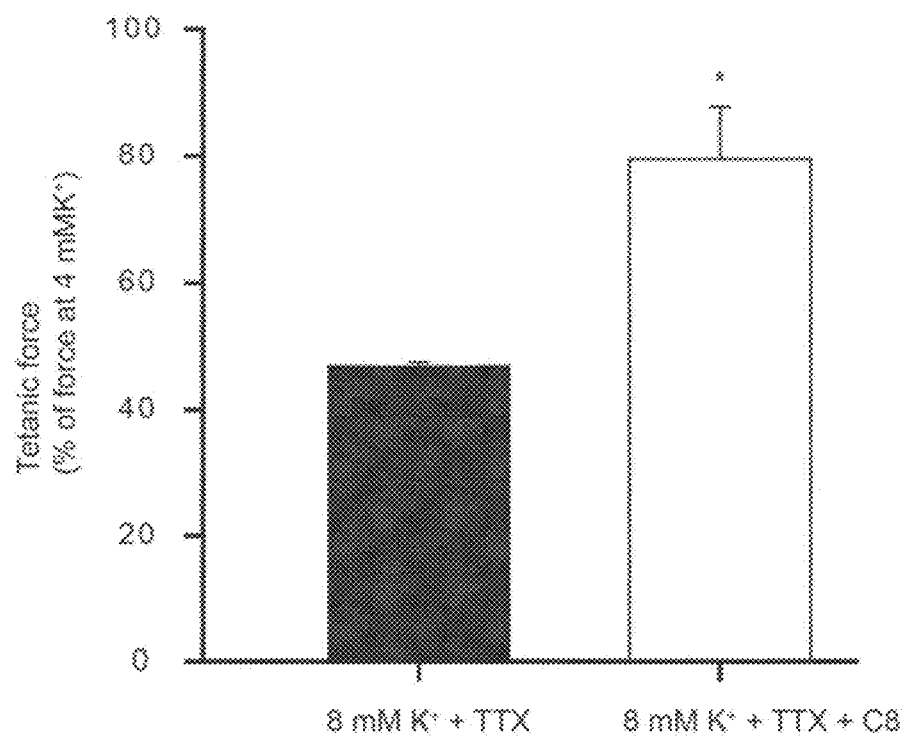

Example 10: ClC-1 Inhibition can Recover Contractile Force in Human Muscles Under Conditions that Mimic Critical Illness Myopathy Critical illness myopathy (CIM) is a condition that develops in around 30% of critically ill patients in intensive care units. The condition is diagnosed from a loss of muscle excitability as evaluated from reduction in compound muscle action potentials. The associated muscle weakness prevents patients from weaning from mechanical ventilation and therefore increases the stay in intensive care units. At the cellular level, CIM is associated with loss of NaV1.4 function and muscle fibers become depolarized. To evaluate whether ClC-1 inhibition can recover muscle function in such conditions, depolarization and loss of NaV1.4 function in CIM were mimicked in experiments with isolated human muscles. Fibers were depolarized by raised extracellular $K^+$, and loss of NaV1.4 function was induced by a small dose of NaV1.4 inhibitor TTX. As shown by FIG. 8, the contractile force declined upon introducing the elevated $K^+$ and TTX. However, contractile force was markedly recovery upon addition of C8. This confirms that compounds that inhibit ClC-1 such as C8 can prevent loss of force due to depolarization and NaV1.4 loss of function—the mechanisms underlying CIM.

Example 11: Pharmacokinetic Analysis of C8 in Rats and Effect of ClC-1 Inhibition in Animal Models of Myasthenia Gravis Before conducting in vivo experiments with animal models of myasthenia gravis, some pharmacokinetic details were obtained for C8 in response to one-bolus I.P. injection. The details from these experiments have been summarized in Table 6:

TABLE 6

PK parameters for C8 tested in rats.

| Parameter | Unit | Value |
|---|---|---|
| $t^{1/2}$ | h | 3.70 |
| Tmax | h | 0.5 |
| Cmax | ng/ml | 44600 |
| C0 | ng/ml | 24533 |
| AUC 0-t | ng/ml*h | 203635 |
| AUC 0-inf_obs | ng/ml*h | 205381 |
| AUC 0-t/0-inf_obs | | 0.9915 |
| VD_obs | ml | 259.62 |
| Cl_obs | ml/h | 48.69 |

Figure 9A:
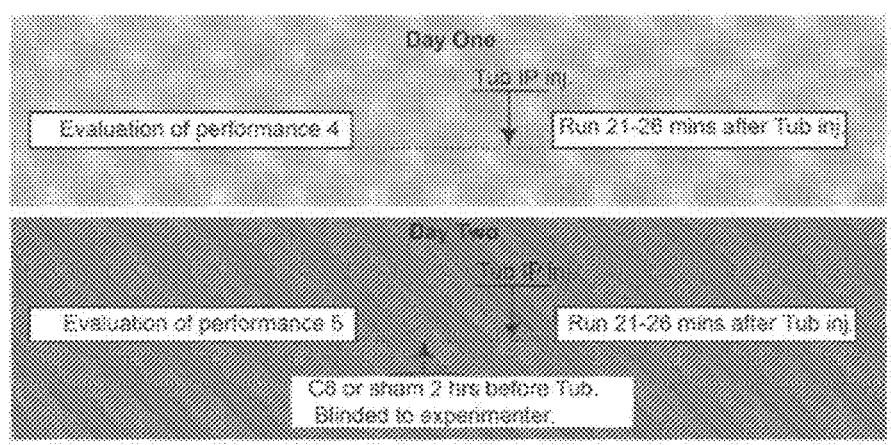
FIGS. 9A-9B. Effects of I.P. C8 injection (20 mg/kg) on running performance of rats after I.P. injection of tubocurarine (0.13 mg/kg).
Figure 9B:
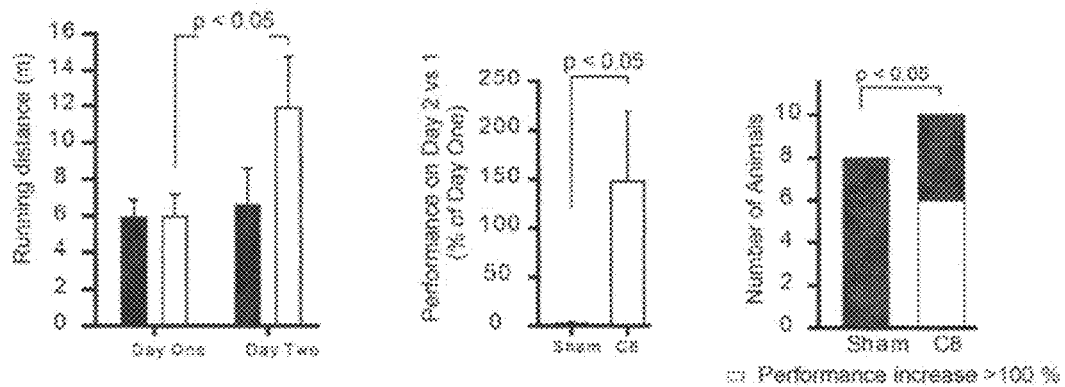

In the first series of in vivo experiments, myasthenia gravis was simply mimicked by I.P. injection of tubocurarine (0.13 mg/kg) in animals that had been familiarized to running on the rotarod. On the first of two consecutive days, tubocurarine was injected I.P. and the running performance of the animal was tested 21 minutes after this injection. On the second day of experimentation, the animals first performed a test run to ensure that they were no longer affected by the tubocurarine injected the day before. Then C8 (20 mg/kg) or sham treatment were injected I.P. and allowed to act for 2 hrs before again injecting tubocurarine. Animals were again tested 21 minutes after this second tubocurarine treatment. This experimental design enabled a paired analysis of whether the sham or C8 injections on the second day changed the response of the animals to tubocurarine. It should also be noted that the experimenter did not know which animals had been given C8 or sham treatment. The design of the experiments has been illustrated in FIG. 9A and the results from the experiments are illustrated in FIG. 9B-D. As can be seen from FIG. 9B, the animals that were administered sham-treatment covered almost identical distances on the two days. C8 treated animals, however, were able to cover significantly longer distance on the rotarod on the second day when compared to their own performance on the first day. Thus, C8 treated animals ran around 150% longer on the second day (FIG. 9C) clearly contrasting that sham-treated animals only ran around 2% longer. To demonstrate that the marked improvement upon C8 administration was a general response of the animals and not just a rare observation in a few animals, FIG. 9D shows the number of animals in the two groups (sham and C8) that had a performance increase of at least 100% on the second day.

Figure 10:
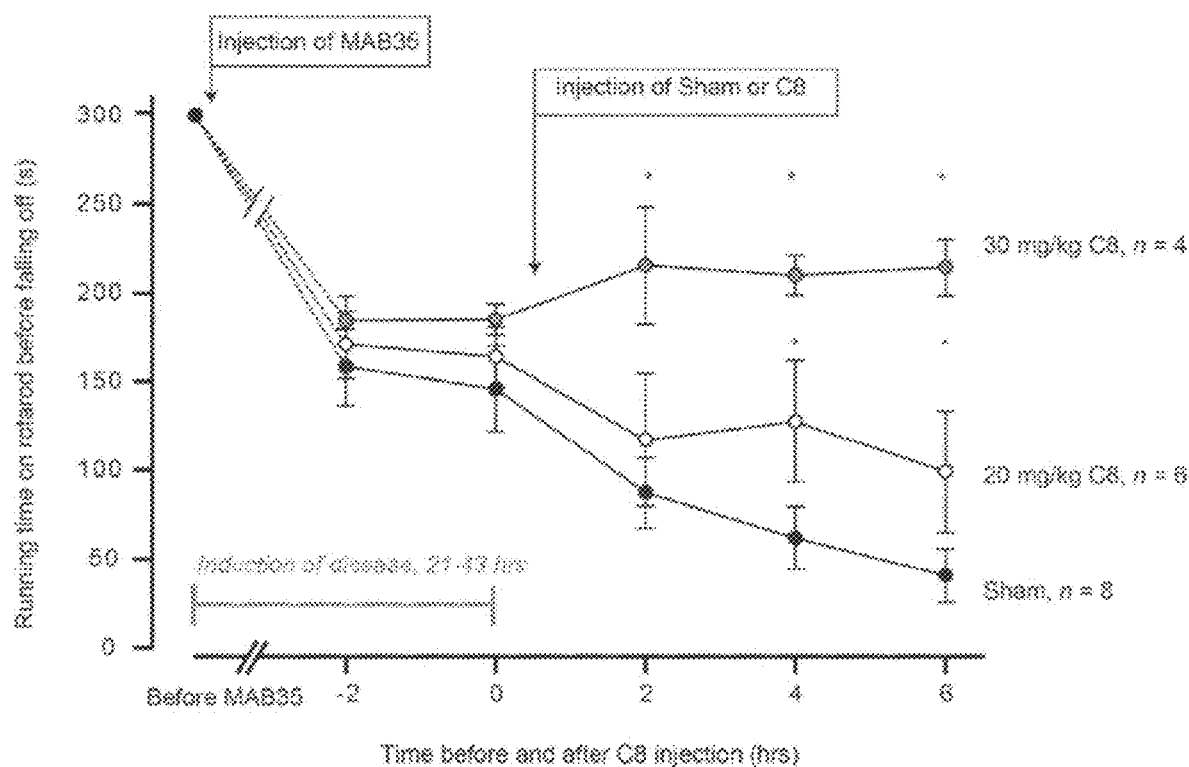
FIG. 10. Effects of C8 on running performance after inducing passive myasthenia gravis in rats using MAB35 monoclonal antibody. Prior to I.P. injection of MAB35 the animals had been familiarized to the rotarod over three training sessions distributed over two days. After I.P. injection of MAB35 the running performance of the animals was monitored regularly and if a stable reduction in performance developed, the animals were given either sham, 20 mg/kg C8 or 30 mg/kg C8. After this treatment performance was monitored every second hour. *Indicates significant different as evaluated using student t-test.
Figure 11A:
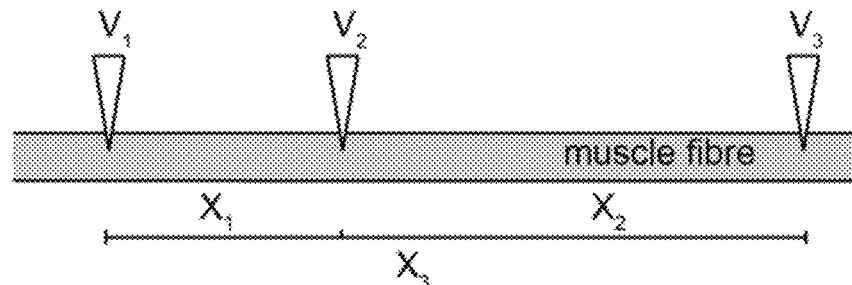
FIGS. 11A-11C.
Figure 11B:
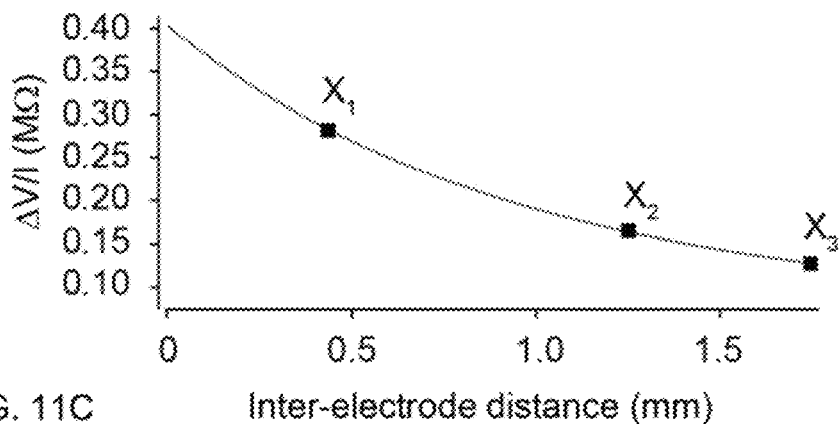
Figure 11C:
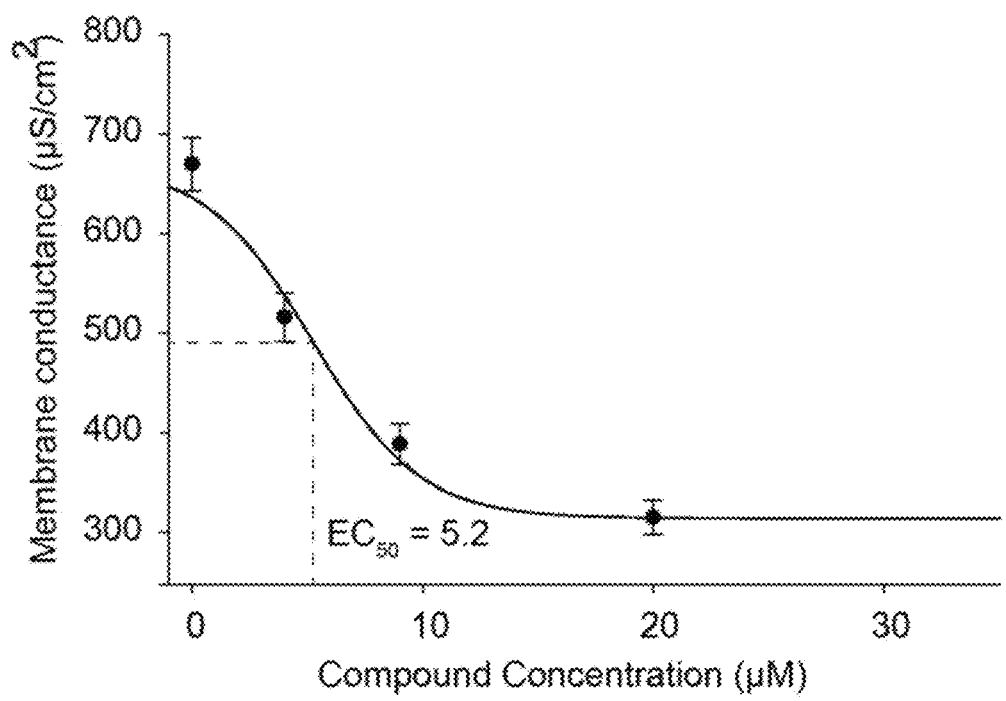
Figure 12A:
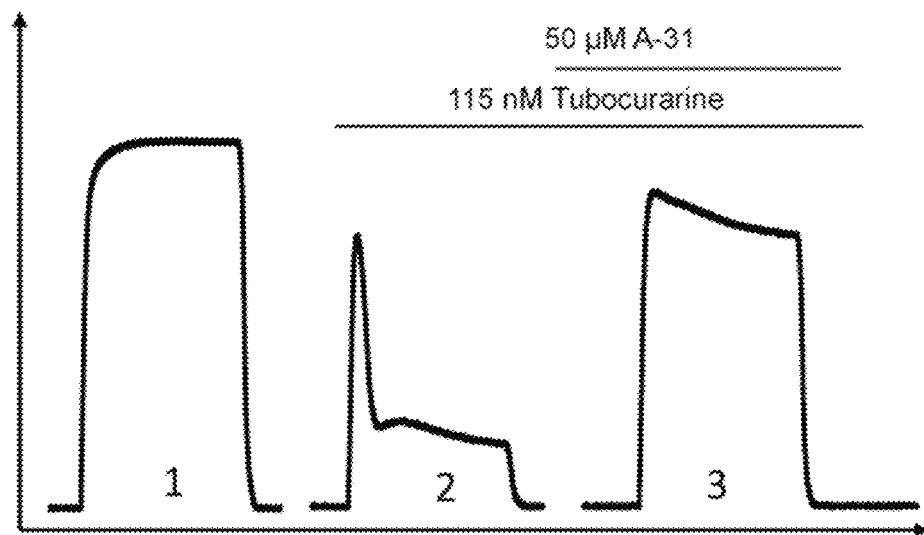
FIGS. 12A-12B.
Figure 12B:
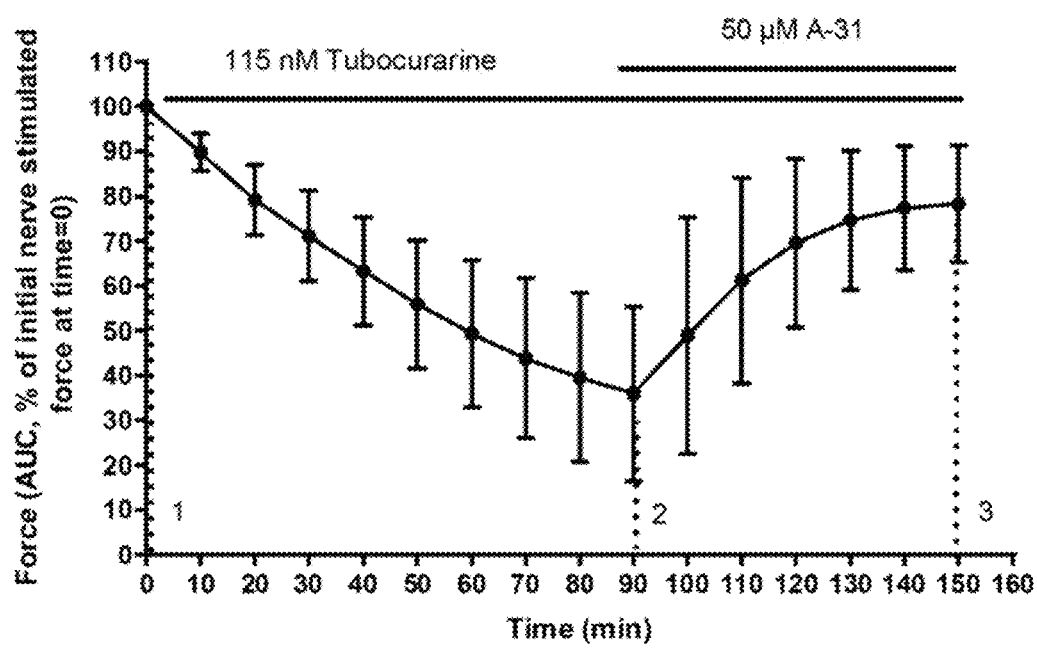

In the last series of experiments, myasthenia gravis was mimicked in rats by inducing an immunological reaction against the motor endplate of muscle fibers using monoclonal antibody against the nicotinic ACh receptor in muscle fibers. Again the animals had been familiarized to the rotarod before the MAB35 injection. As shown in FIG. 10, symptoms of reduced performance developed 21-43 hrs after injection of MAB35. When a stable reduction in performance was observed, the animals were administered either C8 or sham. From FIG. 10 it can be seen that upon injection sham treatment the performance further declined. This decline was reduced when 20 mg/kg C8 was injected and with the larger dose of C8 (30 mg/kg) there was a clear recovery of performance. While there was no difference in performance between the three groups of animals before sham or C8 injections, the performance in the groups of animals treated with C8 was significantly better than sham-treated animals after injection.

Example 12: Electrophysiological Measurement of Compound Inhibition of ClC-1 in Rat Muscle The investigatory goal of these experiments was to evaluate whether compounds inhibit ClC-1 channels in native tissue of rat skeletal muscle fibres. Apparent ClC-1 affinity was reported by the concentration of compound at which 50% of the compound's full inhibition of ClC-1 was observed ($EC_{50}$).

ClC-1 Cl⁻ ion channels generate around 80% of the total membrane conductance ($G_m$) in resting skeletal muscle fibres of most animals including rat and human. Other ion channels that contribute to Gm can therefore be considered negligible, and it is possible to evaluate whether a compound inhibits ClC-1 in rat muscle by comparing $G_m$ measurements before and after exposure to a compound. ClC-1 inhibition would in such recordings be reflected by a reduction of Gm.

Experimentally, $G_m$ was measured in individual fibres of whole rat soleus muscles using a three micro-electrodes technique described in this example and in full detail elsewhere. Briefly, intact rat soleus muscles were dissected out from 12-14 week old Wistar rats and placed in an experimental chamber that was perfused with a standard Krebs Ringer solution containing 122 mM NaCl, 25 mM $NaHCO_3$, 2.8 mM KCl, 1.2 mM $KH_2PO_4$, 1.2 mM $MgSO_4$, 1.3 mM $CaCl_2$, 5.0 mM D-glucose. During experiments, the solution was kept at approx. 30° C. and continuously equilibrated with a mixture of 95% $O_2$ and 5% $CO_2$, pH~7.4. The experimental chamber was placed in Nikon upright microscope that was used to visualize individual muscle fibres and the three electrodes (glass pipettes filled with 2 M potassium citrate). For $G_m$ measurements, the electrodes were inserted into the same fibre with known inter-electrode distances of 0.35-0.5 mm (V1-V2, X1) and 1.1-1.5 mm (V1-V3, X3) (FIG. 1A). The membrane potential of the impaled muscle fibre was recorded by all electrodes. Two of the electrodes were furthermore used to inject 50 ms current pulses of −30 nA. Given the positions of the electrodes, three different inter-electrode distances could be identified (X1-X2, X1-X3, X2-X3) and hence the membrane potential responses to the current injections could be obtained at three distances from the point of current injection. The steady state voltage deflection at each distance was divided by the magnitude of current injected (−30 nA) and the resulting transfer resistances were plotted against inter-electrode distance and the data was fitted to a mono-exponential function from which Gm could be calculated using linear cable theory (FIG. 1B).

To establish a dose response relationship, Gm was first determined in 10 muscle fibres in the absence of compound and then at four increasing compound concentrations with $G_m$ determinations in 5-10 fibres at each concentration. The average $G_m$ values at each concentration were plotted against compound concentration and the data was fitted to sigmoidal function to obtain an $EC_{50}$ value (FIG. 1C). Table 7 shows the $EC_{50}$ values for a range of compounds with n values referring to number of experiments that each reflect recordings from around 50 fibres.

TABLE 7

Inhibition of ClC-1 ion channel using compounds of the invention

| Compound investigated | $EC_{50}$ (μM) |
|---|---|
| Compound A-6 | 7.4 ± 1.4 (n = 4) |
| Compound A-26 | 3.8 ± 0.8 (n = 7) |

TABLE 7-continued

Inhibition of ClC-1 ion channel using compounds of the invention

| Compound investigated | $EC_{50}$ (μM) |
|---|---|
| Compound A-27 | 4.5 ± 1.7 (n = 7) |
| Compound A-31 | 7.2 ± 2.8 (n = 2) |
| Compound A-40 | 4.2 ± 0.6 (n = 3) |
| Compound A-54 | 6.8 ± 1.3 (n = 2) |
| Compound A-58 | 6.3 ± 2.4 (n = 2) |

In conclusion, this example demonstrates that the compounds of the present invention have an $EC_{50}$ value in the range of 3-8 μM.

Example 13: Measurement of Force in an In Vitro Model

The current invention relates to compounds that inhibit ClC-1 ion channels and increase muscle excitability and thereby improve muscle function in clinical conditions where muscle activation is failing. Such conditions result in loss of contractile function of skeletal muscle, weakness and excessive fatigue. In this series of experiments the compounds were tested for their ability to restore contractile function of isolated rat muscle when the neuromuscular transmission had been compromised akin to neuromuscular disorders.

Experimentally, soleus muscles from 4-5 wk old rats were isolated with the motor nerve remaining attached. The nerve-muscle preparations were mounted in experimental setups that enabled electrical stimulation of the motor nerve. Stimulation of the motor nerve led to activation of the muscle fibres and ensuing force production that was recorded. The nerve-muscle preparations were also in these experiments incubated in the standard Krebs Ringer (see example 5) and the solution was heated to 30° C. and continuously equilibrated with a mixture of 95% $O_2$ and 5% $CO_2$, pH~7.4.

Figure 2A:
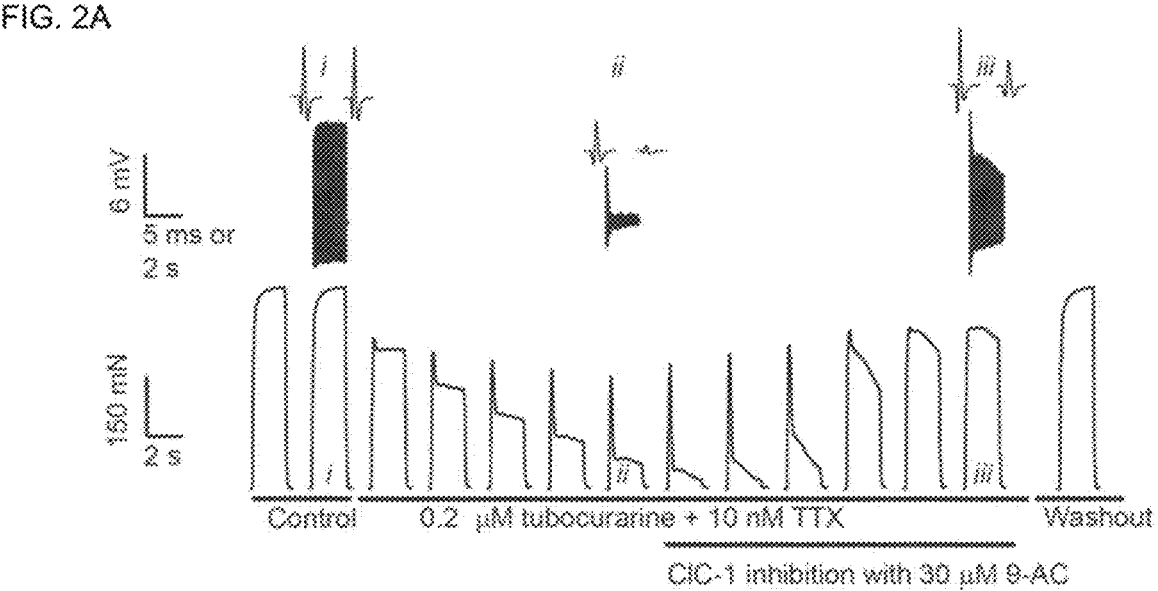
FIGS. 2A-2B. Effect of ClC-1 channel inhibition with 9-AC on nerve-stimulated force in rat soleus muscles exposed to tubocurarine or elevated extracellular Mg$^{2+}$. Muscles were stimulated to contract by activation of the motor nerve using a suction electrode. During experiments, the muscles contracted every 10 min for 2 s in response to 60 Hz stimulation.
Figure 2B:
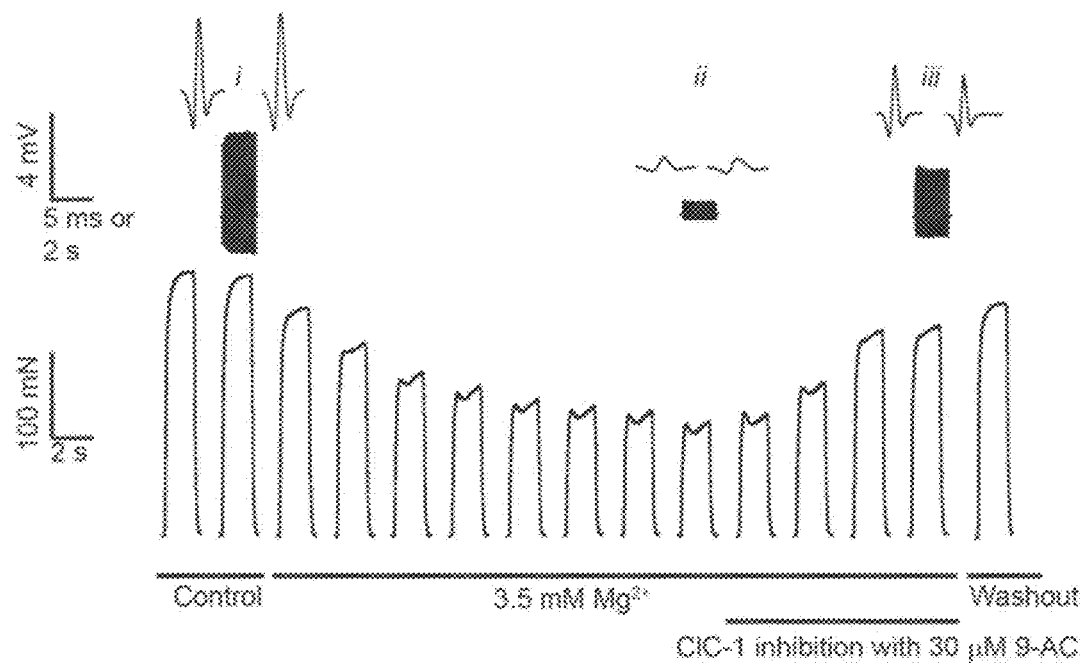
Figure 3A:
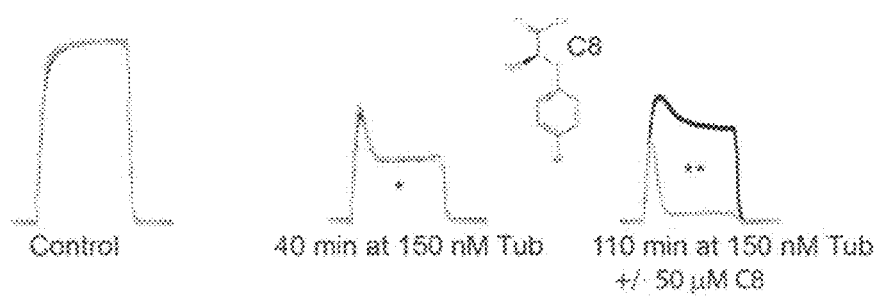
FIGS. 3A-3B. Example of recovery of nerve-stimulated force with a clofibric acid derivative, C8, in muscles exposed to 150 nM tubocurarine. The motor nerve was stimulated every 10 min for 2 s with 30 Hz with field stimulation using short duration pulses.
Figure 3B:
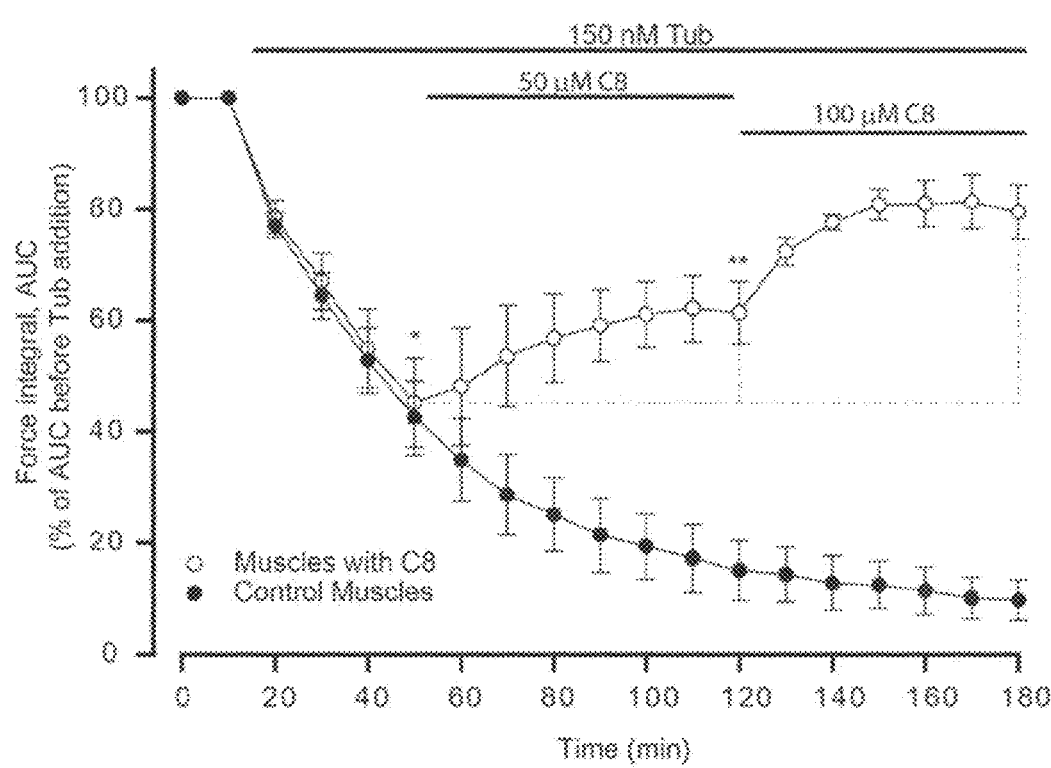

After mounting the nerve-muscle preparation in the experimental setup, the contractile function of the muscle was initially assessed under the control conditions (FIG. 2A). Sub-maximal concentration of tubocurarine (115 nM), an acetylcholine receptors antagonist, was then added to the experimental bath to impose partial inhibition of the ability of the motor nerve to activate the muscle fibres. The experimental condition mimics the failing neuromuscular transmission in a range of neuromuscular disorders. After addition of tubocurarine the contractile force declined over the next 90 mins to 10-50% of the control force. 50 μM of the test compound was then added and the contractile force recovered despite the continued presence of tubocurarine. To quantify the ability of the compound to restore force the percentage of the initial force that was restored was determined after 40 mins of compound exposure (FIG. 2B) and the point increase is reported in Table 8.

TABLE 8

Percentage increase of initial force that was restored

| Compound investigated | Point increase (%) |
|---|---|
| Compound A-6 | 44 |
| Compound A-26 | 39 |
| Compound A-27 | 46 |
| Compound A-31 | 42 |

TABLE 8-continued

Percentage increase of initial force that was restored

| Compound investigated | Point increase (%) |
|---|---|
| Compound A-40 | 20 |
| Compound A-58 | 44 |

In conclusion, this example demonstrates that the compounds of the present invention are able to increase muscle excitability and thereby improve muscle function in clinical conditions. The muscle contractility was recovered by 20-46% points, which meant almost complete restoration of the force.

The invention claimed is:

1. A compound of Formula (II.2):

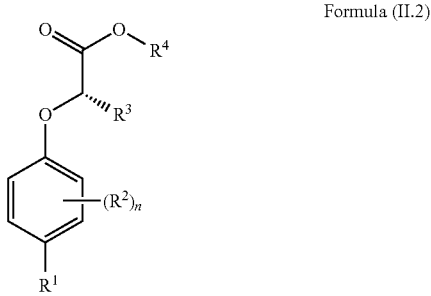

Formula (II.2)

wherein:
R$^1$ is selected from the group consisting of F, Cl, Br, and I;
R$^2$ is independently selected from the group consisting of hydrogen, deuterium, F, Cl, Br, I, —CN, —CF$_3$ and -oxime optionally substituted with C$_1$ alkyl;
R$^3$ is C$_{1-5}$ alkyl substituted with one or more substituents R$^5$;
R$^4$ is H;
R$^5$ is independently F; and
n is an integer 0, 1 or 2;
or a pharmaceutically acceptable salt, hydrate, polymorph, tautomer, or solvate thereof.

2. The compound according to claim 1, wherein
R$^1$ is selected from the group consisting of F, Cl, Br, and I;
R$^3$ is C$_{1-5}$ alkyl substituted with one or more F;
R$^4$ is H; and
n is 0;
or a pharmaceutically acceptable salt, hydrate, polymorph, tautomer, or solvate thereof.

3. The compound according to claim 1, wherein the compound is of Formula (III.2):

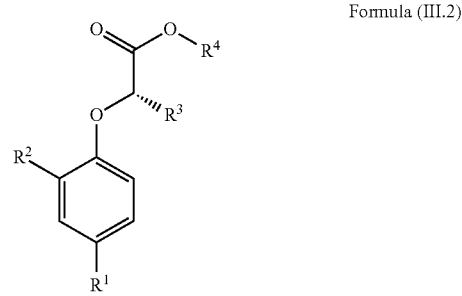

Formula (III.2)

wherein:
R$^1$ is selected from the group consisting of Cl, Br, and I;
R$^2$ is selected from the group consisting of deuterium, F, Cl, Br, I, and
oxime optionally substituted with C$_1$ alkyl;
R$^3$ is C$_{1-5}$ alkyl substituted with one or more F; and
R$^4$ is H;
or a pharmaceutically acceptable salt, hydrate, polymorph, tautomer, or solvate thereof.

4. The compound according to claim 1, wherein the compound is of Formula (IV.2):

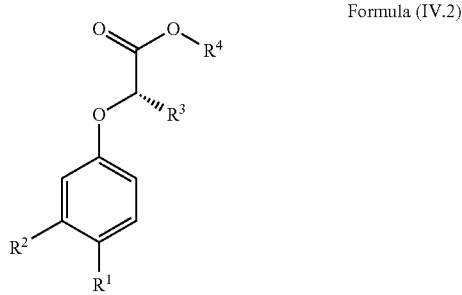

Formula (IV.2)

wherein:
R$^1$ is selected from the group consisting of Cl, Br, and I;
R$^2$ is selected from the group consisting of deuterium, F, Cl, Br, and I;
R$^3$ is C$_{1-5}$ alkyl substituted with one or more F; and
R$^4$ is H;
or a pharmaceutically acceptable salt, hydrate, polymorph, tautomer, or solvate thereof.

5. The compound according to claim 1, wherein the compound is of Formula (V.2) or (VI.2):

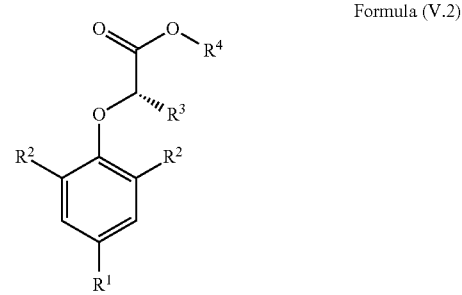

Formula (V.2)

-continued

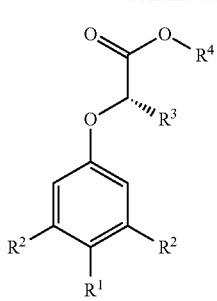

Formula (VI.2)

wherein:
R¹ is Br, Cl or I;
R² is independently deuterium, F, Cl, Br, or I;
R³ is $C_{1-5}$ alkyl substituted with one or more F; and
R⁴ is H;
or a pharmaceutically acceptable salt, hydrate, polymorph, tautomer, or solvate thereof.

6. The compound according to claim 1, wherein the compound is selected from the group consisting of:
(2R)-2-[4-bromo(3,5-H)phenoxy]-3-fluoropropanoic acid;
(2R)-2-[4-bromo(2,6-H)phenoxy]-3-fluoropropanoic acid;
(2R)-2-(4-bromo-2-fluorophenoxy)-3,3-difluoropropanoic acid;
(2R)-2-(4-bromo-2-fluorophenoxy)-3-fluoropropanoic acid;
(2R)-2-(2-bromo-4-chlorophenoxy)-3-fluoropropanoic acid;
(2R)-2-(4-chlorophenoxy)-3-fluoropropanoic acid;
(2R)-2-(4-chloro-2-fluorophenoxy)-3-fluoropropanoic acid;
(2R)-2-(2,4-dibromophenoxy)-3-fluoropropanoic acid; and
(2R)-2-(4-bromophenoxy)-3-fluoropropanoic acid;
or a pharmaceutically acceptable salt, hydrate, polymorph, tautomer, or solvate thereof.

7. The compound according to claim 1, wherein the compound has the following structure:

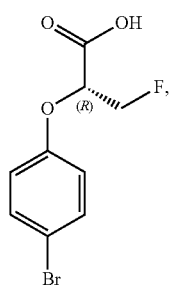

or a pharmaceutically acceptable salt, hydrate, polymorph, tautomer, or solvate thereof.

8. A method of treating and/or ameliorating a disorder in a patient by inhibiting a ClC-1 receptor in a patient, comprising administering to a patient in need thereof a compound according to claim 1 or a pharmaceutically acceptable salt, hydrate, polymorph, tautomer, or solvate thereof, wherein the disorder is selected from the group consisting of amyotrophic lateral sclerosis (ALS), spinal muscular atrophy (SMA), X-linked spinal and bulbar muscular atrophy, Kennedy's disorder, multifocal motor neuropathy, Guillain-Barre syndrome, poliomyelitis, post-polio syndrome, myasthenia gravis, critical illness myopathy (CIM), critical illness polyneuropathy, Charcot-Marie tooth disease (CMT), sarcopenia, Chronic fatigue syndrome (CFS), metabolic myopathy, mitochondrial myopathy, and Lambert-Eaton syndrome.

9. A method of treating and/or ameliorating a neuromuscular disorder in a patient, comprising administering to a patient in need thereof a therapeutically effective amount of a compound according to claim 1 or a pharmaceutically acceptable salt, hydrate, polymorph, tautomer, or solvate thereof.

10. A method of reversing and/or ameliorating a neuromuscular blockade in a patient, comprising administering to a patient in need thereof a therapeutically effective amount of a compound according to claim 1 or a pharmaceutically acceptable salt, hydrate, polymorph, tautomer, or solvate thereof.

11. The method according to claim 9, wherein the neuromuscular disorder is myasthenia gravis.

12. The method according to claim 9, wherein the neuromuscular disorder is amyotrophic lateral sclerosis (ALS).

13. The method according to claim 9, wherein the neuromuscular disorder is spinal muscular atrophy (SMA), critical illness myopathy (CIM), Charcot-Marie tooth disease (CMT) or sarcopenia.

14. The method according to claim 9, wherein the neuromuscular disorder has been induced by a neuromuscular blocking agent.

15. The compound according to claim 1, wherein:
R¹ is selected from the group consisting of F, Cl, Br and I;
R² is independently selected from the group consisting of deuterium, F, Cl, Br and I, and
n is an integer 1 or 2.

16. The compound of claim 1, wherein:
wherein R³ is selected from the group consisting of —$CH_2F$, —$CHF_2$, —$CF_3$, —$CH_2CH_2F$, —$CH_2CHF_2$ and —$CH_2CF_3$.

* * * * *